US011426552B2

(12) United States Patent
Moiler et al.

(10) Patent No.: US 11,426,552 B2
(45) Date of Patent: Aug. 30, 2022

(54) FOAM CUSHION RESPIRATORY APPARATUS

(71) Applicant: ResMed Pty Ltd, Bella Vista (AU)

(72) Inventors: Grant Moiler, Chipping Norton (AU); Nigel Quarmby, Beaumont Hills (AU)

(73) Assignee: ResMed Pty Ltd ( * ) Notice: Subject to any disclaimer, the term of this patent is extended or adjusted under 35 U.S.C. 154(b) by 469 days.

(21) Appl. No.: 15/509,638

(22) PCT Filed: Oct. 7, 2015

(86) PCT No.: PCT/AU2015/050608
§ 371 (c)(1),
(2) Date: Mar. 8, 2017

(87) PCT Pub. No.: WO2016/054692
PCT Pub. Date: Apr. 14, 2016

(65) Prior Publication Data
US 2017/0361048 A1    Dec. 21, 2017

Related U.S. Application Data

(60) Provisional application No. 62/062,444, filed on Oct. 10, 2014.

(51) Int. Cl.
A61M 16/06    (2006.01)
A61M 16/00    (2006.01)
(Continued)

(52) U.S. Cl.
CPC .... A61M 16/0622 (2014.02); A61M 16/0066 (2013.01); A61M 16/06 (2013.01);
(Continued)

(58) Field of Classification Search
CPC .............. A61M 16/022; A61M 16/105; A61M 16/0633; A61M 16/0616; A61M 16/0825;
(Continued)

(56) References Cited

U.S. PATENT DOCUMENTS 4,782,832 A    11/1988  Trimble et al.
4,944,310 A    7/1990   Sullivan
(Continued)

FOREIGN PATENT DOCUMENTS

CN    102149422 A    8/2011
CN    103561820 A    2/2014
(Continued)

OTHER PUBLICATIONS

McMaster-Carr, About Foam, "Lightweight High-Temperature Polyimide Foam Sheets" (Year: 2021).*
(Continued)

Primary Examiner — Bradley H Philips
Assistant Examiner — Savannah L Gabriel
(74) Attorney, Agent, or Firm — Botos Churchill IP Law LLP

(57) ABSTRACT

A mask apparatus for a respiratory treatment can permit delivery of breathable gas to a user. In one example, the mask may employ a frame and cushion to form a seal for both mouth and nose. The frame may be adapted for coupling with a respiratory treatment apparatus so as to permit communication of a pressurized gas from the respiratory treatment apparatus. The cushion, which may be foam, and a frame component may be made in an over-moulding process that moulds the frame onto a pre-formed foam cushion. Such a moulding process may form a mechanical and/or chemical bonding of the foam and mask frame component. The mask frame component may be a shell of plenum chamber, such as for both nose and mouth. Various features of the cushion may further promote sealing and comfort for the under the nose design.

34 Claims, 87 Drawing Sheets

(51) Int. Cl.
*A61M 16/08* (2006.01)
*A61M 16/10* (2006.01)

(52) U.S. Cl.
CPC .... *A61M 16/0616* (2014.02); *A61M 16/0633* (2014.02); *A61M 16/0683* (2013.01); *A61M 16/0825* (2014.02); *A61M 16/105* (2013.01); *A61M 16/107* (2014.02); *A61M 2016/0027* (2013.01); *A61M 2016/0039* (2013.01); *A61M 2205/42* (2013.01); *A61M 2207/10* (2013.01)

(58) Field of Classification Search
CPC .......... A61M 16/0066; A61M 16/0683; A61M 16/06; A61M 16/107; A61M 2205/42; A61M 2916/0039; A61M 2916/0027; A61M 2207/10; B29C 44/005
See application file for complete search history.

(56) References Cited

U.S. PATENT DOCUMENTS

| | | |
|---|---|---|
| 6,532,959 B1 | 3/2003 | Berthon-Jones |
| 6,581,594 B1 | 6/2003 | Drew et al. |
| 2003/0196656 A1 | 10/2003 | Moore et al. |
| 2009/0044808 A1* | 2/2009 | Guney ............... A61M 16/0605 128/206.24 |
| 2009/0050156 A1 | 2/2009 | Ng et al. |
| 2009/0223521 A1* | 9/2009 | Howard ............. A61M 16/065 128/206.23 |
| 2010/0000534 A1 | 1/2010 | Kooij et al. |
| 2010/0018534 A1* | 1/2010 | Veliss ............... A61M 16/0622 128/206.24 |
| 2011/0000492 A1* | 1/2011 | Veliss ............... A61M 16/0666 128/207.13 |
| 2011/0088699 A1 | 4/2011 | Skipper et al. |
| 2011/0146684 A1* | 6/2011 | Wells ................... A61M 16/06 128/205.25 |
| 2012/0125341 A1 | 5/2012 | Gebrewold et al. |
| 2012/0138061 A1* | 6/2012 | Dravitzki ............. A61M 16/06 128/205.25 |
| 2012/0222680 A1 | 9/2012 | Eves et al. |
| 2013/0133660 A1* | 5/2013 | Ng ....................... A61M 16/06 128/205.25 |
| 2013/0139824 A1 | 6/2013 | Mazzone et al. |
| 2014/0021645 A1* | 1/2014 | Rayess ............. B29C 45/14795 264/69 |
| 2014/0083431 A1* | 3/2014 | Burz .................... A61M 16/06 128/206.24 |

FOREIGN PATENT DOCUMENTS

| | | | |
|---|---|---|---|
| EP | 2213324 A1 | 8/2010 | |
| JP | 2012501763 A | 1/2012 | |
| WO | 1998004310 A1 | 2/1998 | |
| WO | 1998034665 A1 | 8/1998 | |
| WO | 00078381 A1 | 12/2000 | |
| WO | 2004073778 A1 | 9/2004 | |
| WO | 2005063328 A1 | 7/2005 | |
| WO | 2006074513 A1 | 7/2006 | |
| WO | 2006130903 A1 | 12/2006 | |
| WO | 2007009182 A1 | 1/2007 | |
| WO | 2009052560 A1 | 4/2009 | |
| WO | 2009100905 A1 | 8/2009 | |
| WO | 2010028425 A1 | 3/2010 | |
| WO | 2010135785 A1 | 12/2010 | |
| WO | 2012052902 A2 | 4/2012 | |
| WO | 2012052906 A1 | 4/2012 | |
| WO | WO-2014085942 A1 * | 6/2014 | ....... B29C 66/12441 |
| WO | 2014110622 A1 | 7/2014 | |
| WO | 2014117227 A1 | 8/2014 | |

OTHER PUBLICATIONS

Supplementary European Search Report including Written Opinion for EP Application No. 15848522.7, dated Apr. 25, 2018.
Chiu, Hsien-Tang et. al., "Study on Mechanical Properties and Intermolecular Interaction of Silicone Rubber/Polyurethane/Epoxy Blends", Journal of Applied Polymer Science, 2003, pp. 959-970, vol. 89.
International Search Report for Application No. PCT/AU2015/050608 dated May 18, 2016.
West, John B., "Respiratory Physiology: The Essentials", Jan. 2012, 9th Edition, Lippincott Williams & Wilkins, Baltimore, MD.
Chinese Office Action issued in corresponding CN application No. 2015800649679 dated Dec. 28, 2018.
"Design Focus: The name of this game is bond—good bond", www.plasticstoday.com, Apr. 1, 2005.
EP examination report dated Aug. 13, 2020 for EP Patent Application No. 729889.
TPE Overmolding, Bonding and Substrate Considerations, https://web.archive.org/web/20131229061928. Dec. 29, 2013.
Naitove, Matthew , "Do's and Don'ts for Overmolding Liquid Silicone onto Thermoplastics," Plastics Technology, https://www.ptonline.com/articles/do's-and-don'ts-for-overmolding-liquid-silicone-onto-thermoplastics, Aug. 11, 2020.
The Extended European Search Report for European Patent Application No. 22159330.4, dated Jul. 11, 2022.

* cited by examiner

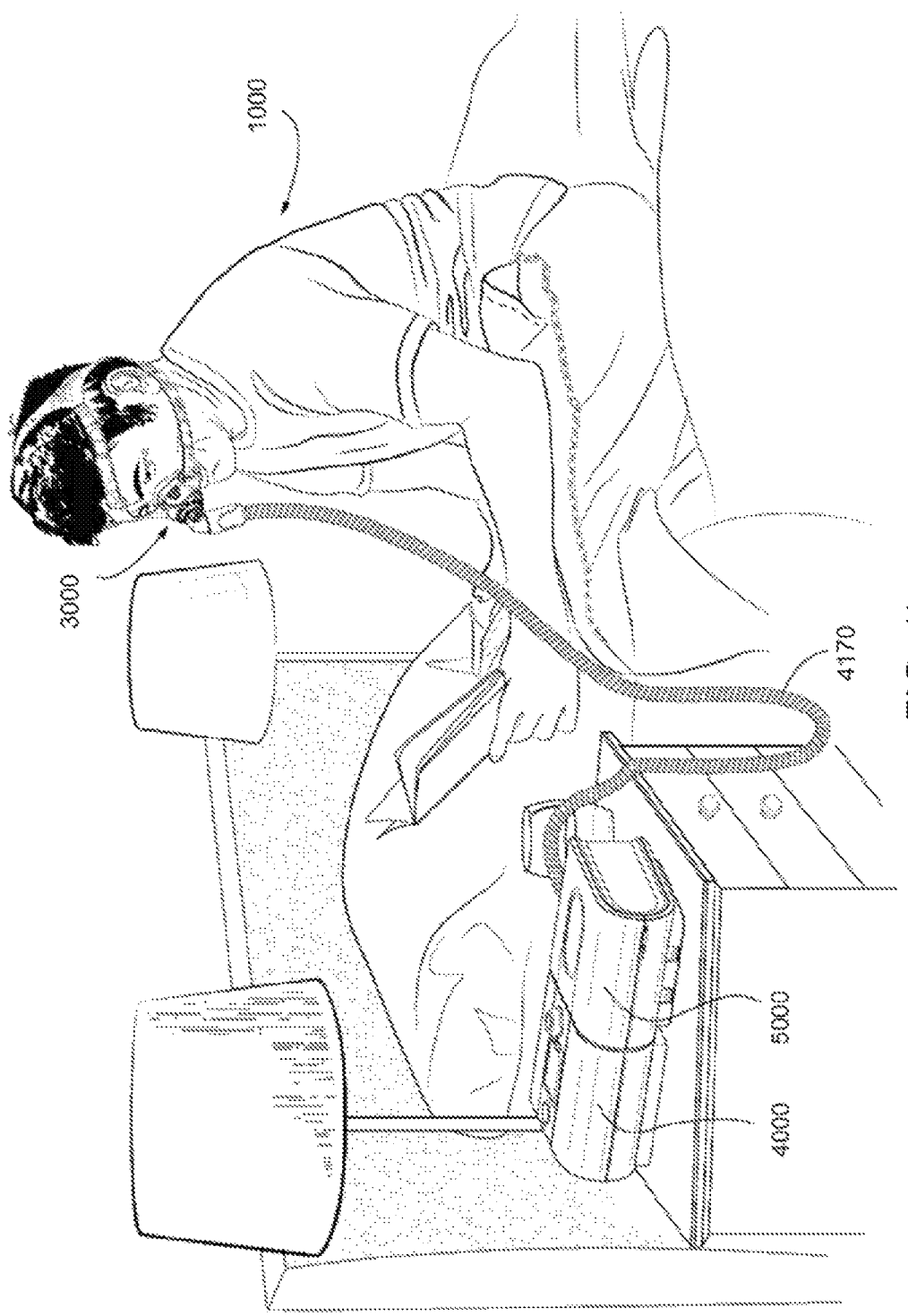

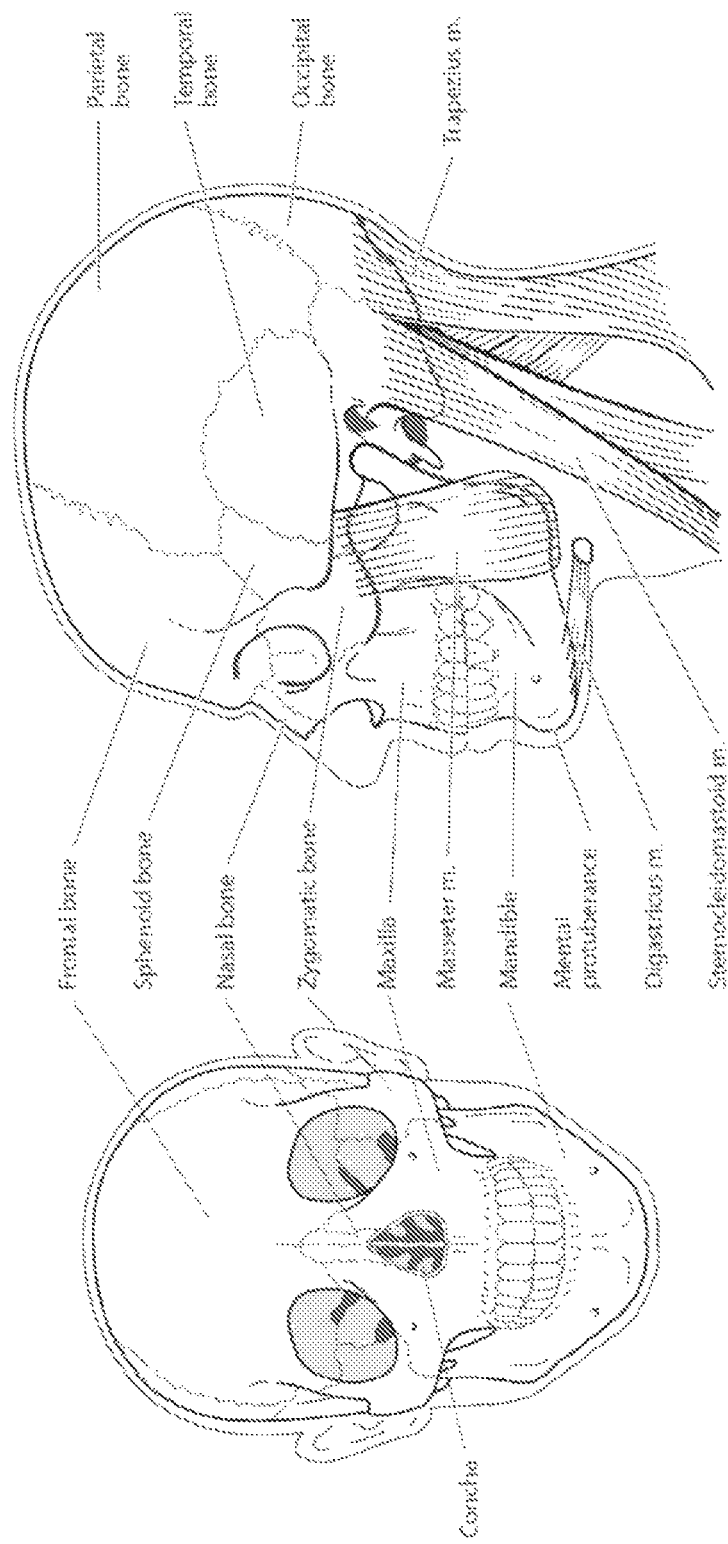

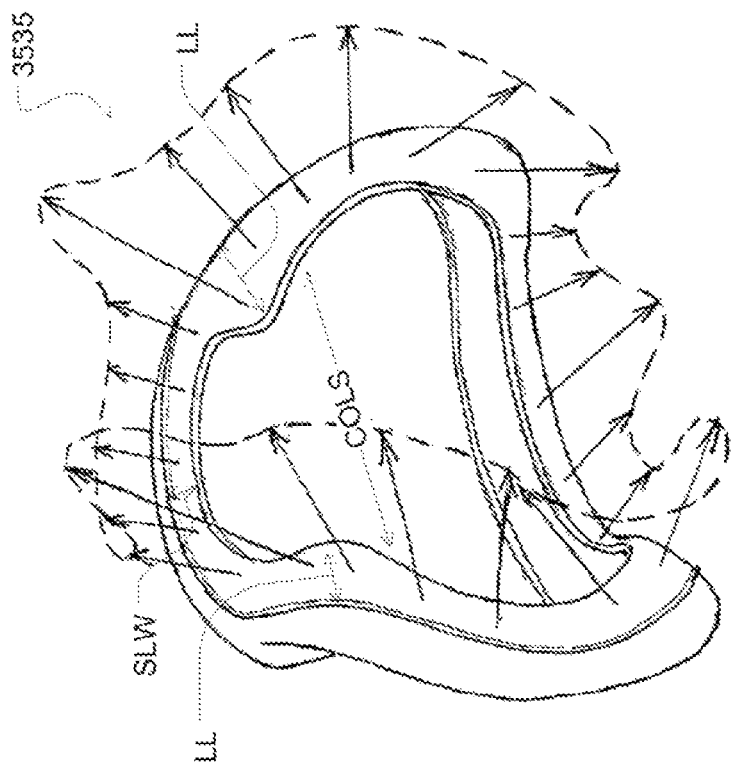
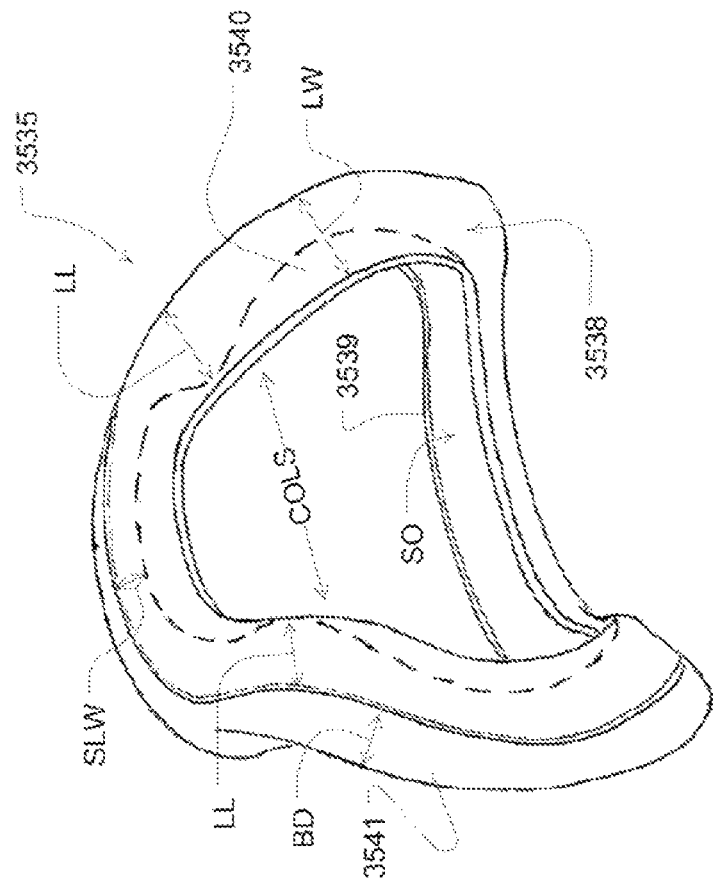
FIG. 19
FIG. 18

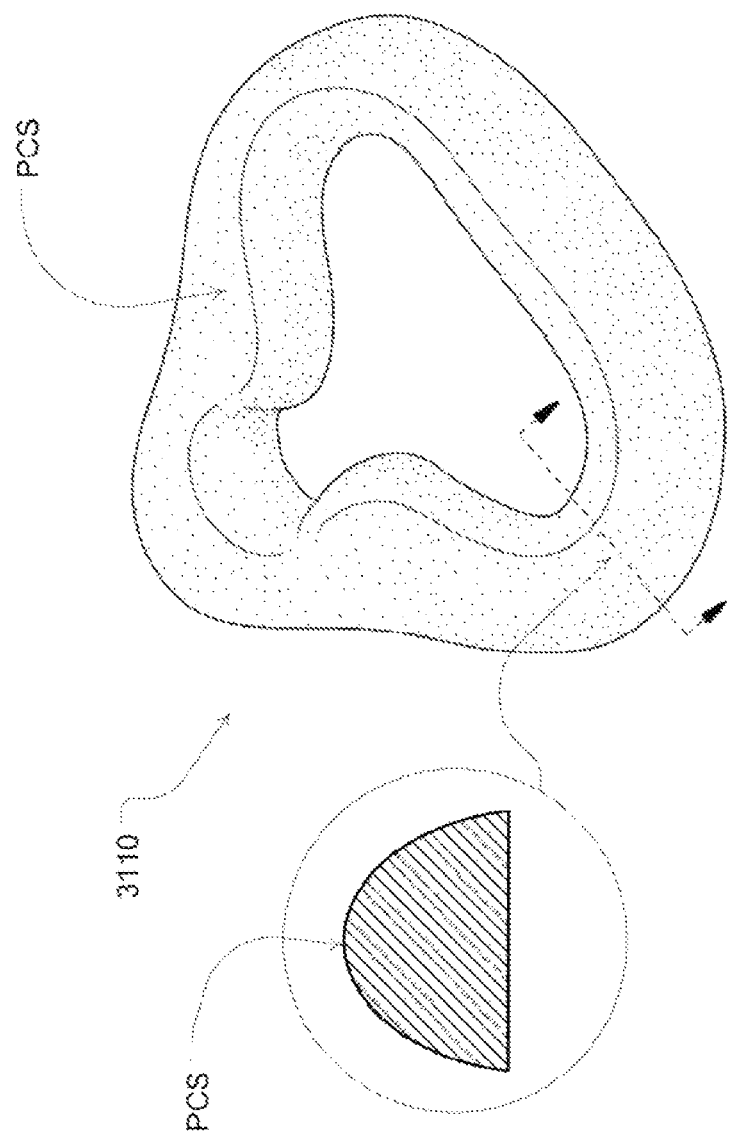

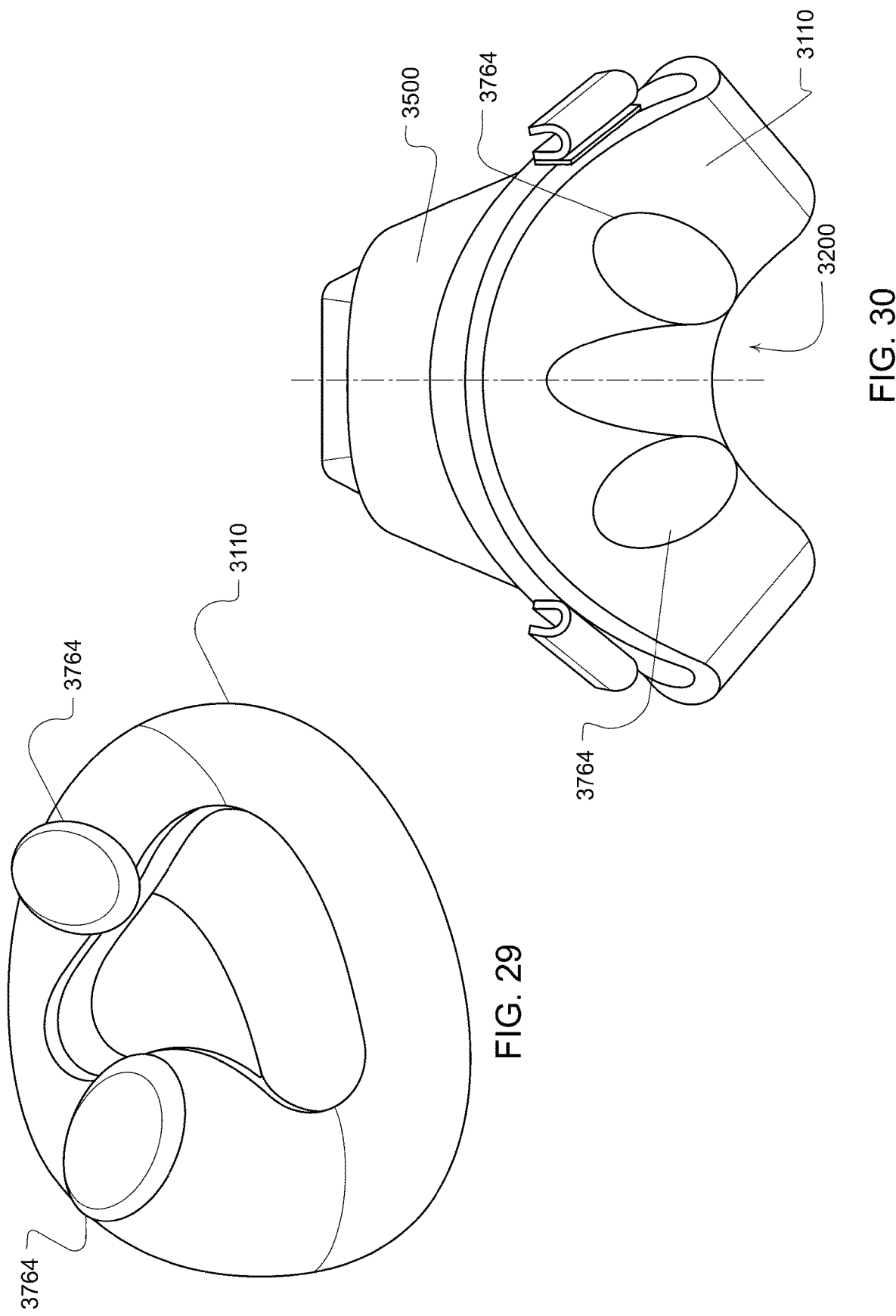

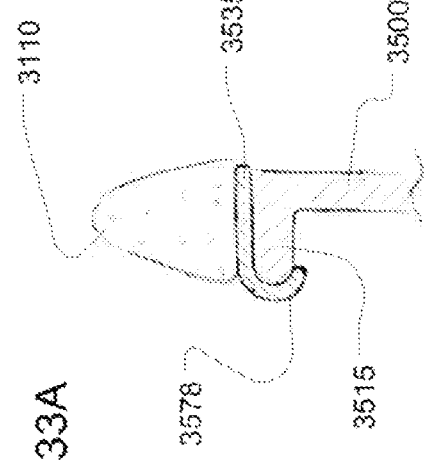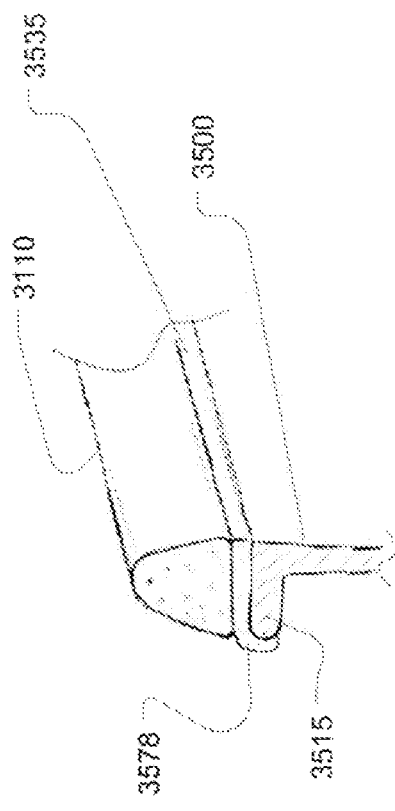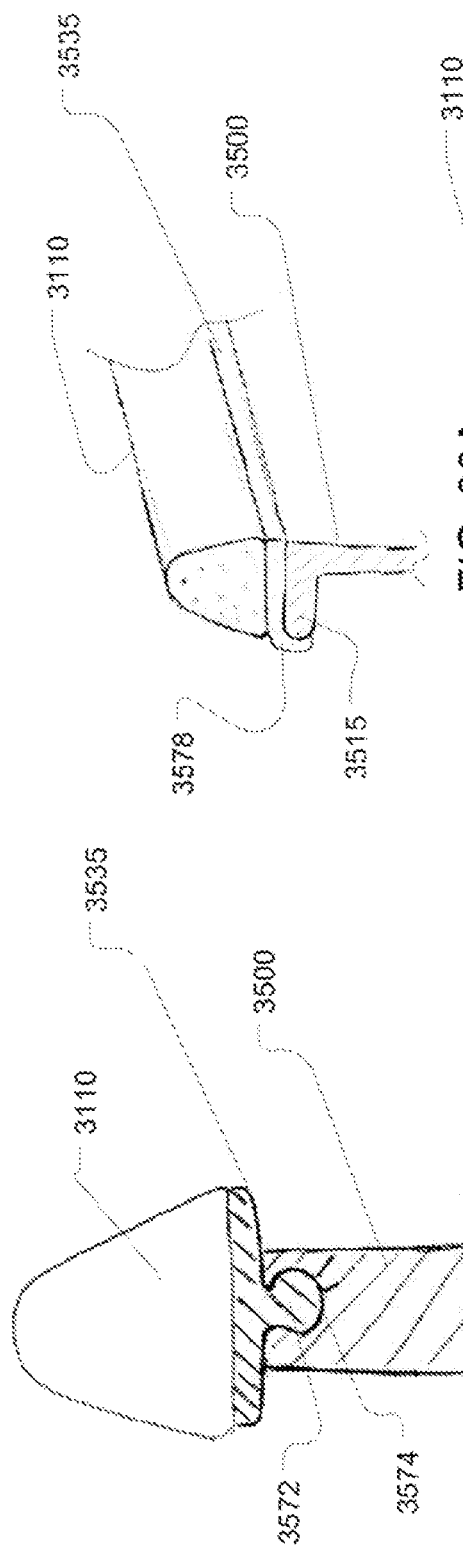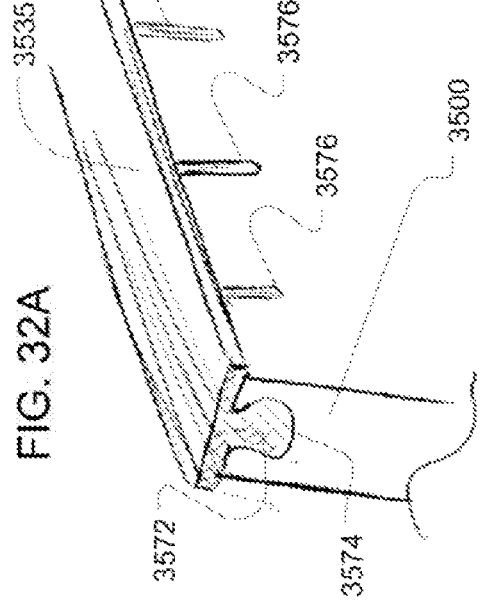

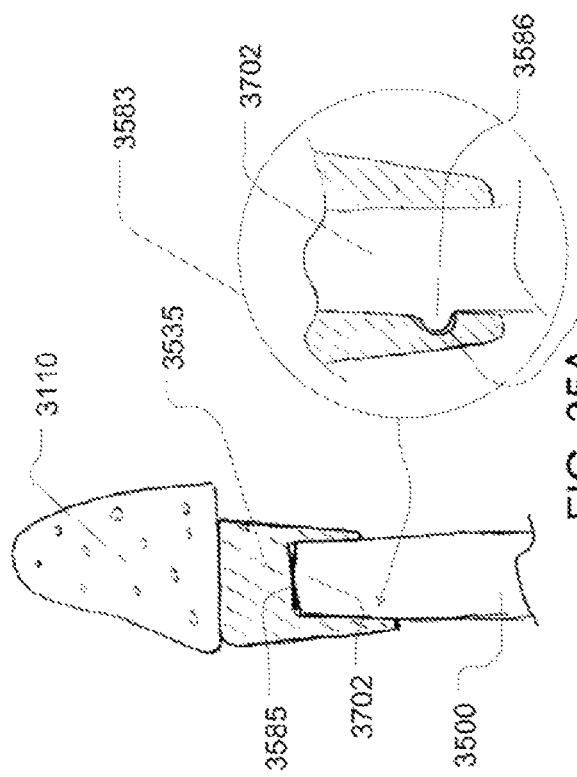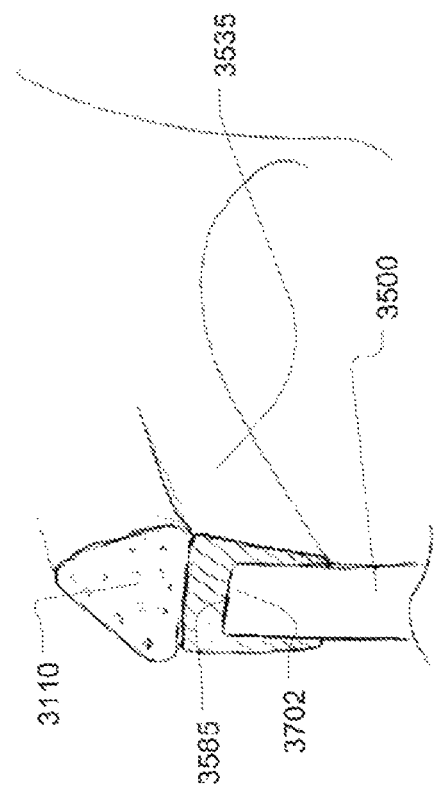
FIG. 35A
FIG. 35B
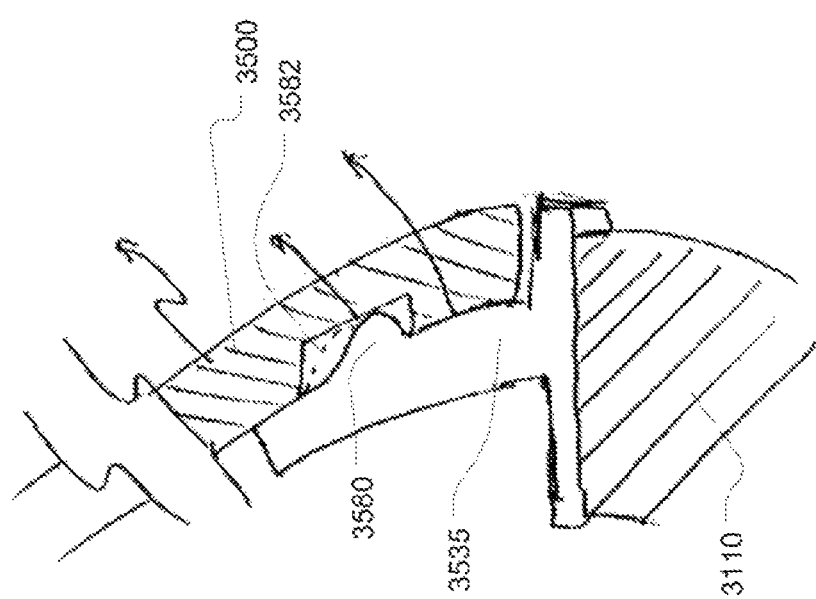
FIG. 34

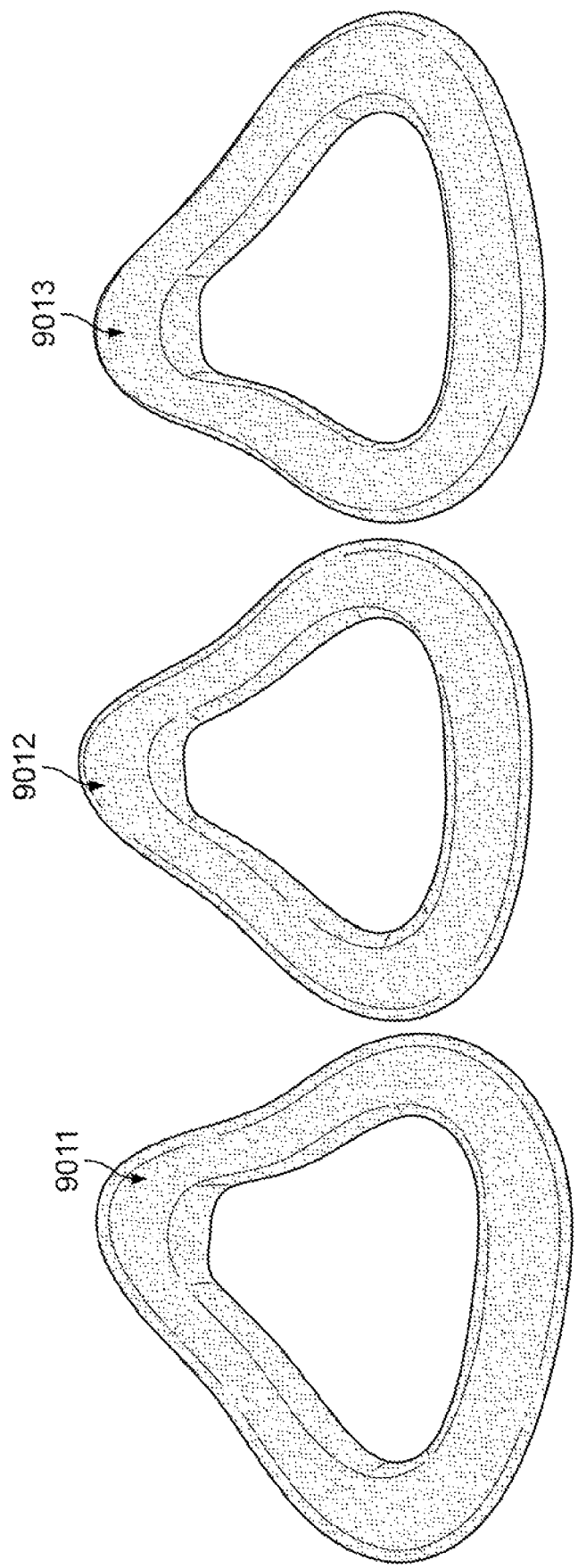

FOAM CUSHION RESPIRATORY APPARATUS

CROSS-REFERENCE TO RELATED APPLICATIONS

The present application is a national phase entry under 35 U.S.C. § 371 of International Application No. PCT/AU2015/050608 filed Oct. 7, 2015, published in English, which claims priority from U.S. Provisional Patent Application No. 62/062,444 filed Oct. 10, 2014, all of which are incorporated herein by reference.

2 BACKGROUND OF THE TECHNOLOGY

2.1 Field of the Technology

The present technology relates to one or more of the detection, diagnosis, treatment, prevention and amelioration of respiratory-related disorders. In particular, the present technology relates to medical devices or apparatus, and their use. Such devices may include an interface for directing a treatment to a patient respiratory system.

2.2 Description of the Related Art

The respiratory system of the body facilitates gas exchange. The nose and mouth form the entrance to the airways of a patient.

The airways consist of a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2011.

A range of respiratory disorders exist.

Obstructive Sleep Apnoea (OSA), a form of Sleep Disordered Breathing (SDB), is characterized by occlusion of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnoea on exertion, chronic cough and sputum production.

Neuromuscular Disease (NMD) may encompass many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnoea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnoea on exertion, peripheral oedema, orthopnoea, repeated chest infections, morning headaches, fatigue, poor sleep quality and loss of appetite.

Otherwise healthy individuals may take advantage of systems and devices to prevent respiratory disorders from arising.

2.2.1 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) provides ventilator support to a patient through the upper airways to assist the patient in taking a full breath and/or maintain adequate oxygen levels in the body by doing some or all of the work of breathing. The ventilator support is provided via a patient interface. NIV has been used to treat CSR, OHS, COPD, MD and Chest Wall disorders.

Invasive ventilation (IV) provides ventilatory support to patients that are no longer able to effectively breathe themselves and is provided using a tracheostomy tube.

Ventilators may control the timing and pressure of breaths pumped into the patient and monitor the breaths taken by the patient. The methods of control and monitoring patients typically include volume-cycled and pressure-cycled methods. The volume-cycled methods may include among others, Pressure-Regulated Volume Control (PRVC), Volume Ventilation (VV), and Volume Controlled Continuous Mandatory Ventilation (VC-CMV) techniques. The pressure-cycled methods may involve, among others, Assist Control (AC), Synchronized Intermittent Mandatory Ventilation (SIMV), Controlled Mechanical Ventilation (CMV), Pressure Support Ventilation (PSV), Continuous Positive Airway Pressure (CPAP), or Positive End Expiratory Pressure (PEEP) techniques.

2.2.2 Systems

One known device used for treating sleep disordered breathing is the S9 Sleep Therapy System, manufactured by ResMed. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit.

A system may comprise a PAP Device/ventilator, an air circuit, a humidifier, a patient interface, and data management.

2.2.3 Patient Interface

A patient interface may be used to interface respiratory equipment to its user, for example by providing a flow of breathable gas. The flow of breathable gas may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 cm H2O. For other forms of therapy, such as the delivery of oxygen, the patient interface may not include a seal sufficient to facilitate delivery to the airways of a supply of gas at a positive pressure of about 10 cm H2O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, mask designed as part of personal protection equipment (e.g. filter masks), SCUBA masks, or for the administration of anaesthetics may be tolerable for their original application, but nevertheless be undesirably uncomfortable to be worn for extended periods of time, e.g. several hours. This is even more so if the mask is to be worn during sleep. An uncomfortable mask may impact on patient compliance.

Nasal CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is not easily replaceable or difficult to clean (e.g. difficult to assemble or disassemble), patients may not replace or clean their mask and this may impact on patient compliance.

For these reasons, masks for delivery of nasal CPAP during sleep form a distinct field.

2.2.3.1 Seal-Forming Portion

Patient interfaces may include a seal-forming portion.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

One type of seal-forming portion extends around the periphery of the patient interface, and is intended to seal against the user's face when force is applied to the patient interface with the seal-forming portion in confronting engagement with the user's face. The seal-forming portion may consist of an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

2.2.3.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

2.2.3.3 Vent Technologies

Some forms of patient interface systems may include a vent to allow the washout of exhaled carbon dioxide. Many such vents are noisy. Others may block in use and provide insufficient washout. Some vents may be disruptive of the sleep of a bed-partner 1100 of the patient 1000, e.g. through noise or focused airflow.

ResMed Limited has developed a number of improved mask vent technologies. See WO 1998/034,665; WO 2000/078,381; U.S. Pat. No. 6,581,594; US Patent Application; US 2009/0050156; US Patent Application 2009/0044808.

Table of noise of prior masks (ISO 17510-2: 2007, 10 cmH$_2$O pressure at 1 m)

| Mask name | Mask type | A-weighted sound power level dBA (uncertainty) | A-weighted sound pressure dBA (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |
| ResMed Mirage FX | nasal | 26 (3) | 18 (3) | 2010 |
| ResMed Mirage Swift (*) | nasal pillows | 37 | 29 | 2004 |
| ResMed Mirage Swift II | nasal pillows | 28 (3) | 20 (3) | 2005 |
| ResMed Mirage Swift LT | nasal pillows | 25 (3) | 17 (3) | 2008 |
| ResMed Mirage series I, II (*) | full face | 31.7 | 23.7 | 2000 |
| ResMed UltraMirage | full face | 35 (3) | 27 (3) | 2004 |
| ResMed Mirage Quattro | full face | 26 (3) | 18 (3) | 2006 |
| ResMed Mirage Quattro FX | full face | 27 (3) | 19 (3) | 2008 |

(* one specimen only, measured using test method specified in ISO3744 in CPAP mode at 10 cm H$_2$O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.3.4 Nasal Pillow Technologies

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), U.S. Patent Application 2009/0044808 (describing amongst other things aspects of ResMed SWIFT LT nasal pillows); International Patent Applications WO 2005/063, 328 and WO 2006/130,903 (describing amongst other things aspects of ResMed LIBERTY full-face mask); International Patent Application WO 2009/052,560 (describing amongst other things aspects of ResMed SWIFT FX nasal pillows).

2.2.4 Respiratory Apparatus (PAP Device/Ventilator)

Examples of respiratory apparatuses include ResMed's S9 AutoSet™ PAP device and ResMed's Stellar™ 150 ventilator. PAP devices or ventilators typically comprise a flow generator, such as a motor-driven blower or a compressed gas reservoir, and are configured to provide a controlled supply of breathable gases (e.g., air) to the airway of a patient. In some cases, the flow of air or other breathable gases may be supplied to the airway of the patient at positive pressure may be supplied to the airway of a patient by a PAP device such as a motor-driven blower. The outlet of the blower PAP device or the ventilator is connected via a flexible delivery conduit an air circuit to a patient interface such as those described above.

Ventilators or PAP devices typically include a flow generator, an inlet filter, a patient interface, an air circuit delivery conduit connecting the flow generator to the patient interface, various sensors and a microprocessor-based controller. The patient interface may include a mask or a tracheostomy tube as described above. The flow generator may include a servo-controlled motor, volute and an impeller that forms a blower. In some cases a brake for the motor may be implemented to more rapidly reduce the speed of the blower so as to overcome the inertia of the motor and impeller. The braking can permit the blower to more rapidly achieve a lower pressure condition in time for synchronization with expiration despite the inertia. In some cases the flow generator may also include a valve capable of discharging generated air to atmosphere as a means for altering the pressure delivered to the patient as an alternative to motor speed control. The sensors measure, amongst other things, motor speed, mass flow rate and outlet pressure, such as with a pressure transducer or the like. The apparatus may optionally include a humidifier and/or heater elements in the path of the air delivery circuit. The controller may include data storage capacity with or without integrated data retrieval and display functions.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

An aspect of the present technology relates to apparatus used in the treatment or prevention of a respiratory disorder.

One form of the present technology involves an interface that directs a treatment, such as a positive pressure breathable gas, to a patient respiratory system.

Another aspect of one form of the present technology involves such an interface that directs a treatment to the nares and/or mouth of the patient respiratory system.

Another aspect of one form of the present technology is a patient interface that is moulded or otherwise constructed with a clearly defined perimeter shape which is intended to match the face profile of an intended wearer.

A mask apparatus for a respiratory treatment can permit delivery of breathable gas to a user. In one example, the mask may employ a frame and cushion to form a seal for both mouth and nose. The frame may be adapted for coupling with a respiratory treatment apparatus so as to permit communication of a pressurized gas from the respiratory treatment apparatus. The cushion, which may be foam, and a frame component may be made in an overmoulding process that moulds the frame onto a preformed foam cushion. Such a moulding process may form a mechanical and/or chemical bonding of the foam and mask frame component. The mask frame component may be a shell of plenum chamber, such as for both nose and mouth. Various features of the cushion may further promote sealing and comfort for the under the nose design.

Some versions of the present technology may include a mask apparatus for a respiratory treatment. The apparatus may include a frame component adapted to couple with a respiratory treatment apparatus so as to permit communication of a pressurized gas to a respiratory system of a patient from the respiratory treatment apparatus. The apparatus may include a foam cushion adapted to conform to a facial surface of the patient for delivery of the pressurized gas. In some versions, the frame component may be overmoulded to the foam cushion to form a bond at a surface of the frame component and the foam cushion. The foam cushion may include a triangular ring having a common nasal and mouth aperture. The mask frame component may include a shell of a plenum chamber.

In some versions, the foam cushion may be formed of a thermoset foam. The frame component may be formed of a plastic material. The bond may comprise a chemical bond between material of the foam cushion and material of the frame component. The bond may comprise a mechanical bond between material of the foam cushion and material of the frame component. The mechanical bond may include an impregnation of a sub-surface of the foam cushion with material of the frame component. The mechanical bond may include an interlock of a sub-surface of the foam cushion with material of the frame component. The mechanical bond comprises hook and loop connections. The frame component and foam cushion may be joined without adhesive. The materials of the frame component may include thermoplastic polyurethane, silicone, and/or silicone/urethane copolymers. The foam cushion may be a semi-open cell foam. The foam cushion may include a generally flat seal-forming surface. The foam cushion may include a generally curved seal-forming surface. In some versions, the mask apparatus may further include a respiratory treatment apparatus configured to generate a controlled supply of breathable gas at a pressure above atmospheric pressure, the respiratory treatment apparatus including a gas delivery conduit coupled with the frame component to direct the breathable gas to the frame component.

Some versions of the present technology may involve a method of manufacturing a mask apparatus for a respiratory treatment. The method may include positioning a foam cushion within a cavity of a mould. The cavity of the mould may be for forming a mask frame component. The method may include injecting a material into the mould to form the mask frame component. In such a process, the formed frame component may be overmoulded to the foam cushion forming a bond at a surface of the frame component and the foam cushion. The foam cushion may include a triangular ring having a common nasal and mouth aperture. The mould may have a form of a shell of a plenum chamber. The foam cushion may be formed of a thermoset foam. The injected material may be a plastic. The bond may include a chemical bond between material of the foam cushion and material of the frame component. The bond may include a mechanical bond between material of the foam cushion and material of the frame component. The mechanical bond may include an impregnation of a sub-surface of the foam cushion with material of the frame component. The mechanical bond may include an interlock of a sub-surface of the foam cushion with material of the frame component. The mechanical bond may be reinforced by mechanical keying between the foam cushion and the material of the frame component. The mechanical bond may include hook and loop connections. The frame component and foam cushion may be so joined without adhesive. The injected material of the frame component may include thermoplastic polyurethane. The foam cushion may be a semi-open cell foam. The injecting may occur at a pressure range of 20 to 50 mega-pascals. The injecting may occur at a pressure of about 20 mega-pascals. The method may further include inserting a plenum chamber shaped inner moulding core against the foam cushion.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1b shows a PAP device 4000 in use on a patient with a nasal mask type of patient interface;

4.2 Therapy

4.2.1 Respiratory System

Figure 1A:
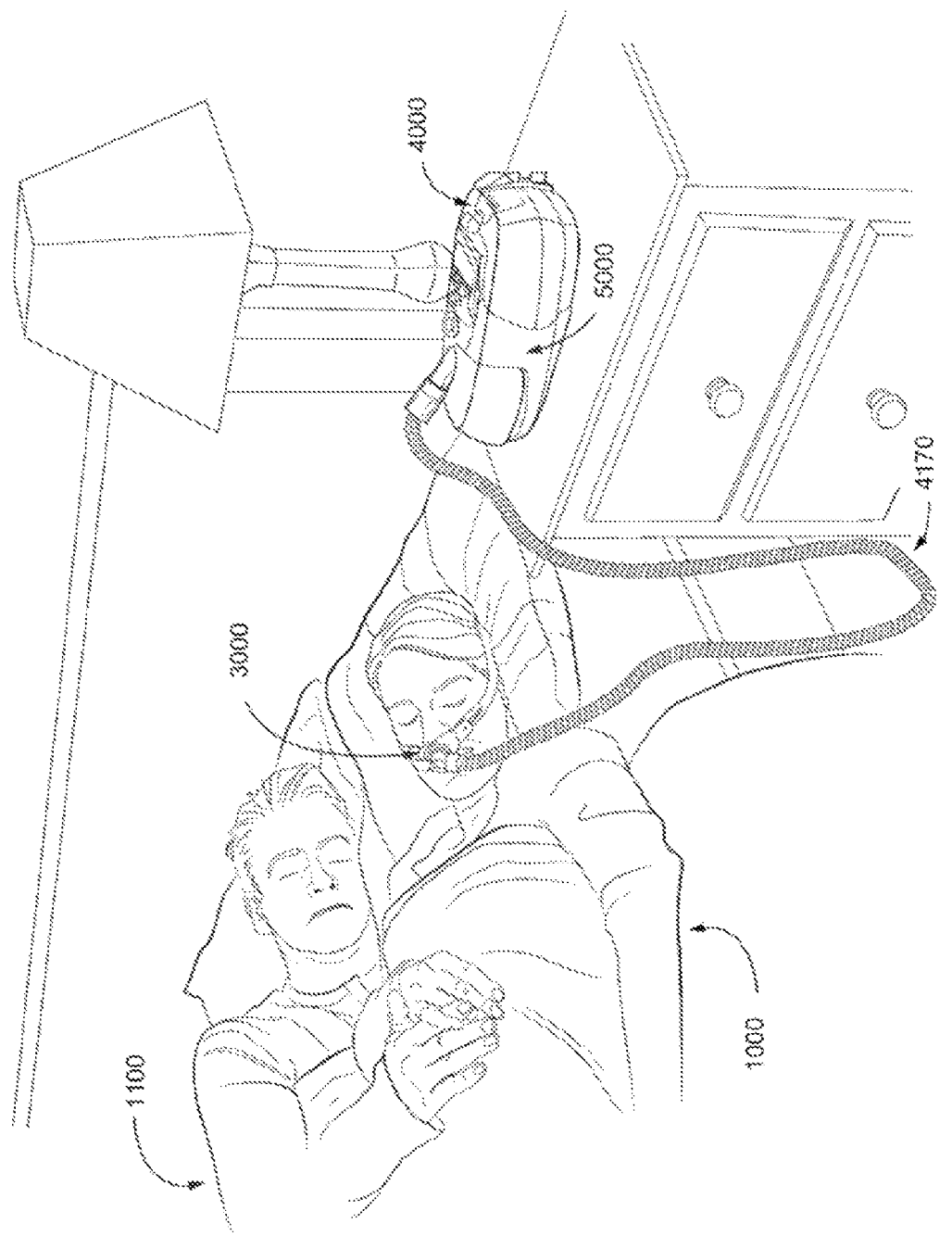
FIG. 1a shows components of a system suitable for use with examples of the present technology. A patient 1000 wearing a patient interface 3000, such as nasal prongs only covering the patient's nose, receives a supply of air at positive pressure from a PAP device 4000. Air from the PAP device is humidified in a humidifier 5000, and passes along an air circuit 4170 to the patient 1000.
Figure 1C:
FIG. 1c shows a PAP device in use on a patient with a full-face mask type of patient interface.
Figure 2A:
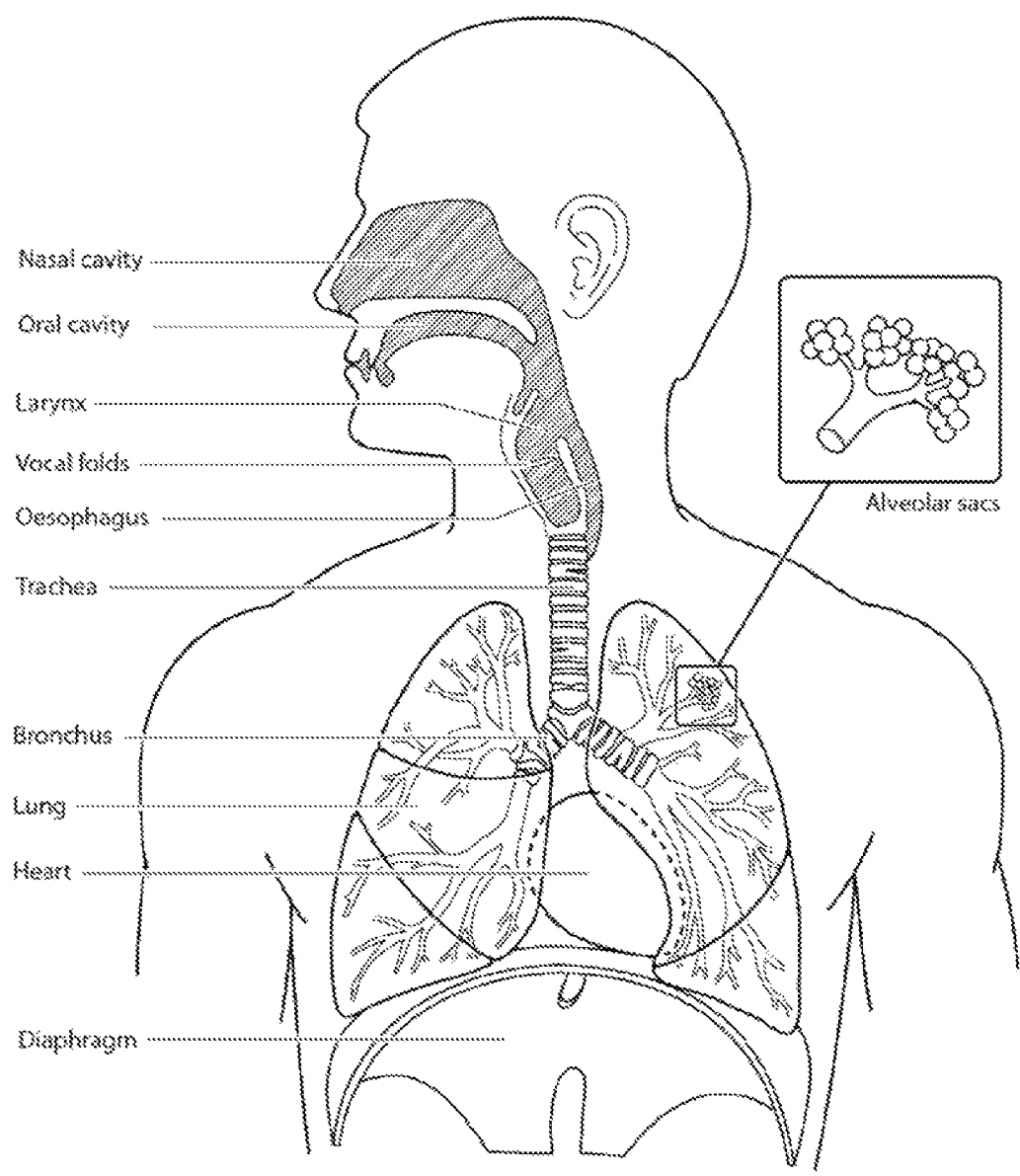
Figure 2B:
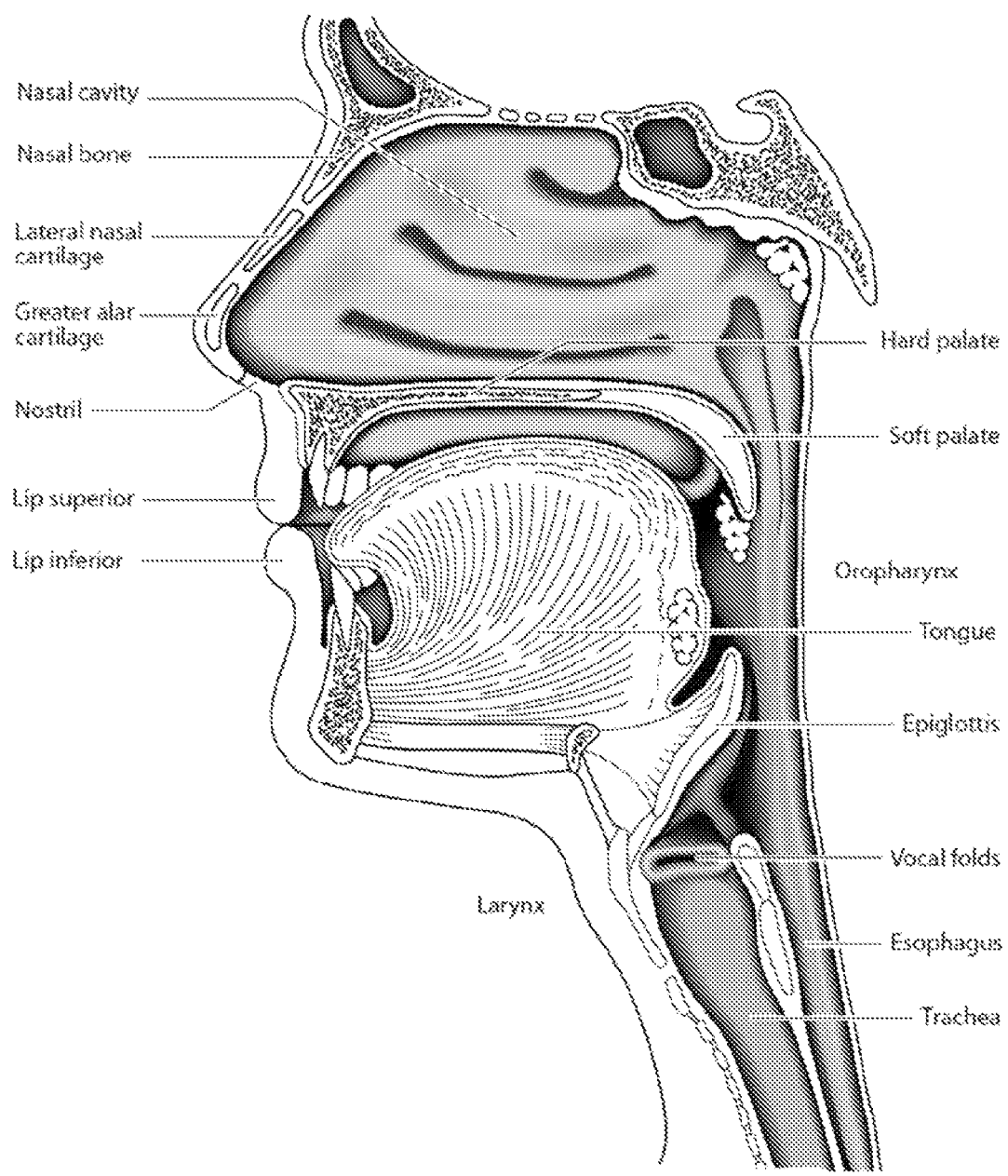

FIG. 2a shows an overview of a human respiratory system including the nasal and oral cavities, the larynx, vocal folds, oesophagus, trachea, bronchus, lung, alveolar sacs, heart and diaphragm;

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea;

4.2.2 Facial Anatomy

Figure 2C:
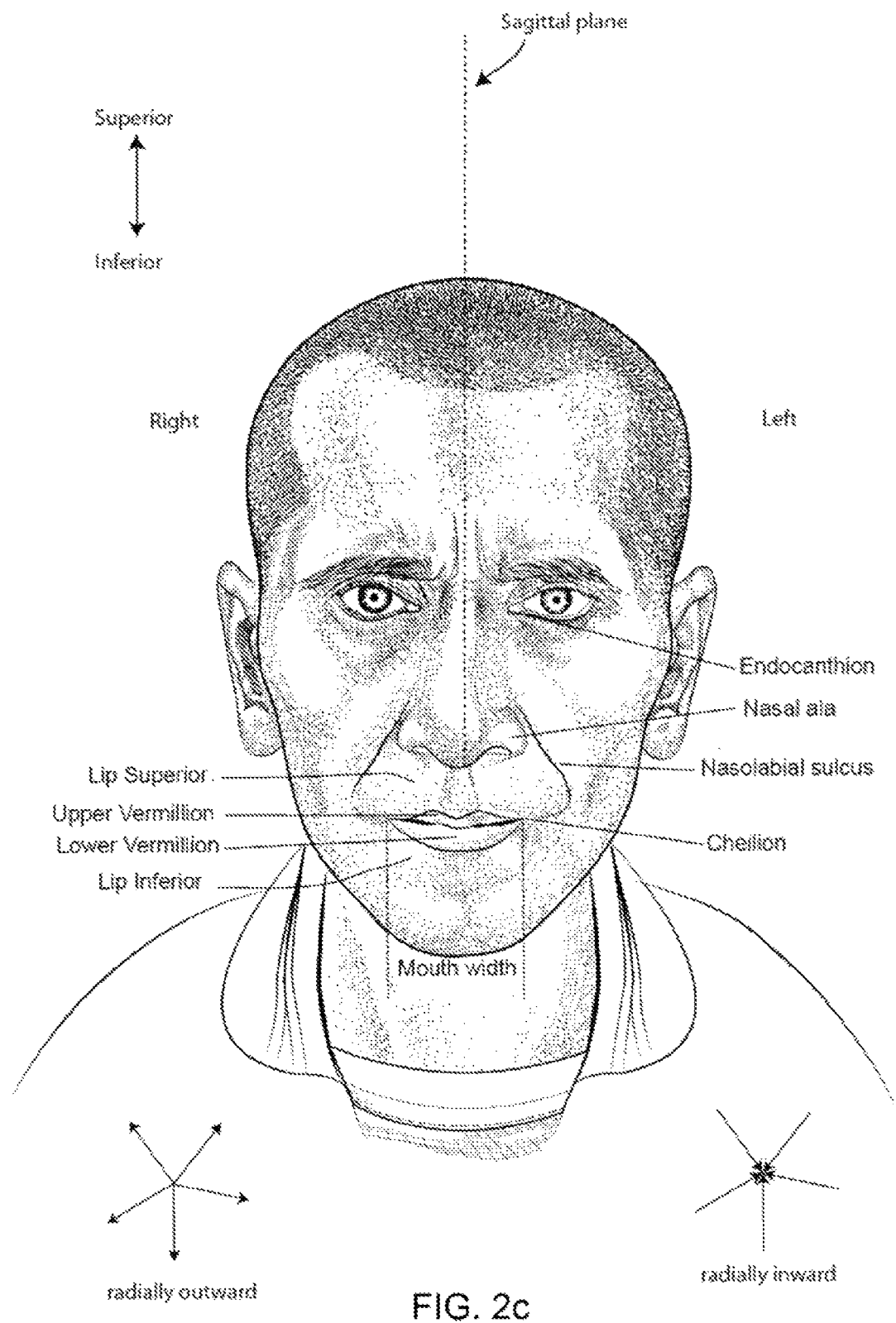
Figure 2D:
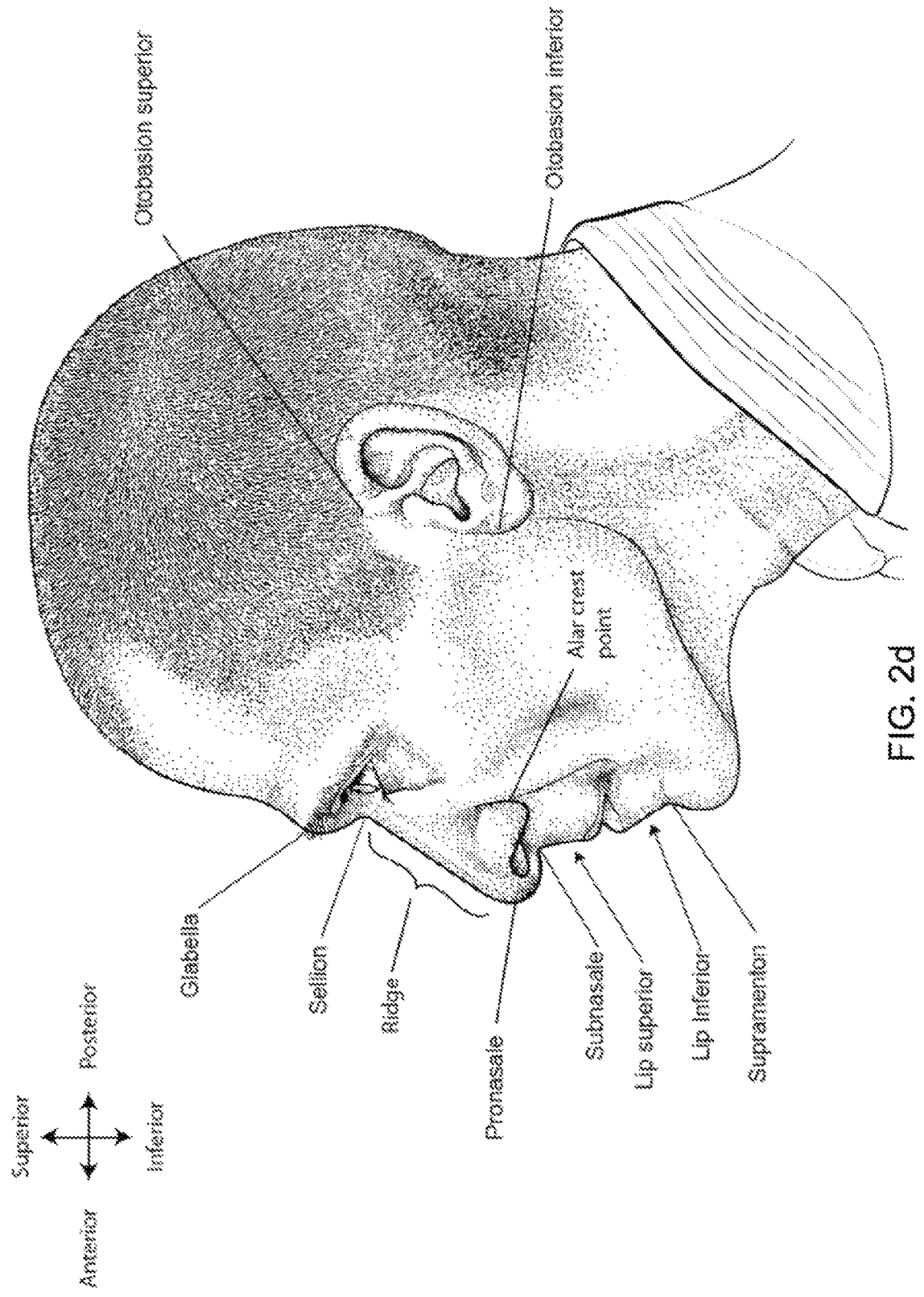
Figure 2E:
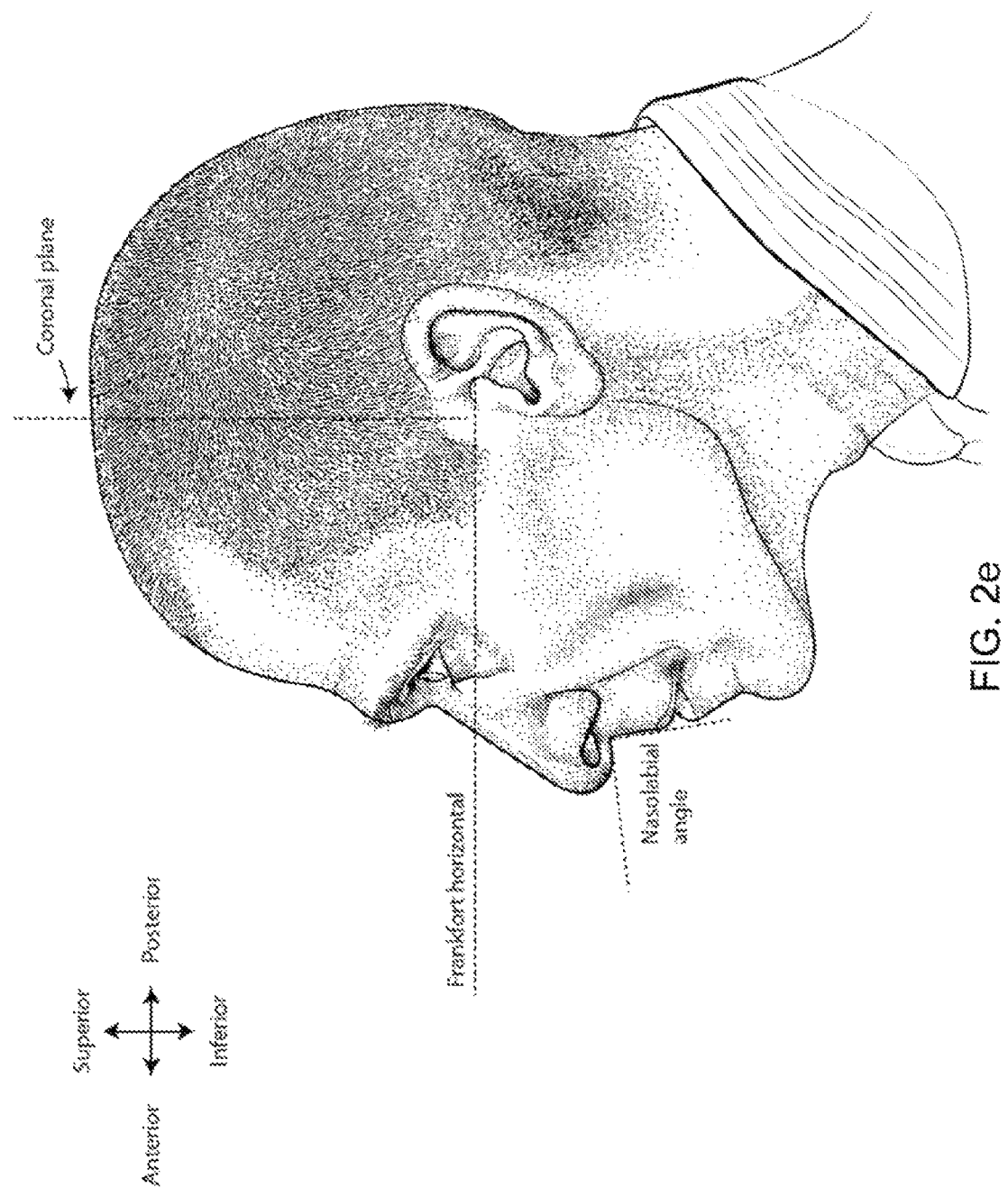
Figure 2F:
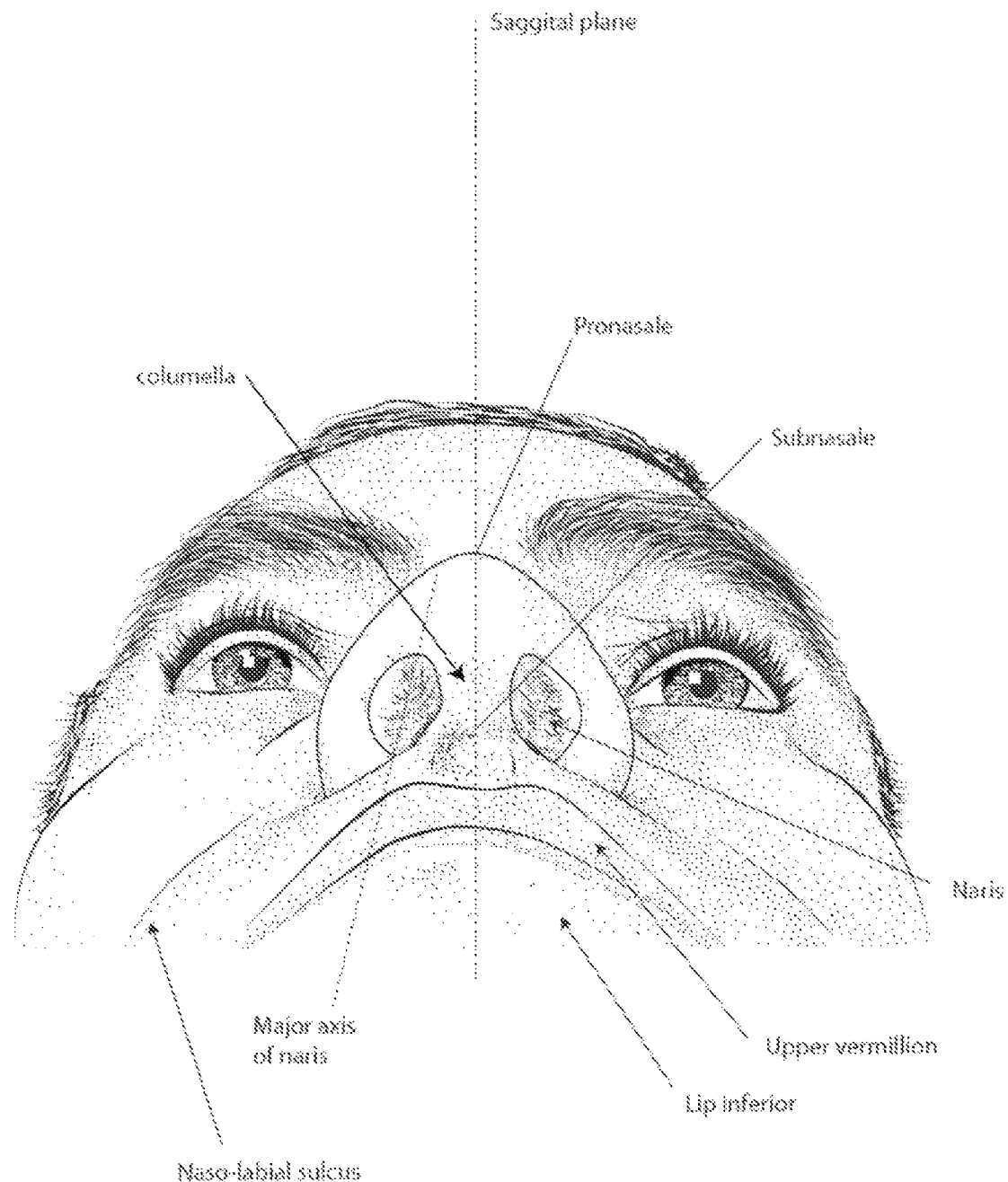
Figure 2I:
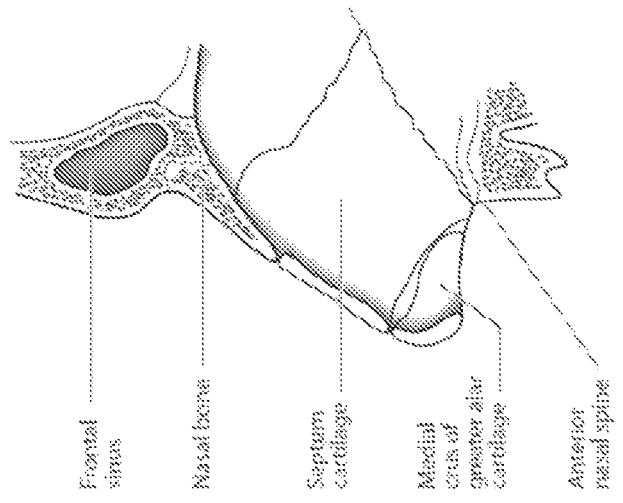
Figure 2H:
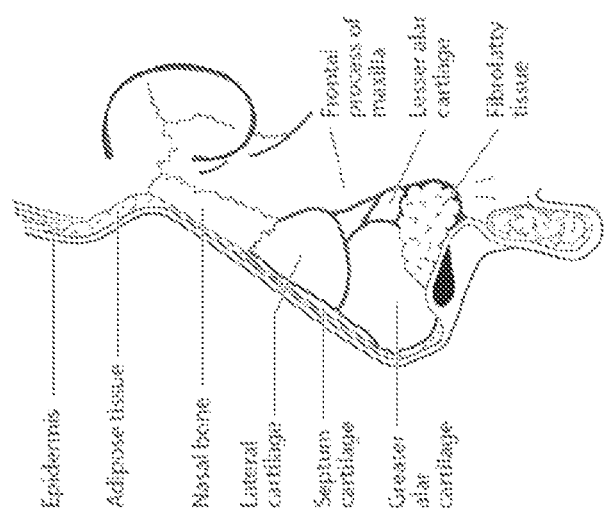
Figure 2G:
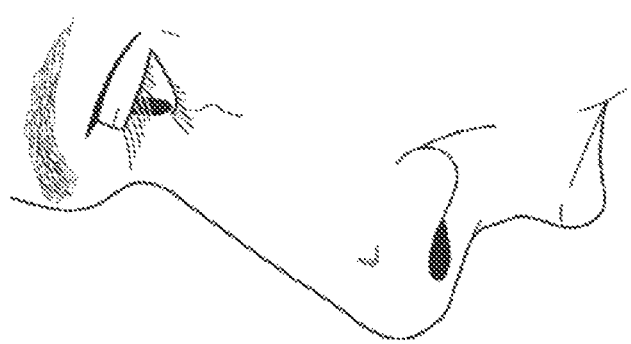

FIG. 2c is a front view of a face with several features of surface anatomy identified including the lip superior, upper vermillion, lower vermillion, lip inferior, mouth width, endocanthion, a nasal ala, nasolabial sulcus and cheilion;

FIG. 2d is a side view of a head with several features of surface anatomy identified including glabella, sellion, pronasale, subnasale, lip superior, lip inferior, supramenton, nasal ridge, otobasion superior and otobasion inferior. Also indicated are the directions superior & inferior, and anterior & posterior;

FIG. 2e is a further side view of a head. The approximate locations of the Frankfort horizontal and nasolabial angle are indicated;

FIG. 2f shows a base view of a nose;

FIG. 2g shows a side view of the superficial features of a nose;

FIG. 2h shows subcutaneal structures of the nose, including lateral cartilage, septum cartilage, greater alar cartilage, lesser alar cartilage and fibrofatty tissue;

FIG. 2i shows a medial dissection of a nose, approximately several millimeters from a sagittal plane, amongst other things showing the septum cartilage and medial crus of greater alar cartilage;

FIG. 2j shows a front view of the bones of a skull including the frontal, temporal, nasal and zygomatic bones. Nasal concha are indicated, as are the maxilla, mandible and mental protuberance;

FIG. 2k shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter sternocleidomastoid and trapezius;

4.3 Pap Device

Figure 3:
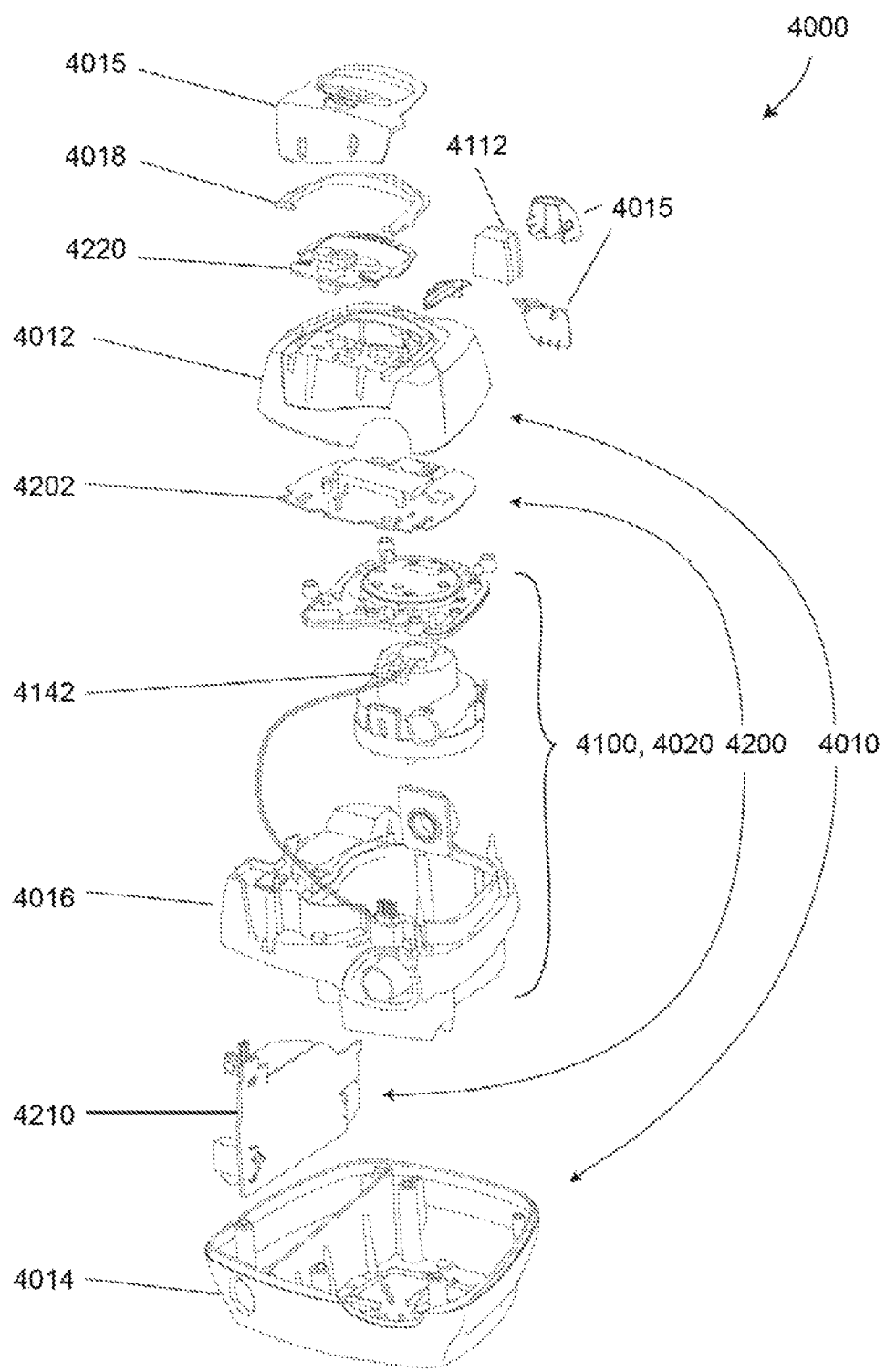

FIG. 3 shows an example PAP device suitable for implementation with examples of the present technology;

4.4 Patient Interface

Figure 4:
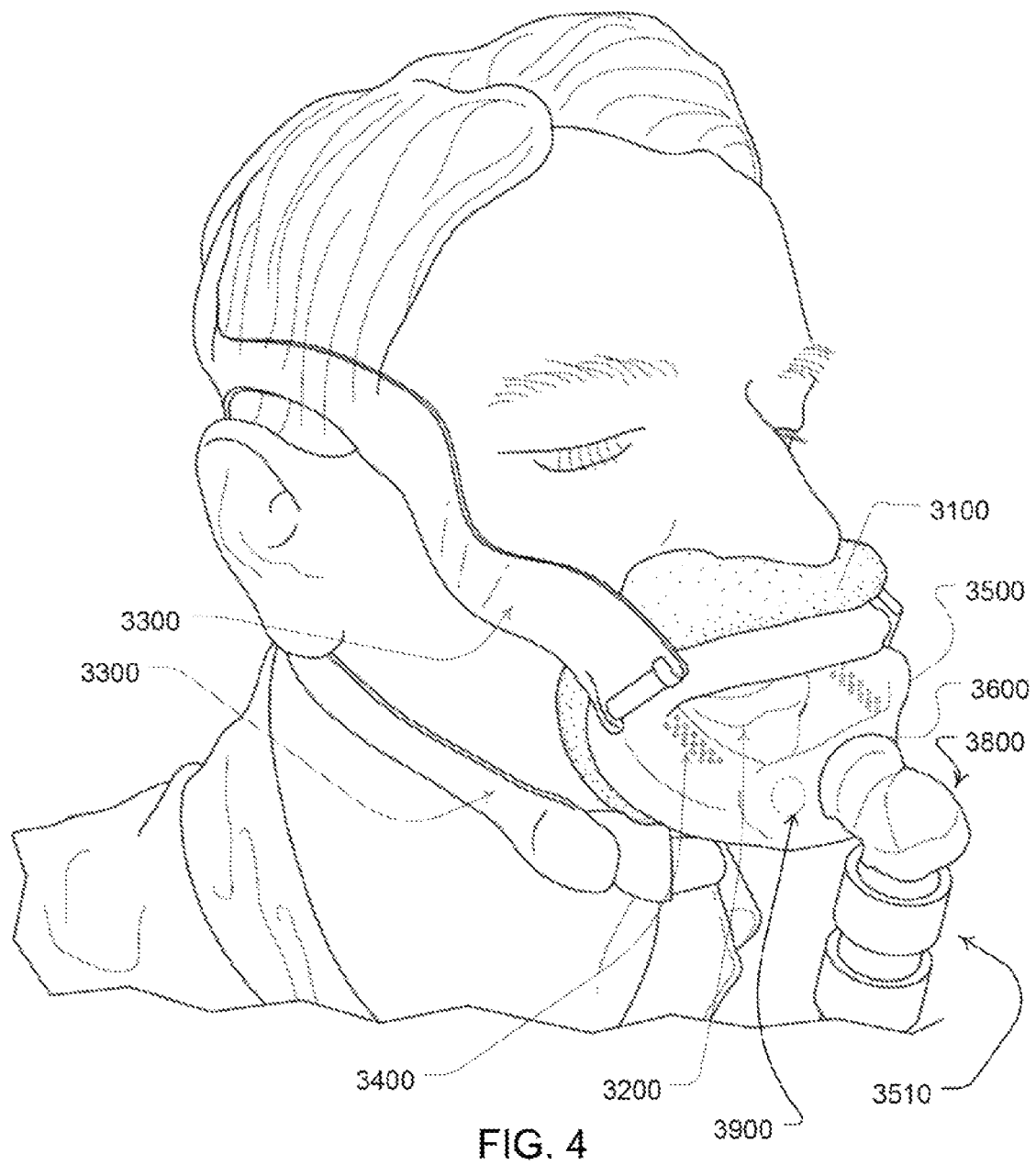
Figure 5:
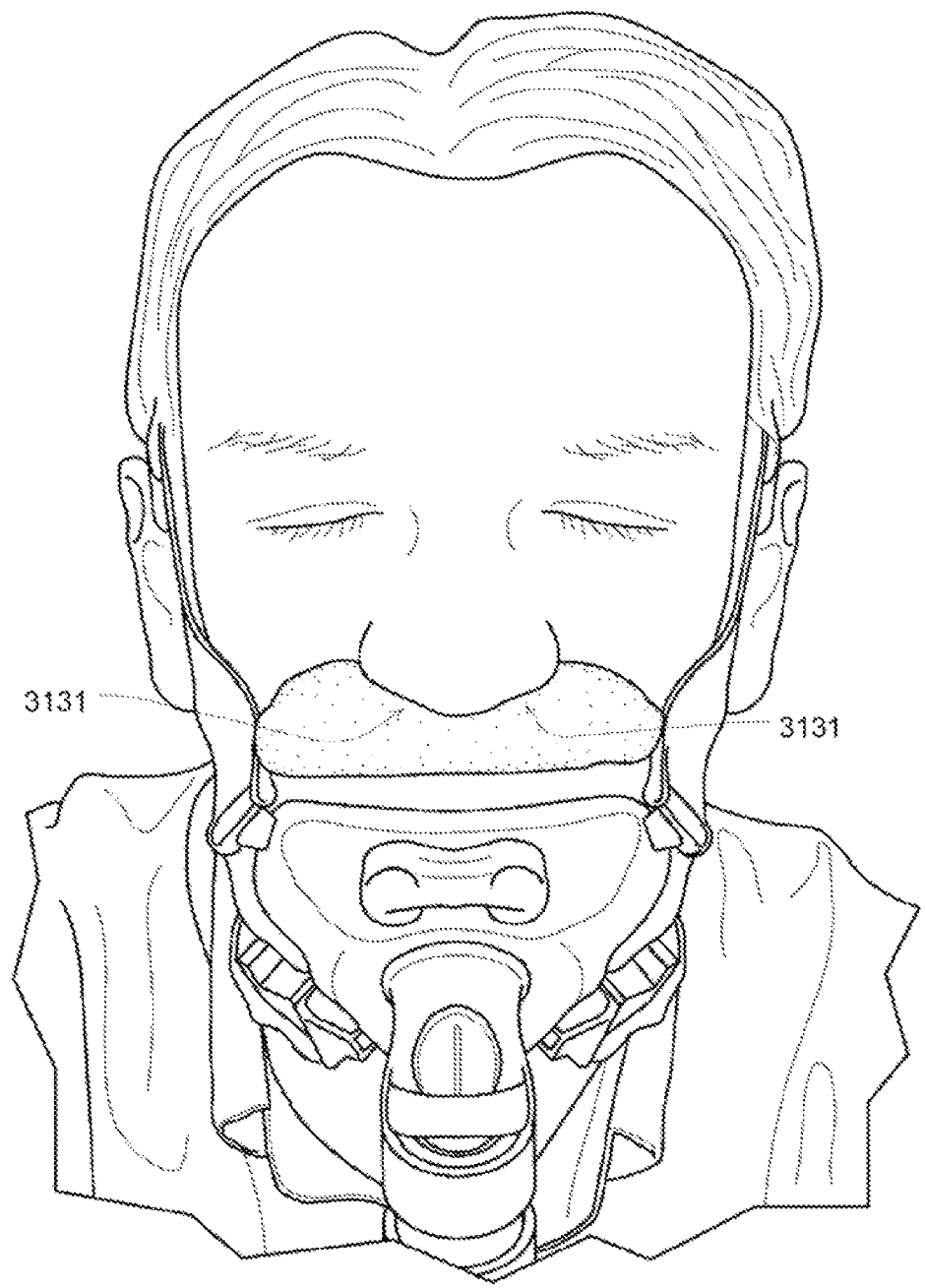
Figure 6:
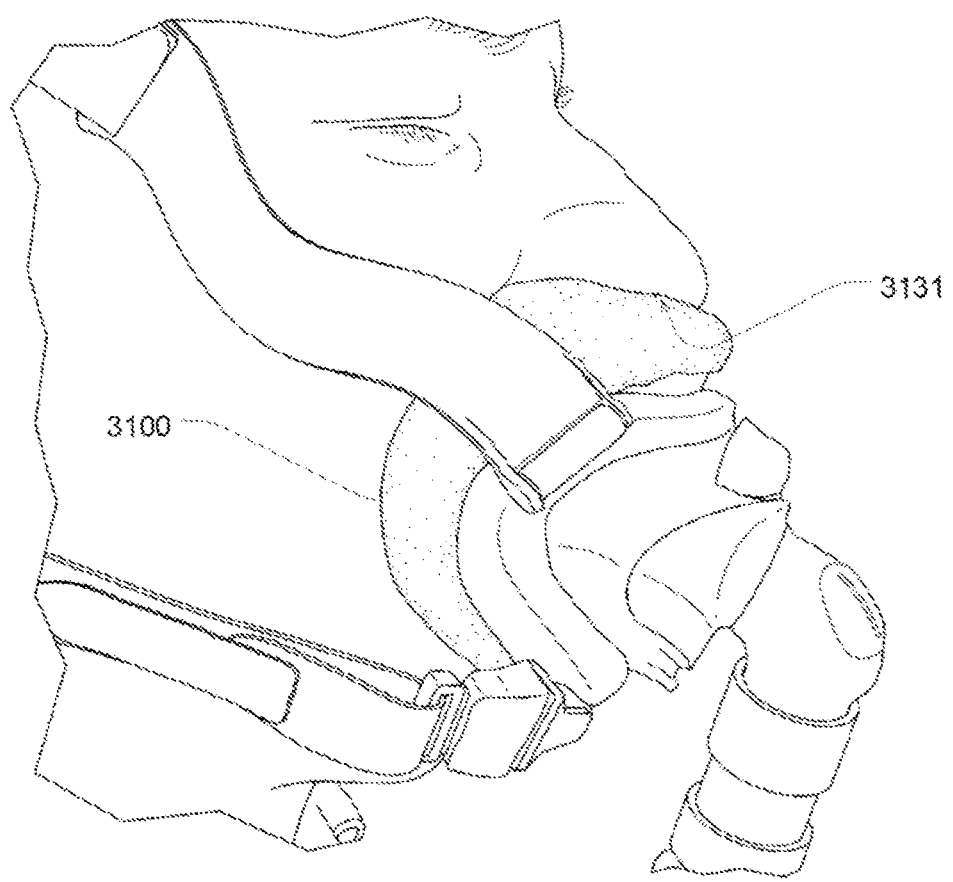
Figure 7:
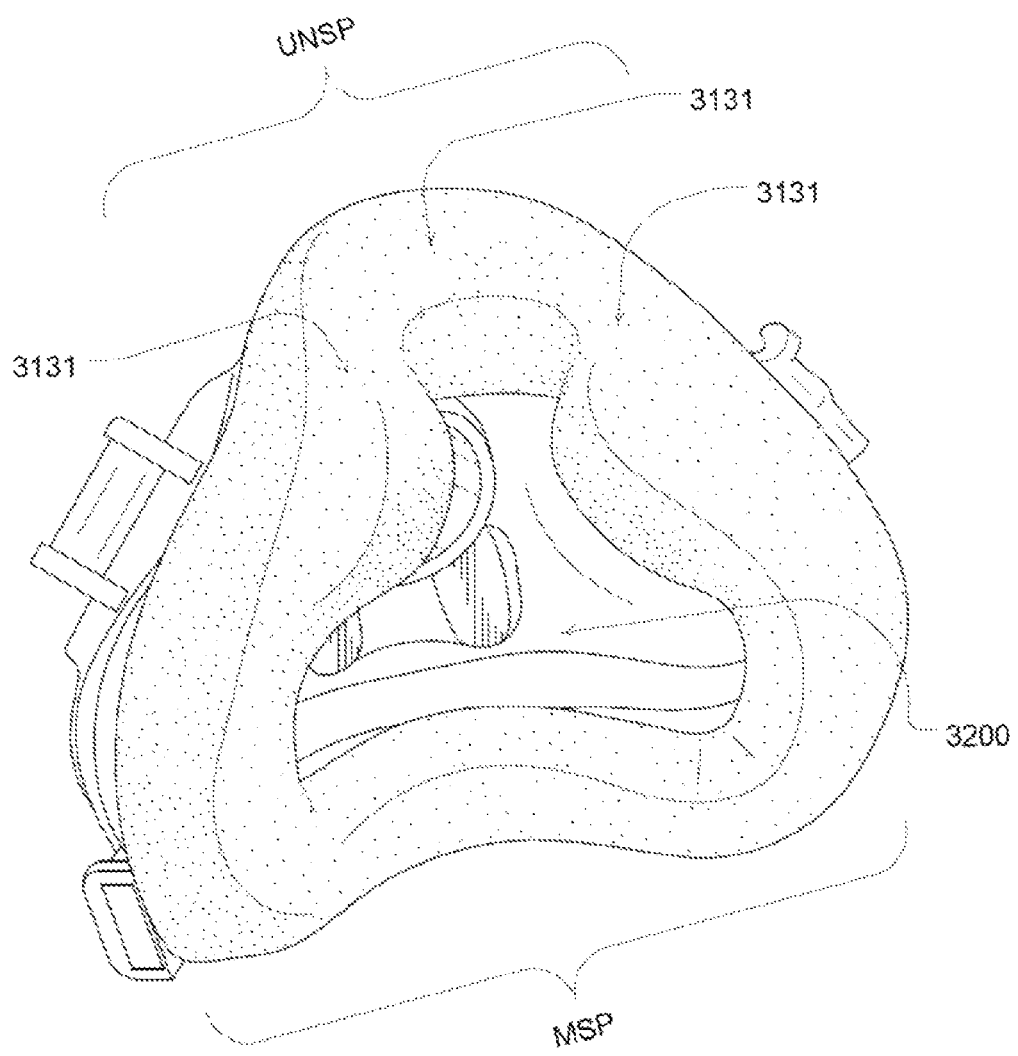
Figure 8:
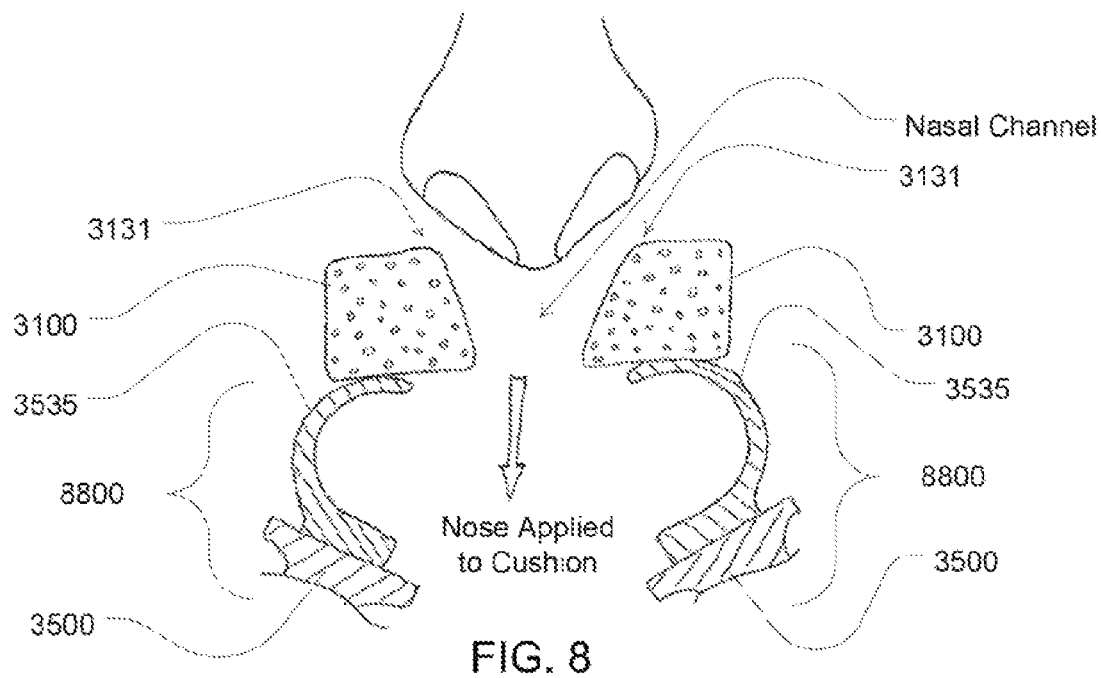
Figure 9:
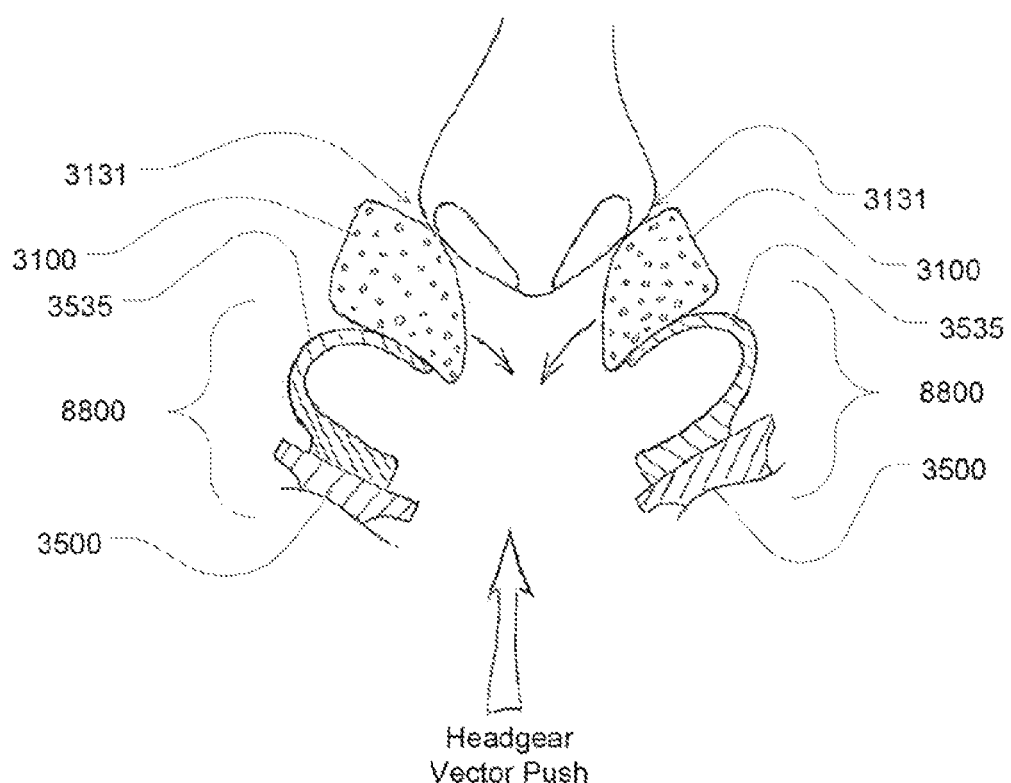
Figure 10:
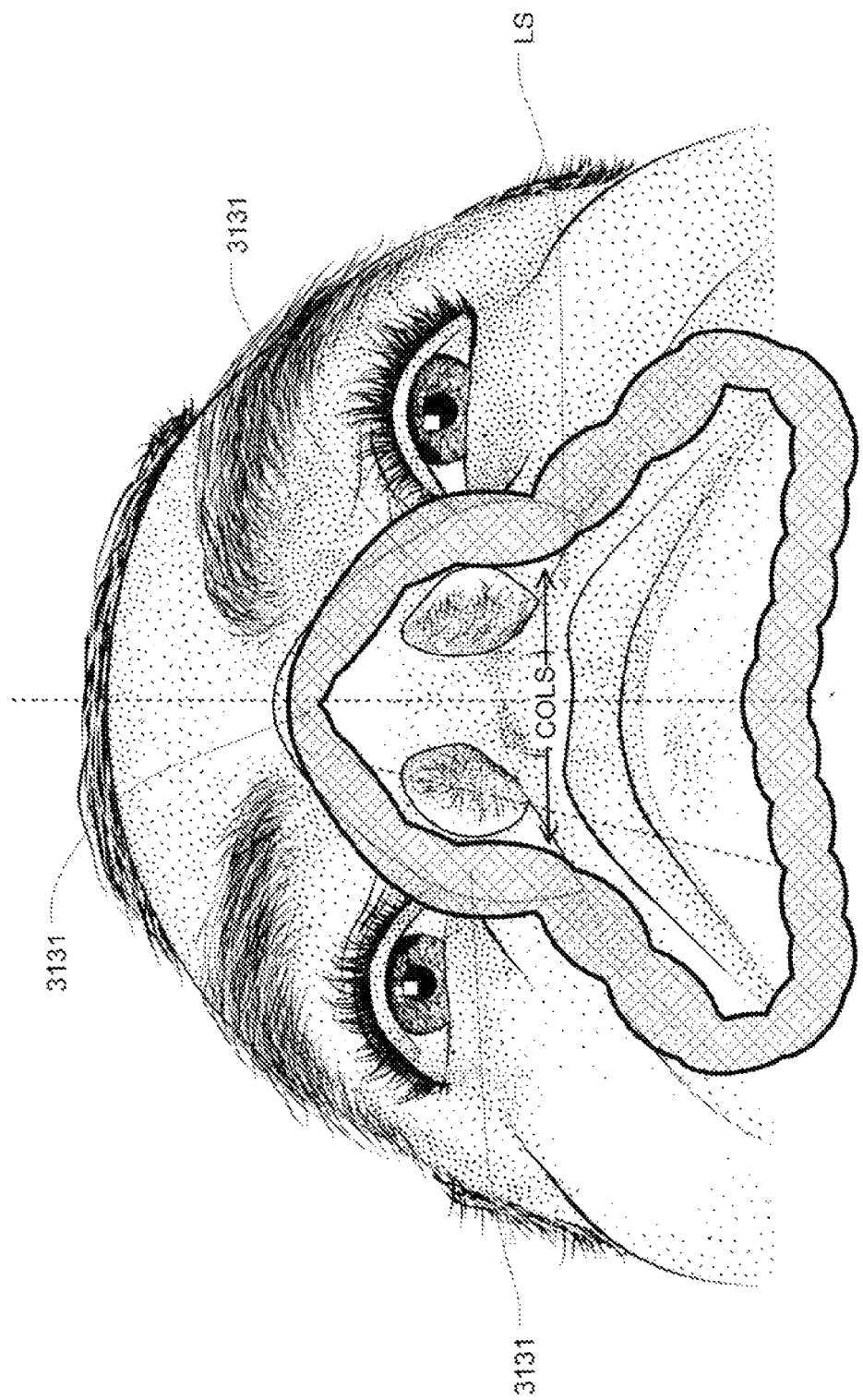
Figure 11:
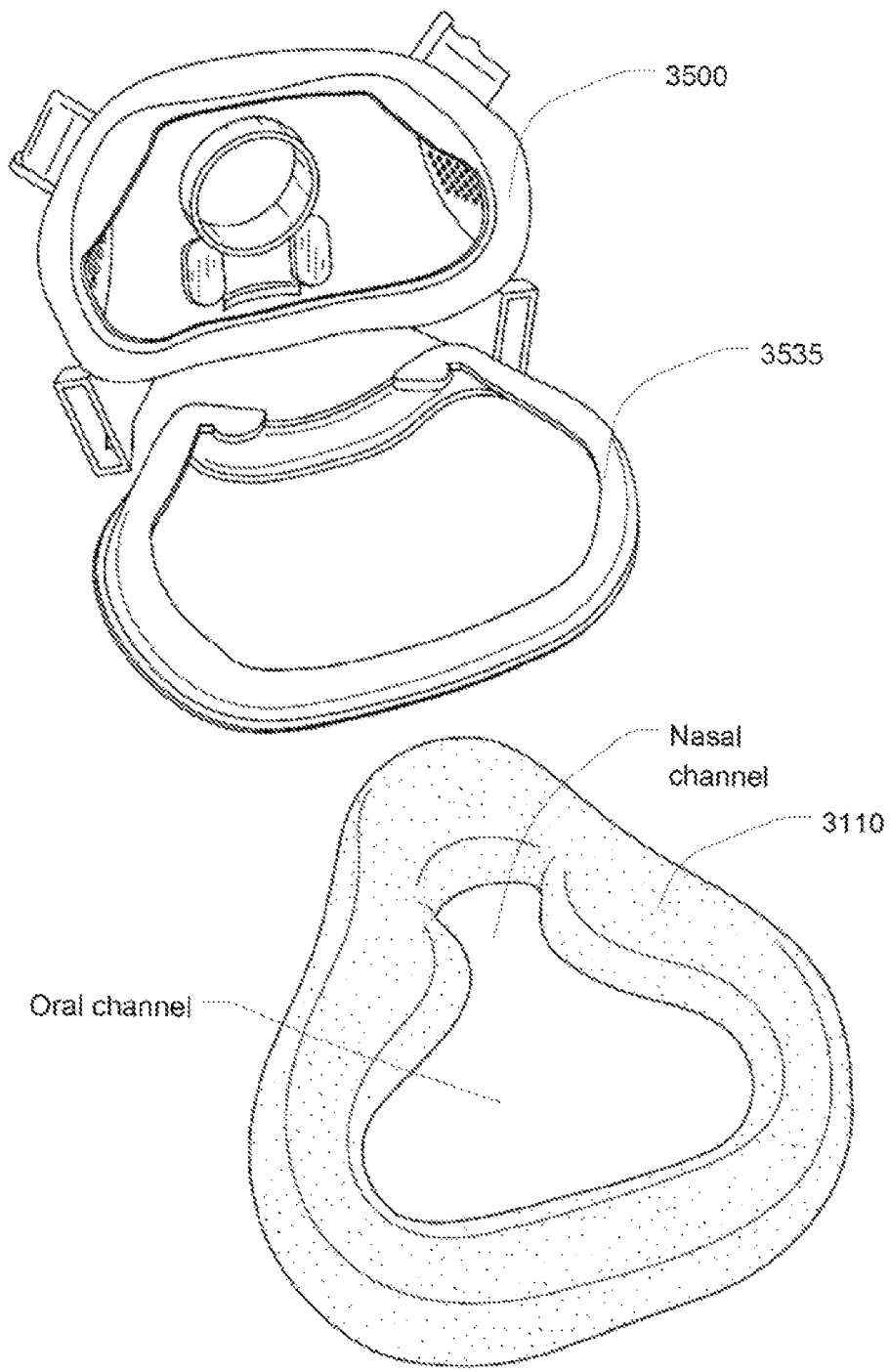
Figure 12:
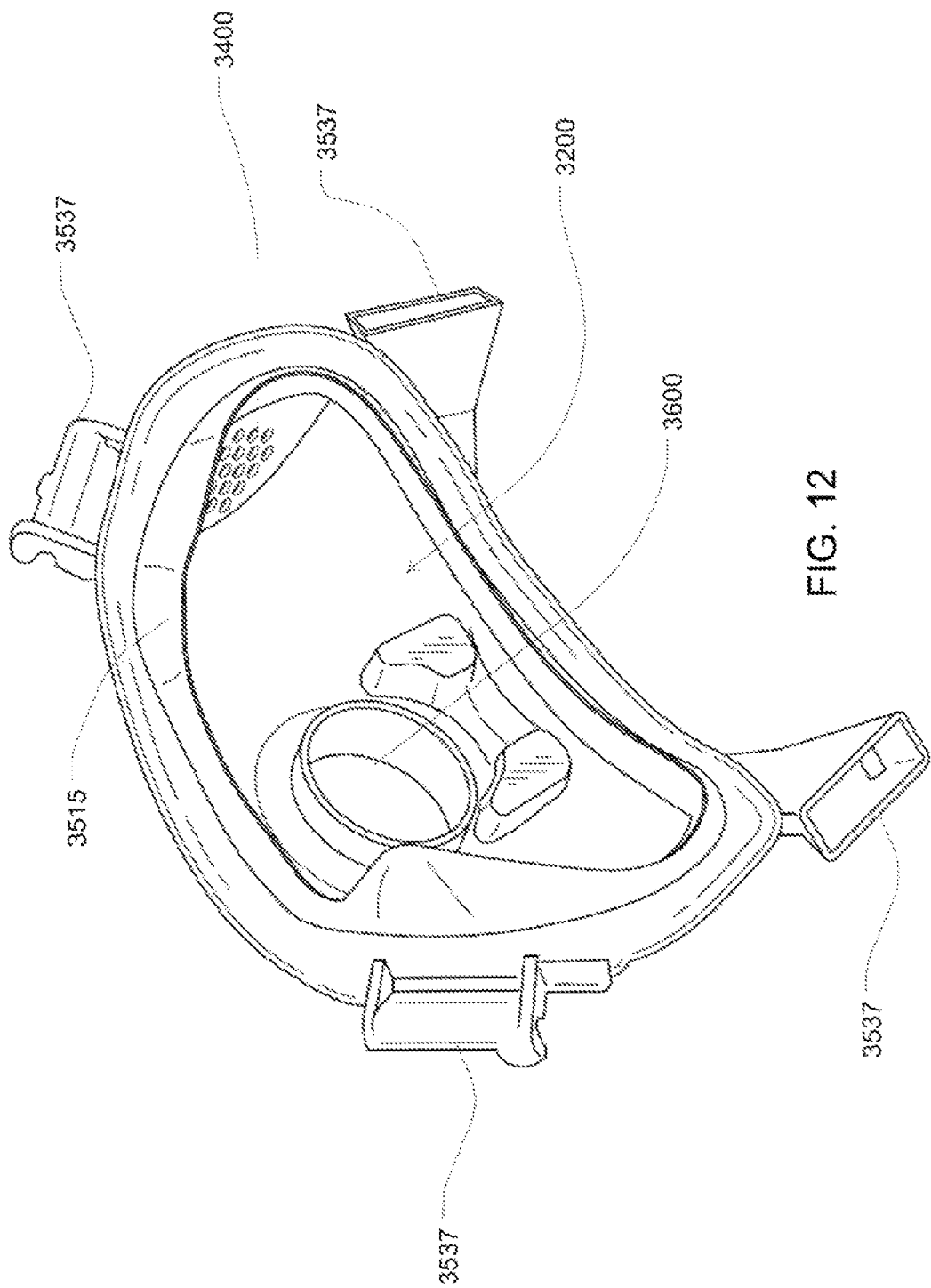
Figure 13:
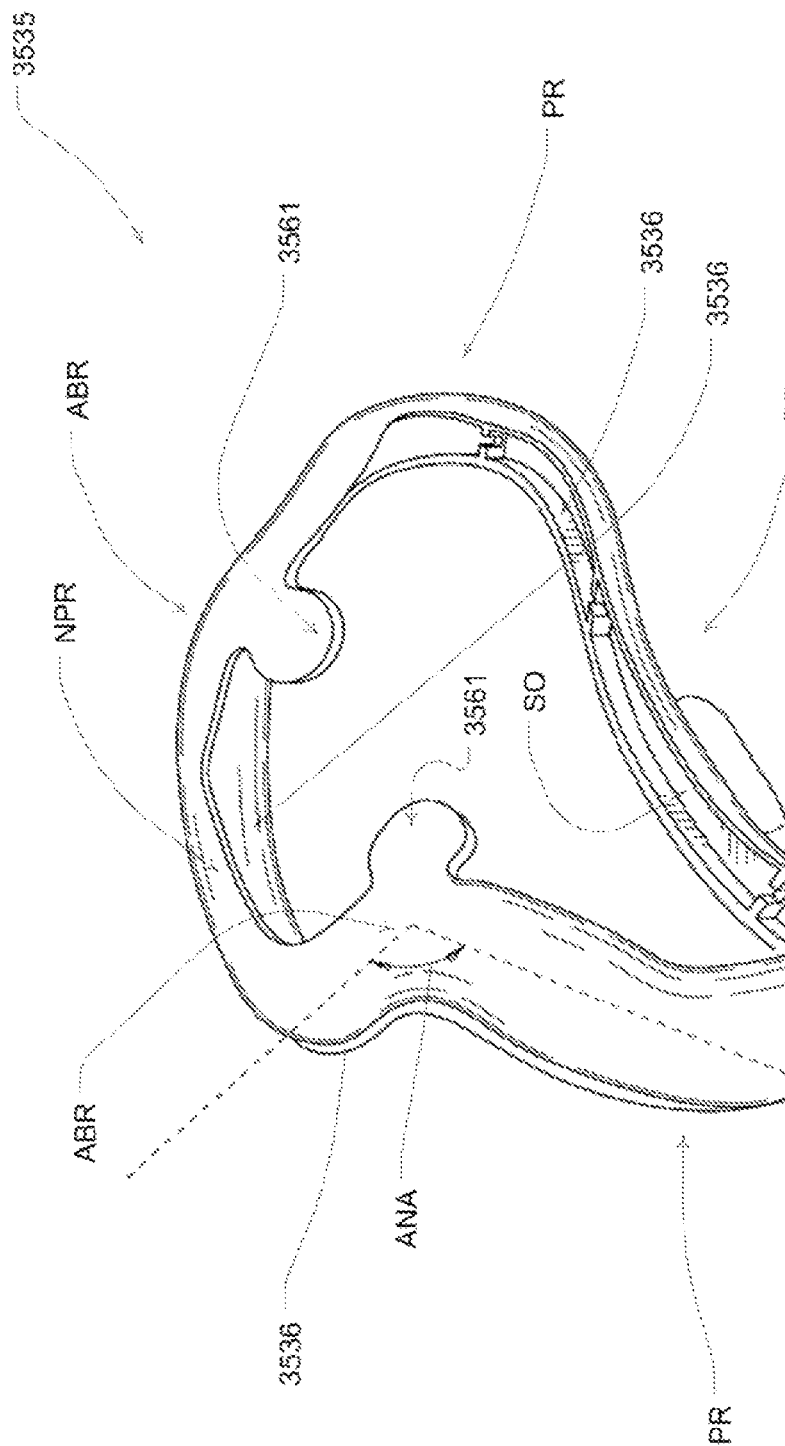
Figure 14:
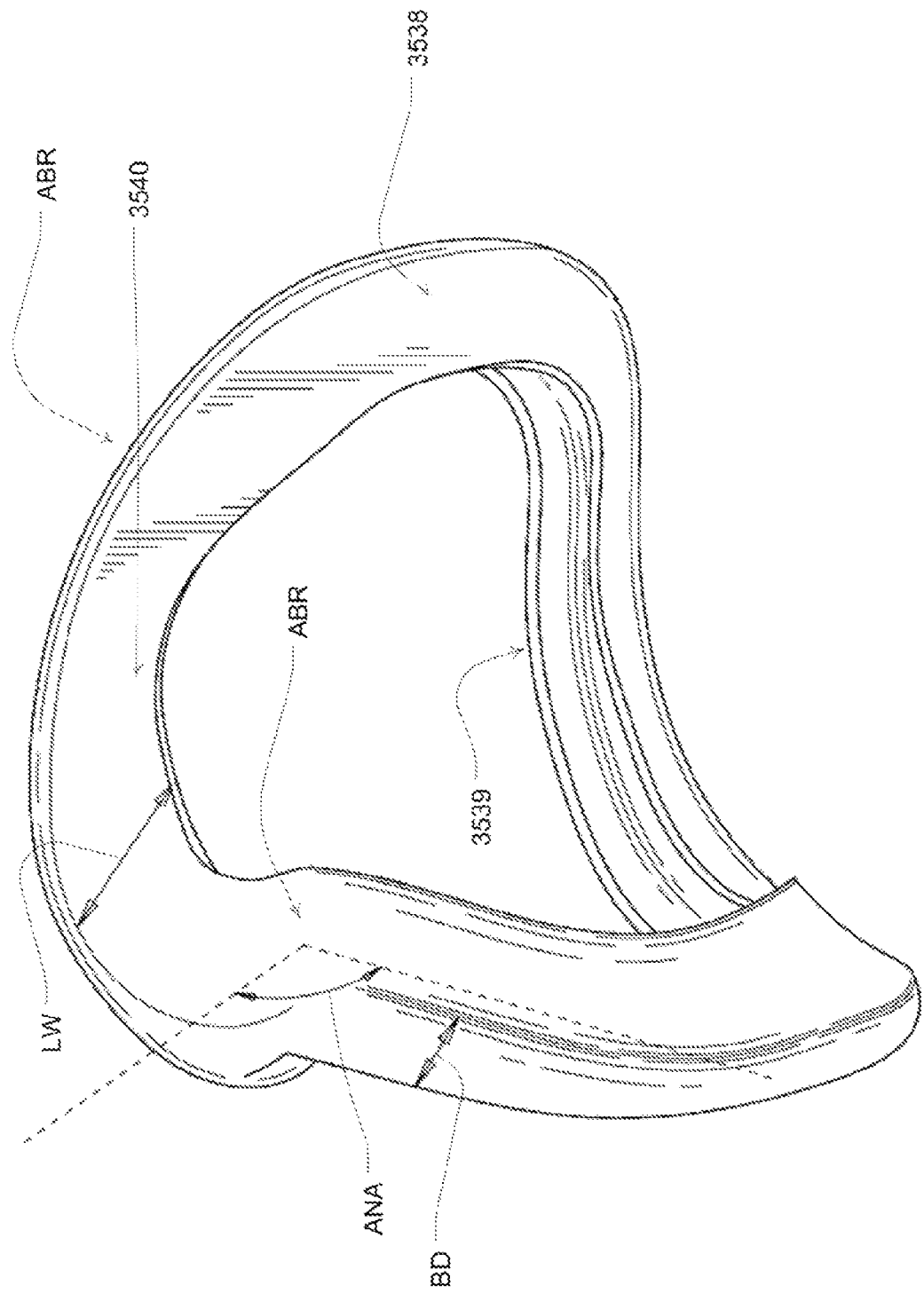
Figure 15:
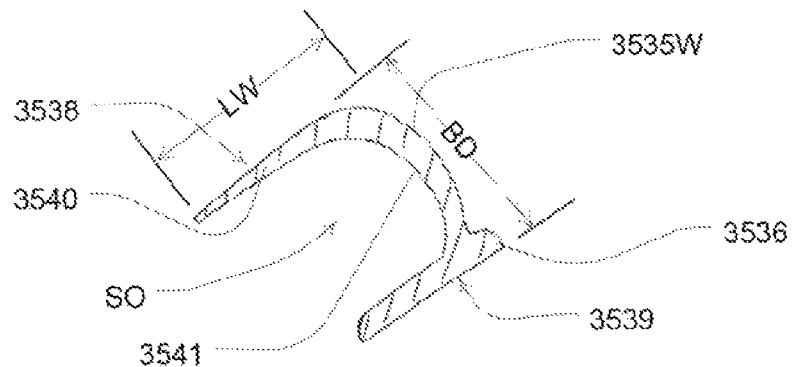
Figure 16:
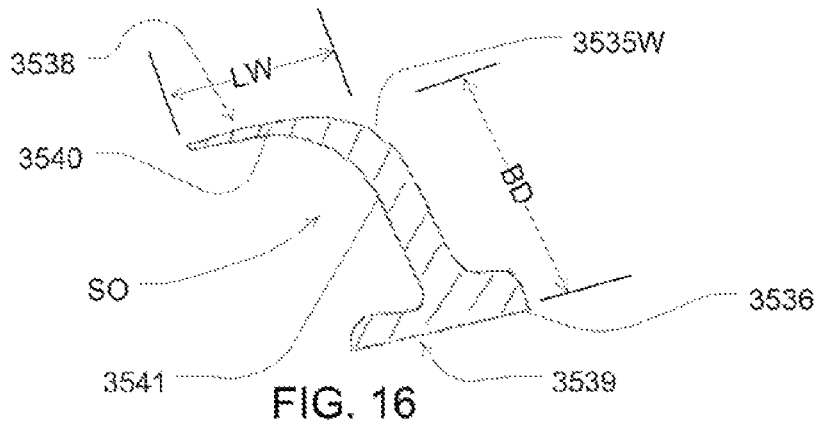
Figure 17:
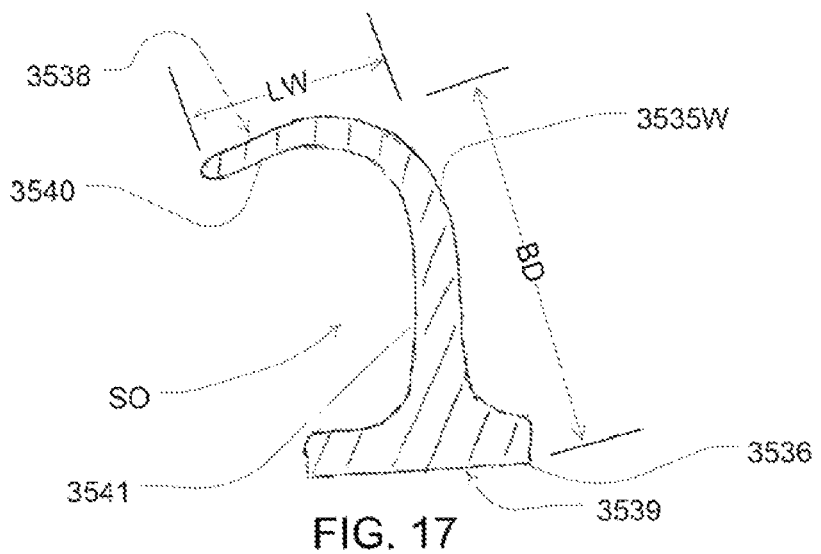
Figure 20:
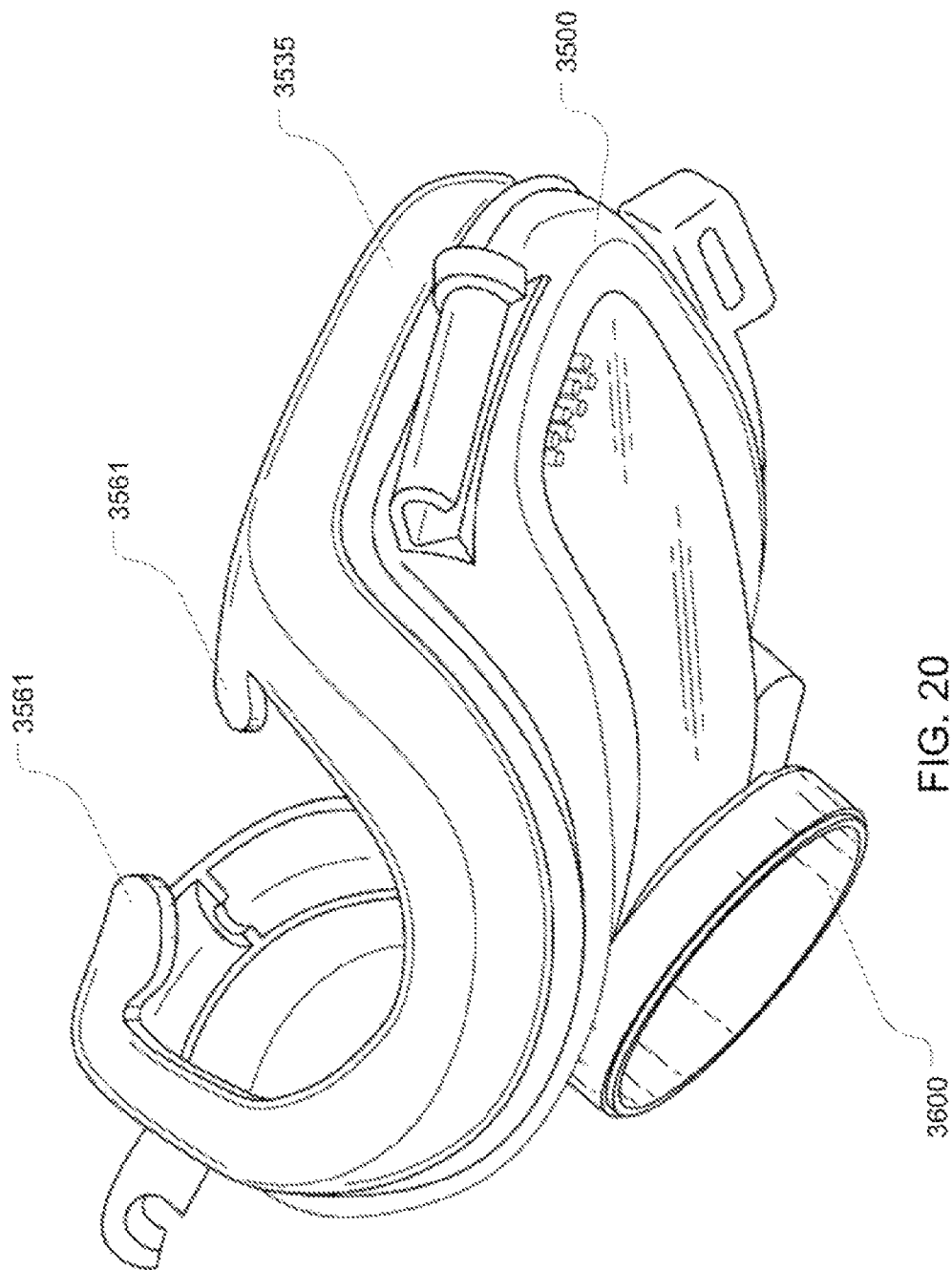
Figure 21:
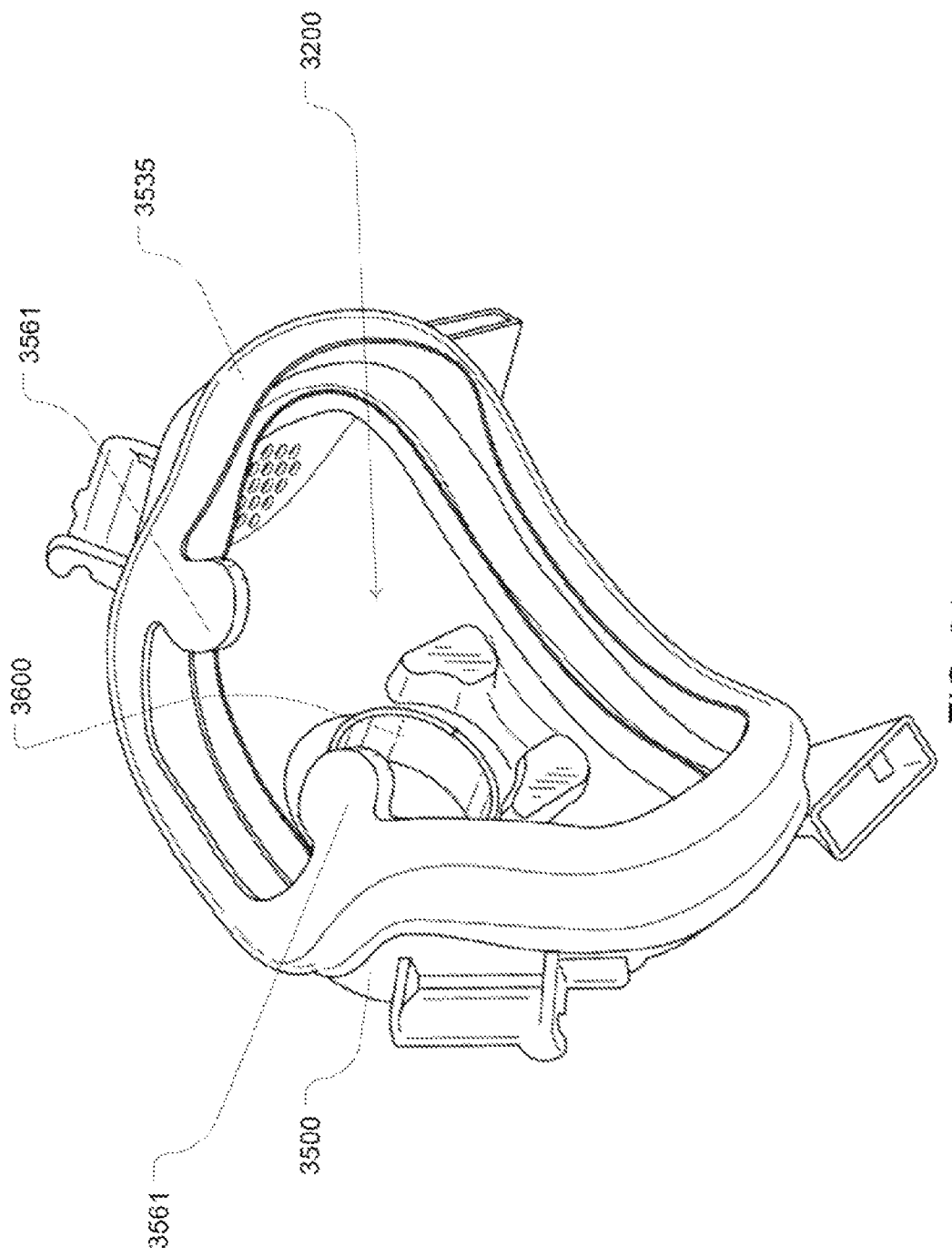
Figure 22:
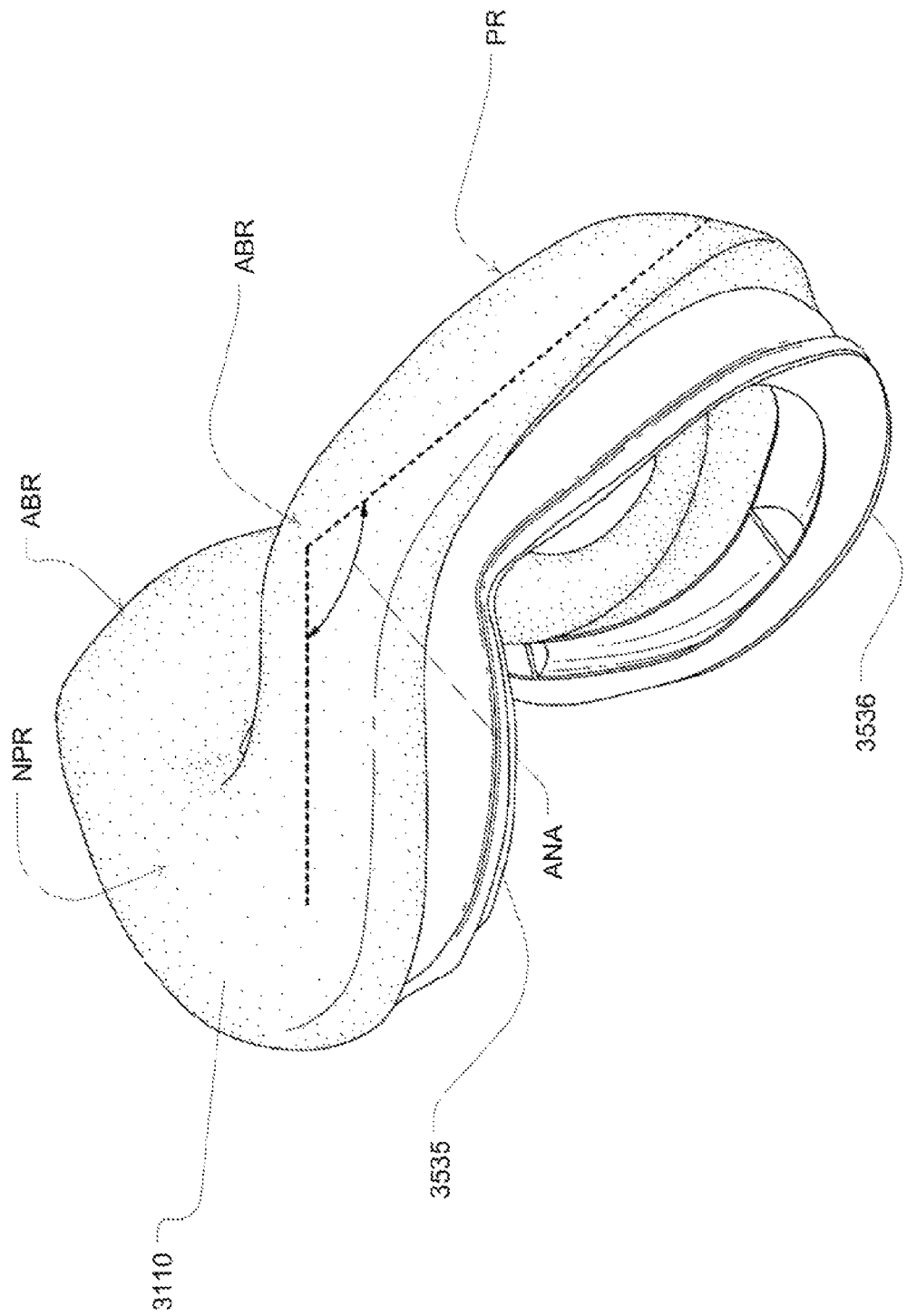
Figure 23:
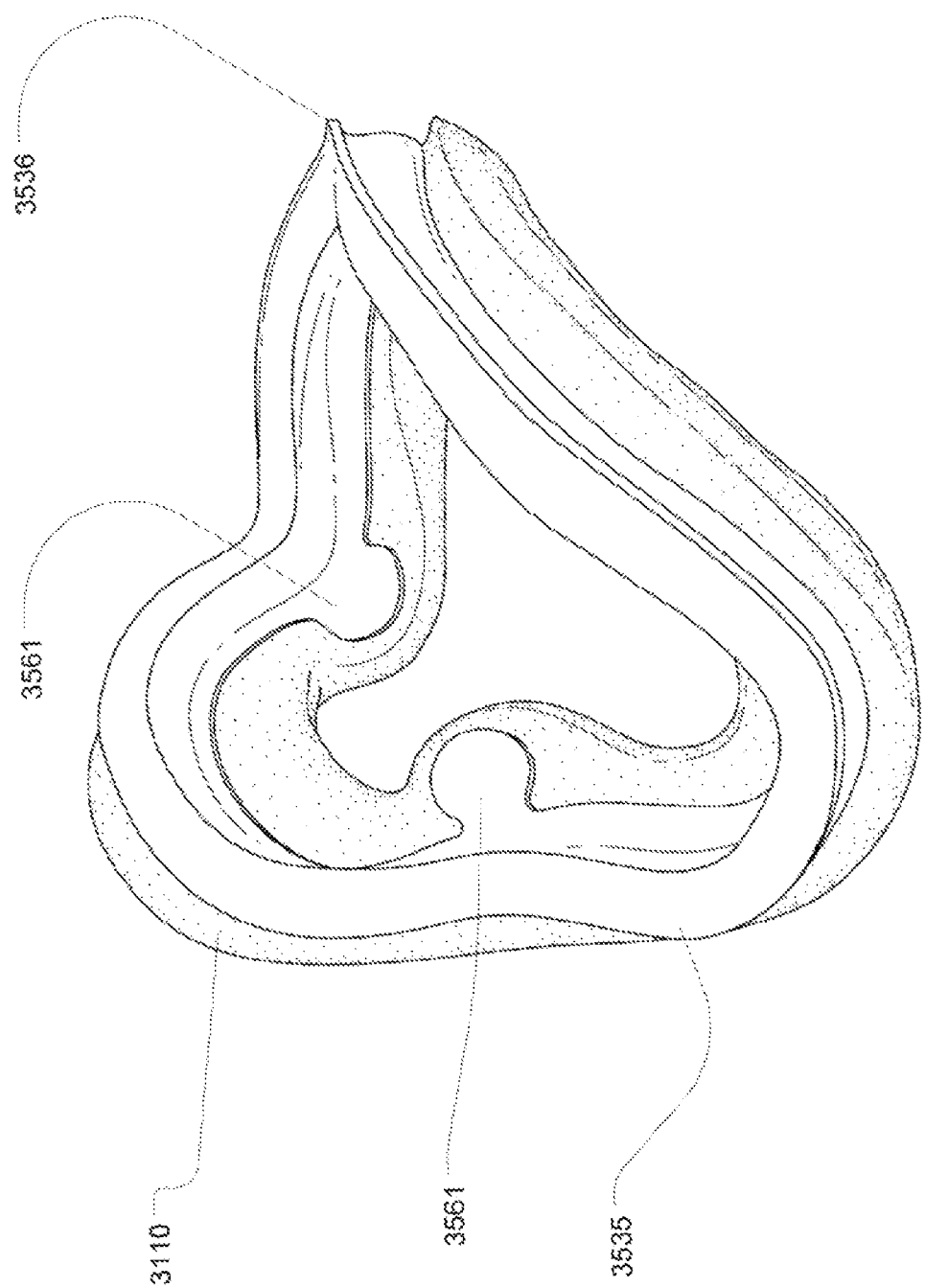
Figure 24:
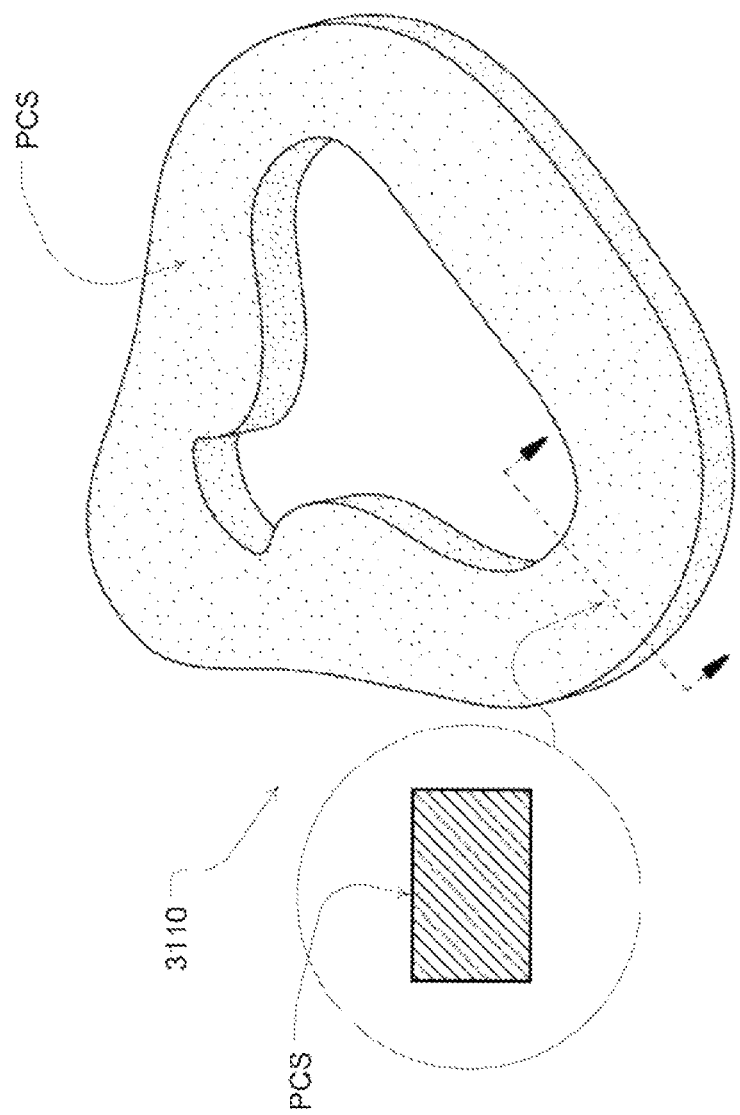
Figure 27:
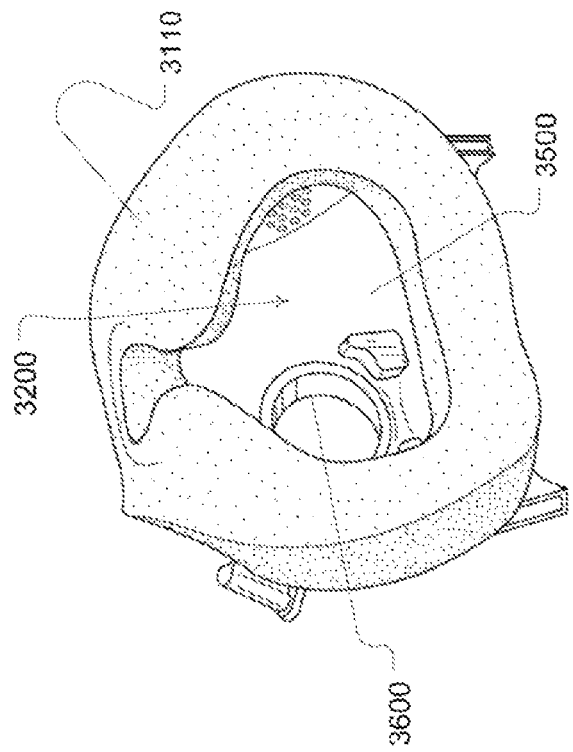
Figure 26:
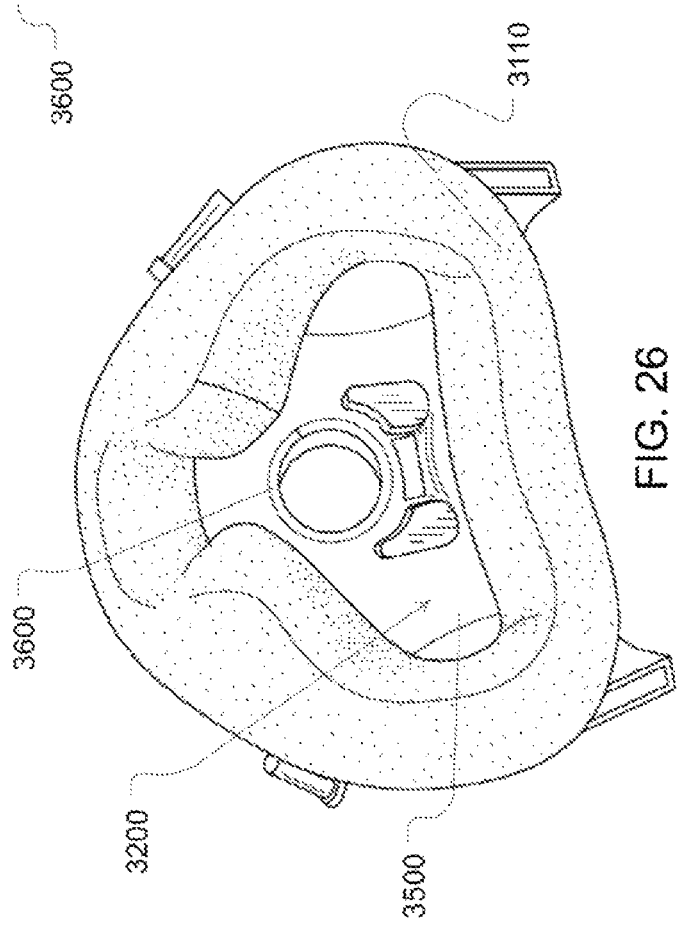
Figure 28:
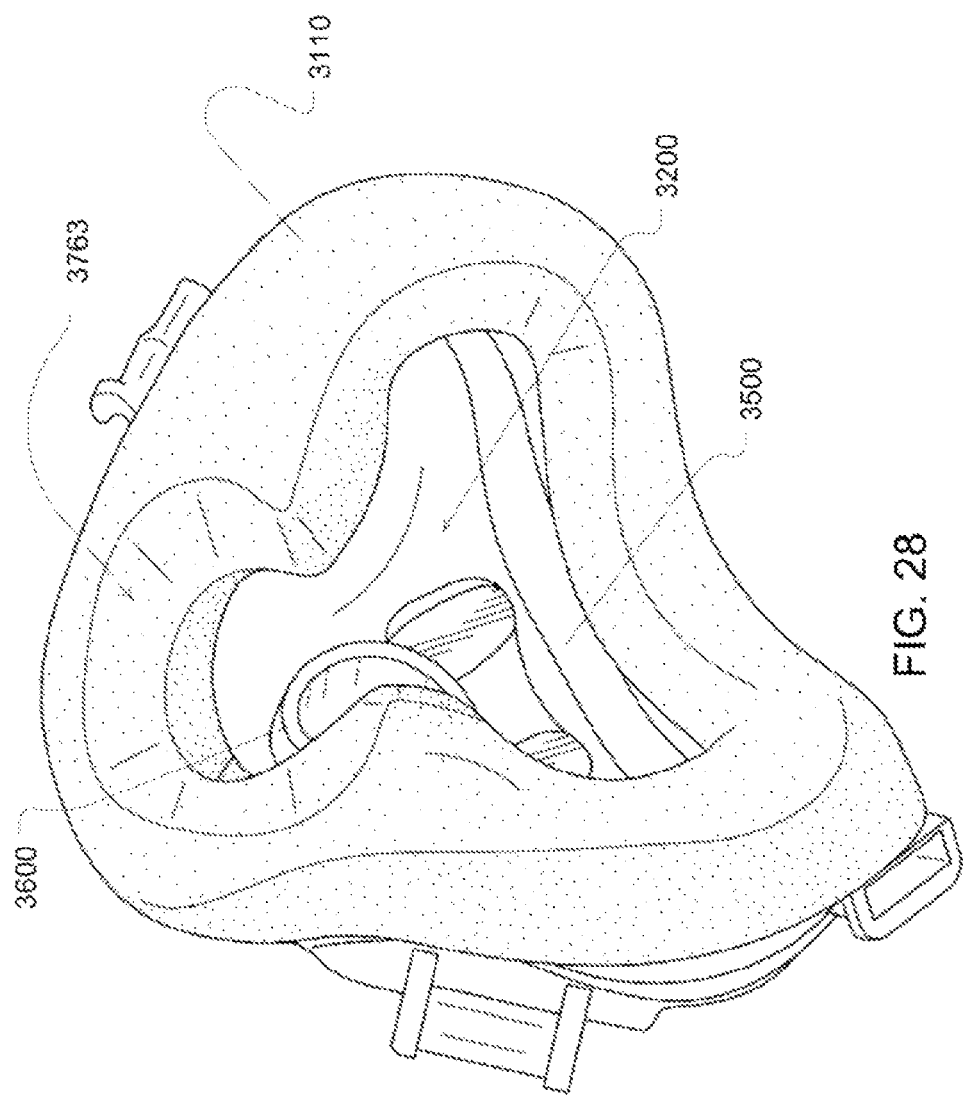
Figure 31:
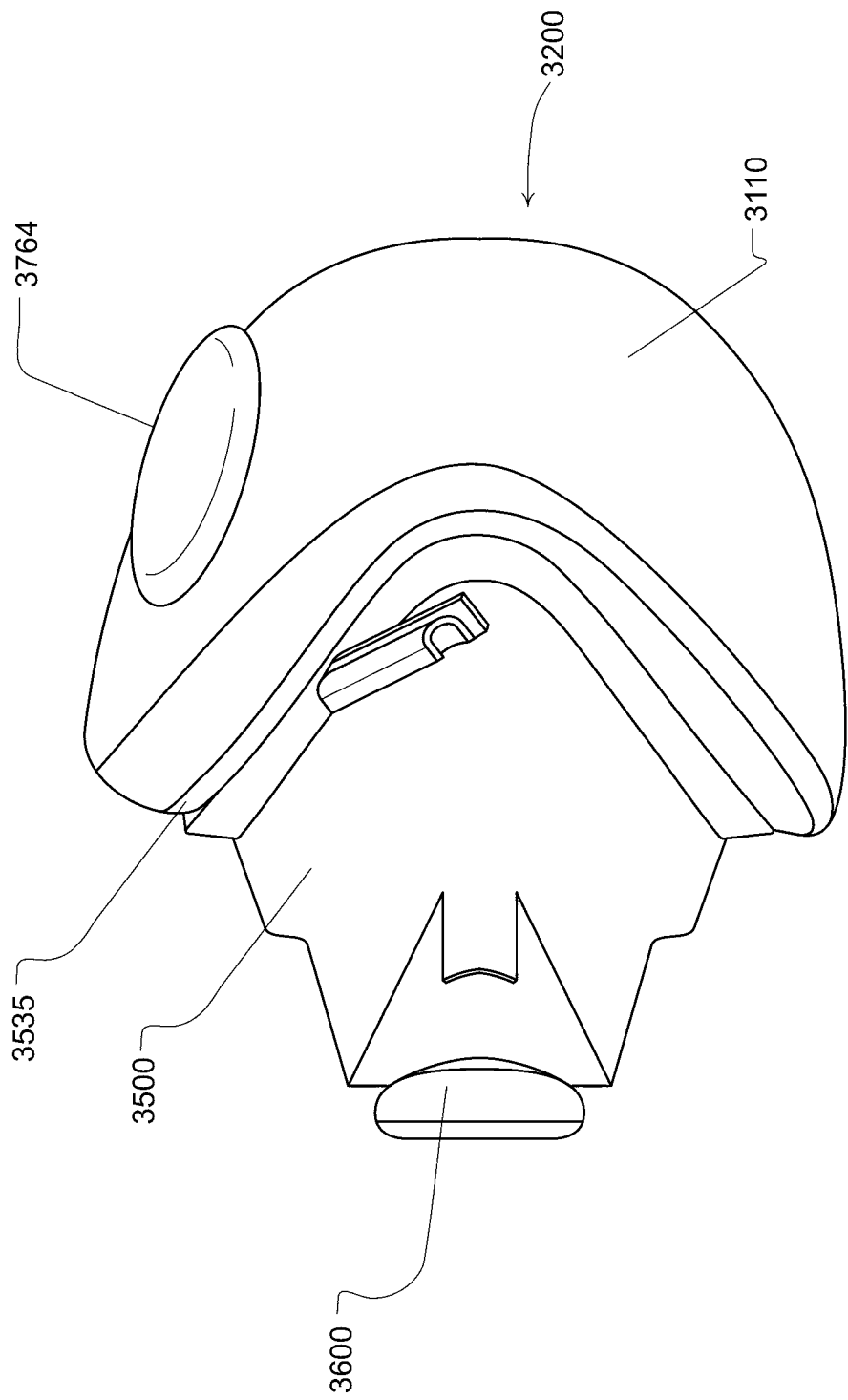

FIGS. 4, 5 and 6 show a patient using an example under the nose patient interface of the present technology;

FIG. 7 is a patient side or proximate view of the cushion of the patient interface of FIG. 4;

FIGS. 8 and 9 are cross sectional views of the patient interface of FIG. 4, particularly showing the nasal region of the patient interface of FIG. 7;

FIG. 10 illustrates facial contact regions of an under the nose mask for some examples of the present technology;

FIG. 11 shows an example frame, cushion support clip and cushion components in some forms of a patient interface of the present technology;

FIG. 12 is an illustration of the example frame component of FIG. 11;

FIG. 13 is an illustration of the example cushion support clip component of FIG. 11;

FIG. 14 is an illustration of another example cushion support clip component;

FIGS. 15, 16 and 17 show cross sectional views of different cushion support regions for the cushion support clip component;

FIG. 18 is a further illustration of another example cushion support clip of the present technology;

FIG. 19 illustrations and example force profile that may be achieved with some examples of the present technology;

FIGS. 20 and 21 show perspective views of a cushion support clip component coupled with a frame component;

FIGS. 22 and 23 illustrate a side view and a perspective view, respectively, of a cushion coupled to a cushion support clip;

FIG. 24 illustrates an example flat contact surface cushion suitable for implementation with some embodiments of the present technology; the figure also includes a callout showing a cross-sectional view of the cushion. Notably, because of the square profile, the surfaces for contacting the underlying supporting surface and the patient's face are both flat);

FIG. 25 illustrates an example curved surface cushion suitable for implementation with some embodiments of the present technology; the figure also includes a callout showing a cross-sectional view of the cushion. The flat surface of the cushion is for contacting the underlying supporting surface and not the patient's face;

FIGS. 26 and 27 illustrate the assembly of the cushions of FIGS. 24 and 25 respectively with a frame;

FIG. 28 illustrates a scalloped nasal region of a cushion in some examples of the present technology;

FIG. 29 illustrates a cushion having left and right nasal support protrusions;

FIGS. 30 and 31 show plan and side views respectively of the cushion of FIG. 29 in a under-the-nose mask assembly of the present technology;

FIGS. 32A and 32B illustrate a clip and frame connector for some examples of the present technology;

FIGS. 33A and 33B illustrate another clip and frame connector for some examples of the present technology;

FIG. 34 illustrates a still further clip and frame connector for some examples of the present technology; and FIGS. 35A and 35B illustrate yet another clip and frame connector for some examples of the present technology.

Figure 36:
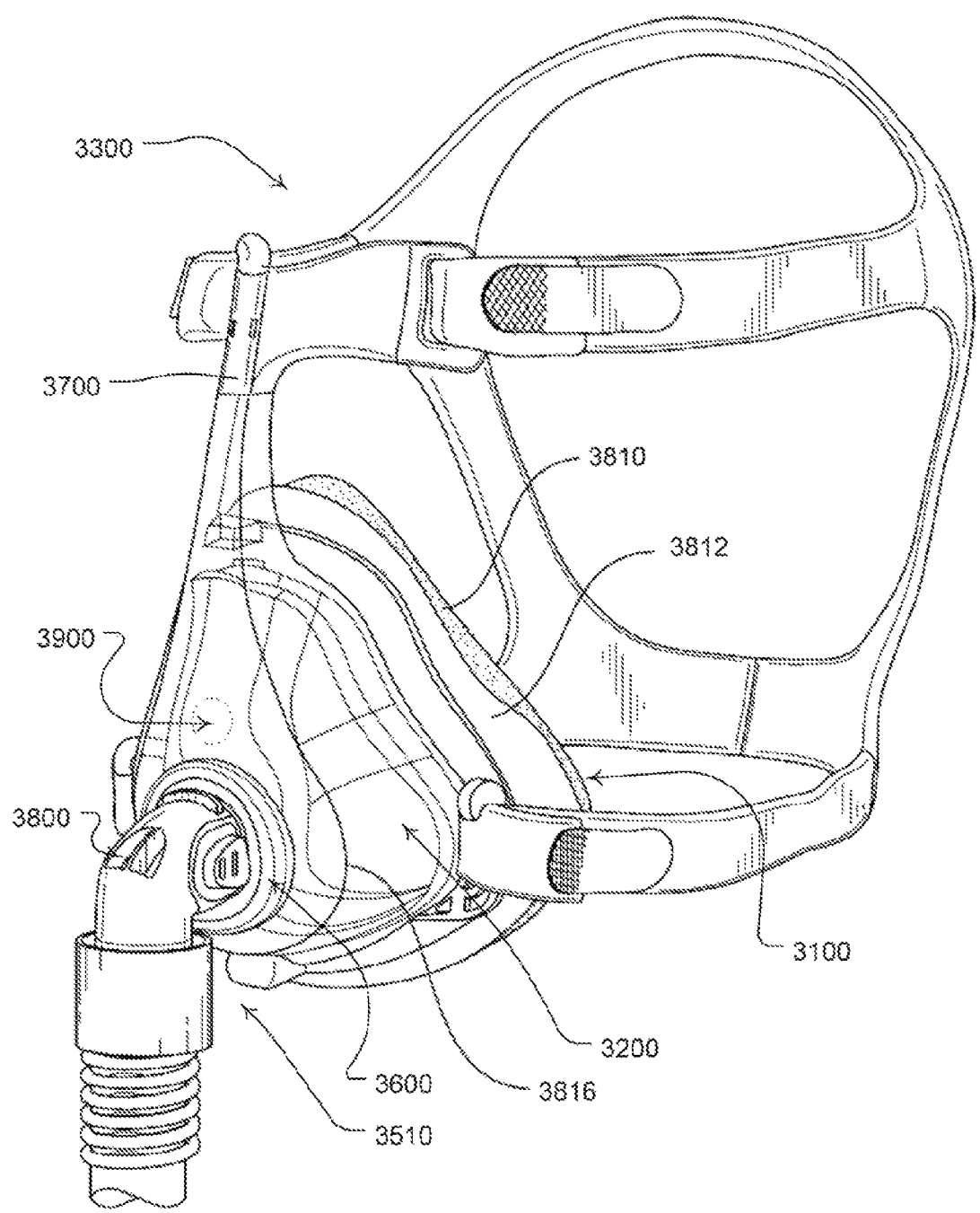
Figure 37:
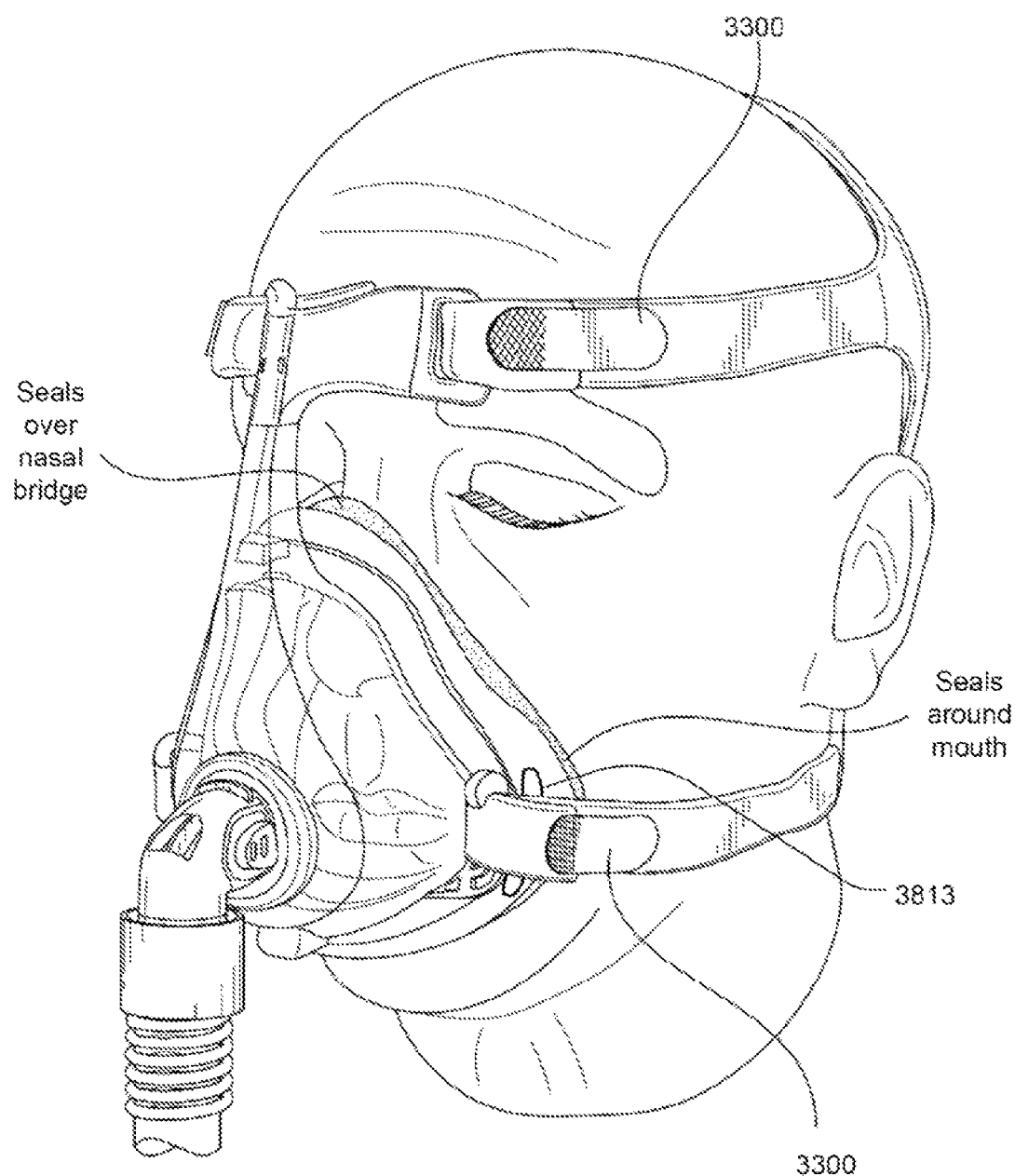

FIGS. 36 and 37 illustrate a foam mask, with headgear, configured for sealing with the mouth and over the nasal bridge.

Figure 38:
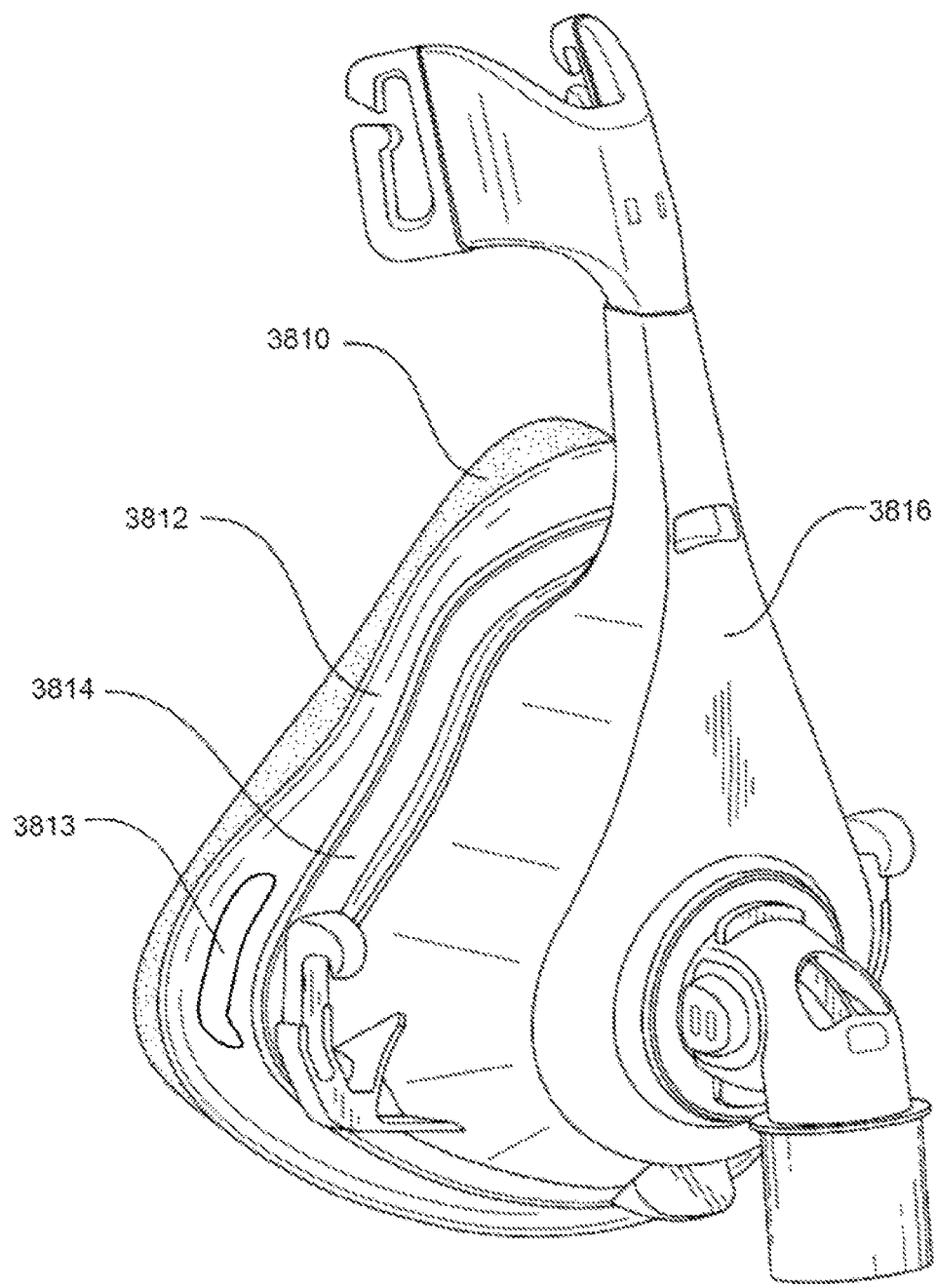

FIG. 38 is another view of the foam mask of FIG. 36 without the headgear.

Figure 39:
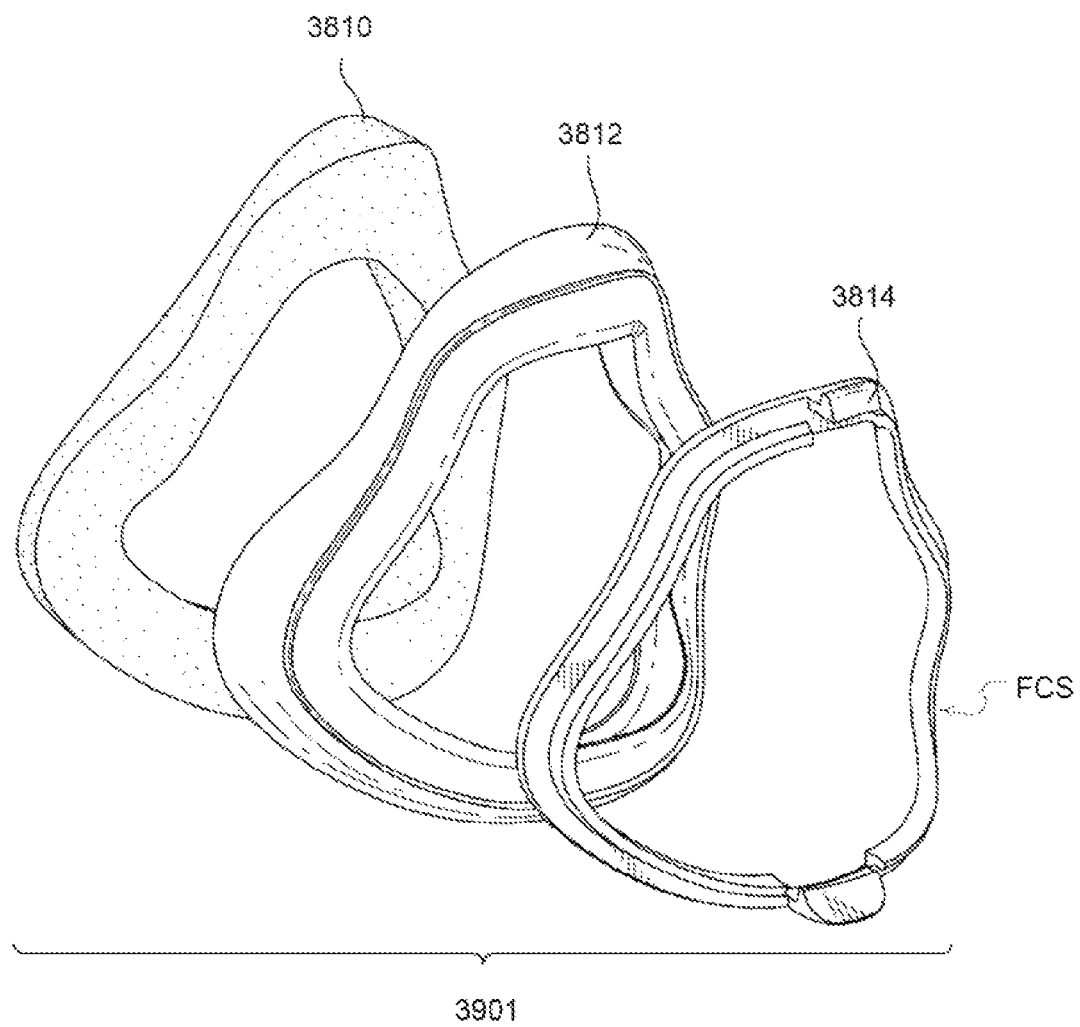

FIG. 39 is an illustration of separated components of a foam cushion assembly such as for the foam mask of FIG. 38.

Figure 40:
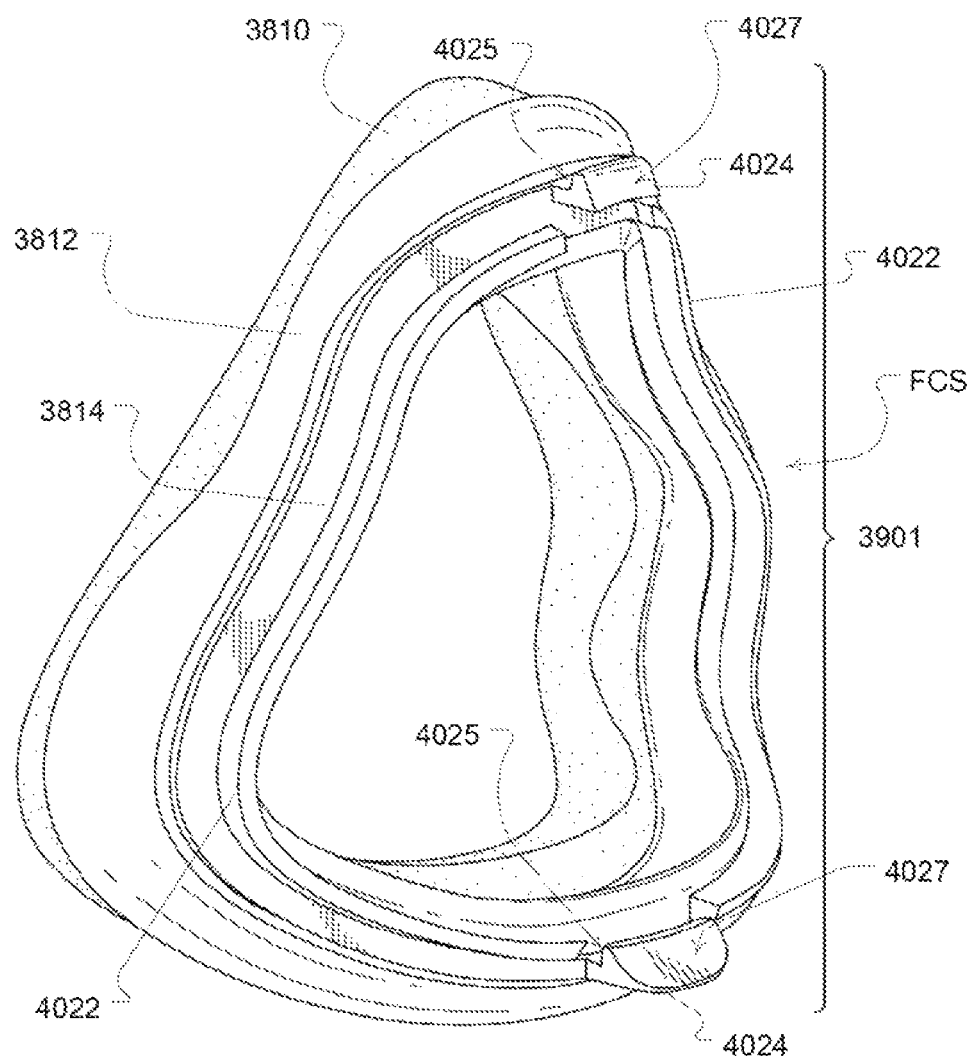

FIG. 40 shows the foam cushion assembly with the coupled components of FIG. 39.

Figure 41:
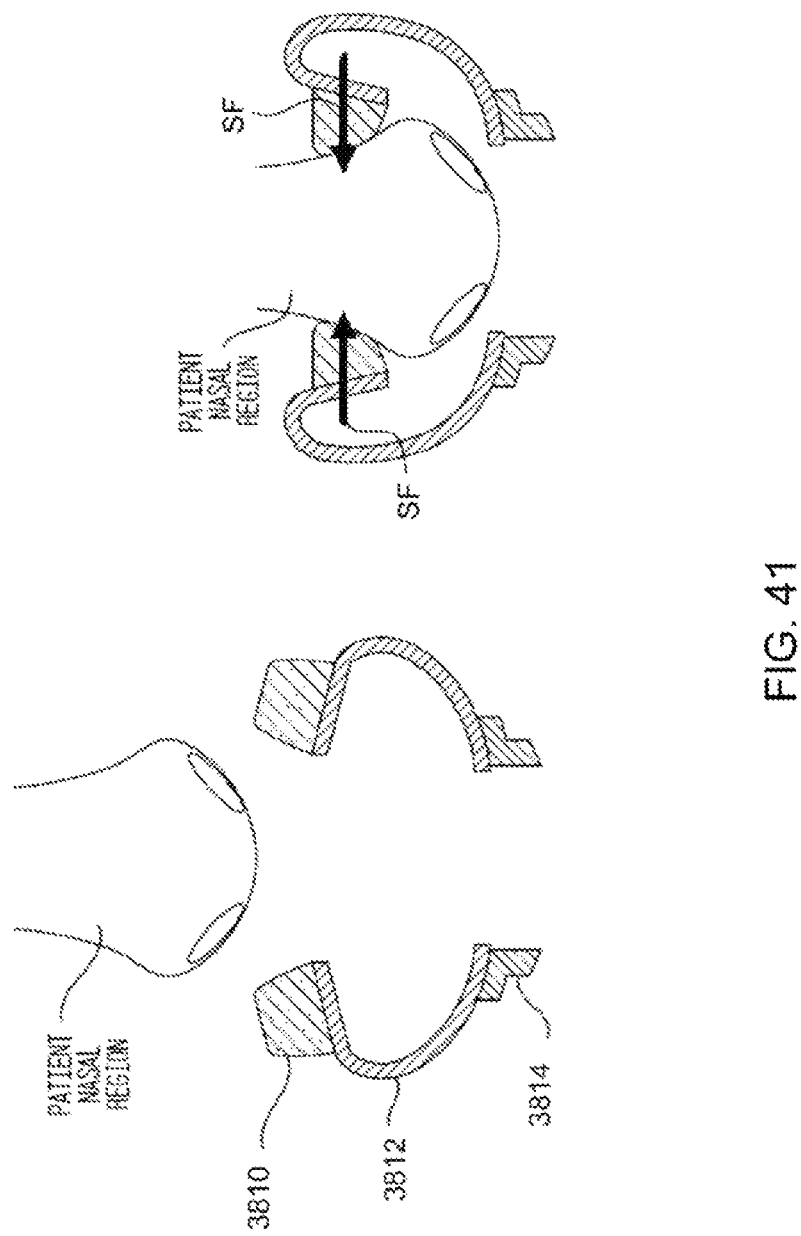

FIG. 41 illustrates mask sealing with a foam cushion in a nasal region with the mask of FIG. 39.

Figure 42:
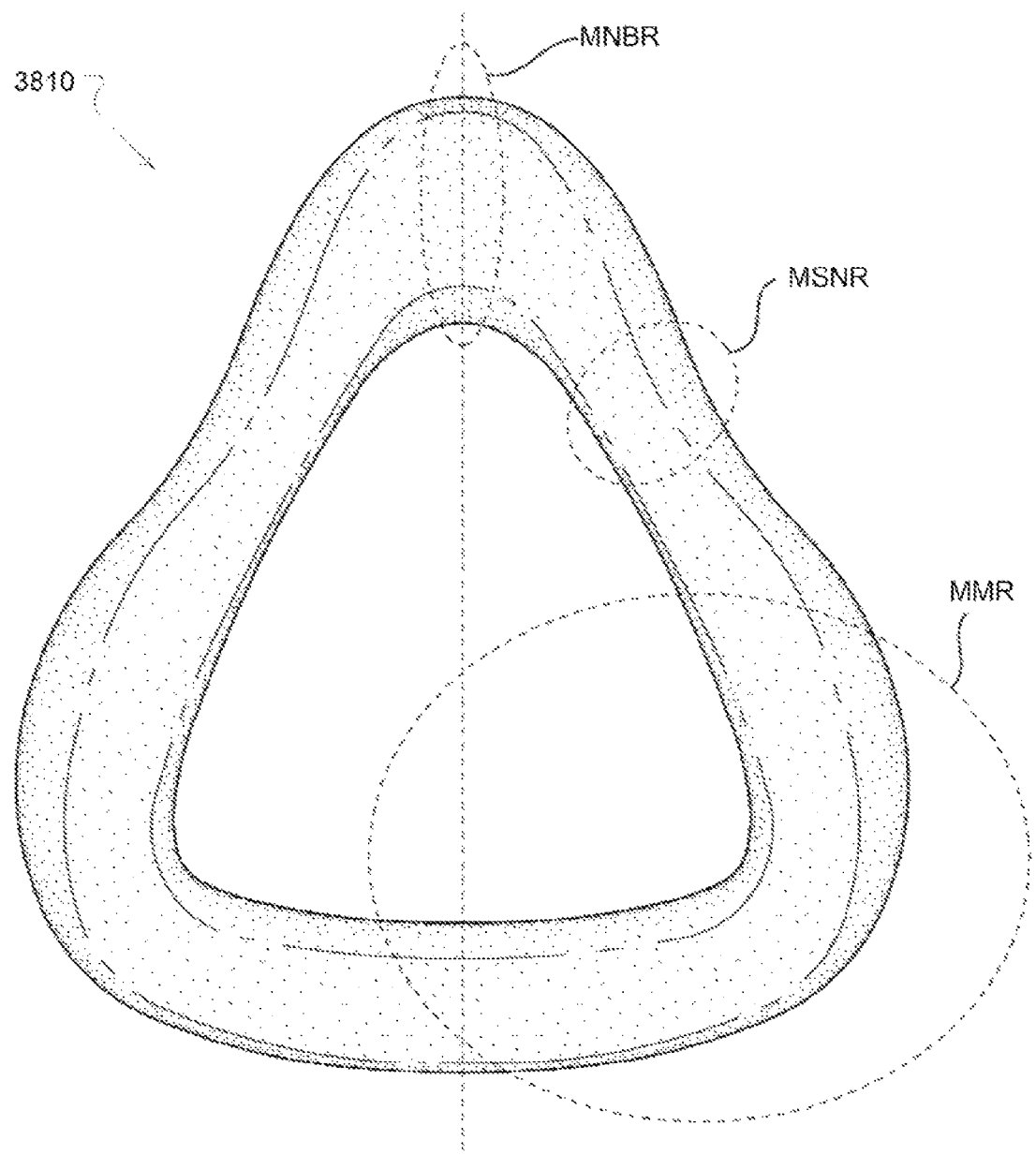

FIG. 42 shows regions of a clip component of the mask of FIG. 39.

Figure 43:
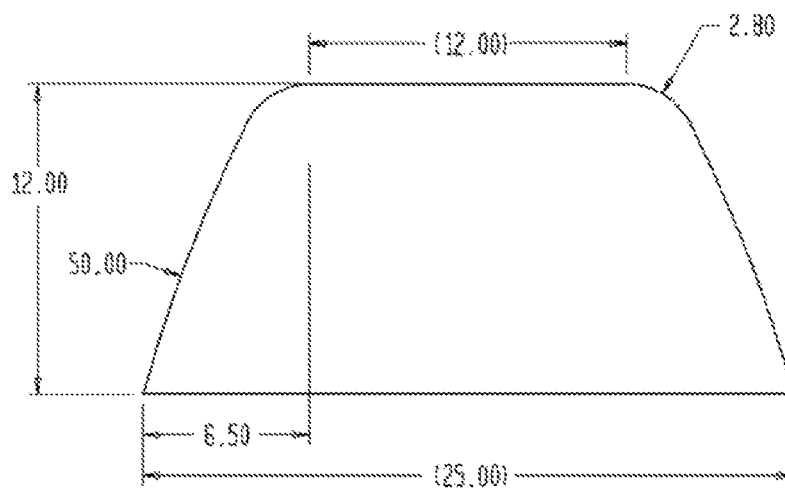
Figure 44:
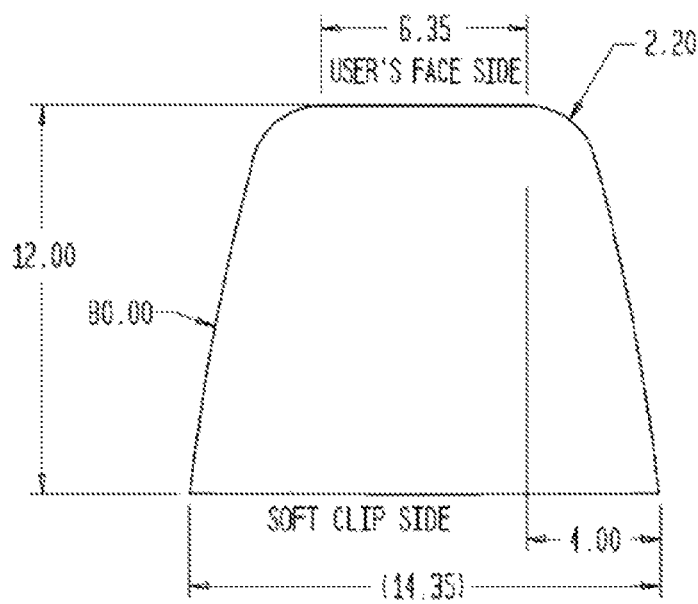
Figure 45:
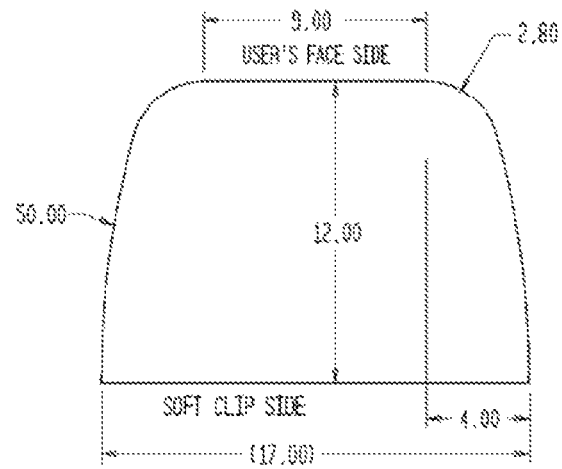

FIGS. 43, 44 and 45 are cross sectional views a portion of a foam cushion in some embodiments of the present technology such as for a nasal bridge region, a side of nose region and side of mouth region.

Figure 46:
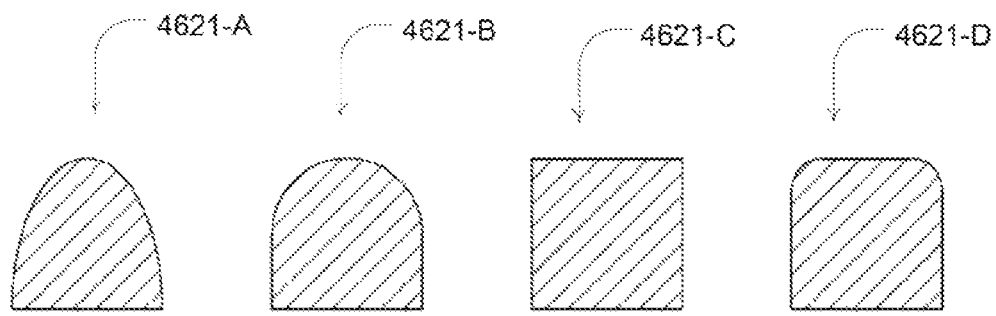

FIG. 46 illustrates several example cross sectional geometries for a foam cushion of any of the foam cushion patient interface embodiments of the present technology.

Figure 47:
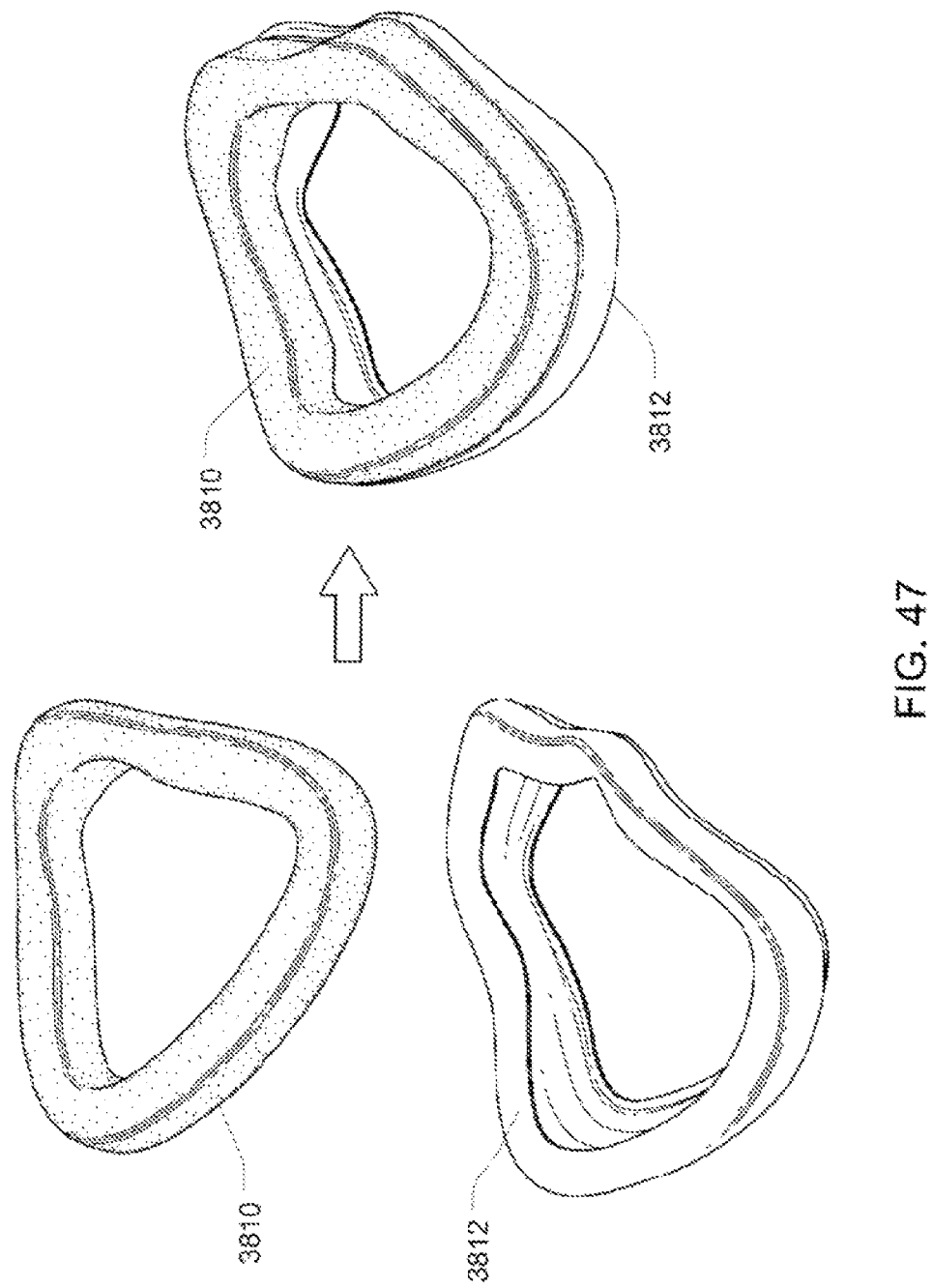

FIG. 47 illustrates foam cushion and clip components, as separate components, as well as in an assembled configuration of the present technology.

Figure 48:
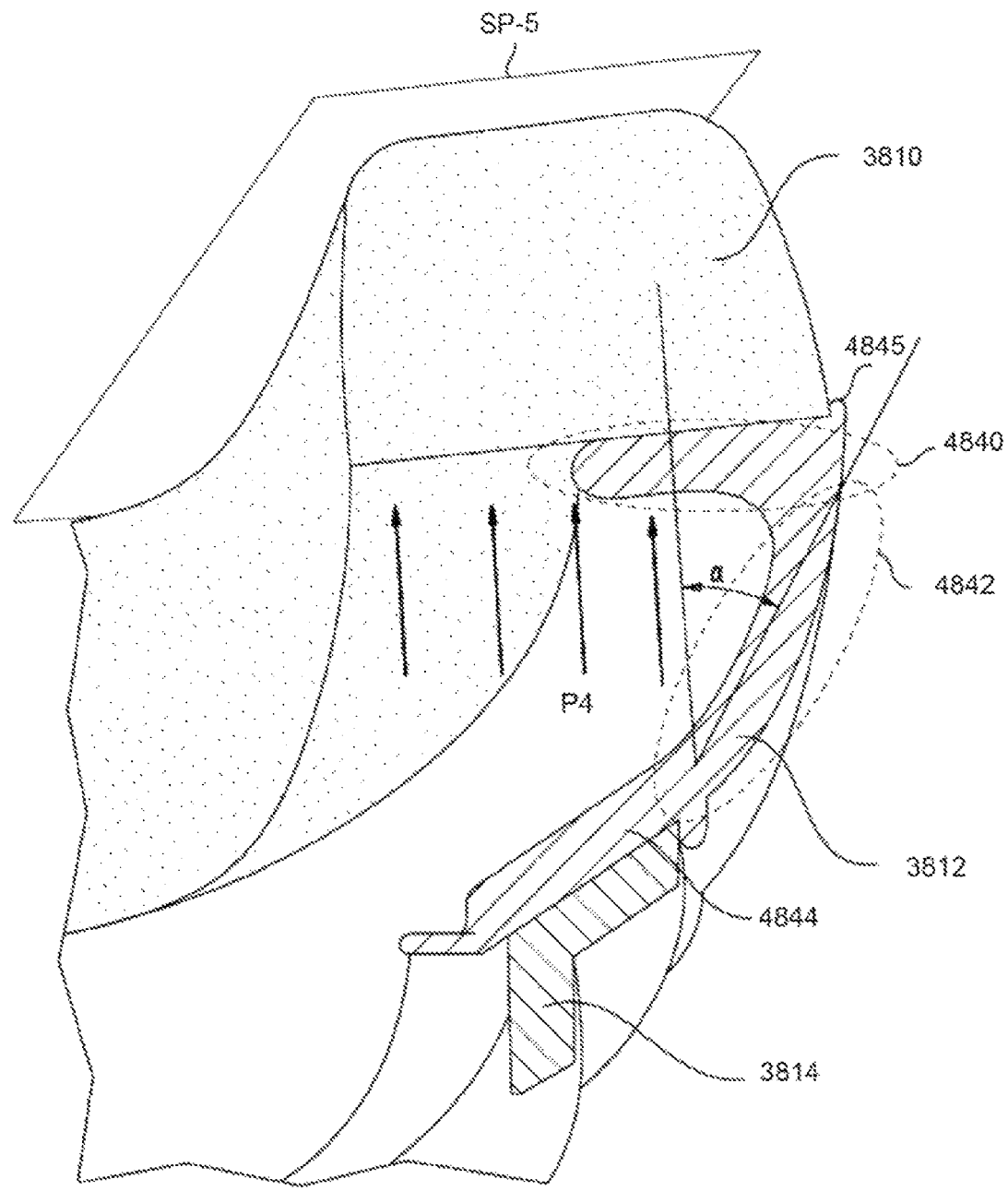

FIG. 48 is a cross sectional view of a cushion assembly in some versions of the present technology having multiple clip components and a foam cushion.

Figure 49:
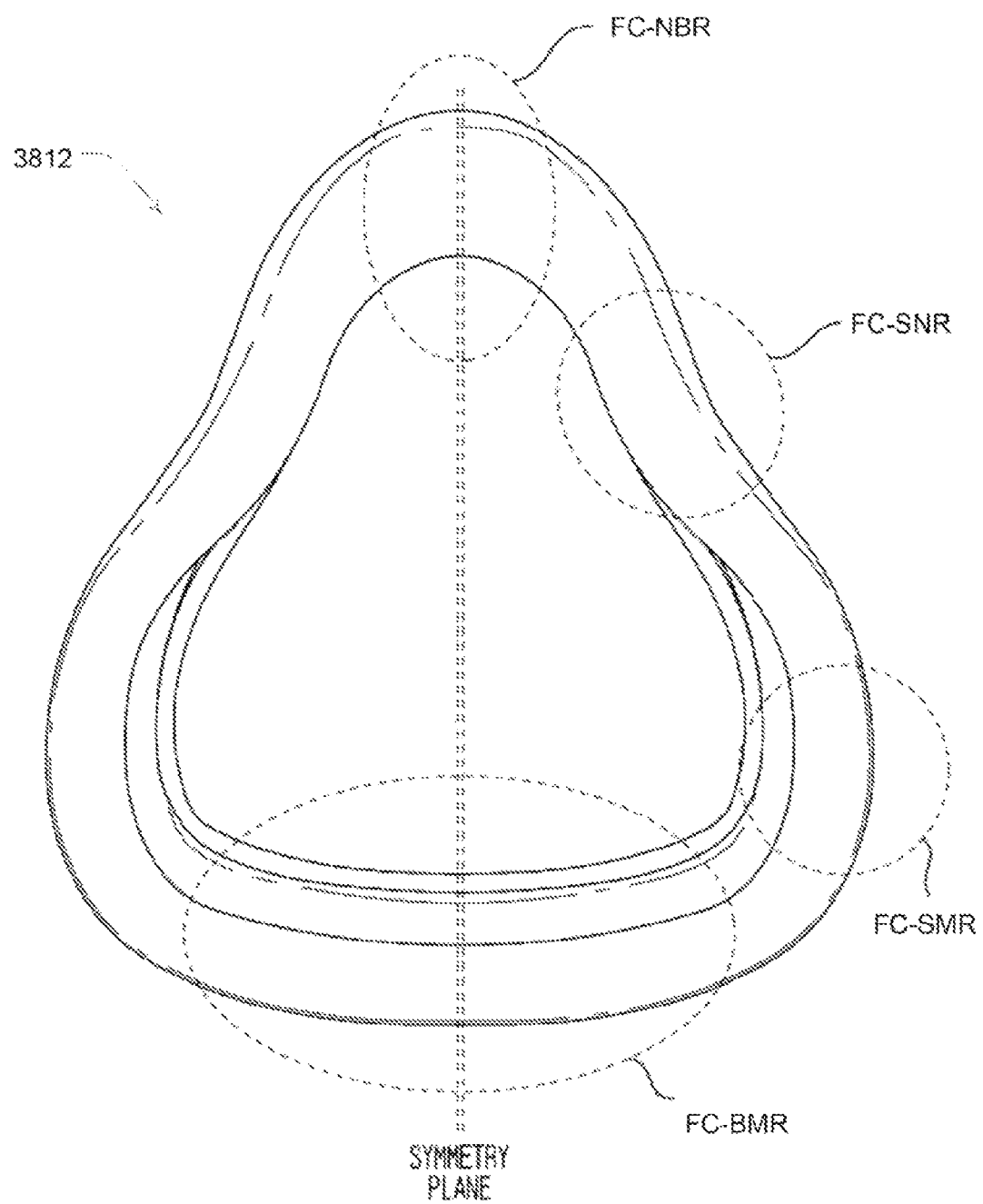

FIG. 49 shows various regions of a flexible clip component for a foam cushion mask.

Figure 50:
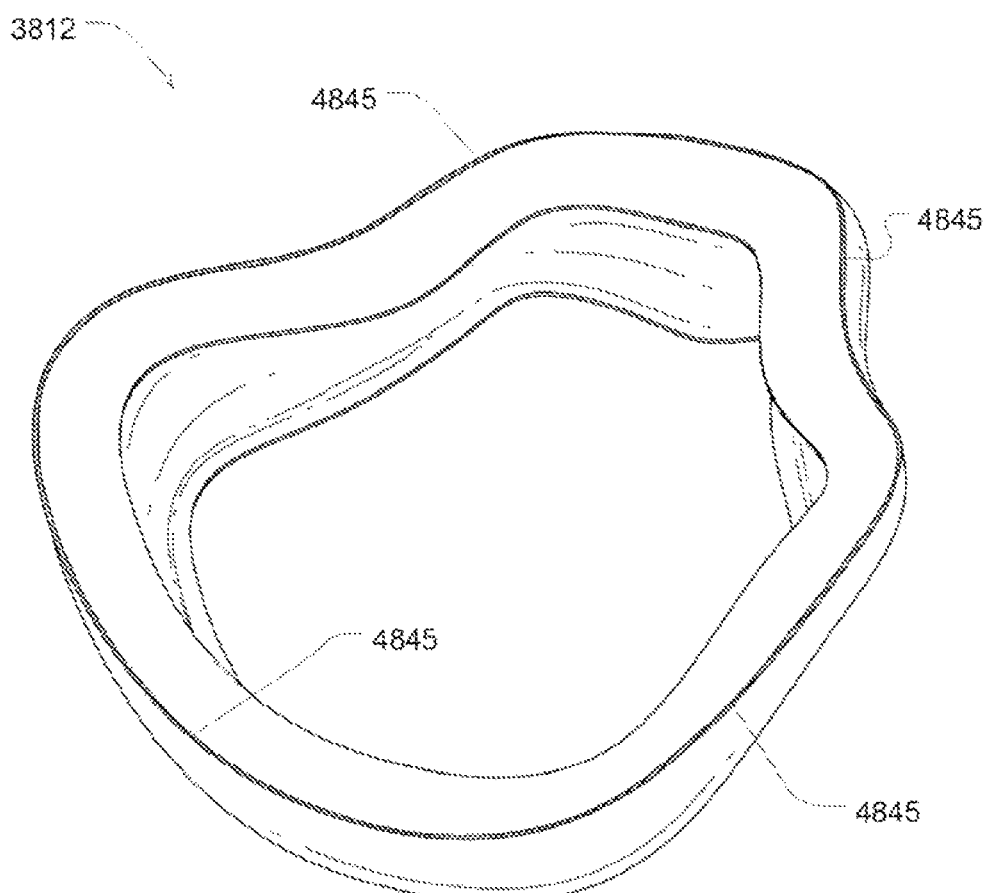

FIG. 50 shows the clip component of FIG. 49 with an optional foam location ridge.

FIGS. 51, 52, 53 and 54 illustrate various cross sectional geometries for various regions of the clip component of FIG. 49 such as for a nasal bridge region, a side of nose region, side of mouth region and a bottom of mouth region.

Figure 55:
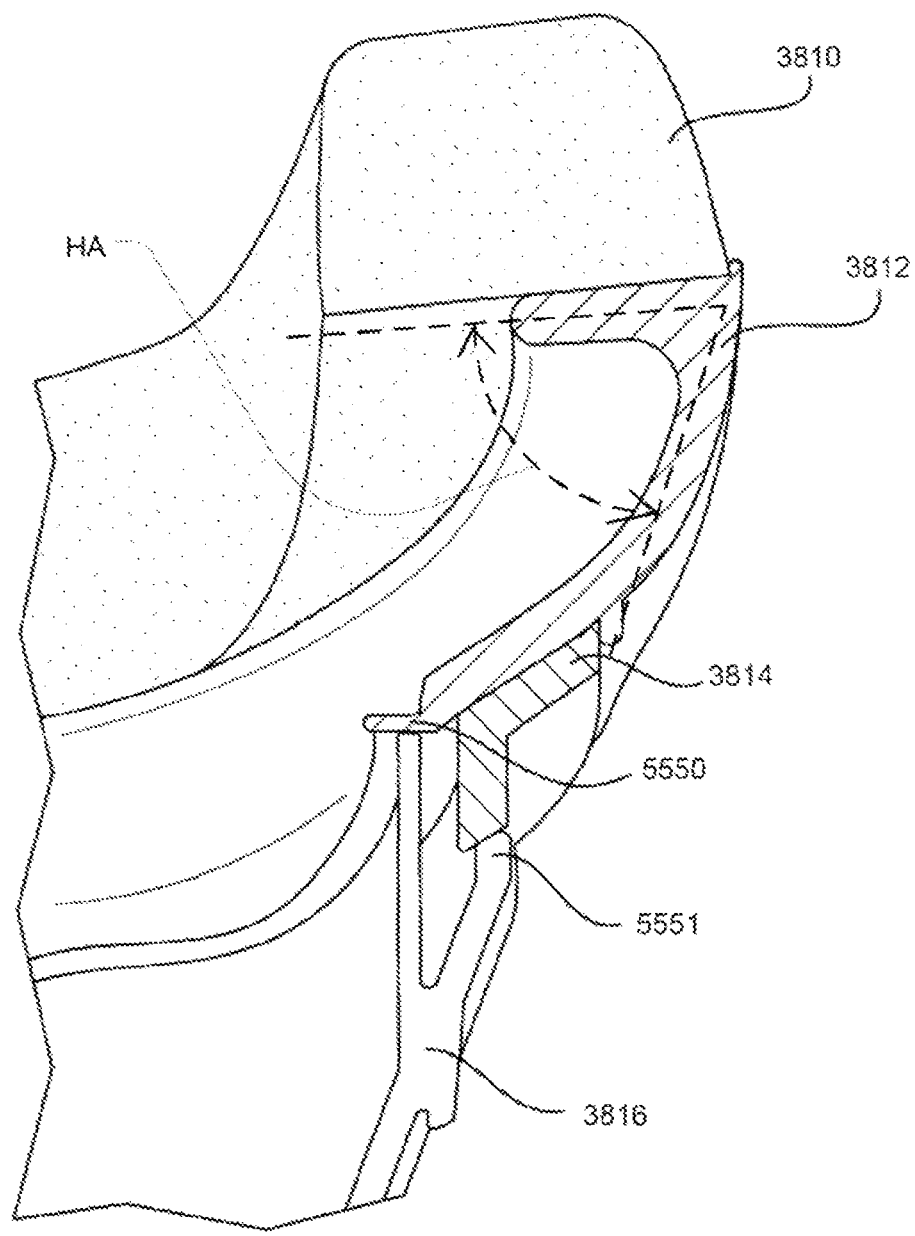
Figure 56:
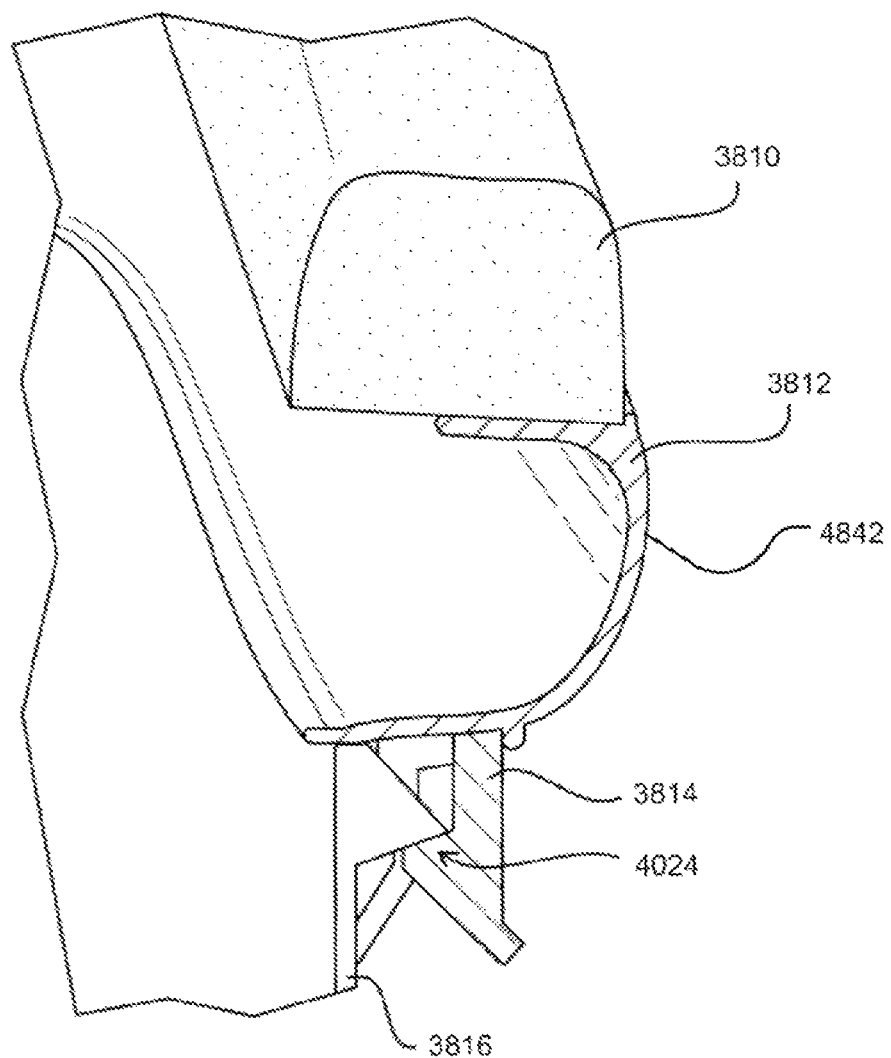

FIGS. 55 and 56 are cross sectional views of several example cushion assemblies coupled with a mask frame.

Figure 57:
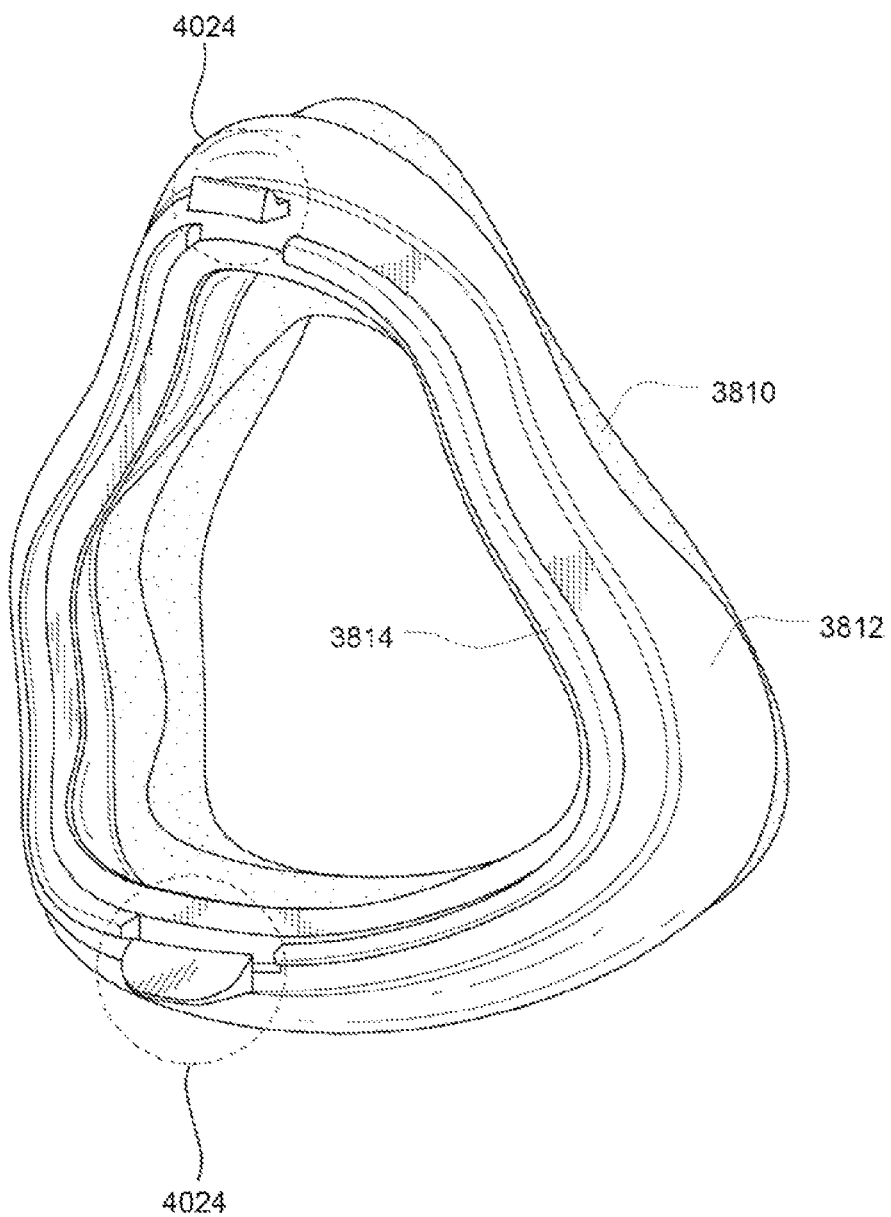

FIG. 57 illustrates several example retention elements for coupling a foam mask cushion assembly with a mask frame.

FIG. 58A is a side view of a cushion and clip assembly in some versions of the present technology.

FIG. 58B is a cross sectional view of the cushion assembly of FIG. 58A.

Figure 59:
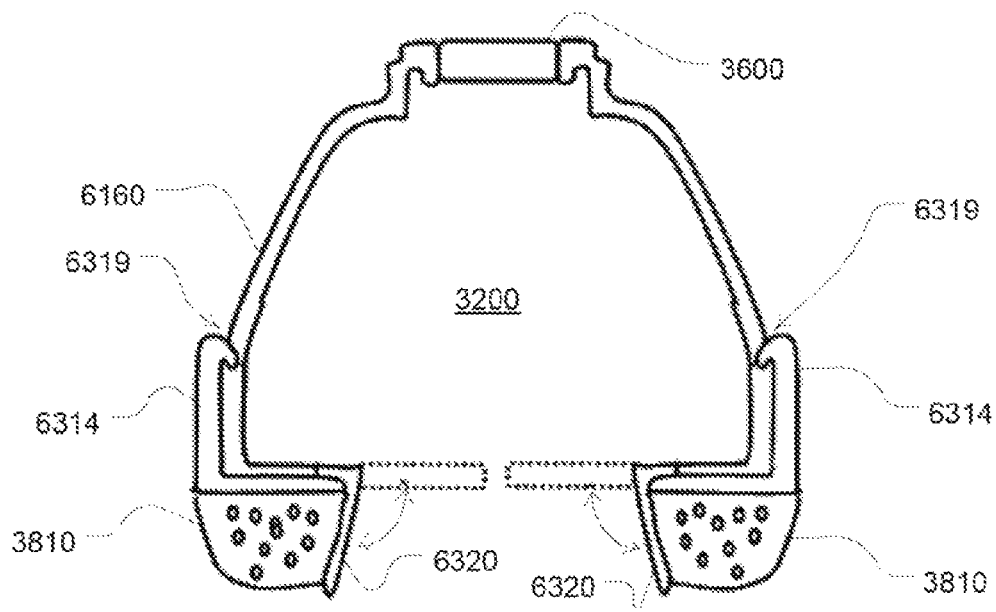

FIG. 59 is a cross section view of a mask and foam cushion assembly in some versions of the present technology.

Figure 60:
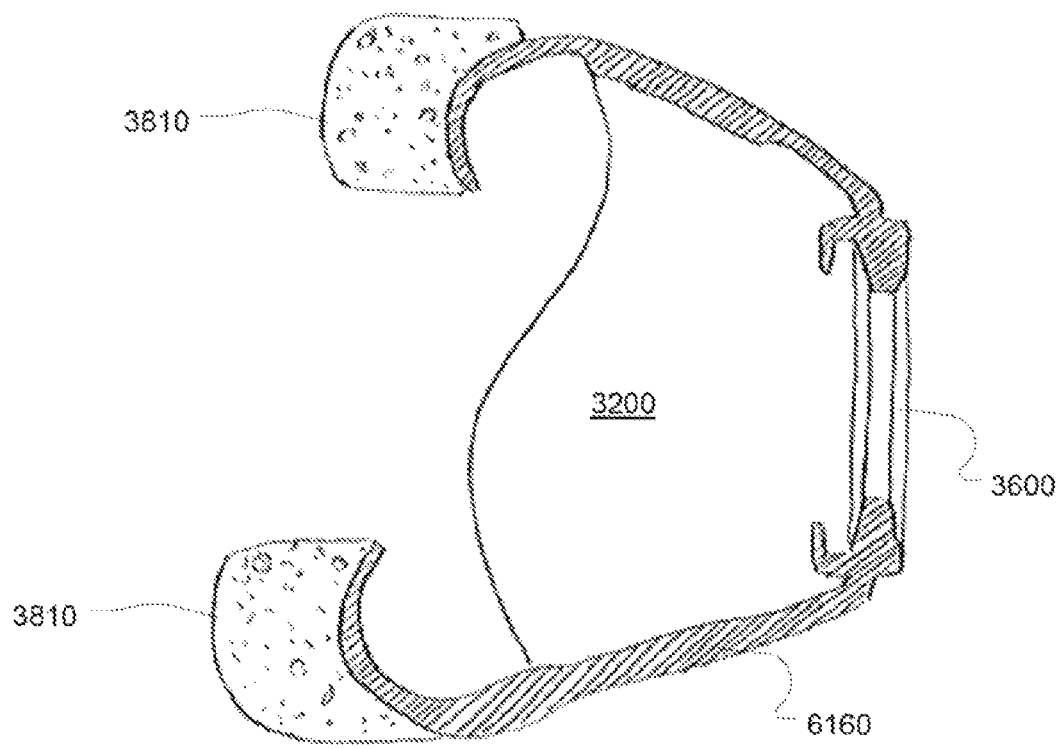

FIG. 60 is a cross sectional view of a flexible shell for a foam mask assembly.

Figure 61:
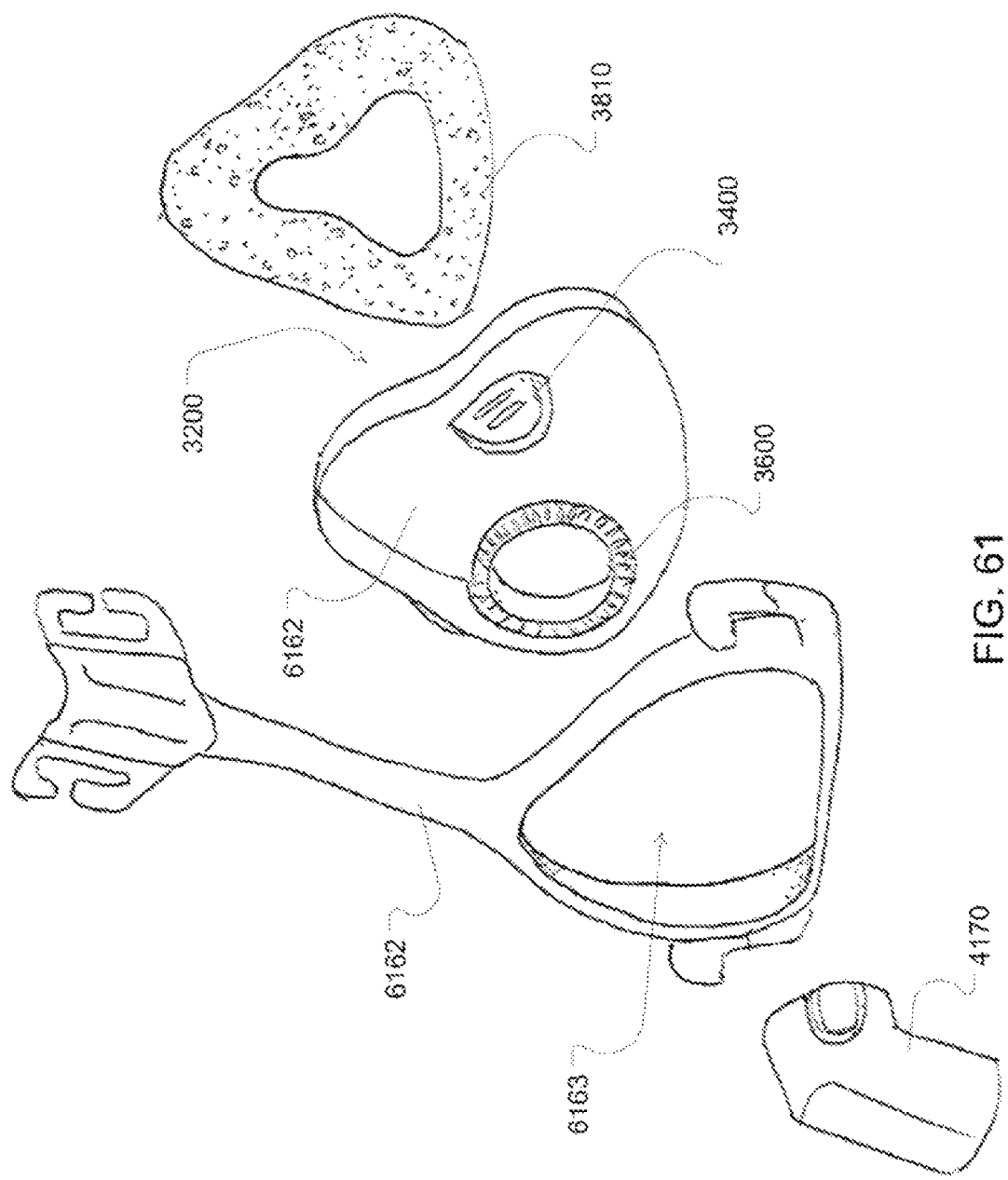

FIG. 61 is an exploded view of components of a foam mask assembly with the shell of FIG. 60.

Figure 62:
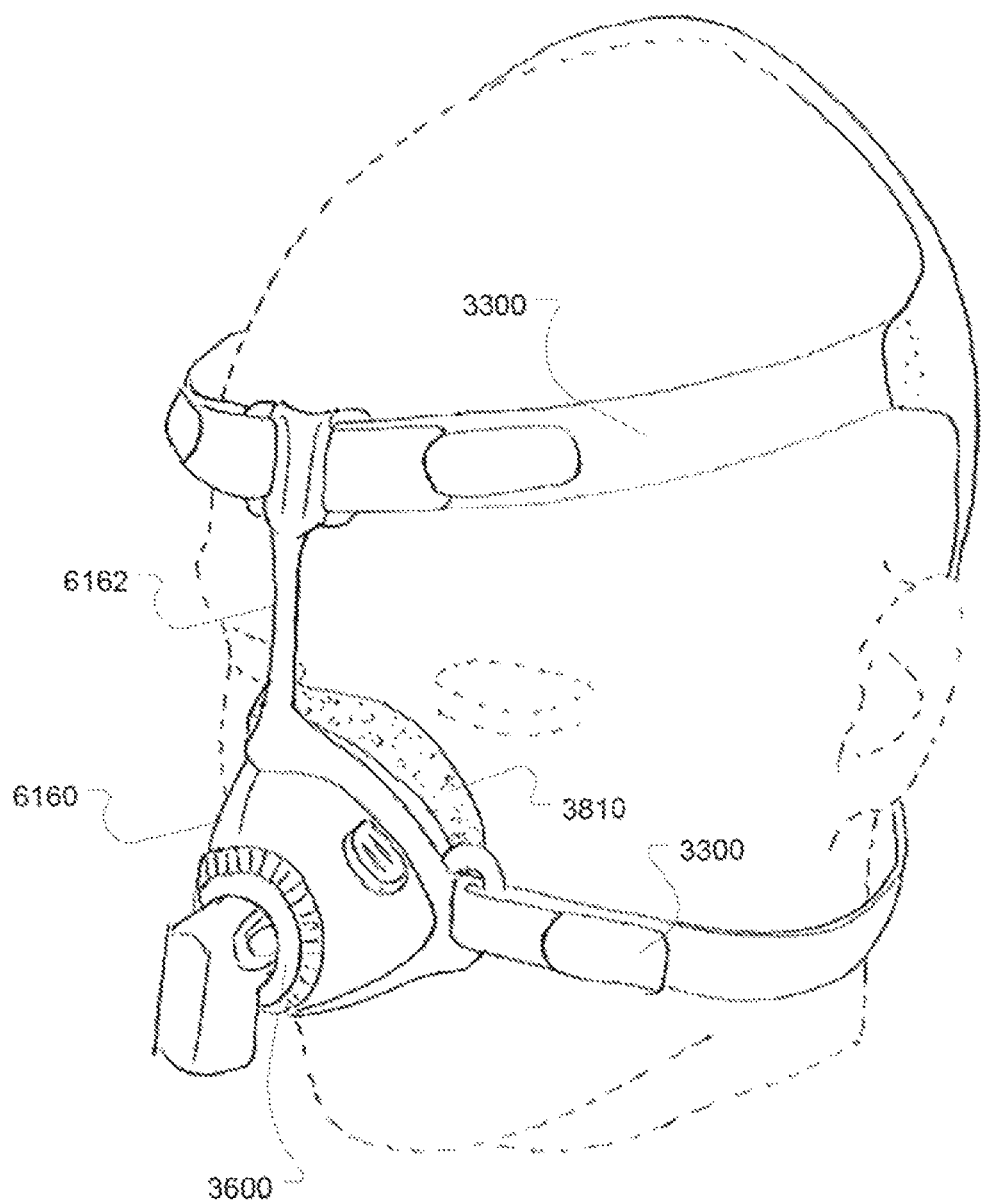

FIG. 62 illustrates the foam mask assembly of FIG. 61 on person.

Figure 63A:
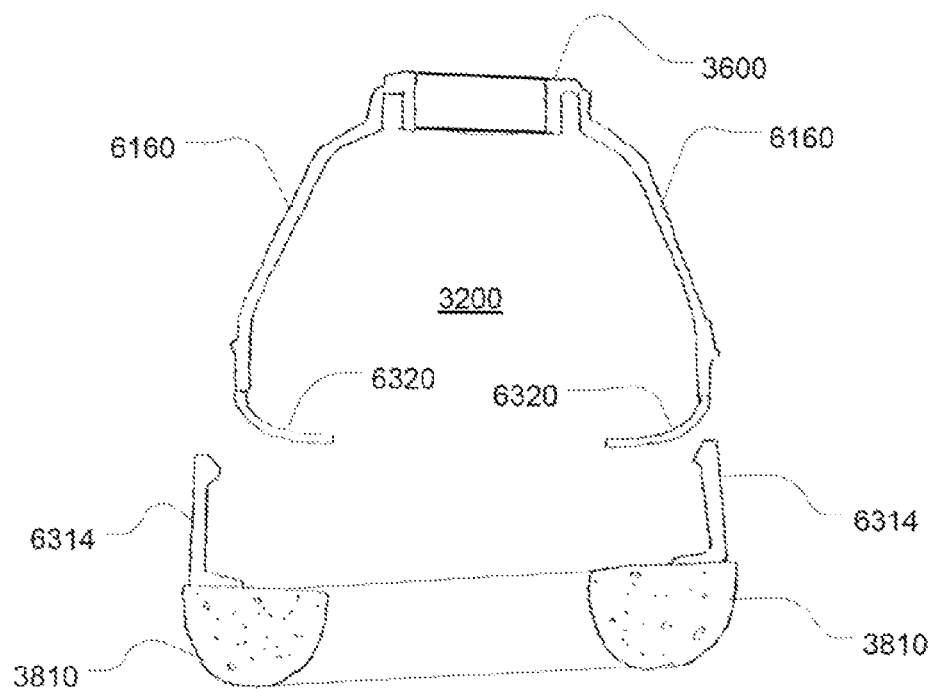
Figure 63B:
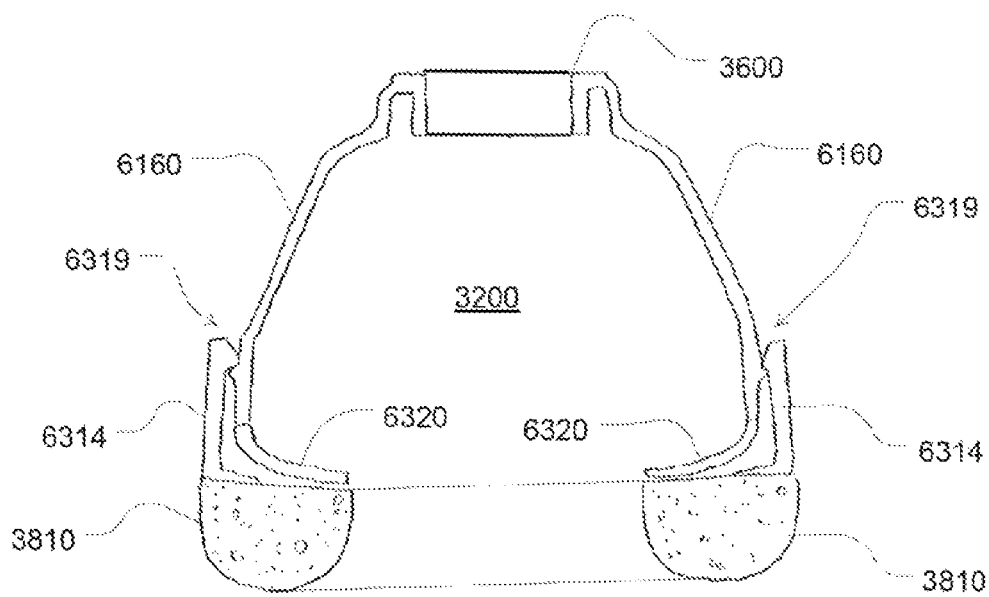
Figure 64:
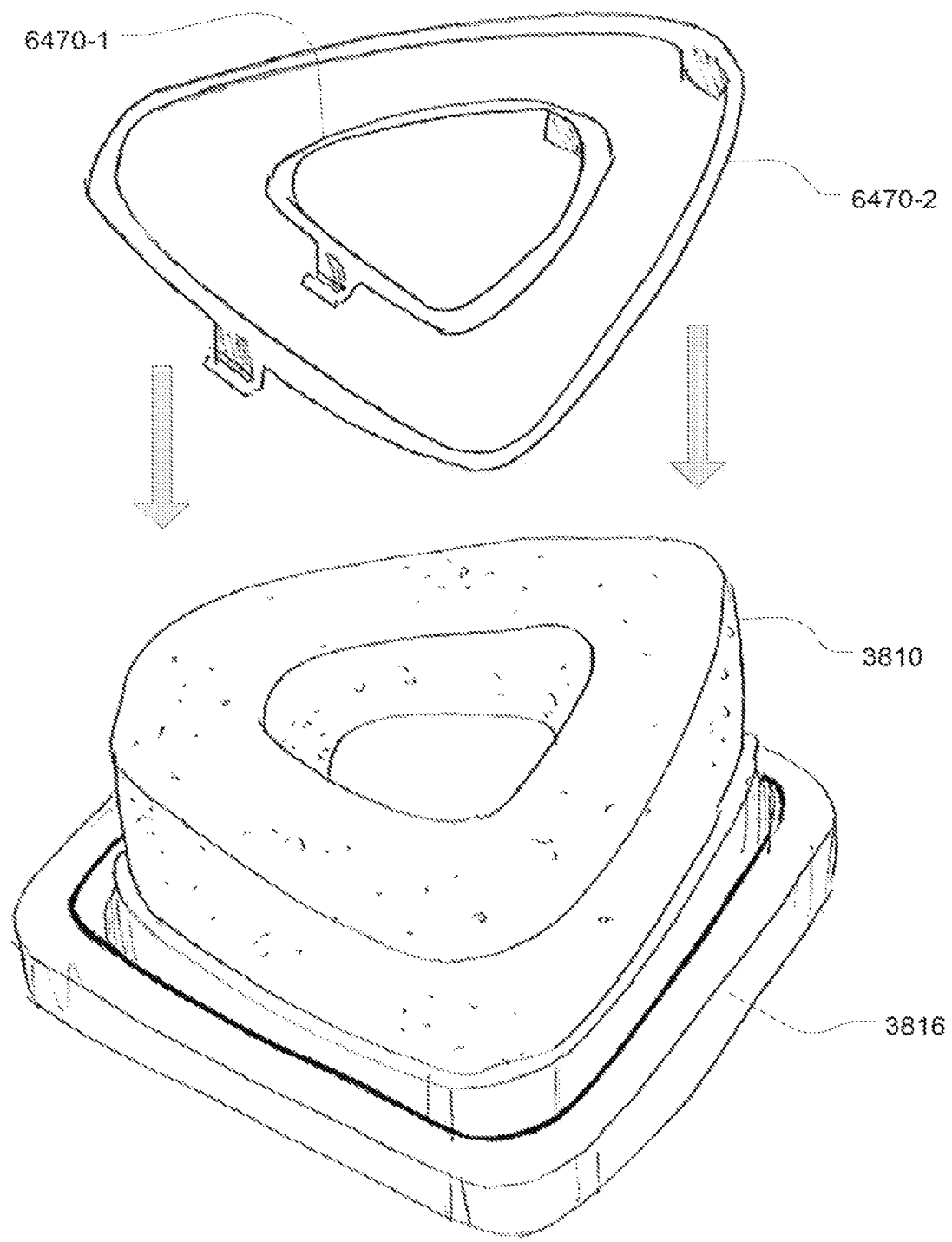

FIGS. 63A and 63B illustrate assembly of a foam cushion and clip in some examples of the present technology.

FIGS. 64, 65, 66A and 66B illustrate assembly of a foam cushion and mask frame with various clips.

Figure 67:
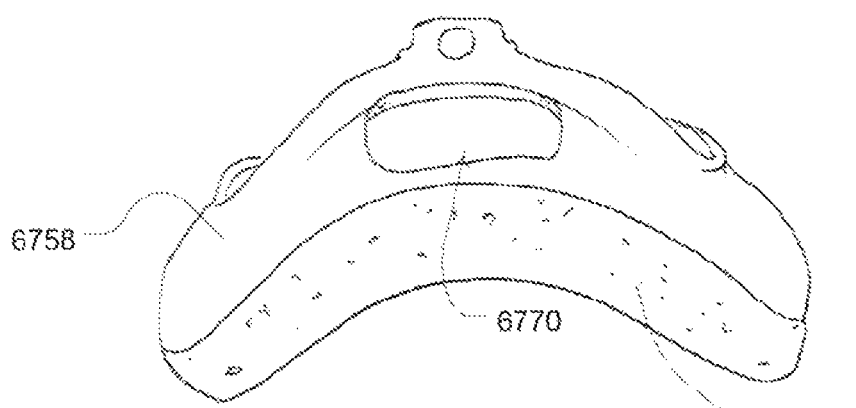
Figure 68:
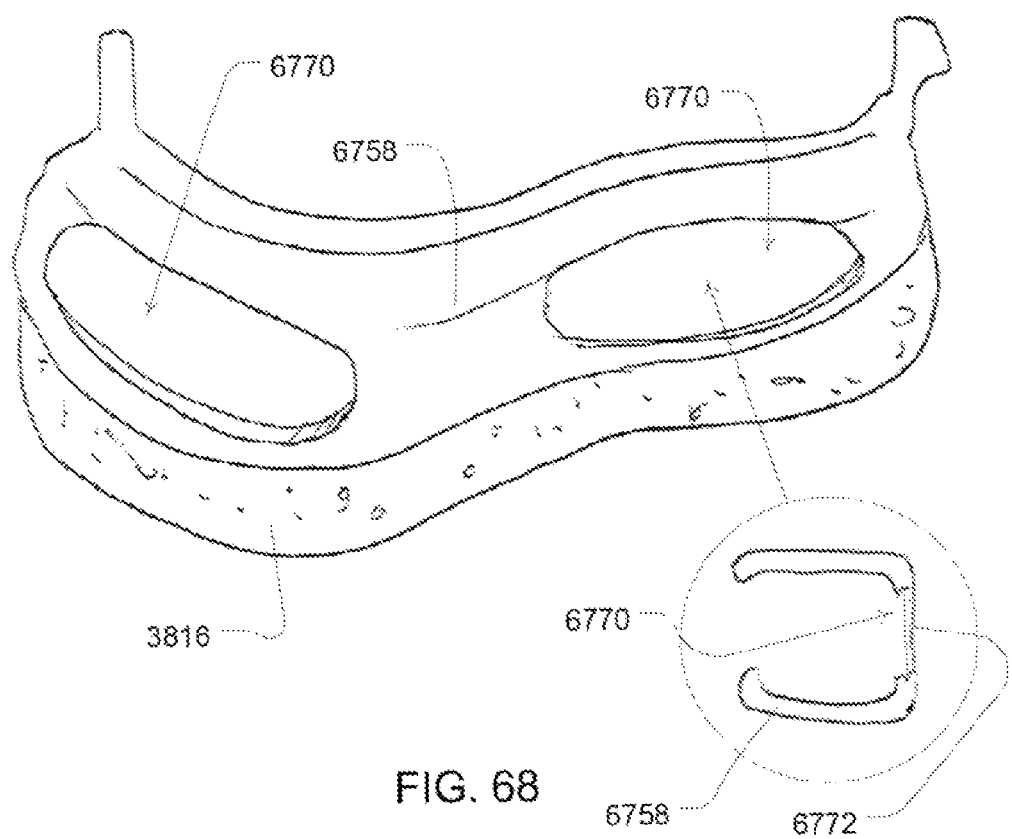

FIGS. 67 and 68 show a foam cushion and clip assembly with some versions of the present technology.

Figure 69:
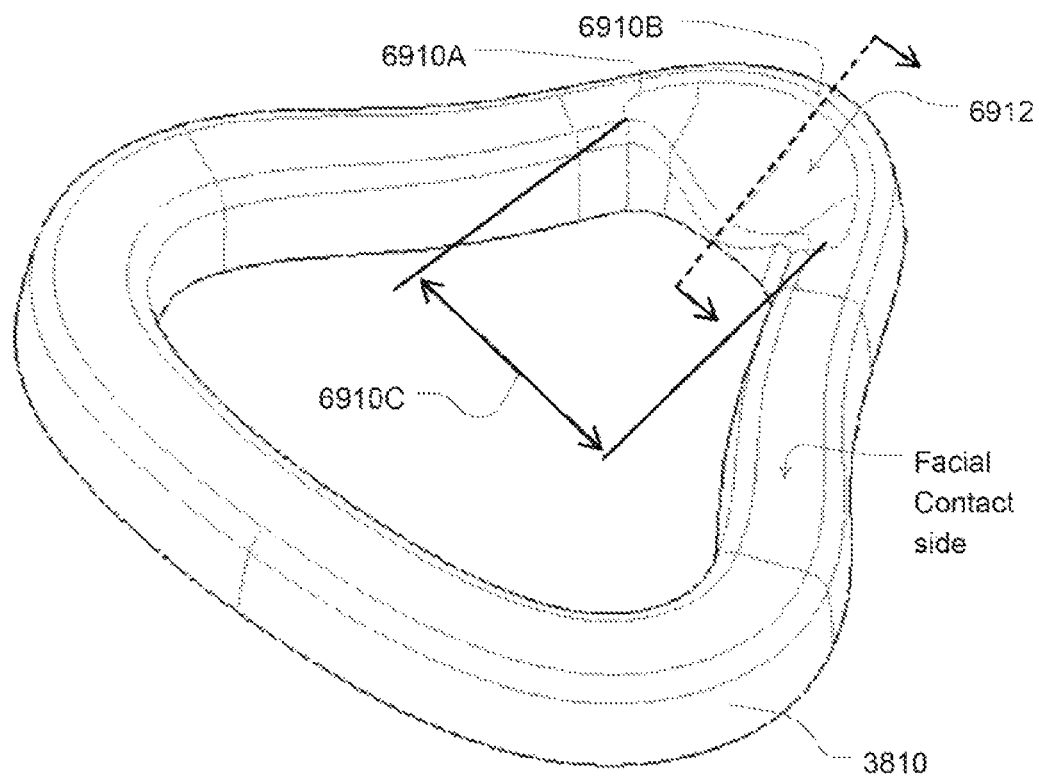

FIG. 69 is an illustration of a foam cushion suitable for some embodiments of the present technology;

FIGS. 70, 71, 72 and 74 illustrate cross sectional geometries of an example clip such as for the foam cushion of FIG. 69.

Figure 73:
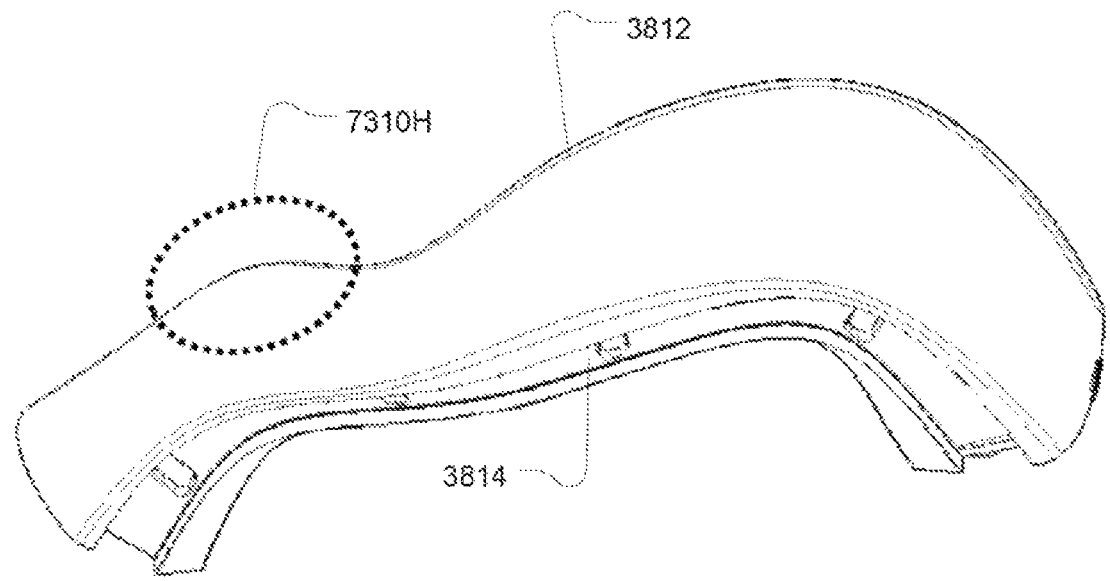

FIG. 73 is a side view of a further example clip assembly for a foam cushion.

Figure 75:
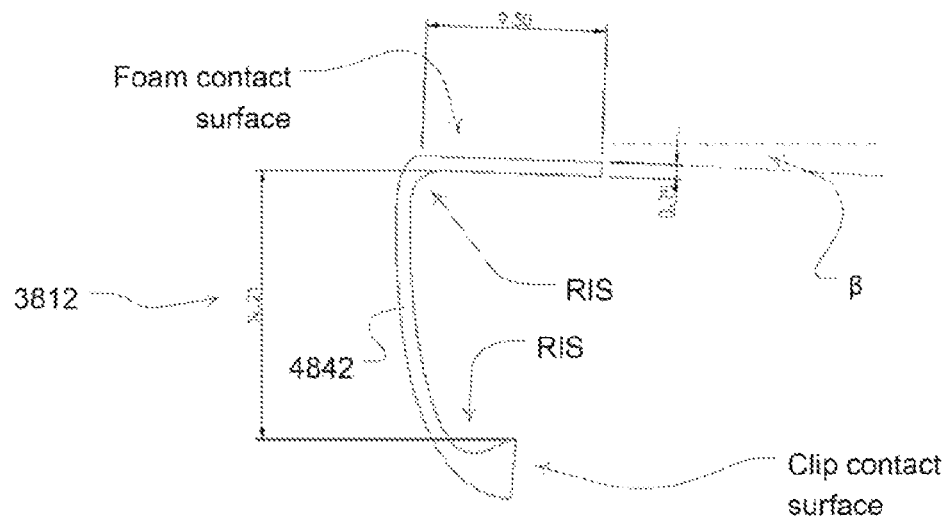

FIG. 75 is a cross sectional view of a portion of an example clip.

Figure 76:
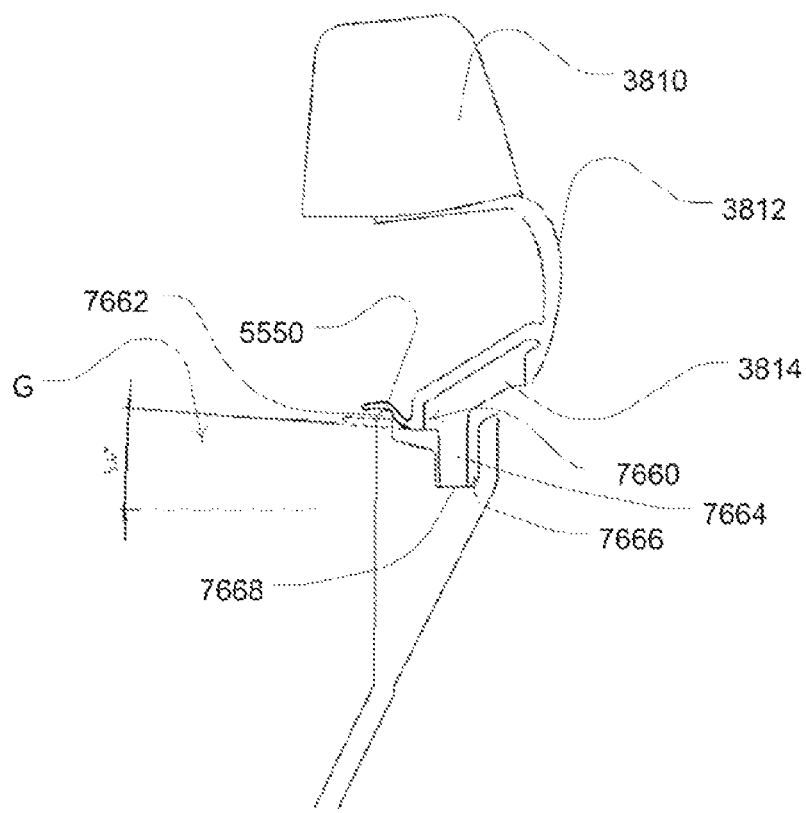

FIG. 76 is a cross sectional view of portions of a foam cushion mask assembly.

Figure 77:
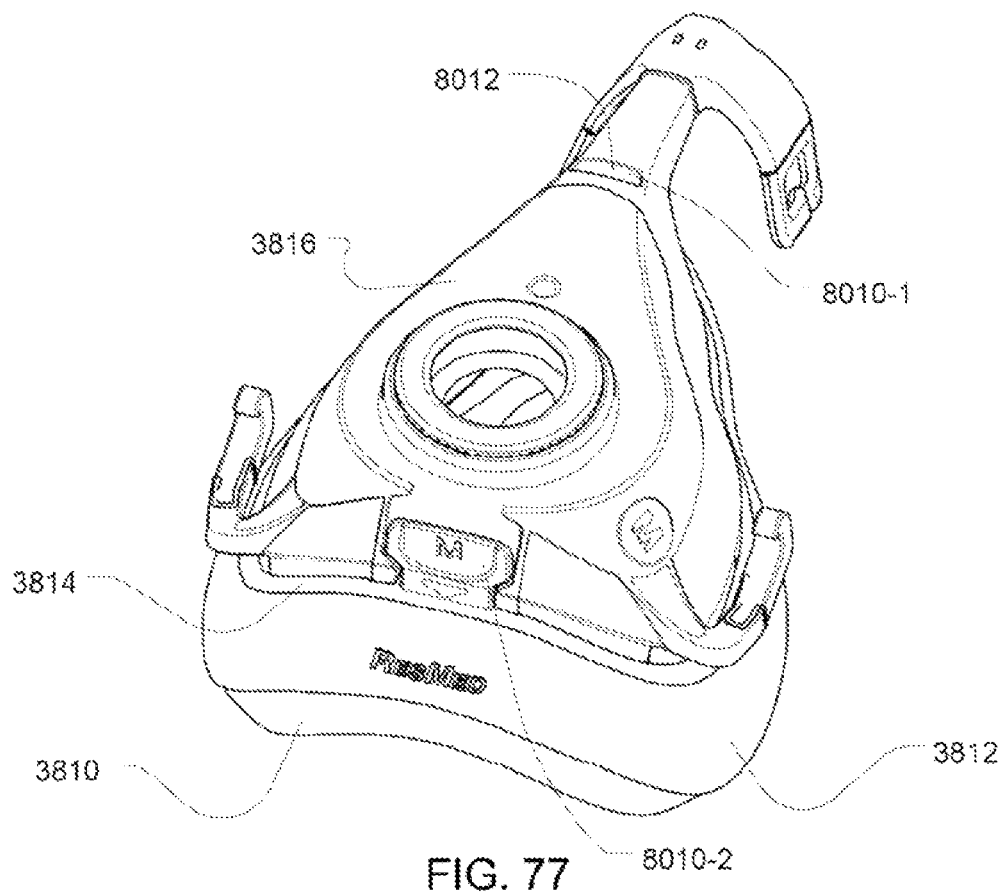

FIG. 77 is a perspective view of an example foam cushion mask assembly of the present technology.

Figure 78:
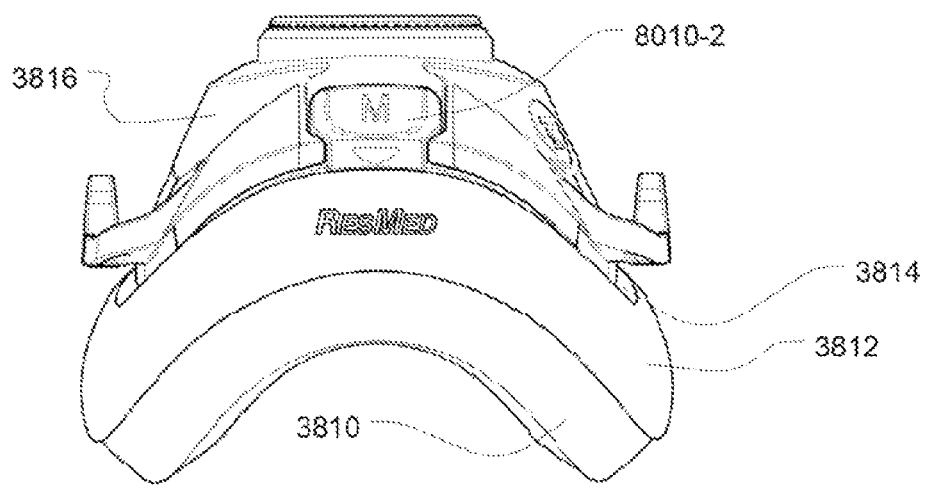

FIG. 78 is a bottom side view of the foam cushion mask assembly of FIG. 77.

Figure 79:
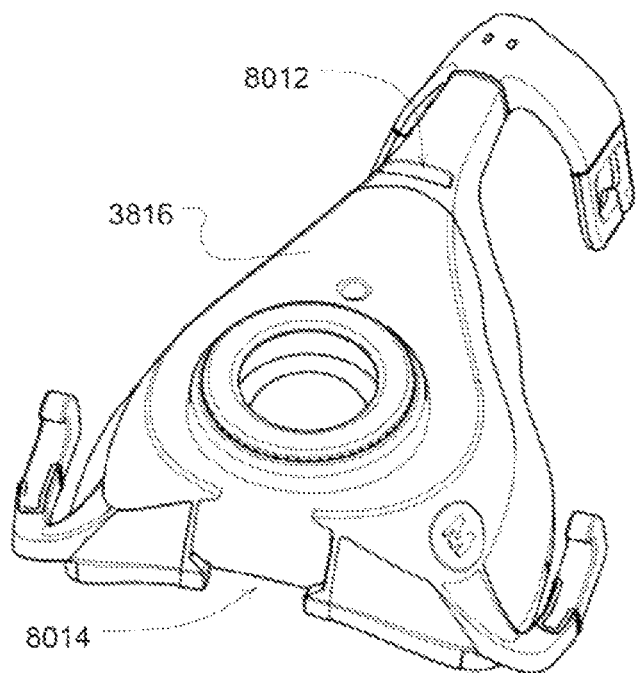

FIG. 79 is a perspective view of a mask frame component of the foam cushion mask assembly of FIG. 77.

Figure 80:
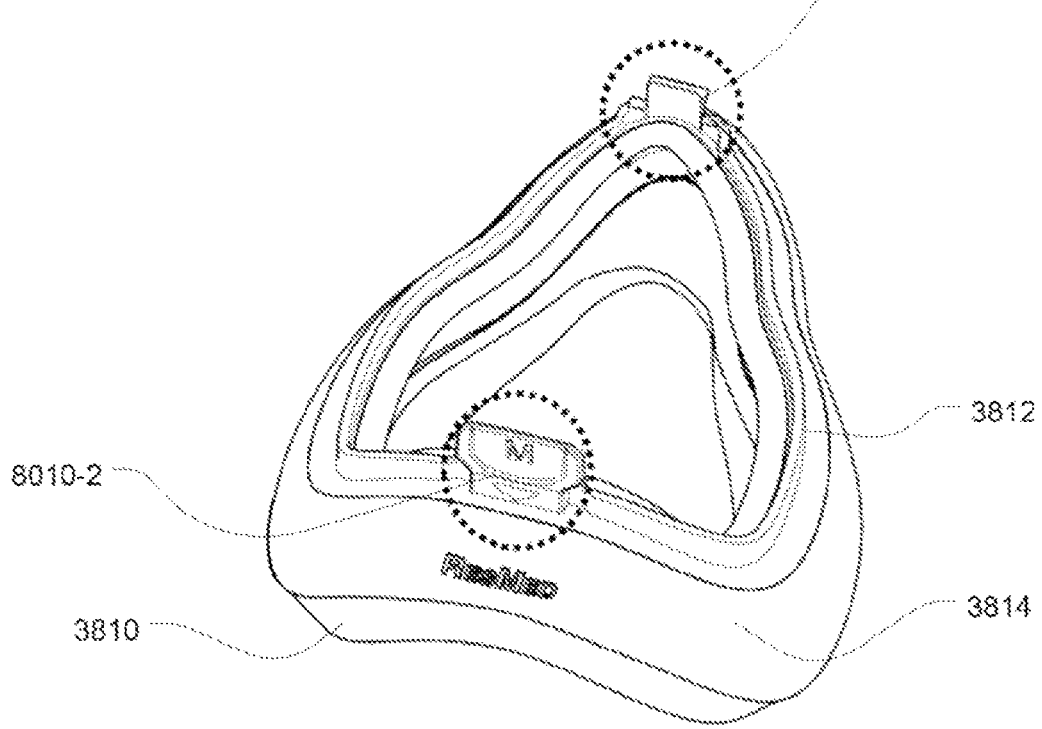

FIG. 80 is a perspective view of a cushion assembly of the foam cushion mask assembly of FIG. 77.

Figure 81:
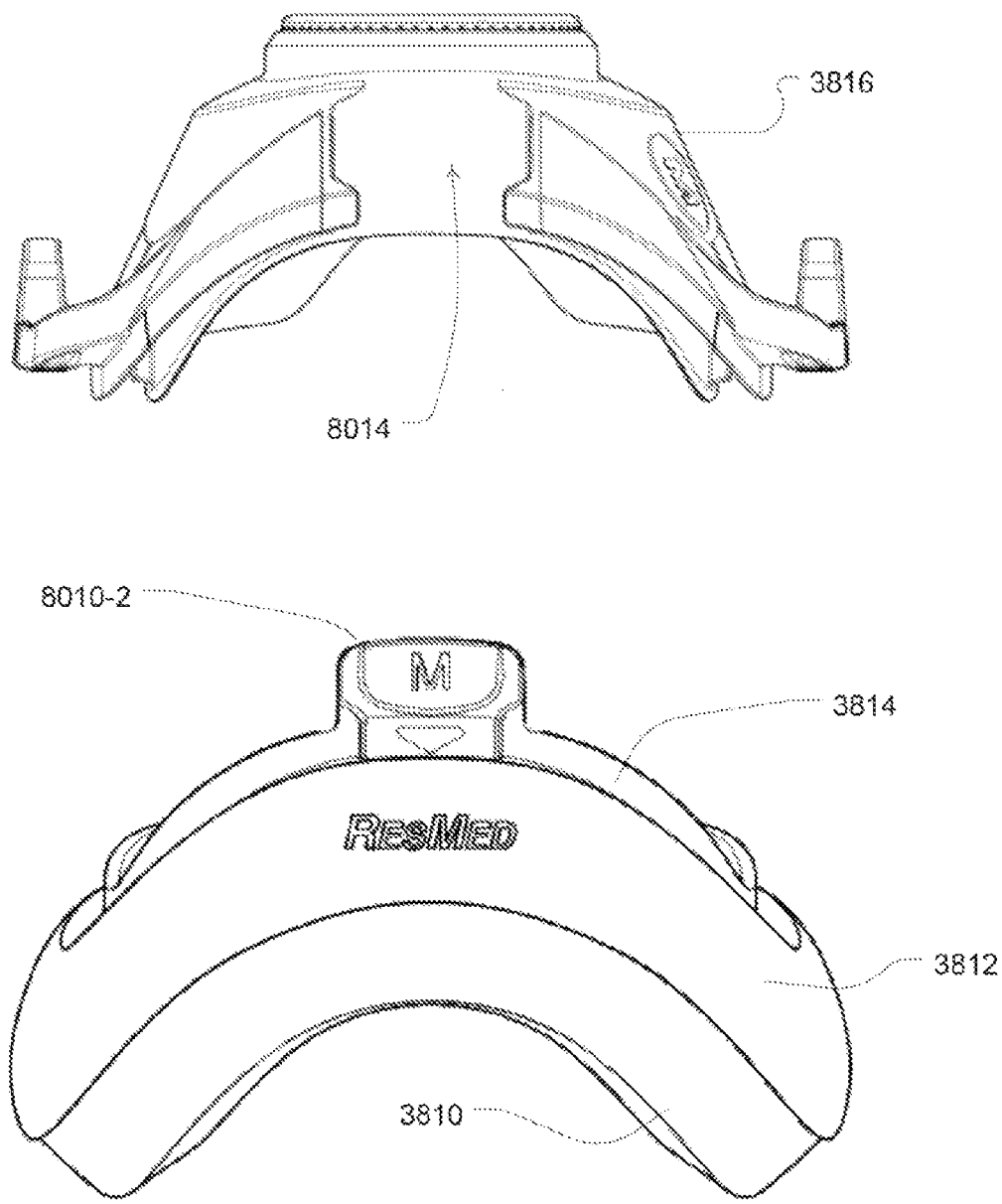

FIG. 81 is a bottom side view illustrating assembly of the mask frame component and cushion assembly of FIGS. 79 and 80.

Figure 82:
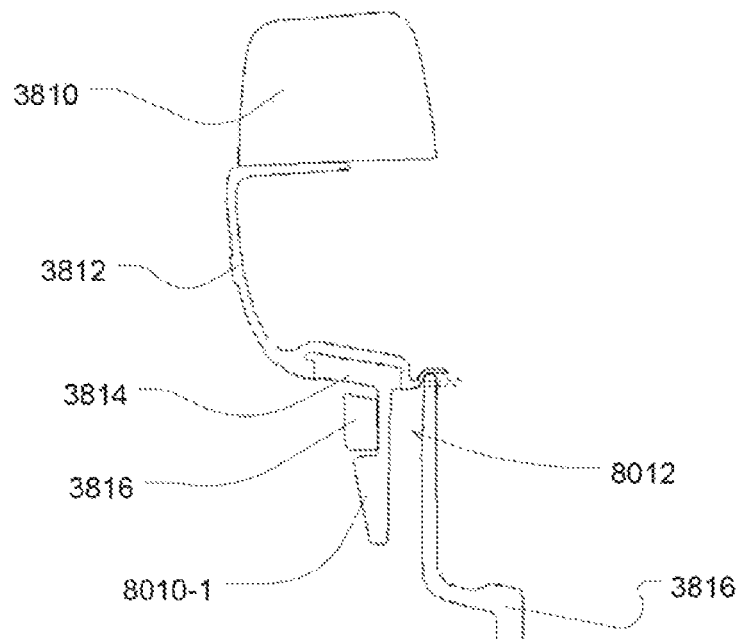

FIG. 82 is a cross sectional view of portions of a foam cushion mask assembly.

Figure 83:
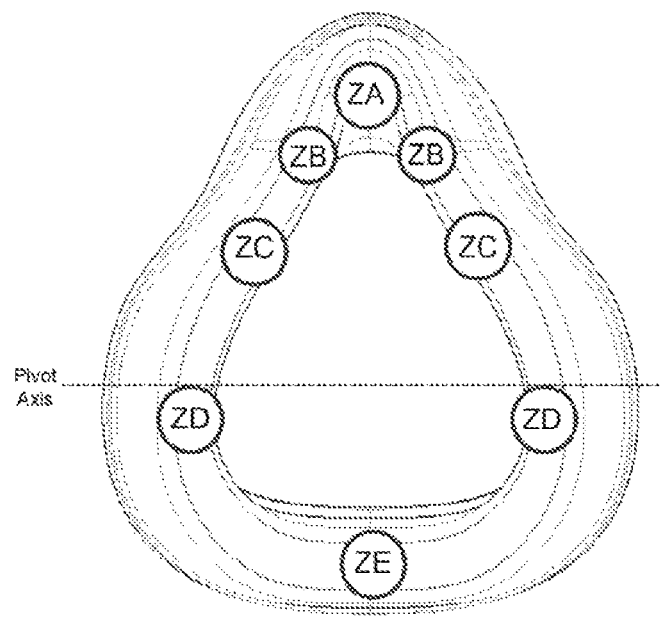

FIG. 83 illustrates various performance regions of a foam cushion of the present technology.

Figure 84:
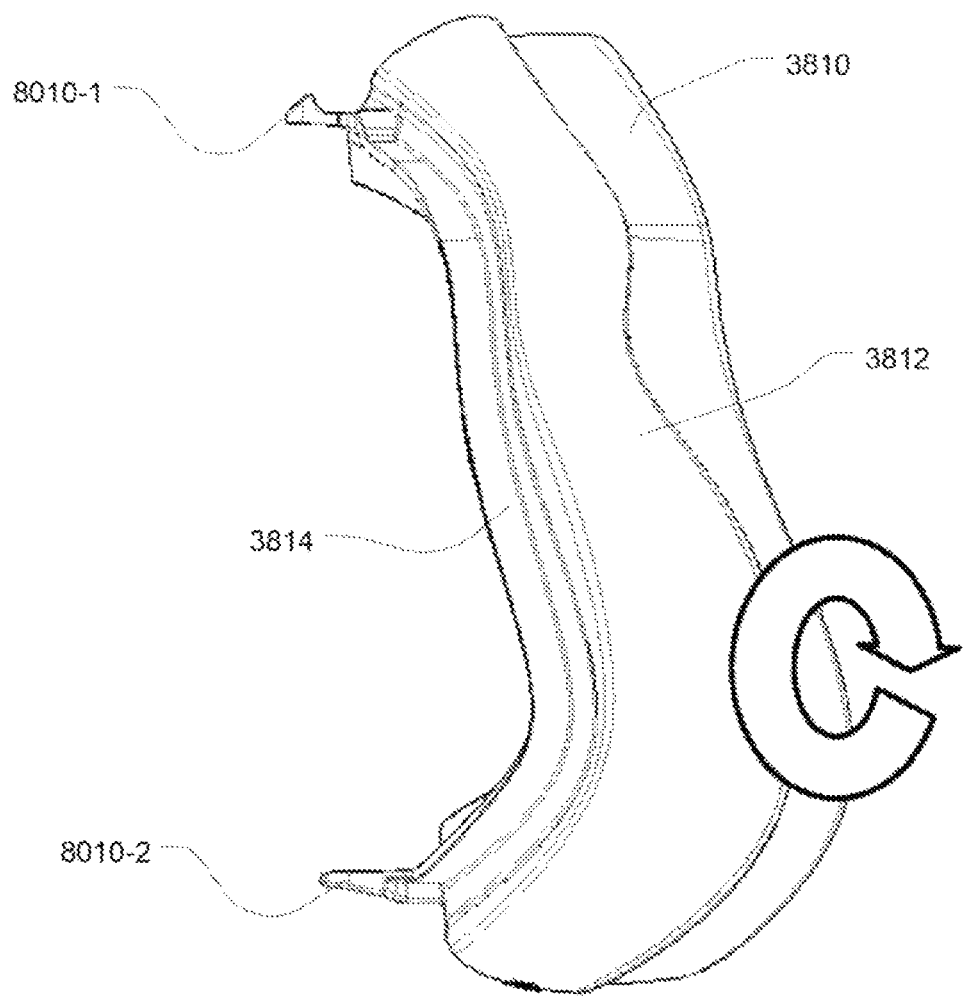

FIG. 84 is a side view of a foam cushion assembly illustrating a pivot point.

Figure 85:
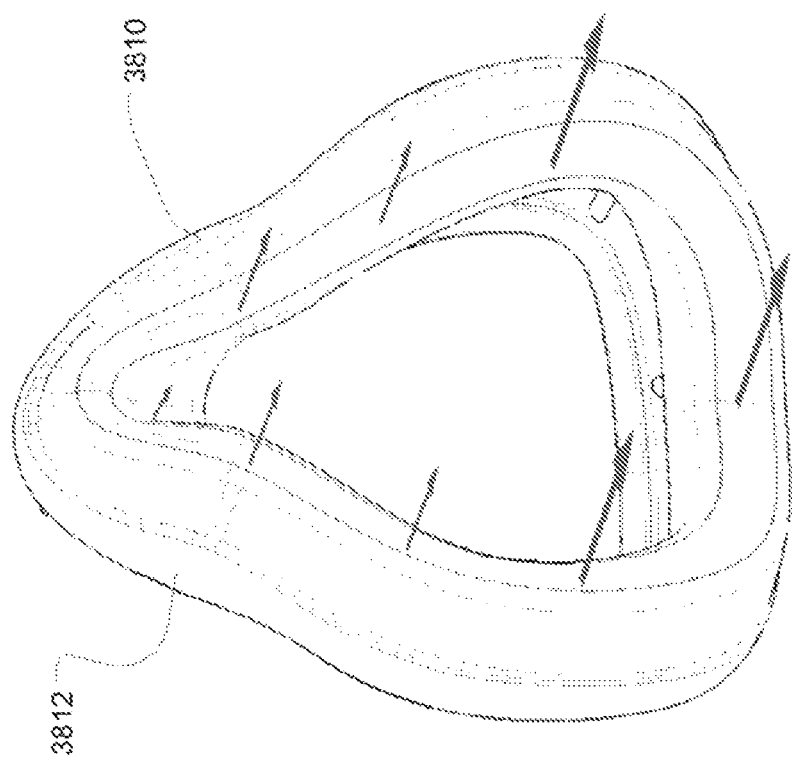

FIG. 85 illustrates cushion pressure performance of example foam cushion assemblies of the present technology.

Figure 86:
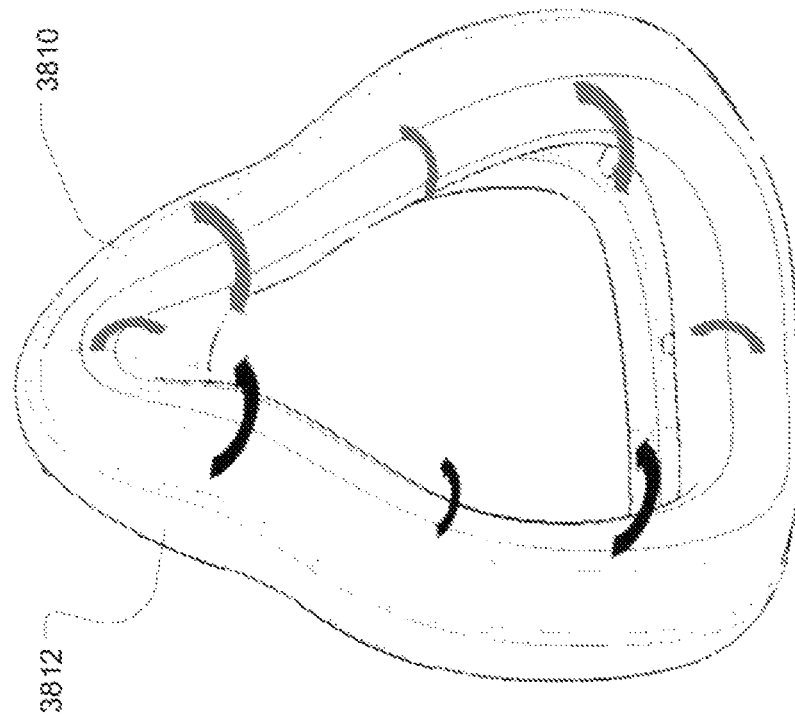

FIG. 86 illustrates cushion roll-in performance of example foam cushion assemblies of the present technology.

Figure 87:
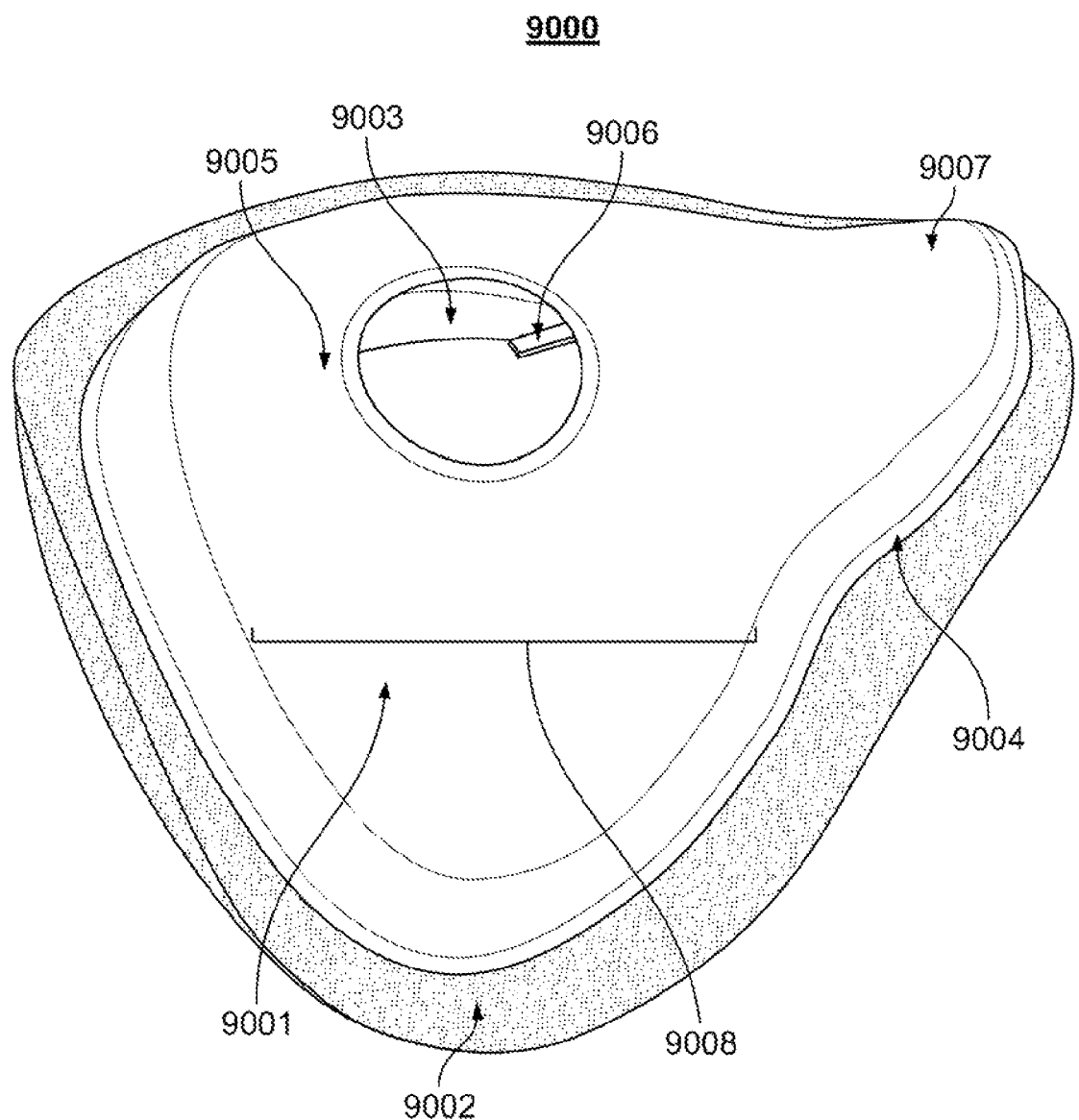
Figure 88:
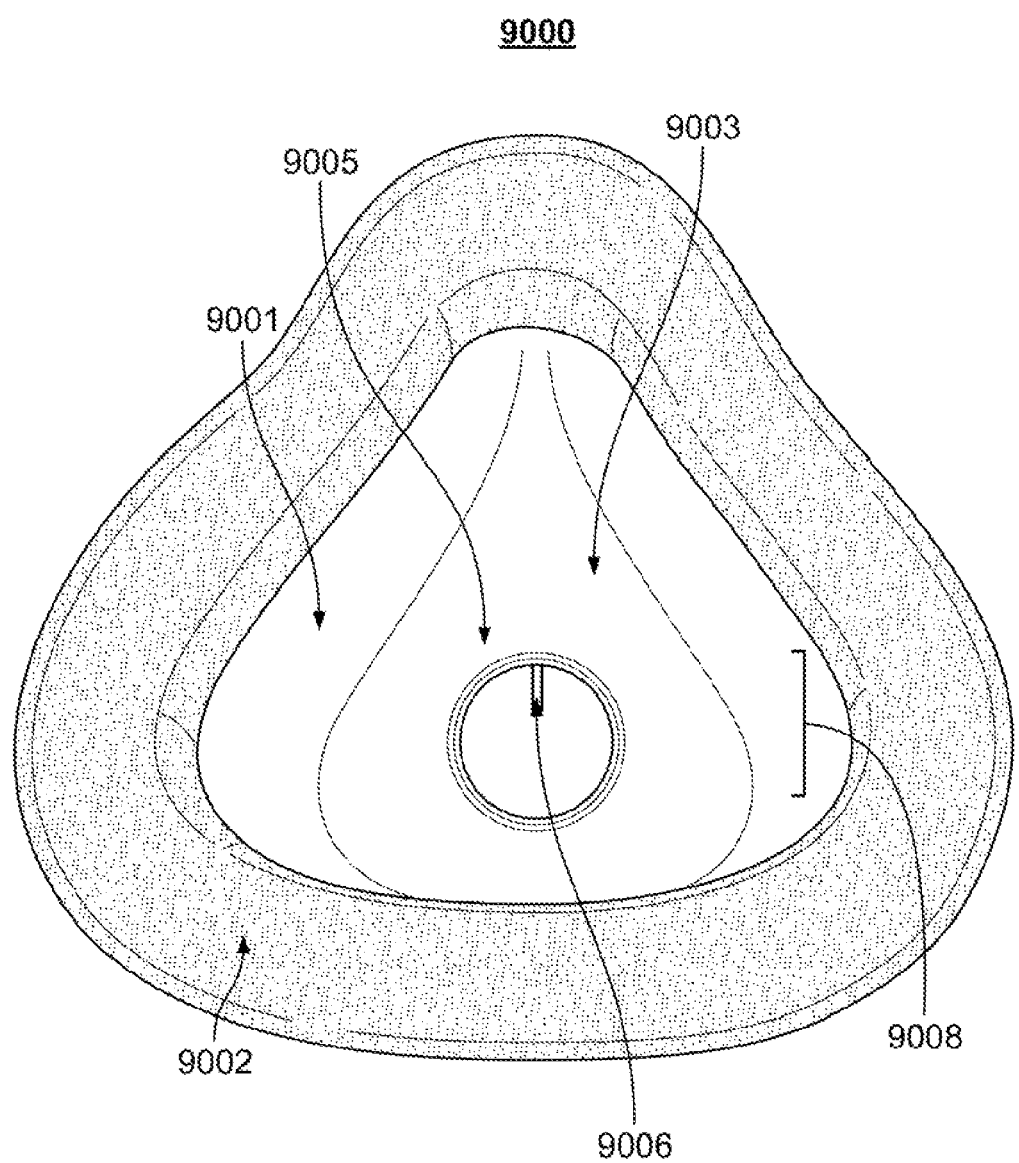
Figure 92:
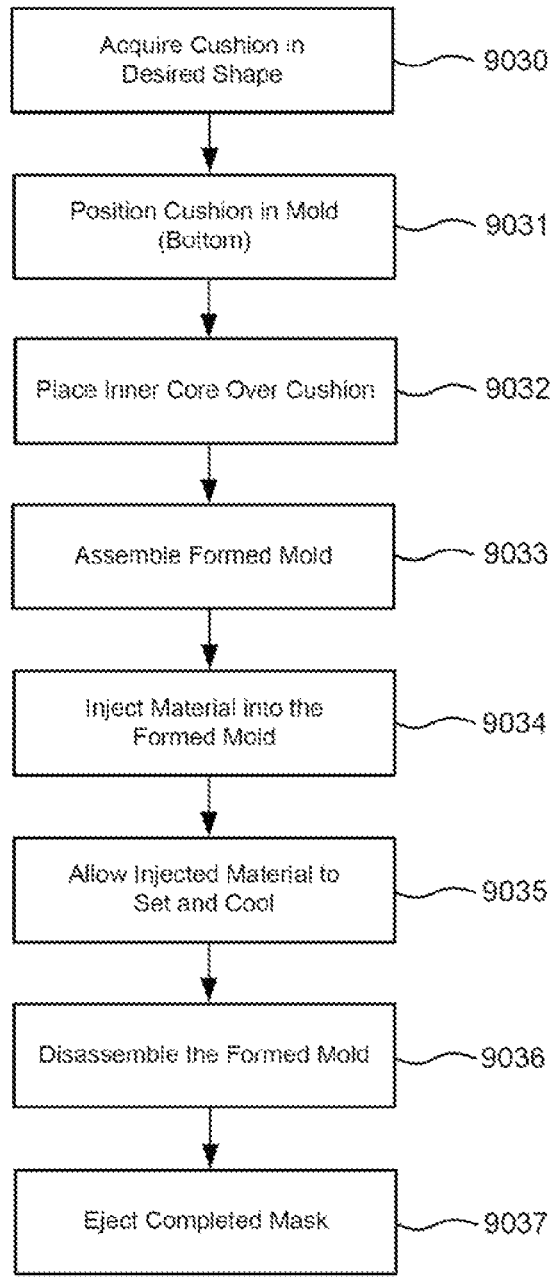
Figure 93:
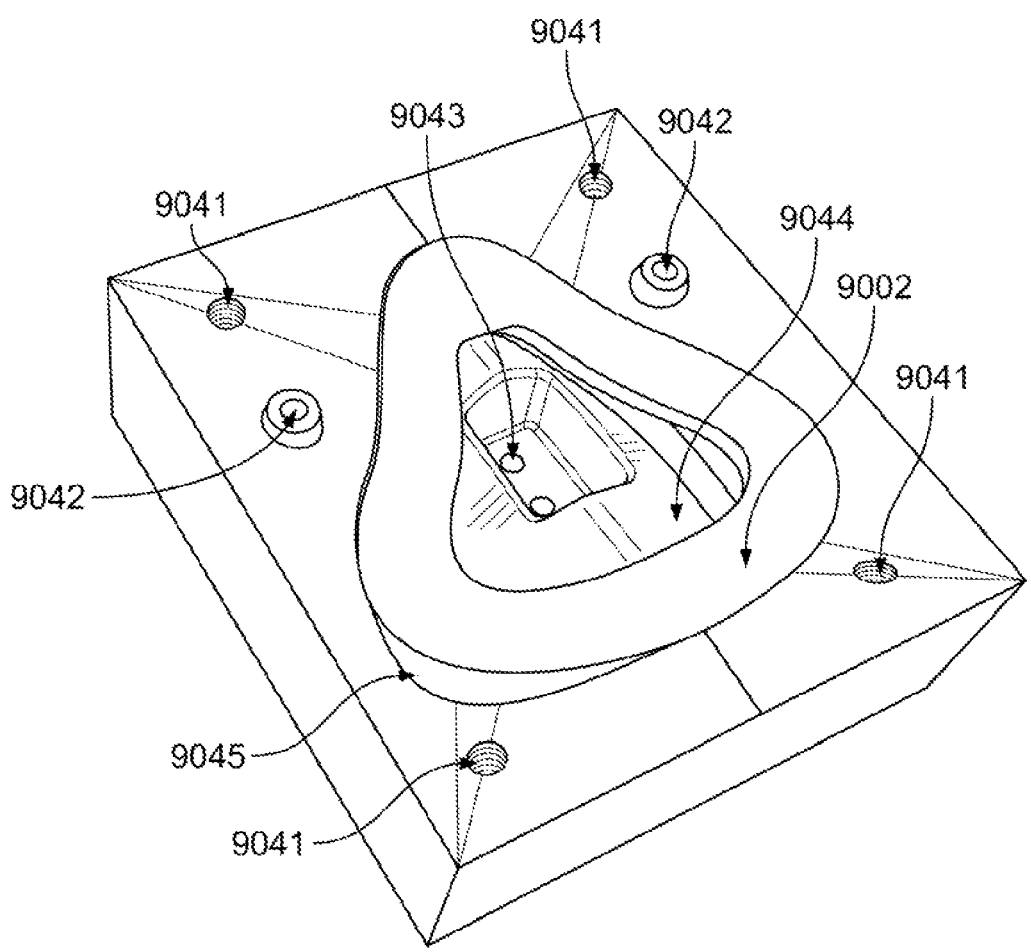
Figure 94:
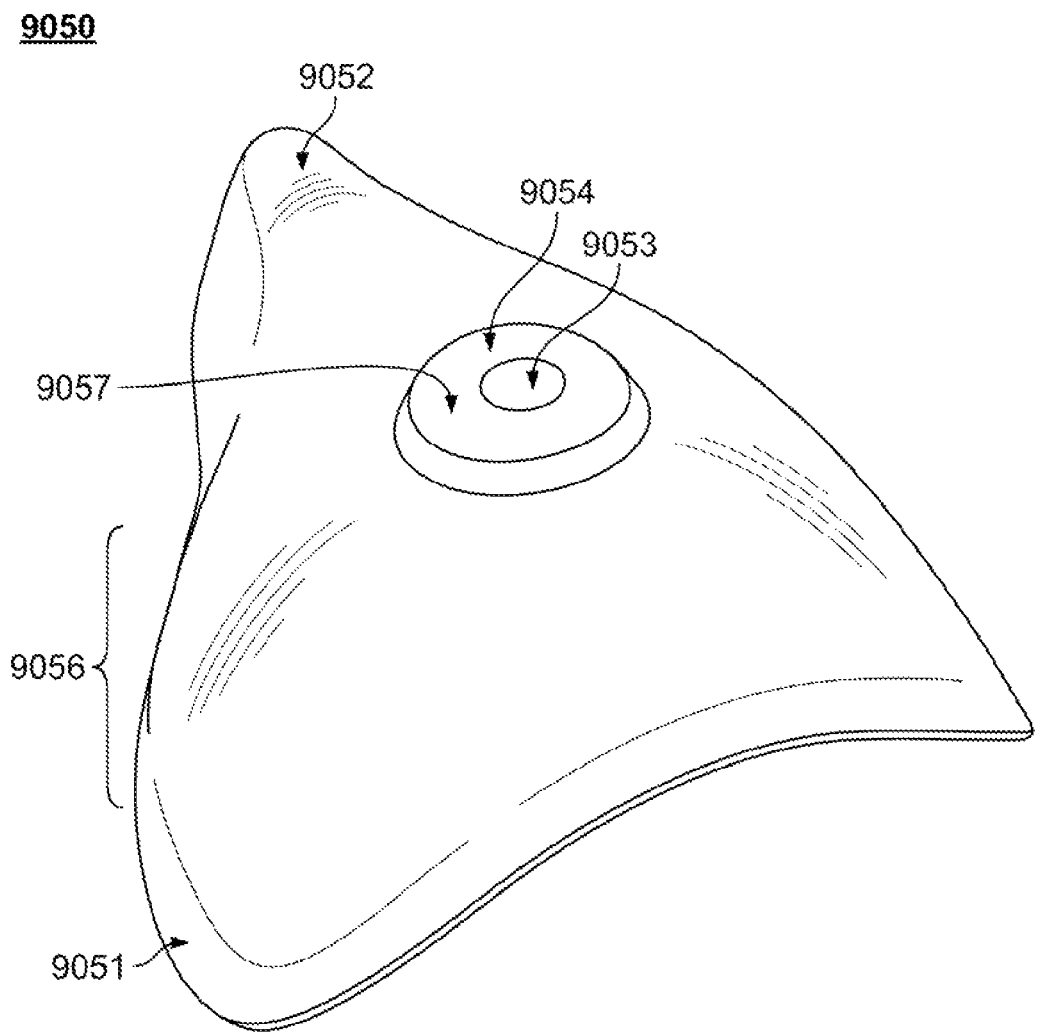
Figure 95:
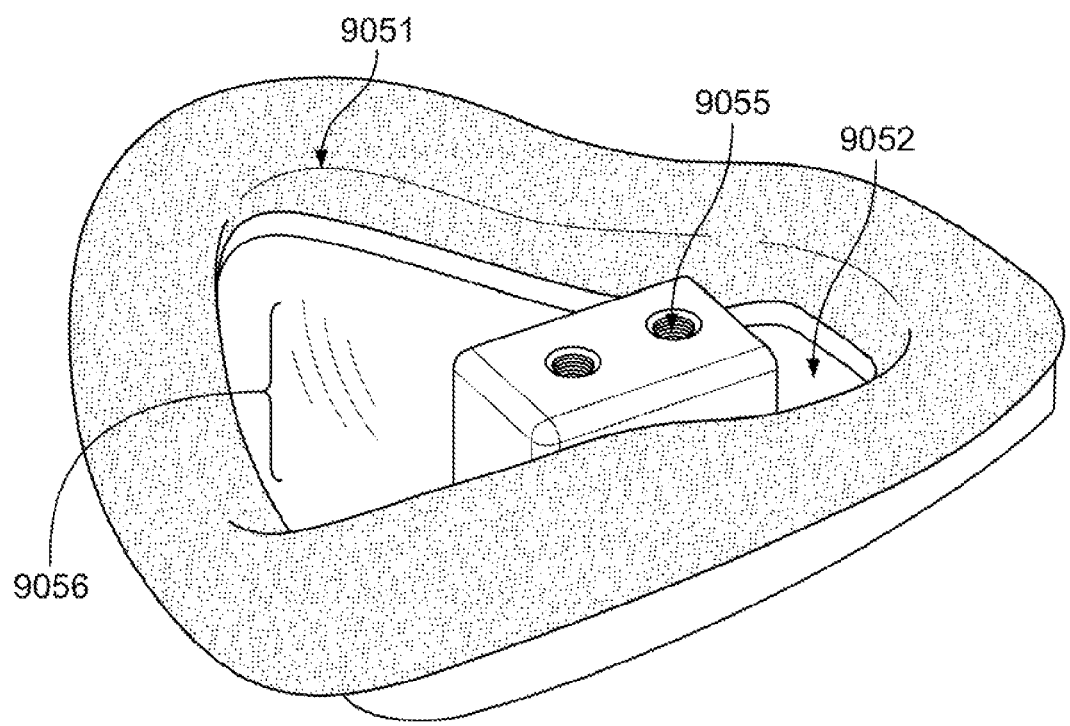
Figure 96:
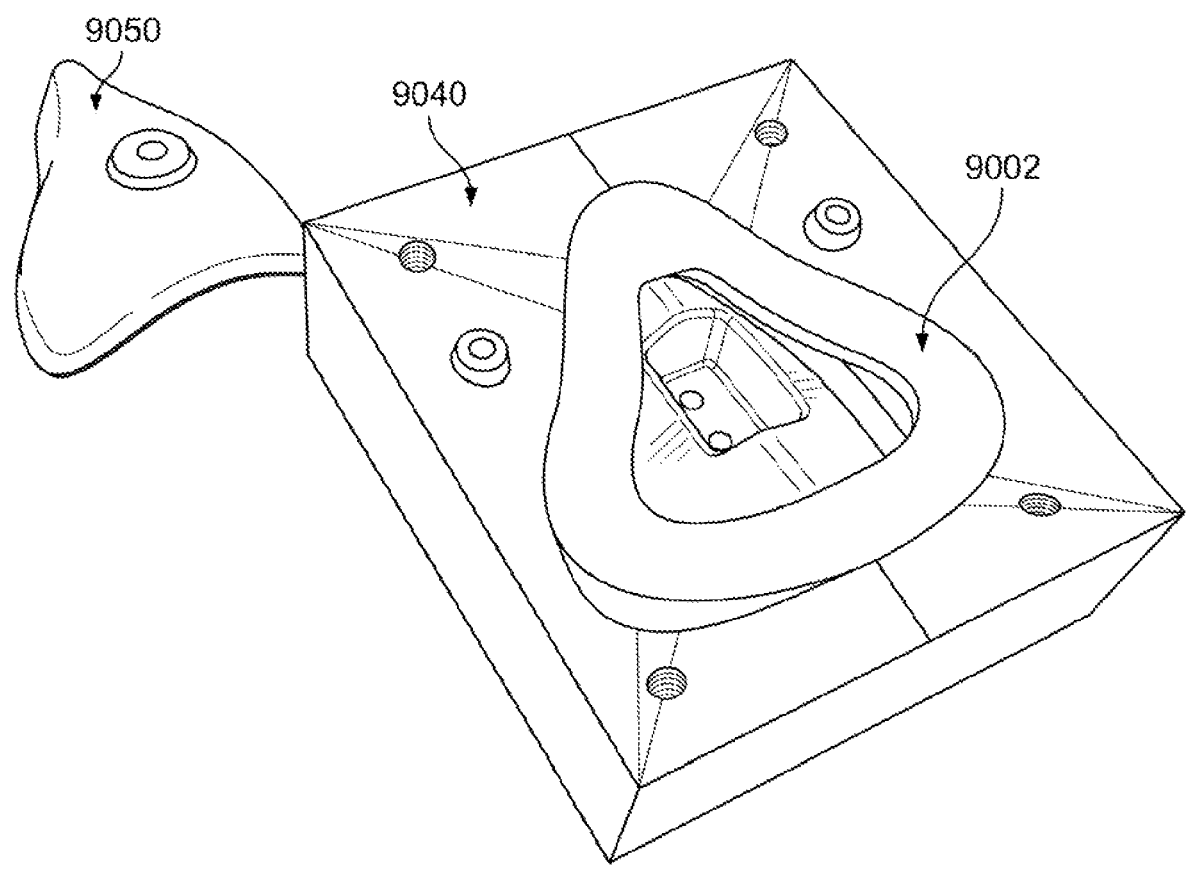

FIGS. 87 and 88 show perspective views of a frame component in the form of a shell of a plenum chamber with a foam cushion joined;

FIG. 89 shows examples of various foam cushions;

FIGS. 90A-D and 91A-B show examples of magnified connection areas between a frame and a cushion;

FIG. 92 is a flowchart illustrating steps of an example manufacturing process for overmoulding a frame component onto a cushion;

FIG. 93 shows a part of a mould and an inserted cushion suitable for the present technology;

FIGS. 94 and 95 show an example of an inner core suitable for the present technology;

FIG. 96 shows another view of a part of a mould, a cushion, and an inner core suitable for the present technology.

Figure 97:
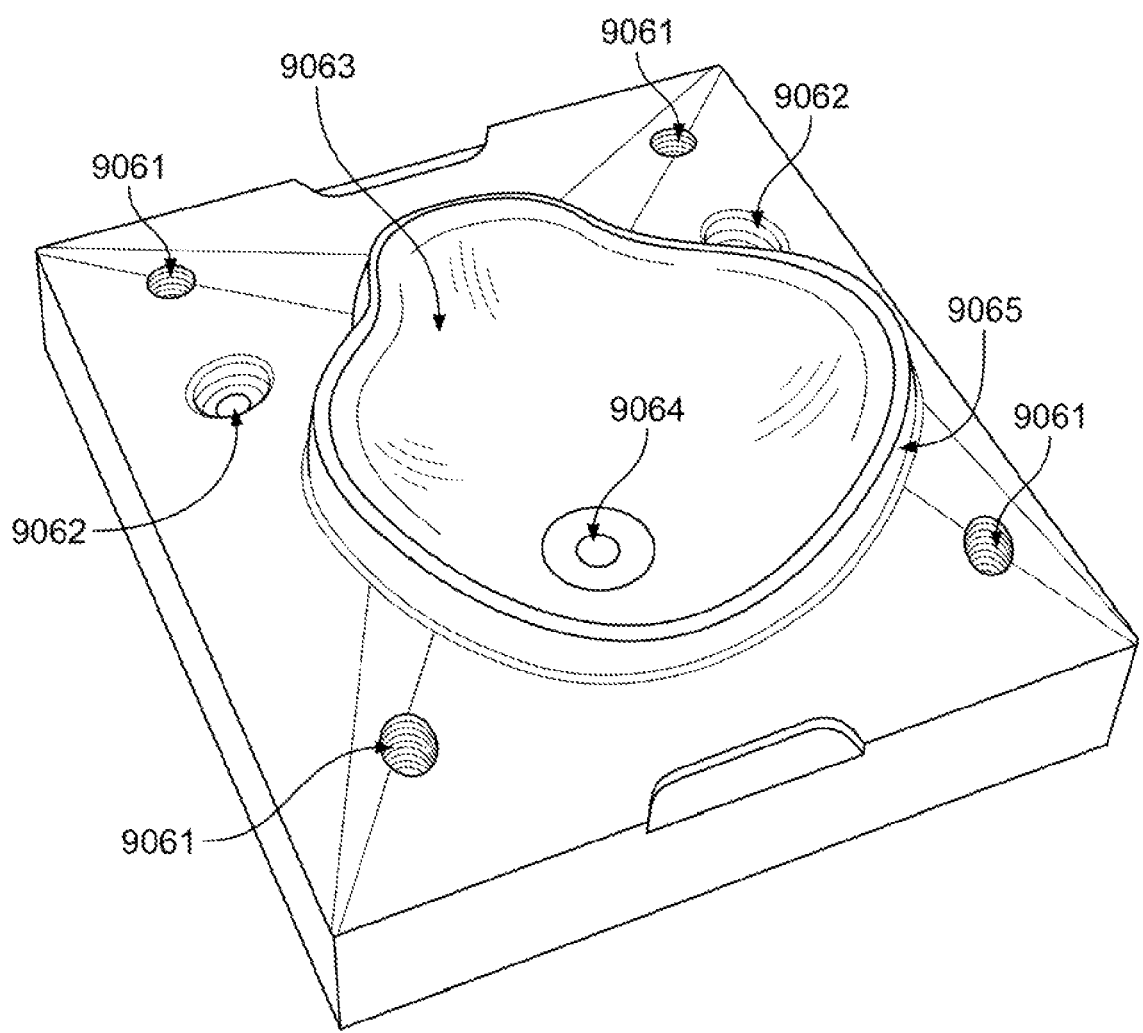
Figure 98A:
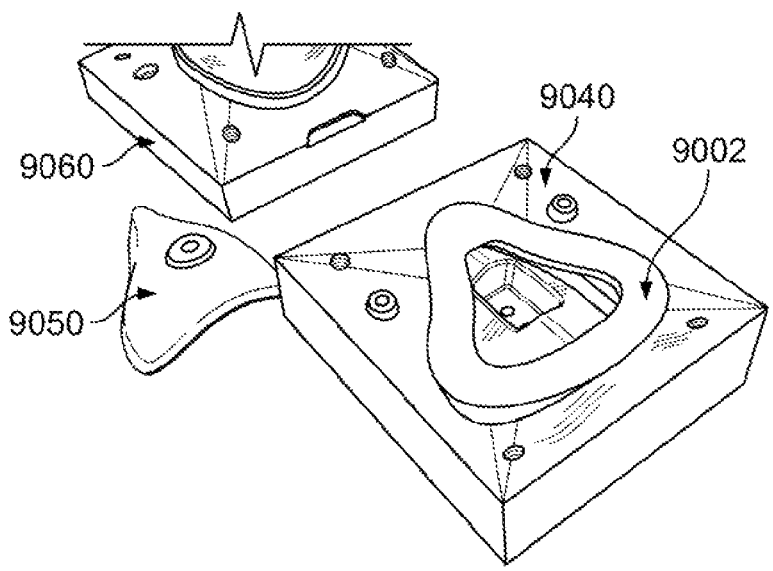
Figure 98B:
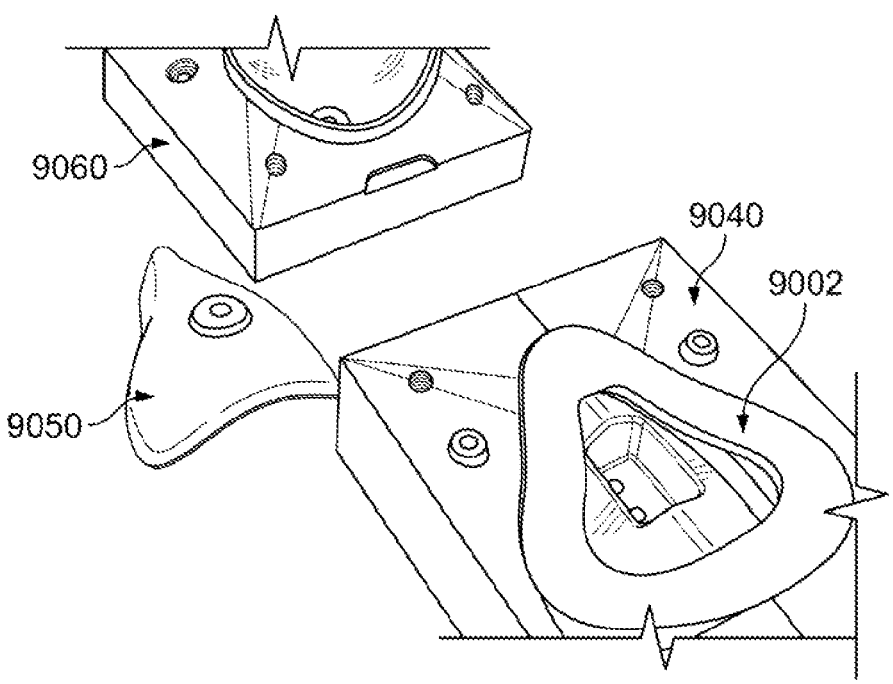

FIG. 97 shows a view of another part of a mould suitable for the present technology;

FIGS. 98A and 98B show mould parts, a top and bottom mould, a cushion, and an inner core suitable for the present technology.

5 DETAILED DESCRIPTION OF THE INVENTION

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

5.1 Treatment Systems

In one form, the present technology comprises apparatus for treating a respiratory disorder. The apparatus may include a flow generator or blower for supplying pressurised respiratory gas, such as air, to the patient 1000 via an air delivery conduit, such as a tube, leading to a patient interface 3000.

5.2 Therapy

In one form, the present technology may involve a method for treating a respiratory disorder by applying positive pressure to the entrance of the airways of a patient 1000.

5.2.1 CPAP for OSA

In one example, the present technology may involve a method of treating Obstructive Sleep Apnea in a patient by applying continuous positive airway pressure to the patient with a patient interface described herein. Other positive pressure treatment therapies may also be provided (e.g., bi-level CPAP, etc.)

5.3 Pap Device 4000

An example PAP device 4000 in accordance with one aspect of the present technology may include mechanical and pneumatic components 4100, electrical components 4200 and is programmed to execute one or more control methodologies or algorithms, such as to control providing the continuous positive airway pressure or any one or more of the positive pressure treatment therapies. The PAP device may include an external housing 4010, which may be formed in two parts, an upper portion 4012 of the external housing 4010, and a lower portion 4014 of the external housing 4010. In alternative forms, the external housing 4010 may include one or more panel(s) 4015. The PAP device 4000 may include a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 may include an inlet air filter 4112, an inlet muffler 4122, a controllable source 4140 of air at positive pressure (preferably a blower 4142), and an outlet muffler 4124. One or more pressure sensors 4272 and flow sensors 4274 may be included in the pneumatic path.

An example pneumatic block 4020 may include a portion of the pneumatic path that is located within the external housing 4010.

The PAP device 4000 may have an electrical power supply 4210, one or more input devices 4220, a processor, a pressure device controller, one or more protection circuits, memory, transducers, data communication interface and one or more output devices. Electrical components 4200 may be mounted on a single Printed Circuit Board Assembly (PCBA) 4202. In an alternative form, the PAP device 4000 may include more than one PCBA 4202.

The processor of the PAP device 4000 may be programmed to execute a series of algorithm modules in use, preferably including pre-processing transducer signals module, a therapy engine module 4320, a pressure control module, and further preferably a fault condition module.

4.4 PATIENT INTERFACE 3000

4.4.0 Features

A patient interface 3000 in any versions of the present technology may typically include optional features such as a seal forming structure 3100, a plenum chamber 3200, positioning and stabilizing structure 3300, vent 3400, decoupling structure 3510, connection port 3600, forehead support 3700, anti-asphyxia valve 3800 and/or one or more ports 3900. Such features may be considered in reference at least to the examples of FIGS. 4 and 36.

4.4.0.1 Seal-Forming Structure 3100

In one form of the present technology, a seal-forming structure 3100 provides a sealing-forming surface, and may additionally provide a cushioning function.

A seal-forming structure 3100 in accordance with the present technology may be constructed from a soft, flexible, resilient material such as silicone or other materials and structures described throughout this specification.

In one form, the seal-forming structure 3100 may include a sealing flange and may further include a support flange. The sealing flange may be a relatively thin member with a thickness of less than about 1 mm, for example about 0.25 mm to about 0.45 mm, that extends around the perimeter of the plenum chamber 3200. Support flange may be relatively thicker than the sealing flange. The support flange can be disposed between the sealing flange and the marginal edge of the plenum chamber 3200, and extends at least part of the way around the perimeter. The support flange is or includes a spring-like element and functions to support the sealing flange from buckling in use. In use the sealing flange can readily respond to system pressure in the plenum chamber 3200 acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology may include: a frusto-cone, at least a portion of which forms a seal on an underside of the patient's nose; a stalk, a flexible region on the underside of the cone and connecting the cone to the stalk. In addition, the structure to which the nasal pillow of the present technology is connected includes a flexible region adjacent the base of the stalk. The flexible regions can act in concert to facilitate a universal joint structure that is accommodating of relative movement—both displacement and angular—of the frusto-cone and the structure to which the nasal pillow is connected. For example, the frusto-cone may be axially displaced towards the structure to which the stalk is connected.

In one form of a non-invasive patient interface 3000, a seal-forming portion forms a seal in use on an upper lip region (that is, the lip superior) of the patient's face.

In one form the non-invasive patient interface 3000 comprises a seal-forming portion that forms a seal in use on a chin-region of the patient's face.

Additional features of the seal-forming structure may be further considered in reference to the additional details of this specification.

4.4.0.2 Plenum Chamber 3200

Preferably the plenum chamber 3200 has a perimeter that is shaped to be complementary to a surface contour of the face of an average person in the region where a seal will form in use. In use, a marginal edge of the plenum chamber 3200 is positioned in close proximity to an adjacent surface of the face. Actual contact with the face is provided by the seal-forming structure 3100. Preferably the seal-forming structure 3100 extends in use about the entire perimeter of the plenum chamber 3200.

4.4.0.3 Positioning and Stabilising Structure 3300

Preferably the seal-forming structure 3100 of the patient interface 3000 of the present technology is held in sealing position in use by the positioning and stabilising structure 3300.

4.4.0.4 Vent 3400

In one form, the patient interface 3000 includes a vent 3400 constructed and arranged to allow for the washout of exhaled carbon dioxide.

One form of vent 3400 in accordance with the present technology comprises a plurality of holes, for example, about 20 to about 80 holes, or about 40 to about 60 holes, or about 45 to about 55 holes.

Preferably the vent 3400 is located in the plenum chamber 3200. Alternatively, the vent 3400 is located in a decoupling structure 3510, e.g. a swivel.

4.4.0.5 Decoupling Structure(s) 3510

In one form the patient interface 3000 includes at least one decoupling structure 3510, for example a swivel or a ball and socket.

4.4.0.6 Connection Port 3600

Connection port 3600 allows for connection to the air circuit 4170.

4.4.0.7 Forehead Support 3700

In one form, the patient interface 3000 includes a forehead support 3700.

4.4.0.8 Anti-Asphyxia Valve 3800

In one form, the patient interface 3000 includes an anti-asphyxia valve 3800.

4.4.0.9 Ports 3900

In one form of the present technology, a patient interface 3000 may optionally include one or more ports that allow access to the volume within the plenum chamber 3200. In one form this allows a clinician to supply supplemental oxygen. In one form this allows for the direct measurement of a property of gases within the plenum chamber 3200, such as the pressure.

4.4.1 Sub Nasal Sealing

A non-invasive patient interface 3000 in accordance with one example of the present technology may be considered with reference to FIGS. 4-7. The patient interface may include any of the following features: a seal-forming structure 3100, such as a cushion 3110, a plenum chamber 3200, a positioning and stabilising structure 3300, such as one or more headgear vectors, and a connection port 3600 for connection to an air/gas circuit 4170. In some forms, one or more such features may be provided by one or more physical components. In some forms, one physical component may provide one or more functional features. In use, the seal-forming structure 3100 may be arranged to be in direct contact with the patient's skin and surround an entrance to the airways of the patient so as to facilitate the supply of air at positive pressure to the airways.

For example, as shown in FIGS. 4-7, the patient interface may be configured as a mask to provide a sealed interface with the mouth and nares of a patient so as to direct a breathable gas under pressure to both the mouth and nares. Such a mask may be configured to be a substantially under-the-nose mask. As illustrated, the plenum chamber 3200 may be formed by a frame 3500 and cushion 3110. The cushion 3110 may also serve as the seal forming structure 3100. The frame may be adapted for coupling with a respiratory treatment apparatus so as to permit communication of a pressurized gas to a respiratory system of a patient from the respiratory treatment apparatus. The cushion may then be adapted to couple with the frame.

In some cases, as illustrated in FIG. 7, the cushion may form a seal with a substantially under nose seal portion UNSP and a mouth seal portion MSP. Such a configuration may be considered in reference to the illustration of FIG. 10. The under nose seal portion may be formed by a sub-nasal ridge 3131 that forms a semi-peripheral sealing boundary about both nares of the patient. In this regard, such a seal may be achieved with both nares and the mouth while in some cases avoiding a seal portion or other mask contact structure at a central region of the lip superior LS. Such a mask may provide a more open and comfortable feel for users such as when compared to mouth masks that may be combined with nasal prongs, while still providing an effective seal.

Obtaining a seal with a single cushion that seals both over the mouth and under the nares of the nose can be difficult to achieve with a nasal cradle design that uses standard silicone cushion materials. It has been discovered that the anthropometrical variations of facial features are large. Some materials, such as standard silicone, may have insufficient flex to achieve both seal and comfort, especially with respect to the intricate facial features surrounding the nose and the mouth.

In some cases, this problem may be overcome by an implementation of foam, such as a semi-open (or semi closed) cell foam. In some examples, the cushion may be a foamed silicone material or a polyurethane foam, etc. In some cases, a very low durometer thermoplastic elastomers (TPE), thermoplastic polyurethane (TPU), thermoplastic polyurethane (TPV), silicone or rubber material might be implemented. The compliant nature of foam allows it to, under relatively small tension force, compress into intricate facial features and affect a good seal. This, combined with the easy adaptability and softness experienced by the patient, provides for a relative fast and easy mask set-up. The porosity of the foam also exhibits better breathability than silicone and may permit wicking away of moisture from the face. Thus, the use of foam may be associated with better cooling and reduced discomfort in the areas of contact or sealing.

In some cases, the cushion and/or frame may define a single chamber, such as the plenum chamber 3200 that is illustrated in FIG. 7, which covers the patient's mouth and the nares of the nose from underneath. As discussed in more detail herein, the cushion may have a substantially oval and/or triangular shape. The sealing surface may continuously extend substantially in two plains—one plane that allows it to seal with the mouth and a second plane that facilitates the seal under the patient's nostrils. The second plane may form an angle with respect to the first plane. The angle may be approximately close to ninety degrees or approximately perpendicular, but may be slightly larger or slightly smaller. Such an angle may approximate the nasolabial angle. Such a single chamber foam cushion may be designed to attach to a frame directly or by way of a clip as discussed in more detail herein.

The seal around the mouth and the nares of such a mask can be produced through the interaction between the patient's face and the combined reaction of the assembly (e.g., frame, flexible clip, and/or cushion) and subject to tension from headgear. The structures of the components when assembled can work together to provide variable amounts of compression around the nose and mouth so that an effective seal is produced in these areas.

FIGS. 8 and 9 show a cross sectional view of a sub-nasal region of a portion of the seal including an example sub-nasal ridge 3131. The figures illustrate a mechanism for achieving the seal in the sub-nasal region.

When the nose is applied onto the cushion (e.g., foam) in the region of the sub-nasal ridge, the headgear may be tightened. The headgear vectors help to enforce a seal at the periphery of both of the nares through the combination of the cushion (e.g., foam) and/or the cushion support structure 8800 (e.g., clip 3535) rolling inwards (illustrated by arrows RR in FIG. 9) and closing around the periphery of the nares. The flexibility of the combination of cushion and/or cushion support structure can enable the cushion to align to the alar angle and to the Nasolabial angle of the nose. As the headgear vectors are further tightened, a greater sealing force can be applied to the periphery of the nares. The reaction force in the cushion and the cushion support (e.g., clip and/or frame), caused by the rolling and compression of them, result in a reaction vector that radiates (approximately perpendicularly) from the frame support back towards the patient. Moreover, the generated gas pressure (e.g., from a flow generator coupled to the mask assembly) that accumulates inside the mask plenum chamber can push the cushion (e.g., foam) outwards. This can ensure an opening up of the air passage to the nostrils and may also compress the cushion upwardly (towards the patient's sub-nasal region), thus generating sealing pressure around the nares.

In some cases, there may be a potential for occlusion of the nares by some cushions during set-up or use. When the seal around the nares is associated with the compression of some foams, it can lead to nasal occlusion occurring at mask set-up before pressure is applied to the mask. In order to minimize the potential for occlusion, a balance can be attained between the foam thickness, the foam profile around the periphery of the nares and cantilever spring characteristics of the support structure (e.g., clip if used).

In the case of implementation of foam, a thin foam section, such as in the nasal region may be suitable. For example, a foam thickness of about 8 to 20 mm (e.g., 13 mm) may noticeably improve/prevent set-up occlusion. In some cases, the foam internal profile may be aligned and/or shaped to match the nares opening such as at their periphery. A soft elastic material (such as silicone, TPE, TPU etc.) may be implemented as a material such as for the cushion support. Such a material can be configured to pass on a light cantilever spring affect onto the nose.

During a pressure treatment, such as a CPAP treatment, occlusion may be avoided at the nares. The internal profile (as illustrated in FIG. 9) of the foam cushion can provide relief around the nares. Generally, the foam may be compressed around the periphery of the nares by the internal CPAP pressure inflating the nostrils. In order to achieve a suitable and comfortable seal, the foam rigidity should be no greater than the reaction force generated by the internal CPAP pressure inflating the nostrils. This situation can hold the nares open during CPAP and no occlusion will result.

The cantilever spring force of the cushion support (e.g., clip and/or frame) can be soft enough to allow the nose to press into the foam cushion at set-up without occluding the nares. Conversely, the spring force of the cushion support can provide enough reaction force to press the foam cushion into all the sealing zones of the mask. This may be significant for areas such as at the corners of the nose.

Example components for a mask assembly of the present technology are further illustrated in FIGS. 11 through 23. In some cases, as shown in FIG. 11, the frame 3500 may be a separable component from the clip 3535 and the cushion. As seen in FIG. 12, the frame may include a set of fasteners 3537. The fasteners may be employed for connection of head gear (not shown) to position and support the mask assembly for use. The frame may also optionally, include a vent 3400. In one form, the vent 3400 may be constructed and arranged to allow for the washout of exhaled carbon dioxide. The vent 3400 may be formed by a plurality of holes, for example, about 20 to about 80 holes, or about 40 to about 60 holes, or about 45 to about 55 holes. The vent 3400 may be located in the plenum chamber 3200. Alternatively, the vent 3400 may be located in a decoupling structure, e.g. a swivel or other coupler.

The frame may typically include a connection port 3600. The connection port 3600 allows for connection to an air circuit 4170, such as for a connection with a respiratory treatment apparatus or flow generator. Such a connection to an air circuit may be by way of a decoupling structure as previously mentioned. In some cases, the patient interface 3000 may include an anti-asphyxia valve (not shown). Optionally, the frame may include one or more additional ports. Such additional ports may permit access to the volume within the plenum chamber 3200. For example, such a port may permit introduction of a supply of supplemental oxygen. Such a port may also serve as a coupler or housing for a sensor for direct measurement of a property of the gases within the plenum chamber 3200, such as pressure.

The frame may contain a flange 3515 around its rear (patient proximate side) periphery such as the one illustrated in FIG. 12. This flange may vary in angle and width around the periphery of the plenum chamber in order to follow the curvature of the sections of the face where a seal is to take place. The flange may extend generally parallel to those areas near where the seal is to exist on the patient's face. A varying angled flange can work together with the headgear vectors to impart a desired amount of cushion compression to the varying parts around the mouth and the nares to achieve a comfortable and effective seal.

In some cases, the mask assembly may employ a clip 3535 as illustrated in FIG. 13 or FIG. 14. The clip may be releasably attachable with the frame so as to permit a convenient replacement of the cushion that may be applied to the clip. In this regard, FIGS. 20 and 21 illustrate the clip (without a cushion) coupled to the frame. However, any one or more of the features of the clip described herein may optionally be integrated with the structure of the frame itself and the cushion applied thereto.

In some cases, the clip's profile can assist in imparting form to the cushion so as to configure the cushion into its multi-dimensional shape (e.g., multi-plane) suitable for conforming to the person's face so as to form a good seal in an under-the-nose configuration. In this regard, as seen in FIGS. 13 and 14, the clip may be formed with a bend or angled region ABR. The angled region ABR permits an angle between a nasal plateau region NPR and a mouth periphery region PR. An approximately nasolabial angle ANA may be formed by a plane of the mouth periphery region and a plane of the nasal plateau region. When the cushion is applied to the clip (and/or frame) such as shown in FIGS. 22 and 23, the characteristics of these regions may be imparted to the cushion in the case that the cushion is not already formed with such regions.

Alternatively, a 2D flat clip may be used. In this case the 3D shape is imparted to the flexible clip/cushion combination by attachment onto a 3-D shaped frame.

Generally, the clip may be permanently coupled to the frame or include connectors 3536, such as those illustrated in FIGS. 13, 22 and 23 to facilitate its removable coupling with the frame. These elements may be formed around one side (e.g., the lower periphery or distal side) of the clip where it interfaces with the frame. Additional examples of such connection elements are explained in more detail herein with reference to FIGS. 32-35. The clip's opposing side (e.g., upper peripheral surface or patient proximate side) provides a connection or landing surface for attachment of the cushion (e.g., the foam ring). In this regard, the features of the clip may serve as a suspension for the cushion.

As the wall thickness of the clip is relatively small (i.e. few millimeters) the clip's body may generally be approximated with a curved surface. The cross-sectional profile of the clip around the clip's periphery may differ in different sections of the clip so as to provide different regions of flexibility/rigidness to the cushion. Examples may be considered with reference to the cross sectional views of FIGS. 15, 16 and 17. For example, the clip may be formed so as to have an open or concave wall 3535W with a cross-section along the clip's periphery that may vary in geometric shape. These cross-sectional shapes may be, for example, formed as a U-shape such as that shown in FIG. 15, an L-shape such as that shown in FIG. 16, or a C-shape such as that shown in FIG. 17. Other examples may include I-shape or Z-shape cross sectional configurations. In some cases it may be formed with some or all of these wall formations. The opening of each shape (shown in FIGS. 13, 15, 16 and 17 with reference character SO) can be directed inwardly towards the center or plenum chamber of the mask. These different wall structures may have different flexibility characteristics. Such cross-sectional shape(s) can enable the clip to act as a spring or cantilever-type spring. Such a spring configuration can permit the foam cushion to further conform to the face and compress towards it once alignment has been achieved, improving cushion compliance to the face.

Accordingly, the clip (or frame) may be formed with a flexible peripheral lip that variably supports the foam cushion. Pressure within the plenum chamber formed between the mask frame, clip, cushion and the face of the patient, acts on the inside of the clip section (e.g., the shape opening SO of the wall) and cushion and pushes the peripheral lip and the cushion towards the patient's face, thereby reinforcing the seal created by the cushion. As pressure increases, so does the force creating the seal. As such, the wall of the clip may also be chosen to have thickness and flexibility to allow the air pressure to create an air spring effect, further contributing to the compliance of the seal.

As previously mentioned, the wall geometry around the periphery of the clip may vary in order to alter the stiffness or flexibility around the nose and mouth sealing regions. Different stiffness/rigidity may be achieved in these different sections of the face to achieve a balance between good seal, comfort and stability. For example, around the nose, a softer seal can be achieved as the nose is sensitive to pressure, whereas the sides of the mouth can withstand larger sealing pressures without discomfort. Thus, the flexibility of the clip (or frame) may impart these different flexibility characteristics.

In some such examples, support for the cushion in the nasal sealing area may be formed as the flexible cross-section "U" geometry illustrated in FIG. 15. The clip wall (concave wall 3535W) may then have a cushion support surface 3538 and a frame coupling surface 3539 for a connector as discussed herein. In some cases, support for the cushion in the sealing area at the sides of the mouth may be formed by a flexible wall having a cross sectional shape resembling an "L" geometry as illustrated in FIG. 16. Moreover, support for the cushion in the sealing areal at the lower part of the mouth, may be formed by a flexible wall having a cross sectional shape resembling the "C" geometry as shown below in FIG. 17.

Similarly, with respect to at least the example clip shown in FIGS. 14, 18 and 19, two active portions of the clip's structure are the peripheral lip 3540 that form an effective cantilever over-hang portion and a middle transverse portion 3541 of the clip's periphery between the frame coupling surface 3539 and the cushion support surface 3538. Both of these components can act as springs and provide a sealing reaction force through their deformation. Distribution of the clip-contributed sealing force around the mouth may be governed by the clip's material and geometry. Moreover, the force may be controlled by the user depending on the amount of tightening of the headgear of the mask.

In this regard, the combination of a foam cushion and the flexible support structure of the clip can provide reasonable results. However, for achieving optimal seal comfort, the flexible clip may be provided with an oversized peripheral lip that increases the support of a foam cushion width that may be larger than the support surface of the peripheral lip. Such variations in the width of the peripheral lip can produce different reaction forces around the periphery of the mouth cushion. Beam and bending principles may show that, in isolation, a shorter peripheral lip will produce a stiffer mechanical system as there will be less clip deflection for a certain unit force than there will be for a longer peripheral lip.

Such a clip may be considered with reference to the cushion support structures of FIGS. 14, 18 and 19. Sizing of the width (shown in FIG. 18 as arrow LW) of the peripheral lip also allows for introducing variations in the seal geometry. For example, different (e.g., narrower) widths in the peripheral lip area proximate to the nose and mouth may help to achieve different reaction sealing forces in these areas. As illustrated in FIG. 18, the profile for the clip's peripheral lip may be changed to that shown by the dashed line. The resulting clip is illustrated in FIG. 19. As illustrated, a shorter lip width (shown at arrow SLW) may be provided at the peak of the nasal plateau region for less flexibility. A relatively longer lip width (shown as arrows LL) may be provided proximate the centrally open lip superior region COLS for more flexibility. As shown in FIG. 19, the reaction force of such a clip can vary around the periphery as a result of such changing widths of the peripheral lip or cantilever arm. In some such cases, the width of the cushion may be similarly varied. However, the width of the cushion may be relatively constant despite the change in support structure width around its periphery such as shown in FIG. 23. In this sense, the foam's geometry profile may not follow the clip's geometry exactly. As a result, the final force profile of the mask can be affected by the combination of the clip and the compressing foam.

Adjustments to flexibility around the sealing periphery may also be achieved by varying the thickness of the lip. For example, a lip thickness value along the sides of the mouth toward the nasal peak portion may be approximately double that of the thickness along the bottom of the mouth. Such a ratio can provide less flexibility in the nasal region and relatively more flexibility in the lip inferior region. In one such example, and depending on the clip materials, peripheral lip thickness may be in a range of about 1.5 mm to 2.5 mm, such as about a 2.2 mm (+/−0.1 mm) relatively constant thickness from the region proximate to the sides of the mouth to the nasal peak region. The region of the peripheral lip proximate to the lip inferior (around the bottom of the mouth) may be in the range of about 0.75 mm to 1.25 mm, such as about a relatively constant 1.0 mm (+/−0.1 mm) thickness.

Generally, the body depth (illustrated in FIG. 14 as arrow BD) may be relatively constant about the periphery of the clip. In the example of FIGS. 14, 18 and 19, the body depth of the clip (that portion that does not connect to the cushion or the frame) may be in a range, for example, from about 8 mm to 15 mm or for example a depth in a range of about 11 mm to 13 mm.

In some cases, additional features may be formed with or applied to the cushion support structure to further affect the performance of the seal, such as flexible nasal protrusions. Such an example is illustrated with respect to the clip of FIG. 13, which is also shown applied to a frame in FIGS. 20 and 21. In the example of FIG. 13, the clip also contains extra cantilever protrusions 3561 that may further serve as cantilever springs. With these elements, the clip can press the foam into hard-to-seal areas such as the corners of the nose, effectively providing a variable level of cushion compliance.

As previously mentioned, the cushion support (clip or frame), or portions thereof, may be molded from different grades of thermoplastic elastomers TPE. Grades of different hardness may be used. Generally, a TPE material may be more beneficial to silicone as it may be more easily molded onto some cushions (e.g., foam) and its processing time may be faster than silicone. However, other elastic or flexible materials may be used such as thermoplastic polyurethane (TPU), thermoplastic polyurethane TPV or rubber, etc. By way of further example, in some cases, the flexible support structure (e.g., clip) may be formed with silicone, such as a room temperature vulcanizing RTV silicone.

As mentioned previously, because of their flexible nature, the cushion and cushion support structure (e.g., clip) work in unison to respond to the compression force imparted to the frame by the headgear vectors. However, the cushion, such as when foam is used, may play a greater part in conforming to the face of the user purely because it is the softer component and therefore may compress more. Eventually, when the headgear tension has been applied and the frame is pulled towards the patient's face, the foam and flexible support structure will reach an equilibrium shape, in which a seal is created.

Example cushions for the mask assemblies of the present technology are illustrated in FIGS. 24 and 25. The cushions may be foam and form a triangular or oval shaped ring and may have a common nasal and mouth aperture. The corners may be rounded. In the example of FIG. 24, the cushion has a generally flat patient contact surface PCS. In some such cases, the edges may be rounded. For example, as illustrated in FIG. 25, the cushion profile along is periphery may have a generally curved patient contact surface PCS. Other cushion profiles may also be implemented. The frame or clip contact side of the cushion may be generally flat or otherwise conform to the contact surface of the cushion support structure.

With these example generally uni-planar cushions, when connected to the clip or frame as illustrated in FIGS. 26 and 27, the cushion may deform to a multi-planar shape as previously discussed that is better for sealing. The triangular shape, when so deformed, enables the cushion to produce its seal around the outer periphery of a portion of the nares, into the corners of the nose and around the side and the bottom of the mouth while maintaining a substantially under-the-nose configuration and providing for a centrally open lip superior region. Thus, the mask may have a substantially non-contact area in the central lip superior region between the upper vermillion and the columella in the sub-nasal region. Moreover, this non-contact region may be within the plenum chamber during use.

While the cushions of FIGS. 26 and 27 are generally uni-planar and are deformed by the frame or clip to have their multi-planar use configuration (e.g., with an nasolabial angle between the nasal plateau region and the mouth periphery region), in some cases the cushion or foam may be pre-formed or pre-cut in the multi-planar shape consistent with the shape of the clip or frame.

Generally, there should be an air tight seal between cushion and its support structure (e.g., the clip). Various methods may be employed to implement such a joining of the cushion. For example, the cushion may be adhered to the support structure such as with glue, spray adhesives or hotmelts, etc. In some cases, it may be adhered by ultrasonic welding. In some cases, the cushion may be sewn and adhered. The join may also be implemented with an intermediary material such as a tape (e.g., a double sided adhesive tape). In some cases, the support structure (e.g., clip) may be over molded to the cushion.

Similarly, such methods may be employed for joining the cushion to the frame, such as without an interfacing clip. In this regard, the frame may provide the shape forming structure and surface to hold the cushion (e.g., foam) in the desired profile for patient sealing. In such an embodiment, the cushion foam may provide some or all of the necessary spring and softness to effect the seal and provide comfort to the patient. Otherwise, some of the previously described flexible features (e.g., cantilever components of the clip) may be formed with the frame to assist with the seal and comfort effectiveness. In some such clip-free cases, some of the flexible properties of the clip may be imparted to the foam by using a secondary layer of cushion rather than the clip. Such a secondary cushion layer may be applied to the patient contact foam layer and may have different flexibility/rigidity properties when compared to the first foam layer. In such a case, the second layer of the dual cushion may be applied directly to the frame without the clip.

In some cases the foam cushion may be a replaceable item (in some embodiments the replaceable item may include the cushion/clip combination). The cushion may be directly attached to the frame through an adhesive membrane located on the foam (or on a surface of the respective clip (either flexible or rigid). In such a case, the cushion may be simply removed, and a different cushion, with a new adhesive strip, may then be attached to the reusable frame (or reusable clip). In some cases, the foam cushion and frame may be co-molded. In some such cases, the cushion and frame unit may then be discarded together.

In some examples, the cushion 3110 may include additional features. For example, as shown in FIG. 28, the cushion may include an indent, such as a scalloped notch 3763, such as in the nasal plateau region of the cushion as an alternative to being a generally flat sealing surface. The indent may be formed by a semi-peripheral cut of an edge of the cushion in the nasal portion of the seal. In some examples, the cut may form a rising edge from a centrally lower position to a radially higher position. Such a semi-peripheral area may provide a cupping support around the nose. The cupping geometry may provide a greater surface area (bearing surface). In this regard, the scalloped edge shape feature may replicate the topography under the user's nose. As such, the scalloped notch may also improve sealing in the sub-nasal ridge area and may provide improved nasal comfort. It may also serve to minimize nose inflation. The feature may also provide a perceptively distinct landing area for patients to place their nose, resulting in a more intuitive set-up. In some cases, the notched area or the nasal plateau region may be marked to provide an indication of nasal location for user installation. For example, the area may have a distinct color with respect to the remaining areas of the cushion.

The shape of such a notch may be defined from any of the following anthropometric features: width between the labial insertions of the alar base; length of the ala; nasal ala-slope angle; inclination of the columella; nasal tip protrusion; width of nose. In some cases, the depth of the indent detail may be based on any of: the inclination of the columella; patient perception with respect to providing sufficient indication as to where the under nose section of the mask should be worn; sufficient surface to seal around the edge curvature of the nose; sufficient support around the periphery of the nose to prevent the nose from blowing out such as due to pressure from a pressure treatment.

Other versions of the geometry of the indent may include a simple chamfered edge following the periphery of the nose. When the foam has sufficient compliance for the chamfer to fit the nose an improved seal can result. Similarly, other variations in the overall triangular shape of the scalloped nasal feature may be achieved since foam has sufficient compliance to conform to facial features in a range of sizes.

As previously mentioned, the indent, such as the scalloped nasal detail, can effectively cup the lower periphery of the nose and may provide additional surface area for sealing and comfort. Thus, it may work in conjunction with other components of the mask assembly (clip and frame) during use to effectively serve as a seal. In terms of sealing and depending on the specific anthropology of the nose, the sealing interface may shift or extend or both, from under the nose to under and/or partially up the sides of the nose. In terms of comfort, the force applied to the nose from the headgear and the treatment pressure from the seal interface, may thereby be distributed over a larger surface area, resulting in better comfort.

The geometry of the indent in the foam cushion can change to accommodate a range of nasal sizes. A nose that is pressed into the scalloped detail, for example, during set-up of the mask will displace foam until the foam conforms to the nose. The flexible spring nature of the cushion support structure (e.g., clip and/or frame) can provide a resistive force at this stage to prevent the nose from fully pushing through the foam. Under treatment pressure, the foam can be pressed back against the nose which helps to provide an effective seal.

In some cases, the indent may be manufactured as part of a complete compression cutting process for the cushion. Alternatively, the feature may be manufactured by a secondary process such as thermoforming, ultrasonic welding or cutting. In some cases, the whole cushion including the scalloped nasal detail may be manufactured from a single compression cutting or thermoforming process.

In some further examples, the cushion may also include one or more protrusions. Such protrusion(s) may be included on the surface of the cushion. For example, one or more protrusions can be so disposed so that, when the mask is fit on the patient's face, the protrusions extend further out of the cushion into a portion of the patient's face. As such, the protrusions may provide additional structural support and a better seal. For example, a set (e.g., pair) of protrusions 3764, such as one or more approximately oval projections or of another shape, are illustrated in the cushion and mask of FIGS. 29, 30 and 31. These protrusions are disposed so as to extend on the left and right sides of the nose (e.g., left and right nasal ala protrusions). For example, each protrusion may be configured to ply adjacent to a nasal ala of the patient. As such, they may assist with buttressing the cushion's seal at the difficult sealing areas on both sides of the nose. The nasal protrusions, while useful, are optional. An effective seal in these difficult regions may also be achieved by other means, including increasing the thickness and varying the shape of the foam cushion in these areas. For example, a narrowing may be introduced at the sides of the nasal area of the cushion to facilitate a better seal.

As previously mentioned, the connection between the clip and frame may be implemented with various structures. Some examples are illustrated in FIGS. 32 through 35. Generally, in the case of an implementation of a clip, there should be an air tight seal between the clip and the frame. The cushion/clip assembly can be detachable from the frame so as to permit regular replacement of the cushion in the case that the cushion may have a shorter useful life when compared to the frame.

Some example connection structures for anchoring the clip to the frame may include: tongue and groove geometry; a stretchable periphery skirt to extend around an edge of the frame; a peripheral edge that connects by interference fit, such as one similar to air-tight food containers; a tongue and slot interface with secondary lip seal or gasket present. In some cases, the connection structures of the clip may correspond to existing mask frames to permit retrofitting of the cushion designs described herein with existing mask frames.

In the connector example of FIGS. 32A and 32B, the clip and frame may be coupled together by a bulbous ridge 3572 and channel 3574. For example, the frame may be formed with the channel and the clip may include the ridge. A cross sectional view of the ridge and channel may appear as a ball and socket. The soft flexible (e.g., TPE, silicone or other flexible material) bulbous ridge may be pressed into the rigid channel frame (e.g., plastic) to provide a seal and mechanical retention. Optionally snap fingers 3576 may also aid assembly and component de-molding.

In the connector example of FIGS. 33A and 33B, the clip and frame may be coupled together by a skirt 3578 and flange 3515 such as the flange extending continuously around the plenum chamber of the frame 3500. In such a case, the skirt 3578 of the clip may be a semi-rigid element (e.g., TPE, polypropylene or other similar semi-rigid material) continuously extending around the ring of the clip. Plying the skirt so as to cup it over the flange may then serve as a seal and provide mechanical retention.

In the connector example of FIG. 34, the clip and frame may be coupled together by a snap shoulder 3580 and engagement cavity 3582 continuously or semi-continuously extending around the periphery of the clip and frame. Such a snap may be formed on a rim of the clip 3535. The rim and snap may be displaced by a more rigid frame upon engagement, such as when the snap shoulder, which may be a semi-rigid material (e.g., plypropylene) is plied into the engagement cavity 3582. The surface engagement of the rim and frame may provide a seal and the snap shoulder and engagement cavity coupling can provide a mechanical retention.

In the connector example of FIGS. 35A and 35B, the clip and frame may be coupled together by a taper lock (shown in exploded view 3583). In such an example, a peripheral rim 3702 of the frame, which may be rigid, may be retained in a peripheral channel 3585 of the clip. A taper element 3586 of the frame may couple with a taper receiving channel 3587 of the clip, which may be flexible (e.g., silicone, TPE, etc). The taper element and the taper receiving channel may be formed so as to continuously or semi-continuously extend around the periphery of the clip and frame. The taper element and taper receiving channel may then aid mechanical retention of the frame and clip components.

4.4.2 Supra Nasal Sealing

Traditional Full Face mask (also referred to as a patient interface) obtains a seal with the user's face by way of a silicone cushion that seals both around the mouth and over the bridge of the nose. The main issue with this is that, due to the nature of the silicon material, often comfort issues are experienced by the user (i.e. facial markings or other skin irritations).

This problem may be overcome by the implementation of foam such as the foam previously discussed. In some embodiments, the foam cushion can be in direct contact with the patient's skin. The compliant nature of foam allows it to, under relatively small tension force, compress into intricate facial features and affect a good seal. This, combined with the easy adaptability and softness experienced by the patient, provides for a relative fast and easy mask set-up. The foam also exhibits better breathability than silicone. Thus, the use of foam is associated with better permeability (associated by many users with a "different feeling on the face verses silicone") and reduced discomfort in the areas of contact in the sealing areas.

The comfort associated with the permeability of the foam has to be balanced with the increased leak associated with high permeability. As in the case of the under nose mask configuration, the foam cushion may generally be formed by open cell foam, in which the majority of cells are open; by closed cell foam, in which the majority of cells are open or by semi-open (or semi-closed) cell foam, which is formed by a mixture of open and closed cells. In one example, the discussed technology may use a semi-open cell foam in which the number of open cells is significantly higher than that of the closed cells. This ensures limited permeability and a smaller leak through the cushion. The specific range of permeability values having such limited permeability and found suitable for the disclosed technology is discussed later in the text. Other ratios between the number of open and closed cells can also be used. In the case of higher permeability, various actions may have to be taken to mitigate the increased permeability. As discussed elsewhere in the text, one such action is extending the flexible clip or other non-permeable membrane to cover the inner surfaces of the foam cushion and reduce the overall permeability. It is envisaged that open cell foams or closed cell foams may also be used according to the discussed technology.

In order to achieve comfortable fit, a good seal and stability, current Full Face foam masks are larger in footprint when compared to masks with traditional silicone seals.

In effort to achieve certain flow characteristics, some foam cushions previously used are either not permeable or may include a secondary layer over the foam to stop air from passing through the foam. Both options remove the breathability benefit of a foam seal. Only traditional foam full face masks having sealed or non-permeable foam cushions were compatible with current respiratory therapy for obstructive sleep apnea (OSA).

Some prior foam masks also involve separate individual components that together form the cushion. In one example, a foam layer may be attached to a silicon cushion to improve the sealing quality and the comfort associated with the mask. In some circumstances, such arrangements, may be large in size and less comfortable, and may make it more difficult for the user to disassemble, assemble and clean the mask.

In some versions of the present technology, such as when a mask is configured for sealing with the mouth and over the nasal bridge as shown in the example of FIGS. 36 and 37, a foam cushion may be implemented.

For example, a foam cushion assembly can be configured to seal around the mouth and over the nasal bridge, and can achieve a comfortable and effective seal. Such an assembly may include a foam cushion portion and a cushion support structure (e.g., a support clip portion). Here the expression "over the nasal bridge" should be construed as "across" the nasal bridge and not as "above" the nasal bridge. The support clip portion may be a flexible (or soft) clip portion configured to complement the compliance of the cushion so as to allow a reduction in the size of the cushion. The foam cushion can be externally attached to the cushion support clip. Such an external attachment can permit the foam surface of the cushion to be configured for direct contact with a patient's skin.

In one example, the cushion 3810, which may be made with foam, defines a single area that peripherally covers the patient's mouth and nose (approximately midway up the nasal bridge, but this can vary depending on the face anatomy of the specific patient). The foam cushion may, for example, be made from any suitable material such as one or more of the following example materials: Polyethylene, Polyurethane, Ethylene vinyl acetate (EVA). In some cases, the foam cushion may be a semi-open closed cell foam, such as one made of polyurethane. The cushion of semi-open cell foam may have a limited permeability such as in the ranges described in more detail in this specification.

The cushion 3810 may have a substantially triangular or pear-like shape with a sealing face that follows the contours of a user's face. The single chamber foam cushion is designed to be attached to a first support (e.g., flexible) clip 3812 that is itself attached to a second, more rigid, clip 3814 (as shown in FIG. 38) or directly to the mask frame 3816. In one embodiment, the first support clip 3812 can be a flexible clip that is more rigid than the foam cushion, but softer or more flexible than the second clip 3814. It is the combination of the foam and a flexible clip that defines the physical properties of the overall sealing interface. The flexible clip allows the interface to accommodate major variations, and to successfully conform to the contours of the patient's face. The compliant nature of the foam cushion provides micro-adjustment and forms a comfort interface layer that interacts with the patient's skin.

In some versions of the cushion assembly or cushion mask may include a protrusion, or an alignment protrusion, that may be configured, when in use, to be depressed by a headgear strap so as to apply pressure on a respective region of the foam cushion. For example, a protrusion 3813 may optionally be included on the outer surface of the first support clip 3812 (e.g., flexible support clip) on both sides of the mouth (e.g., both symmetrically located about the mouth), in such a manner that a respective headgear strap may pass over each protrusion, as shown in FIG. 37. Such an arrangement may allow for better sealing at the sides of the mouth when dealing with facial width variations. When tightened, the headgear may depress the protrusion toward the patient's face. Such a pressure will be transferred to the foam cushion, depressing the cushion towards the patient's face and enhancing the sealing in this region of the mouth. The additional pressure can be modified by changing either the height of the protrusion, the tension of the headgear or both. A height of between 2 mm and 6 mm, 3 mm to 5 mm, and preferably of about 4 mm, is considered sufficient for such modification. Instead of being located on the surface of the flexible clip, the protrusion may be located on the outer surface of the foam cushion or the rigid clip. Protrusions of different height/thickness and located on different components (i.e. one located on the rigid clip and the other on the flexible clip) can also be used, e.g. to create a gradient of inwardly directed pressure along the side of the mask. In another embodiment, the projection may extend across both the foam cushion and the flexible clip. In yet a further embodiment, a flange may be formed to extend from the frame to apply inwardly directed force and enhance the seal in a similar manner.

In some examples, the flexible clip or even both the flexible and the rigid clips may be omitted by directly applying a foam-only cushion assembly to the frame. Such a design, however, may require the cushion to be of a substantial thickness and height. The implementation of a clip, even of a rigid one, and especially of a flexible clip or a combination of soft and rigid clips as described here, allows reduction in the dimensions of the foam cushion, without compromising on compliance, sealing and comfort. One role of the rigid clip is to facilitate removable attachment of the foam/clip assembly to/from the frame for cleaning or replacement. Components of a foam cushion assembly 3901 are shown in FIG. 39. An assembled view of the foam cushion assembly 3901 is shown in FIG. 40.

As illustrated in FIGS. 39 and 40, a frame coupling side FCS of a rigid second clip 3814 may include structures for removeably coupling the second clip to a mask frame 3816. For example, a coupling ridge 4022 may be provided to engage with a corresponding structure of the mask frame. The coupling ridge 4022 may help to form a seal, such as with an interference fit, to prevent escape of treatment pressure at contact surface of the mask frame and the second clip at the frame coupling side FCS. One or more optional engageable snap elements 4024, may permit a snap-fit or snap-lock of the second clip to the mask frame. Such a snap element may be flexibly resilient so as to bend against a corresponding receptacle of the mask frame until a ridge stop 4025 may engage with an edge of the receptacle or aperture of the mask frame. A taper 4027 at the top edge of the snap element may induce the bending of the snap element during coupling of the second clip to the mask frame until the ridge stop 4025 passes into the receptacle or aperture of the mask frame and thereby locks within the receptacle or aperture of the mask frame. In some cases, the snap element may be formed on the mask frame and a corresponding receptacle may be formed on the second clip. A manual bending of the snap element(s) may then permit the removal of the second clip from the mask frame.

In one example implementation of the foam, flexible clip and rigid clip are formed together or permanently attached to each other, as shown in FIG. 40, forming an integral cushion assembly. The foam and flexible clip form the compliant portion of the assembly, while the rigid clip provides the mechanism to attach the cushion assembly to the mask frame. This allows the cushion assembly to be removed for cleaning and/or replacement. A rigid clip can enable a rigid connection between the cushion assembly and the mask frame which makes the mask more convenient for handling and more durable. Thus, the components of the cushion assembly (e.g., the foam cushion, the flexible clip and the more rigid clip) can be permanently attached in one integral assembly. However, alternatively they may be separable elements, as shown in FIG. 39. These three elements may be arranged to be separately formed, assembled together, but dissembled and assembled again, if necessary. Alternatively, the foam cushion and the flexible clip can be permanently attached to each other, but detachably connected to the rigid clip. In another example, the flexible clip and the more rigid clip can be permanently attached to each other but detachably connected to the foam cushion.

The mechanisms of such removable attachment may be those known in the art and may include adhesive layers (for attaching the foam to the flexible clip), interference fits and snap-locking engagements. The periphery of the more flexible components, such as the flexible clip, can also be stretched over the periphery of the more rigid component, such as the frame or the rigid clip.

Any combination of the three components is possible and alternative design variants could include a cushion assembly comprising only a foam cushion; a foam cushion and a flexible clip or a foam cushion and a hard clip.

In some cases, a foam cushion may itself be formed as a slip-over foam cover component for other mask components, assemblies or mask cushions. For example, a foam cushion overlay may be formed as or with a stretchable engagement skirt. The skirt or foam skirt may then be stretched over an underlying structure defined by any mask component, such as a frame, a clip or even a silicon cushion. Once the foam cushion has been slipped on to fit over an edge of an underlying component, it can serve as a comfortable sealing layer contacting the patient's face. As such, the slip-over foam cushion may even serve as an easily replaceable cover component to improve comfort of existing silicone or foam cushion masks.

5.4.2.1 Sealing Mechanism

With the mask example of FIGS. 36 and 37, the foam cushion is arranged to be in direct contact with the patient's skin. The seal around the mouth, the sides of the nose and the nasal bridge is produced through the interaction between the patient's face and the combined reaction force of the frame (which may be applied to the cushion assembly by way of the hard clip); the flexible clip and the foam cushion, to the headgear tension. Each of these three components is discussed in more detail below. These components when assembled together can work in unison to provide variable amounts of foam compression around the nose and mouth so that an effective seal is produced in these areas. In this regard, the illustration of FIG. 41 shows the mechanism that is created to, through the combination of these three components, achieve seal.

As illustrated in FIG. 41, by applying the foam cushion onto the user's face and tightening the headgear vectors (seen in FIG. 37) a seal is generated along the foam's contact surface with the patient's face, such as over the nasal bridge and around the sides of the nose and mouth. The seal is caused by a combination of foam compression and/or deflection and compression of the flexible clip.

The flexibility in the combination of foam and flexible clip can enable the foam mask to conform well to the patient's facial profile.

As the headgear vectors are further tightened, a greater sealing force SF will be applied.

The reaction forces in the cushion and the flexible clip, caused by the deflection and compression of the cushion and clip by the headgear, result in a reaction vector that is directed from the frame support and towards the patient.

The structure of the foam cushion and the flexible clip is such that the treatment pressure (e.g., CPAP) accumulated inside the mask plenum chamber also acts upon the inner surface of the flexible clip and the foam, pushing them outwardly and compressing the foam against the user's face. Thus, the arrangement utilizes further the pressure in the plenum chamber and helps maintaining sealing pressure. As mentioned above, because of their flexible nature, the foam and clip work in unison to respond to the compression force imparted to the frame by the headgear vectors. Eventually, when the requisite headgear tension has been applied and the frame is pulled towards the patient's face, the foam and clip will reach an equilibrium shape, in which a seal is created and retained. In some examples, through its greater stiffness, the clip may provide a reaction force that is substantially larger than that provided by the foam cushion. The reactions forces of both the clip and the foam cushion may vary along their periphery.

Similarly, the compressed foam may provide relatively small elastic reaction force in some sections of the cushion periphery, and a larger force in other sections.

Similar to the mask examples previously described in this specification (e.g., sub-nasal mask), the flexible clip may be peripherally and inwardly concave so as to have a concave profile or inwardly concave shape. This can allow for the pressure to act upon the inner surface of the clip so as to enhance the sealing of the mask.

Different portions of the flexible clip can serve different functions. For example, the spring constant provided from the mid area of the shape (e.g., 'C') may act as a support beam that creates the main reaction force in response to the tension force applied by the headgear. A peripheral lip for supporting the foam can serve as a cantilever that presses the foam towards the patient's face to strengthen the sealing engagement. Additionally, the overall open (concave, C-shaped or L-shaped) structure of the clip allows the air pressure in the mask to be applied to the inside surface of the peripheral lip. This surface is located opposite to the foam supporting (also sealing) surface. Thus, the mask pressure pushes the peripheral lip, and therefore compresses the foam cushion towards the patient's face, thus further strengthening the sealing engagement and potentially assisting with reducing any air permeability of the foam. In the absence of the clip the pressure will still be applied to the foam cushion. However, because of the semi-open cell type of the used foam, the applied pressure may leak through the foam. Thus, the concave shape of the clip means that at least a portion of the lower surface of the foam cushion 3810 is covered by a non-permeable material of the flexible clip, as best seen in FIG. 41. This can be used to control the leak through the cushion and increase the pressure within the mask plenum chamber. This concept can be taken further and the clip can be extended to cover at least a portion of the outer side wall of the cushion 3810, as long as it does not get in contact with the patient's skin. On the other hand, for various reasons, one may wish to leave some of the surface of the foam exposed. As will be discussed later in the text, one positive outcome of such a design may be the fact that a portion of the foam is unsupported by the flexible clip and, as a result, the foam may tend to "roll-in" when the headgear is tightened. Such a roll-in effect may be beneficial for the sealing in some areas of the nose, for example.

5.4.2.2 Foam Cushion

In the example of the cushion shown in FIG. 42, the foam has a varying cross section from the bridge of the nose to the bottom of the mouth, and is symmetric through the center plane. During use, he the geometry of the foam is affected by the anthropometric data used in the overall design of the flexible clip as well as the specification of the foam material (e.g., hardness, compression set, permeability, compression stress strain, density etc.).

The cushion may be configured with a varying cross section that can be divided into three regions, nasal bridge MNBR, sides of nose region MSNR and sides of mouth region MMR, with a smooth transition between each of the regions. Each section may be configured with a profile that is optimized for the specific area of the face with which it seals.

The cross section of the foam is designed to take into account of the following, and the geometry is design to address each of the areas:

(a) Comfort

It was found with an increase in the amount of foam (both height and width) there is an increase in overall comfort. Depending on the specific cross section of the first clip, the first clip becomes noticeable so as to be felt through the foam for heights of about less than (<) 8.0 mm. (In the example of FIG. 42, the range for the height of the foam is about 8 mm-16 mm. Similarly, the comfort of the cushion was significantly impacted for widths less than (<) about 12 mm. For the foam of an example, the width can be in the range of about 12 mm to 30 mm, and may be desirable at about 15-20 mm.

(b) Seal

It was found the seal is improved with an increase in width for the surface of the foam that is directly in contact with the patient.

(c) Stability

It was found the stability of the seal is negatively impacted by an increase in the height of the foam, whilst being positively impacted by an increase in the width of the foam.

(d) Encroachment

The main risk of encroachment is the potential for the cushion assembly to intrude/obstruct the user's eyes. In some cases, the width of the foam may be reduced in these areas of the eye.

By minimizing either one or both the height and the width of the foam cushion in the noted ranges, one can minimize the overall size of the mask.

5.4.2.2.1 Foam Cross Sections (a) Nasal Bridge Region MNBR—FIG. 43

In some examples a nasal bridge region of the cushion, such as that illustrated in FIG. 43 may be configured (in its cross section) with a trapezium shape. The units of all dimensions shown in the example of FIG. 43 are in mm. This may provide good stability characteristics. The top corners may be rounded for comfort and for a better aesthetic appeal. For example, a width of about 12 mm (or in a range of 0-25 mm) may be suitable for the surface portion that contacts the user's nasal bridge. This may be kept substantially higher than other regions in order to increase the sealing surface in this region.

(b) Side of Nose Region MSNR—FIG. 44

In some versions, a side of the nose region of the cushion, such as that illustrated in FIG. 44, may be configured (in its cross section) with a trapezium shape. The units of all dimensions shown in the example of FIG. 44 are in mm. This may provide stability characteristics. The top corners may be rounded for comfort. The width of the surface contact portion at the user's face may be about 6.35 mm (in a range of about (0-14 mm)) in order to avoid the cushion intruding into the patient's eyes.

(c) Mouth Region MMR—FIG. 45

In some versions, a mouth region of the cushion, such as that illustrated in FIG. 45, may be configured (in its cross section) with a trapezium shape. The units of all dimensions shown in the example of FIG. 44 are in mm. This may provide good stability characteristics. The top corners may be rounded for comfort. The width of about 9 mm (within a range of about 0-17 mm) may be suitable for the surface contact portion and may be a compromise between comfort/seal and overall mask size.

Although these distinct regions have been illustrated with trapezium cross sectional geometry, other cross sectional geometries shown in FIG. 46. Such may include; a rounded top geometry 4621-A, a straight edge rounded top geometry 4621-B, a rectangular geometry 4621-C and a rectangular with rounded edges geometry 4621-D. The rounded top geometry 4621-A has a cross section with a fully rounded top surface. This increases clearance between the user and the foam and improves overall stability. The rectangular geometry 4621-C has a rectangular cross section, which may perform similarly to the trapezium geometry, which for performance purposes is similar to a rectangular cross section with rounded corners. The rounded corner increases the overall comfort of the cushion since, by removing the sharp corners, not as much foam is compressed in these areas during use of the mask.

In some examples of the cushion, a combination of geometries can be implemented in a single foam cushion within and/or between different regions. For example, the foam may be configured with a transition of geometries between regions. In one example, the cushion may transition from a cross sectional geometry having a flat top (e.g., rectangular top for comfort and a better seal) to a round top to increase clearance around specific facial areas.

The example cross sectional geometries shown in FIGS. 45 and 46 each have a foam height of about 12 mm. However, in some examples, the height of the foam may also transition between and/or within regions with suitable heights greater or lesser than 12 mm. Suitable heights may be chosen to change the performance as needed in the individual sections of the cushion.

5.4.2.2.2 Foam Manufacture

An example embodiment of the foam may be produced by compression cutting, but it may be produced by, or with a combination of, any of the following methods including, die cutting, thermoforming, moulding, grinding, compression cutting, etc. For example, the foam may be compression cut to a flat profile as illustrated in FIG. 47. In this flat profile, the foam's shape is somewhat two dimensional, as its shape is mainly defined in two dimensions, but is planar in the third dimension. Once the foam is attached to one or both of the clips (e.g., soft/flexible) clip, it not only changes its two-dimensional shape, but also bends in the third plane (dimension) and becomes truly 3-dimensional. Thus, the clip(s) may impart contour (such as for variations to improve facial contact) into the foam when assembled. In the example of FIG. 47, the foam is held in a contoured shape by the first clip. A better view of the 3-dimensional (3D) aspect of the cushion, in an attached configuration, is shown in FIG. 84. Also, instead of having the 3D shape imparted on the cushion by one of the clips, the cushion itself may be formed in a 3D shape, or such may be imparted to any one or both of the clips and/or the cushion by the frame.

5.4.2.2.3 Assembly Method

The foam can be assembled onto a clip or other mask structure such as the soft/flexible clip by adhesive (e.g., glue and/or tape); by flame lamination; by moulding (e.g., moulding of foam onto the clip, or vice versa); by welding; mechanical connection between foam and clip; by sewing; etc. The foam may be formed or cut with a generally flat or planar contour. Although it will have a facial contour when used as a mask on a patient (see, e.g., facial contours of cushions of FIG. 58A and FIG. 22.) In some cases, the foam cushion of any of the masks described in this specification may simply be bent or deformed to have a facial contour that corresponds to the contour of the clip on which it is installed. Thus, the foam may be dependent on the clip to have a facial contour. However, in some cases, the foam may be formed with the facial contour such as by moulding or cutting the foam. In such cases, the facial contour of the foam may be independent of any clip or other structure.

5.4.2.3 First Flexible Clip (e.g., Also Occasionally Referred to as a "Soft" Clip)

As shown in the cross-sectional view of the cushion assembly illustrated in FIG. 48, the first soft/flexible clip includes a cushion coupling portion 4840, a support portion 4842 and a base portion 4844. The cushion coupling portion 4840 provides a contact surface to which the cushion is attached. The supporting portion 4842 is flexible, but with a specific degree of rigidity so as to provide appreciable reaction support to the cushion when the headgear is tensioned and the mask is in use. The base portion 4844 attaches to the rigid second clip or, in some embodiments, to the frame. One or more additional support portions 4842, for example having different rigidity/flexibility characteristics, can be included between the coupling portion 4840 and the base portion 4844.

Again, because of the relative small thickness of its walls (a few millimeters) the general shape of the body of the clip is a curved concave surface with the opening being directed inwardly towards the center of the plenum chamber of the mask. The cross-sectional profile of the flexible clip varies in shape, but can generally be described as L or C, or even Z-shaped, a simple gusset, or variations in wall section etc. The open or concave nature of the clip allows the pressure inside the mask plenum chamber to be applied to the cushion (illustrated by the arrows P4 of FIG. 48) in a way that enhances the cushion-to-patient seal. The support portion 4842 may be generally perpendicular to the sealing plane SP-5 (for example—see the C-shaped cross section and its respective support portion 4842 in FIG. 56). The material properties of the clip, the shape and the dimensions (in particular the thickness and the height) of the support portion of the clip can be chosen so that the flexible clip offers appreciable support to the cushion, but at the same time is also able to, when the mask is in use, change its configuration and act as a cantilever spring. The reaction force associated with the rigidity of the clip compresses the attached foam cushion towards the patient's face, improving the seal to the face, whilst the compliance introduced (i.e., by the cantilever spring nature of the clip) assists the foam cushion to conform to the face. The rigidity of the clip, especially in a lateral direction (up and down or sidewise with respect to the face) also provides lateral stability of the mask. Such stability is especially beneficial for wearing the mask at night, when movements of the patient's head tend to disturb the mask and compromise the sealing engagement.

A minimum height of about 5 mm is desired in the flexible clip to allow for sufficient movement during usage, so the user does not "bottom out" on the flexible clip. In this context, "bottoming out" can occur when the flexible clip has reached its deflection limits or when compressed completely flat to a stop and there is a sharp rise in the tension force acting on the user's face and experienced by the user. The height can be chosen to be a height within a range of about 5 mm to 30 mm, depending on the area of the face covered by the clip.

The entire flexible supporting clip or the middle support portion 4842 may represent a curved surface having, for example, a "Z", "C" or "L" cross sectional geometry. The cushion coupling portion 4840 may be in the form of a peripheral lip that connects to the foam to form an effective cantilever over-hang portion. Depending on the structure and the material characteristics of the various section of the clip cross-sectional profile (shown in FIG. 48), the cantilever spring effect may be predominantly confined to a specific portion of the flexible clip, such as the overhanging lip formed by the cushion coupling portion 4840 with respect to the top edge of support portion 4842, or the combination of portions 4840 and 4842, with respect to the boundary between the flexible support portion 4842 and the frame attached portion 4844.

When the headgear is tensioned, the support portion 4842 of the clip deforms and creates a reaction force that tries to return the clip to its original shape. This force depresses the foam towards the patient's face, enhancing the sealing engagement.

The configuration of the entire support clip is configured to offer a balance between support and flexibility. By varying the dimensions (mainly the wall thickness and the height), the rigidity and the cross-sectional shape along the perimeter of the clip, different levels of support and flexibility are provided in the different sections of the mask. Whilst support portion 4842 of the clip is generally perpendicular to the sealing plane SP-5, as it can be seen in FIG. 48, in some embodiments, the support portion and a perpendicular to the sealing plane may form an angle α there between. In some examples of the technology, the cross-sectional shape of the flexible support clip is at least partially characterized by the angle α and/or the relative length of the arms of the L, C or Z shape. For example, as it will be discussed later in relation to FIGS. 51-54, where higher softness and lower support is needed, such as in the sensitive area of the nasal bridge, the clip may use one, or combination of two or more of the following features: higher support portion 4842, a thinner support portion 4842 or an increased angle α. For example, angles between 20° and 50°, and more specifically between 30° and 40°, may be suitable for such applications. Variations in the overall physical structure of the first flexible clip, such as changing the overall shape of the clip (i.e. from C to L-shaped) or changing the relative lengths of various sections of the clip (e.g. changing the relative length of cushion coupling portion 4840 or support portion 4842) can also be implemented to achieve similar results.

The cantilever springe effect resulting from the flexible nature of the clip was already described in previous paragraphs. However, the flexible nature of the clip may define a broader self-adjustment effect that may be distributed along the length of the clip and that goes beyond the cantilever springe effect. In particular, such an adjustment occurs when the mask is in an operational configuration—it is attached to the user, the headgear straps are tightened and the plenum chamber of the mask is pressurized. In this instance a certain balance is established between the forces acting on the clip. For example, in a direction perpendicular to the contact plane SP-5, such forces include forces depressing the clip (such as the tension force of the headgear applied via the mask frame, the applied pressure P4 and the reaction force applied by the foam cushion) and the clip's spring constant, defined mainly by the supporting portion 4842. However, the applied pressure in the plenum chamber acts not only in the direction indicated as P1, but on the entire inner surface of the clip. The overall balance of forces and the flexibility of the clip may lead to a dynamic change in the entire configuration of the cross-sectional profile of the clip, once the mask is in its operational configuration. Thus, the shape of the clip (such as the generally L shape shown in FIG. 48) may undergo changes, which may be different in the different peripheral sections of the clip. Some of the changes may include any one of the following: inwardly or outwardly directed bending in any section of the supporting portion 4842, modification of the angle between the portions 4840 and 4842 (not shown in FIG. 48, but being complimentary to angle α) and change of the angle of inclination of the cushion supporting portion 4840. An inward rotation of the cushion coupling portion 4840 (the cushion supporting surface) towards the plenum chamber defines a roll-in effect for the cushion. The changes may vary along the periphery of the clip. For example, in some sections around the periphery of the clip, the surface of the clip at cushion coupling portion 4840 (and therefore the cushion) may roll-in, whilst in others, they may roll-out.

The direction and the extent of modification of the configuration of the clip will depend on the above discussed balance of forces, on the patient's face profile and on the material properties of the clip, such as its rigidity/flexibility. These characteristics may be modified by way of changing the clip's shape, dimensions (e.g., thickness and/or height) and/or material properties. The specific dimensions and material (more specifically the mechanical) properties of at least some embodiments of the clip that facilitate such a modification of the cross-sectional profile of the clip, when in use, are described further in the text. The modification represents a self-adjustment mechanism that allows the flexible clip and the attached foam cushion to accommodate a wide variety of face geometries and features and provide comfortable and reliable seal. The effect of such a self-adjustment mechanism may be further enhanced by a purposeful change of the mechanical properties and the general spatial relationship (or angle) between the portions 4840 and 4842 around the periphery of the flexible clip, as will be discussed in relation to FIGS. 51-54.

In some instances, the support portion 4842 of the clip may be chosen to have dimensions (height and thickness)

and mechanical properties (i.e., flexibility) that would allow the air pressure to create an air spring effect. This is to say that, as shown in FIG. 48, because of the flexibility of the supporting clip, the pressure P4 in the plenum chamber may be used to assist the overall sealing of the mask cushion by depressing the foam cushion towards the patient's face. As pressure increases, so does the force creating the seal. The spring effect may also vary around the periphery of the clip.

All of the effects described in the previous paragraphs allow the flexible clip to compliment the flexibility of the supporting clip. Their effect, however, is limited by the rigidity of the clip. The clip meeds to have sufficient overall rigidity in order to provide significant structural support to the foam.

In some specific embodiments, if for any reason a substantial compliance and softness is required, the dimensions and the material properties of the clip may be selected so as to enable the clip to at least partially expand in a balloon like manner, under the pressure applied to the mask when in use. Such an arrangement will exhibit increased compliance, but reduced stability.

In the example shown in FIG. 49, the soft/flexible first clip has a varying cross section from the bridge of the nose to the bottom of the mouth, and is symmetric through the center plane. The geometry of the flexible clip will largely be affected by the overall design of the foam and the specification of the clip material. For one particular embodiment, the thickness of the flexible clip in both the coupling portion 4840 and support portion 4842 may vary between about 1 mm to 2 mm. However, other thicknesses may be implemented.

A location ridge 4845 shown in FIG. 48 and in FIG. 50 may be included on an external periphery of the surface of the flexible clip that contacts the foam. This structure may then aid alignment in the manufacturing process of the foam to the foam mounting surface provided by the coupling portion 4840 of the flexible clip. The location ridge is designed to be small and does not come into contact with the user's face. For example, it may be about 0.5 mm in height and width with a full round on the top. Other heights may be chosen and may be in a range of about 0.2 mm to 2 mm.

5.4.2.3.1 First Clip Regions

The first clip may be implemented with different characteristics in different regions of the clip. For example, different cross sectional geometries and/or properties in the various portions of the clip is intended to impart different properties to the associated sections of the mask and allow efficient sealing with the respective regions of the user's face, as described in detail below. Example regions are illustrated in FIG. 49. The regions may include a nasal bridge region FC-NBR, a sides of nose region FC-SNR, a sides of mouth region FC-SMR and a bottom of mouth region FC-BMR.

Figure 51:
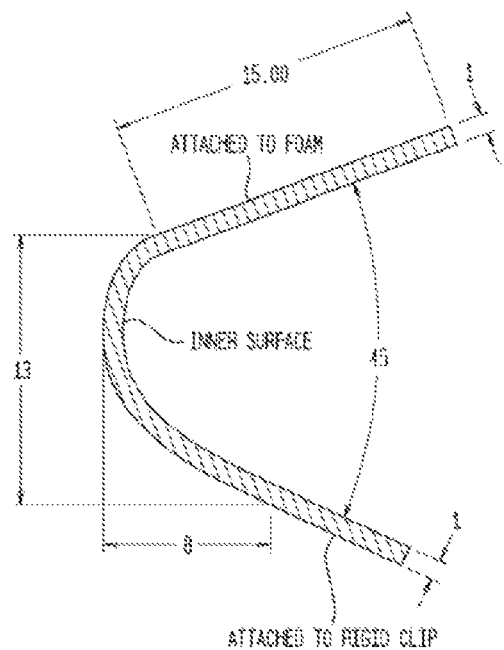

(a) Nasal Bridge Region—FIG. 51

The example of the cross sectional geometry in this region shown in FIG. 51 may be 'C' shaped and allows the foam cushion to move substantially perpendicularly to the user's face to accommodate a wide range of nasal bridge depth. It may be the softest/most flexible part of the first clip and have a thickness in its support portion 4842 of about 1 mm. However, this thickness in some versions may be in a range of about 0.25 mm-1.5 mm. The movement is generated by the angle between the inner face (in this case 45°) (with a range 0° to 90°) and the overall size of the 'C' section.

The surface that attaches to the foam at cushion coupling portion 4848 may be the largest in this area (e.g., about 15 mm) but can be in a range of about 10 mm-25 mm. This sizing is done to reduce the likelihood of the seal blowing out on the sides of the nose, since it restricts the outward movement of the flexible clip in this region.

The height of the clip measured, as indicated in FIG. 51, from the boundary of the area used to attach the flexible clip to the rigid clip, to the boundary of the area used for attachment to the foam, is indicated as 13 mm. However this may vary between 10 and 20 mm. For an indicated thickness of the clip of about 0.25 mm to 1.5 mm, this will define a height to thickness ratio of between 5 and 80.

The combination of these values may define the overall sealing and comfort quality.

Figure 52:
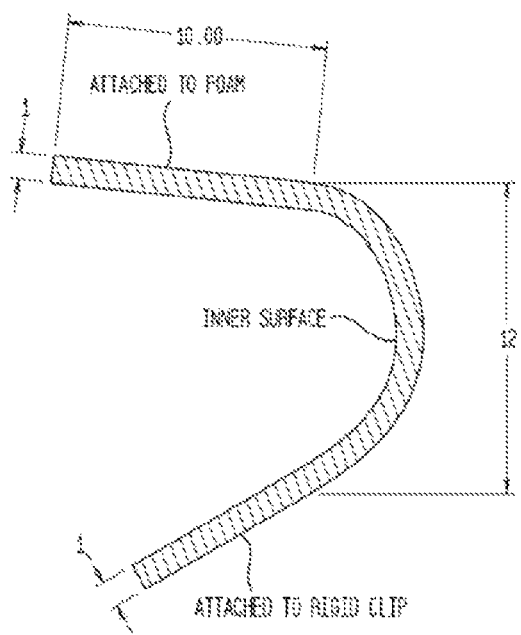

(b) Sides of Nose Region—FIG. 52

The example cross sectional shape of the first clip in this region shown in FIG. 52 may also be 'C' shaped and may allow the foam to pivot and match the facial geometry at the sides of the user's nose. This allows the foam contact surface to be parallel with the user's nose. The flexible clip support portion 4842 in this region of the flexible clip may have a thickness of about 1 mm. However, this thickness in some versions may be in a range of about 0.25 mm to 1.5 mm. The height of about 12 mm gives the range of movement necessary to conform to the user's nose. However, this height in some versions may be in a range of about 8 mm to 20 mm.

The height of the clip is measured, as indicated in FIG. 52, from the boundary of the area used to attach the flexible clip to the rigid clip, to the boundary of the area used for attaching the clip to the foam cushion. The above noted thickness and height of this section of the periphery of the clip define a height to thickness ratio of between 5 and 80.

Figure 53:
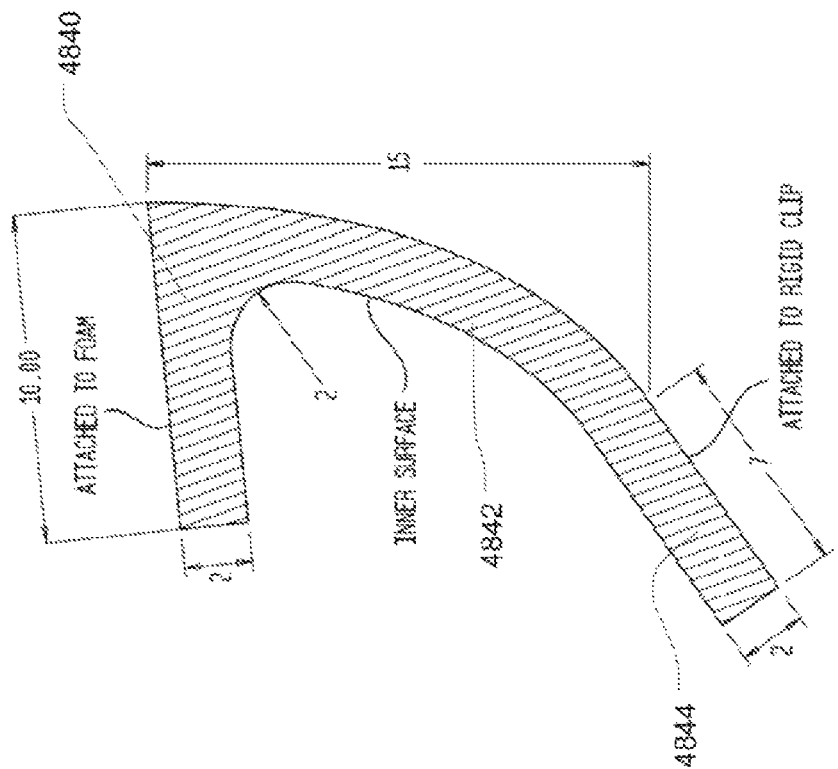

(c) Sides of Mouth Region—FIG. 53

The example clip cross sectional geometry illustrated in FIG. 53 at the region on both sides of the mouth may be 'L' shaped and can be the most rigid portion of the clip, effectively forming an anchor point around the sides of the mouth. The support portion and the cushion coupling portion can also be angled with respect to each other for increased stability and better sealing. The more rigid configuration is suitable since these side of mouth regions of the face are deemed to be the least pressure sensitive. Furthermore this angled configuration allows the foam to be pivoted into the user's face to allow for varying facial profiles. The flexible clip and more particularly its support portion 4842, can have a thickness of about 2 mm but other thickness in a range of about 1.5 mm to 3 mm) may also be implemented to provide the increase in stiffness. In some versions, a 'C' shaped geometry may also be implemented for these regions of the flexible clip. However, this may result in an increase in overall mask footprint.

The height of the clip measured, as indicated in FIG. 53, from the boundary of the area used to attach the flexible clip to the rigid clip, to the boundary of the area used for attachment to the foam cushion, is indicated as 15 mm. However this may vary between 10 and 20 mm. For an indicated thickness of the clip, this will define a height to thickness ratio for this section of the periphery of the clip of between 3 and 80.

Figure 54:
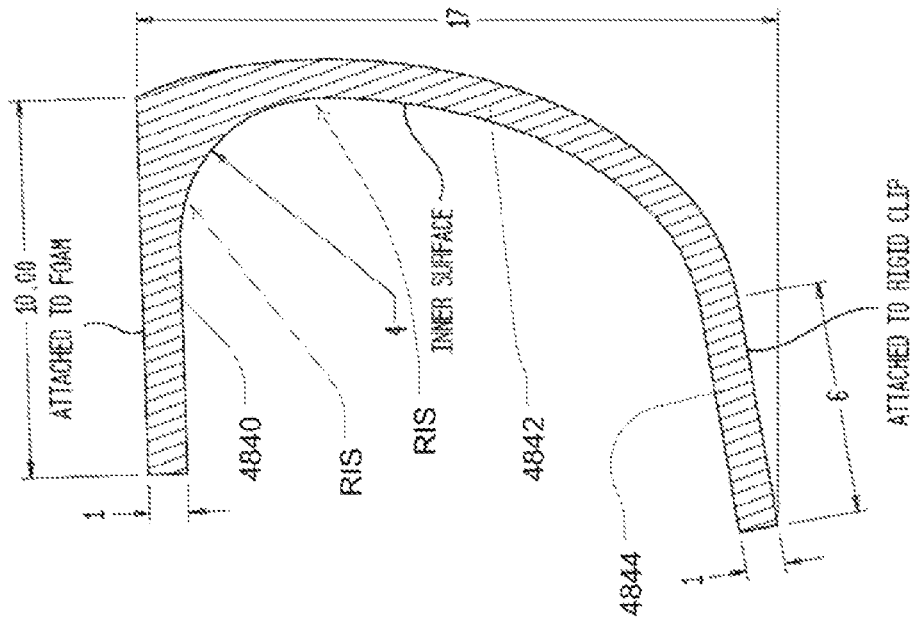

(d) Bottom of Mouth Region—FIG. 54

The example clip cross sectional geometry for the bottom of the mouth region illustrated in FIG. 54 is 'L' shaped and is configured to allow the flexible clip to roll-in. This permits the foam to move upwards and downwards relative to the face (left and right with respect to FIG. 54) and maintain a parallel top sealing surface with respect to the user's face. This feature allows for movement of the user's jaw without losing the cushion-to-patient seal (i.e., jaw drop during usage). The flexible clip can have a thickness in this region of 1 mm (with a range of 0.25-1.5 mm). The roll-in action is possible with the rounded inner surface RIS, this action is further aided by having a sufficiently large radius (for example, about 4 mm, but may be any radius within a range of about 2 to 10 mm) that prevents the lip surface attached to the foam (the cushion coupling portion 4840) from folding inwards. The flexible clip can have a height of about 17 mm but may be a height in a range of about 15 to 25 mm) in this region. This height range permits sufficient movement of the foam cushion. The height of the clip is measured, as indicated in FIG. 54, from the boundary of the area used to attach the flexible clip to the rigid clip, to the boundary of the area used for attachment to the foam. Although an 'L' cross sectional geometry is illustrated, in some versions, a 'C' shaped geometry may be configured in this area, but would result in an increase in overall mask footprint.

The indicated thickness and height of the clip will define a height to thickness ratio for this section of the periphery of the clip of between 10 and 100.

5.4.2.3.2 First Clip Interfacing

In some versions, the flexible clip may include a lip seal 5550, such as the examples illustrated in FIGS. 55 and 56. The lip seal serves as a portion of the flexible clip that seals the flexible clip with the mask frame. Thus, the lip seal 5550 is used between the flexible clip and the mask frame to ensure a seal is maintained between the two components. The lip seal may be part of the flexible clip and may extend around an internal periphery of the flexible clip. The lip seal can be flexible. For example, when the flexible clip is coupled to the mask frame, such as with the hard clip attachment features, a more rigid portion of the mask frame may be depressed against the more flexible lip seal to create a tight/effective seal between them. This may result in some movement or displacement of the more flexible lip seal 5550. In other configurations, the lip seal 5550 may be part not of the first support clip 3812 (e.g., flexible clip), but of the rigid second clip 3814 or the frame 3816.

The interfacing between the second clip (or more rigid clip) and the mask frame is also shown in FIGS. 55 and 56. The rigid clip can serve as a hard stop 5551 to prevent the cushion assembly with the flexible clip from being pushed too far into the mask frame. Thus, the rigid clip may assist with ensuring proper alignment of the lip seal 5550. An incorrectly assembled cushion could lead to leaks through the lip seal, the mask frame protruding too far and contacting the patient, move the headgear attachments on the mask frame too far and causing contact with the patient.

The performance characteristics (how it behaves under load, e.g., increase/decrease in sealing force) can be altered in the individual sections of the flexible clip by modifying any one or more the following: material properties, soft clip thickness, overall flexible clip height and width and/or soft clip geometry.

5.4.2.3.3 First Clip Materials

Generally, unlike the foam cushion which may be permeable to air, the first clip is typically not made of foam and can itself be air impermeable or impermeable to air. The first clip is considered "flexible" or "soft" in that it may be flexible in use or made from an elastic material that will deform under load. This includes but is not limited to, silicone, TPE, TPU and natural rubbers.

TPE material is desirable as it has a higher potential to be adhered to/moulded to the foam and/or the rigid clip.

5.4.2.3.4 First Clip Manufacture

The manufacturing process for the flexible clip may include injection moulding. It may be moulded with any one or more of the following techniques. It may be moulded as a separate component. It may be overmoulded onto another component or components such as any one of the hard clip, mask frame and foam cushion. For example, it may be moulded to both the foam and the hard clip.

Depending on the manufacturing process, if the flexible clip is manufactured as a separate component, it could be assembled to the hard clip by one or more techniques. For example, it may be adhered such as with an adhesive, glue or tape. It may be assembled by flame lamination, ultrasonic welding, injection moulding, such as a 2K or two-shot injection molding process that employs multiple (e.g., two) different polymers by a single injection moulding process.

5.4.2.4 Second Clip (e.g., Hard Clip)

As illustrated in FIGS. 56 and 57, the optional second clip 3814, which may be more rigid with respect to the flexible clip, can allow for easy assembly and disassembly of the cushion assembly to and from the mask frame. This can permit ease of cleaning of the mask frame and for the replacement of the cushion assembly. While different structures may serve as the mechanism for attachment of the rigid clip to the mask frame, FIGS. 56 and 57 represent an example in which a plurality of retaining features (e.g., snap elements 4024 or clips) lock to respective surfaces of the frame and abuttingly support the rigid clip (as well as the entire cushion assembly), to the frame. These features of the retention mechanism have been described with reference to FIG. 40. Alternative assemblies are also possible.

Generally, the second clip 3814 allows for a harder interface between the flexible clip/foam assembly and the mask frame. Whilst the use of the hard clip may increase usability, it is not essential for the operation of the mask. Alternate attachment mechanisms can be used to attach the cushion assembly to the mask frame. Similarly, a mask assembly may be designed that may not necessarily include a support clip that is not flexible. As mentioned earlier in the text, the use of a larger amount of foam will be necessary in such a case.

An alternative assembly mechanism between the foam cushion and the mask frame, some of which do not include rigid or even flexible clip, may include a tongue and groove geometry between the flexible clip and the mask frame.

In some versions, a portion of the flexible clip may be configured to attach to the mask frame by stretching and gripping a coupling edge of the mask frame. In some examples, the he flexible clip may be configured for coupling with the mask frame or rigid clip by an interference fit similar to air-tight food containers. In some versions, the flexible clip and the mask frame may have a tongue and slot interface between them and a secondary lip seal or gasket may be present to prevent air/pressure leak. In some versions, the cushion assembly may be permanently attached to the mask frame. In some versions, an adhesive, such as an adhesive tape, may be employed between the cushion assembly and the mask frame.

The rigid second clip can provide structural integrity to the cushion assembly due to the soft/flexible nature of the flexible clip and foam cushion. The rigid clip can also allow the cushion assembly to maintain its shape even when disassembled from the mask frame.

5.4.2.4.1 Second Clip Materials

The hard clip can be made of any suitable rigid material. For example, the second clip may be made from a rigid thermoplastic material. Such materials may include, for example, acrylonitrile butadiene styrene (ABS), Nylon and/or Polycarbonate.

The second clip may, for example, be manufactured by injection moulding.

4.4.3 Supra Nasal Sealing Additional Examples

Figure 70:
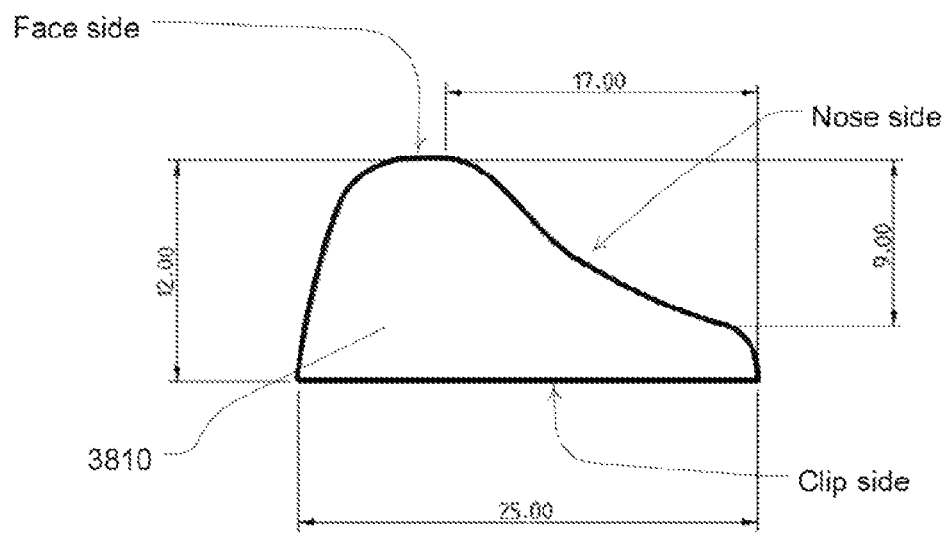

Another example foam mask of the present technology may be considered with reference to FIGS. 69 to 86. The mask may be suitable for sealing around the mouth and over the nose. The foam cushion 3810 is illustrated in FIG. 69. The cross section geometry of the cushion may be generally trapezium in shape with the corners contacting the patients face rounded for comfort. This generally trapezium shape provides stability. As shown in FIG. 70, the flat contact surface has been partially removed to form a nasal recess 6912 adapted to receive a user's nose and reduce the pressure applied by the mask to the nasal bridge area. The height of the recess (in a vertical direction parallel to the nose height) can be about 17 mm. (See cross-section of FIG. 70.) In some versions, it can optionally be any height up to the width of the foam, e.g. 25 mm). Moving from vertical (the direction along the length of the user's nose) to horizontal direction (the direction of the width of the user's nose), the recess gradually decreases until the recessed surface starting from point 6910A joins the non-recessed surface at point 6910B. The width 6910C of the recess in the horizontal direction is between about 10 and 35 mm, but may be about 20-25 mm. A well designed recess allows for the user's nose to be hugged by the foam. This increases the mask stability in the region. An increase in the width of the recess can provide additional relief/comfort to the user, but it will have the adverse effect for sealing and stability. The depth of the recess is about 9 mm but it can be in a range up to the full height of the foam, e.g., 9 mm). An increase in the depth of the recess will provide improved visibility and additional relief/comfort to the user, but may adversely affect the overall durability of the foam cushion.

The cross sectional geometry of the foam in the side of nose and mouth region may be that of any of the cushion versions described in this specification. However, there may also be a smooth transition between the new nasal bridge and side of nose regions. The recess may be manufactured concurrently with a compression cutting process for the foam cushion, but it can also be formed during a secondary process by, for example, additional compression cutting, thermoforming and/or grinding.

5.4.3.1 First Clip (e.g., Flexible Clip)

Similar to the prior examples, the mask may include a first clip (e.g., soft/flexible clip) having cross sectional geometries that vary by region of the clip (e.g., nasal bridge region FC-NBR, sides of nose region FC-SNR, sides of mouth region FC-SMR and bottom of mouth region FC-BMR.) Example cross sectional geometries of each of these regions are shown in FIGS. 71, 72, 74 and 75 respectively.

A. Flexible Clip Nasal Bridge Region

The formation of a recess in the foam cushion can be complemented with a reduction of the width of the flexible clip surface supporting the foam cushion in the nasal bridge region. The reduced support increases the compliance and allows the cushion to roll-in, when a pressure is applied, thus further improving the user's comfort in the nasal bridge area.

Figure 71:
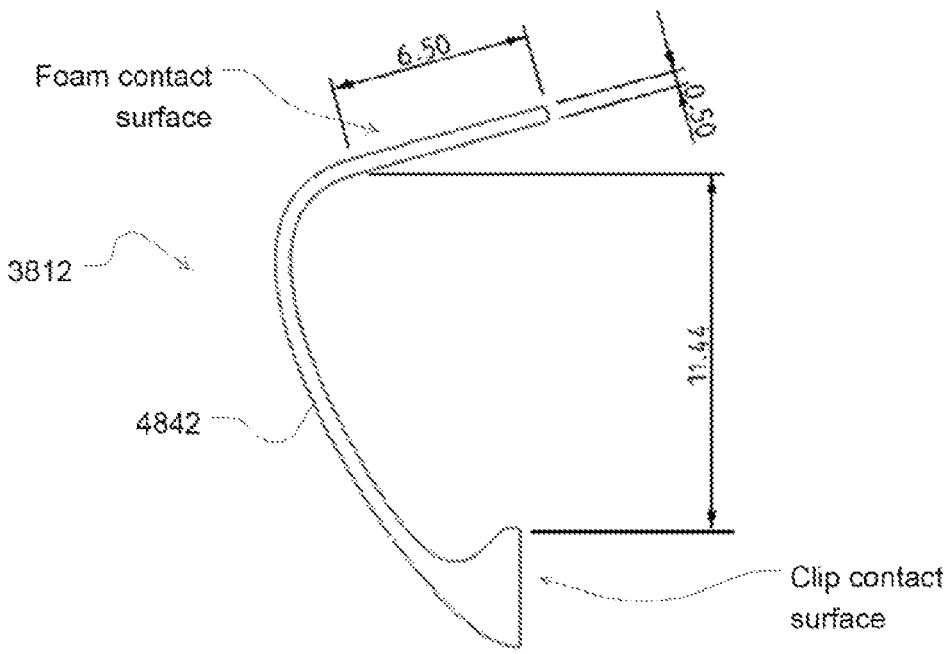

The cross section shown in FIG. 71 of this region of the periphery of the clip is generally 'L' shaped and allows the foam to move substantially perpendicularly to the user's face to accommodate a wide range of nasal bridge depth. It forms the softest (i.e., most flexible) part of the clip and has a thickness (support portion 4842) of about 0.5 mm (but may suitably be a thickness within a range of about 0.25-1.5 mm). The flexibility may be manifested in the flexing of support portion 4842 and the angular movement between support portion 4842 and the portion having the foam contact surface. In this example, the support portion has a height of about 11.44 mm but may suitably be a height within a range of about 8 mm-20 mm. Furthermore, the foam contact surface may be for example about 6.5 mm in width but may be a width in a range of about of about 3-12 mm. This can permit the foam cushion to overlap the contact surface since the foam can be wider. The unattached portion of the foam may the flex independently from the clip. In some versions, this cross sectional portion the clip may be 'c' shaped, but would result in an increase in the overall mask footprint.

B. Flexible Clip Sides of Nose Region

As seen in FIG. 73, in the side of nose region at location 7310H, there is an increased overall height of the foam due to the supporting section of the clip on both sides of the nose, compared to the surrounding areas. This can provide better support and improve seal in this specific region.

Figure 72:
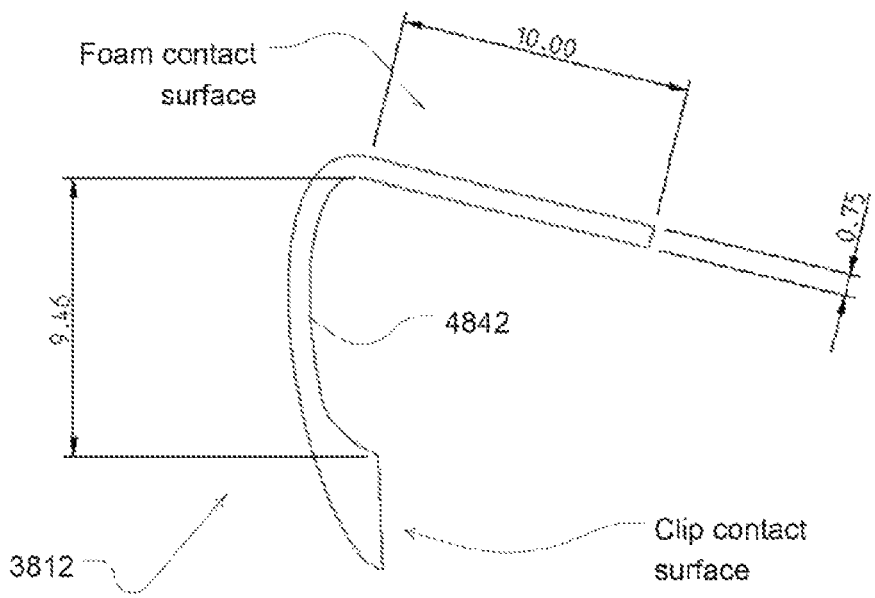

The cross section of the clip in this region of the mask as shown in FIG. 72 is generally 'L' shaped and allows the foam to more easily pivot and match the facial geometry at the sides of the user's nose. The geometry allows the foam contact surface to be parallel to the user's nose. The flexible clip at the support portion 4842 may have a thickness in this region of about 0.75 mm but may be a thickness in a range of about 0.25-1.5 mm.

The height of about 9.46 mm (but may suitably be a height in a range of about 8 mm-20 mm) can give a range of movement necessary to conform to the user's nose. Such a localized increased height in this region allows for, without changing the shape or the thickness of the foam in this region, additional sealing force to be applied to form a better seal around this critical region.

Alternatively, or in addition by combination, to the increased clip height, a similar effect can be achieved through a localised increase at location 7310H in height of the foam cushion in the region of the clip of FIG. 73.

Optionally, a 'c' shaped geometry may be implemented in this region, but would result in an increase in overall mask footprint.

C. Flexible Clip Sides of Mouth Region

Figure 74:
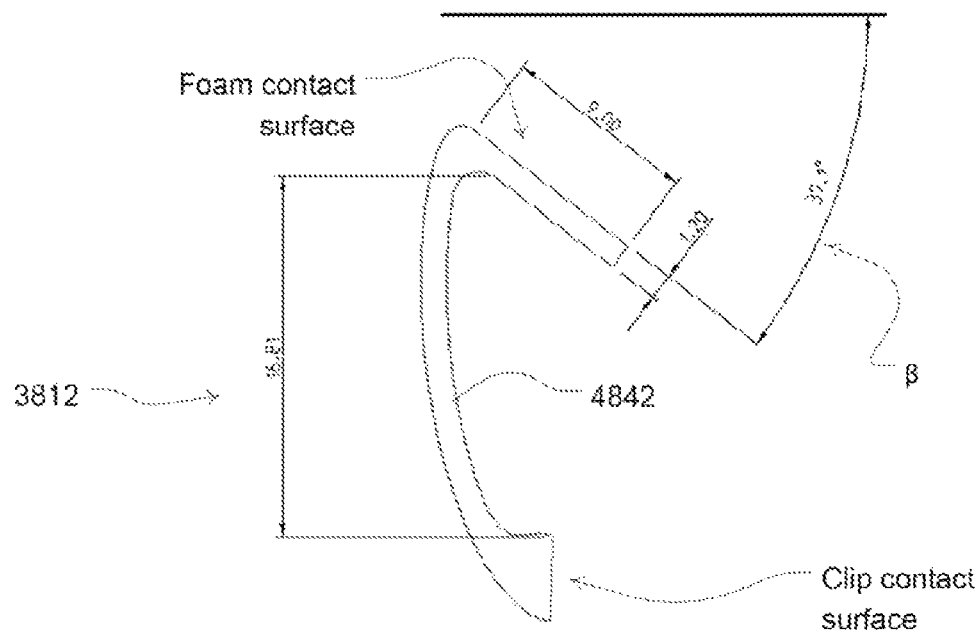

A cross-sectional geometry as indicated in FIG. 74 may be implemented in the sides of mouth region. The region can be configured to have an angle β between a horizontal that is perpendicular to an axis of the supporting portion 4842 and the foam contact surface supporting the foam cushion. This angling permits a roll-in of the foam contact surface inwardly to better hug this region of the face when the foam cushion is applied. It can also improve the overall stability of the system.

This clip cross sectional geometry on both sides of the mouth shown in FIG. 74 is generally 'L' shaped. The large angle α reduces the inward flexing range of the clip and enhances the rigidity of the clip. This allows this section of the mask to better hug the face, effectively forming an anchor point around the sides of the mouth. The rigidity of the flexible clip may be at its highest in this region. Such decreased flexibility in this region of the face may be suitable since it is the least pressure sensitive region of a user. The cross geometry also allows the foam to be pivoted into the user's face to allow for varying facial profiles. The flexible clip and more particularly its support portion 4842, can have a thickness of about 1.2 mm (but may be a suitable thickness in a range of about 1 mm to 2 mm) to provide the desired stiffness. The angle β can be about 37.1 degrees (but may be a suitable angle in a range of about 20-60 degrees).

Optionally, a 'c' shaped geometry design could be used in this area, but would result in an increase in overall mask footprint.

D. Flexible Clip Bottom of Mouth Region

The clip cross sectional geometry shown in FIG. 75 for the bottom of the mouth region is generally 'L' shaped and allows for the flexible clip to roll. The small (close to zero) angle α allows the foam supporting surface to flex. This allows the foam to move upwards and downwards relative to the face (left and right with respect to the illustration of FIG. 75) whilst maintaining a parallel top sealing surface with respect to the user's face. This feature allows for movement of the user's jaw without a loss in seal (e.g., jaw drop during usage). The flexible clip can have a thickness of 0.75 mm (but can suitably have a thickness in a range of about 0.25 mm-1.5 mm). The roll-in action is aided by the smooth rounded internal surface RIS and a height of about 14.21 mm (but may have a suitable height in a range of about 12-25 mm).

Optionally, a 'c' shaped geometry could be implemented in this region, but would result in an increase in overall mask footprint.

5.4.3.2 Second Clip (e.g., Rigid Clip)

Similar to the other versions, the flexible clip as shown in FIG. 76 has a lip seal 5550 that, when the flexible clip is attached to the hard clip, overhangs an edge 7660 of the hard clip (e.g., second clip 3814). The overhanging engagement is such that this peripheral lip seals against the hard clip edge. The angle G the lip seal makes to the horizontal is can be small (e.g., about 5 degrees (with a suitable angle range of about 0 to 20 degrees). This ensures that, when the frame is assembled to the cushion, the lip seal will always be under tension as it is depressed against a more rigid mask frame portion 7662, which improves the sealing engagement and minimizes the change of potential buckling in the lip seal.

The engagement of the soft and hard clips is such that an engagement rib 7664 of the hard clip is received in an engagement groove 7666 of the mask frame. There are a number of points along the engagement groove where stop points 7668 are formed to limit the insertion of the engagement rib into the groove. The hard stop can be a continuous ridge or a set of points localized to a number of positions (e.g., 6) about the periphery of the frame. They can be arranged such that, when the clips are in the engaged configuration, the engagement rib abuts against some or all of these stop points and is prevented from entering the engagement groove any further. Apart from limiting the insertion in a vertical direction, the hard stop points may also constrain the horizontal movement of the frame to cushion assembly. This is achieved by at least one, preferably several, of the hard stop points having a recess that receives the engagement rib. As the width of the opening is arranged to tightly receive the rib 7664, the arrangement limits the movement of the clips in horizontal direction.

As seen in FIGS. 77 to 82, a top attachment snap element 8010-1 can be engaged to the respective frame opening 8012. One way is to pivot the entire clip assembly so that the snap element 8010-1 at a top locking edge of the clip is pivotably inserted in the respective frame opening 8012. This requires minimal effort on behalf of the user. The entire clip assembly is then pivoted back to be parallel to the frame and the lower part of the clip/cushion is depressed against the frame until the bottom snap element 8010-2 clicks into engagement with the respective frame engagement portion. Alternatively, the entire clip assembly may be aligned in parallel and depressed against the frame until both the top and the bottom snap elements of the clip assembly engage with the frame. The engagement of the top attachment in this case requires a slightly larger force which is arranged to be approximately equal to the top headgear tension. Because of that, in the event the top attachment has not been fully engaged during assembly, it will self-engage as the user puts on the mask.

The bottom snap element 8010-2 forms the main interface the user will manipulate during disassembly, and it is sized so a finger can comfortably operate the mechanism. As best seen in FIG. 81, the bottom snap element 8010-2 on the hard clip has two rounds leading to taper edges which increases usability as that will act as lead ins to the corresponding receiving slot 8014 on the mask frame.

In this version, the engagement mechanism (receiving slot 8014) in the frame does not run fully across the bottom, this is specifically designed so during disassembly the user can slide their finger downwards while maintaining full contact with the hard clip.

5.4.3.3 Foam Mask Assembly Operation

Operation/performance of the example masks may be considered in reference to FIGS. 83 to 86. The performance areas around the periphery of the cushion assembly of FIG. 83 include nasal bridge region ZA, Sides of nose region ZB, upper cheek region ZC, sides of mouth region ZD and bottom of mouth region ZE. The design intent of the cushion in terms of how it reacts to a user's face is further described herein.

The cushion is configured to apply a different amount of load or reaction force to individual regions of a user's face. The nasal bridge region ZA is the least loaded as it is the most sensitive region. Then there is an increase in loading in regions ZB and ZC as a more robust seal in this region would decrease the likelihood of leak into the user's eye. In comparison, region ZD and ZE is the most heavily loaded and acts to anchor the cushion to a user's face. There may be uniform loading across regions ZD and ZE, but this can change due to individual user's facial profile.

The cushion has a pivoting motion as the top and bottom headgear straps are tightened or loosened. The approximate pivot axis is shown with the arrow of FIG. 84. By tightening the top head gear straps regions ZA, ZB and ZC pivot into the user's face, and region ZD) and ZE pivot away. When the bottom straps are tightened region ZA, ZB and ZC pivot away from the user's face and region ZD and ZE pivot into the user's face. The inverse will happen with the loosening of the top and bottom headgear straps.

FIG. 85 provides an approximate indication of the relative pressure/reaction force in the various respective regions of the mask. The arrows indicate the pressure/force applied by the mask to the user's face, when the headgear is tensioned to support the mask on the user's face. The different sizes of the arrows indicate the relative pressure differences in each respective region. Thus, the mask may be configured (for example by virtue of the characteristics of the clip(s) and/or foam cushion) to apply different reaction forces in different regions of its patient contact surfaces. In the illustrated example of FIG. 85, the mask is configured for smaller forces to be applied in the upper regions of the mask (e.g. the sensitive nasal bridge region ZA, sides of nose region ZB and/or upper cheek region ZC). The mask may be configured for greater forces to be applied in lower regions of the mask (e.g., sides of mouth region ZD and/or bottom of mouth region ZE). In this example, the mask is configured for the smallest force at the nasal bridge region ZA. These forces may typically be symmetric from side to side of the image of FIG. 85 (e.g., approximately the same on the left side as the right side in the respective regions). Other force distributions/variations may also be applied.

As discussed earlier in the text, the cushion may also exhibit a roll-in effect as it is applied to the user's face. As region ZA is depressed by the user's nose bridge, region ZB can roll into the sides of the user's nose, which acts to increase the compliance of the cushion's seal to the user's face. As region ZE is depressed by the user's chin, region ZD rolls into the sides of the user's mouth, forming a more effective anchor as it wraps around the user's face.

FIG. 86 shows approximate roll-in response in the respective regions of the mask. The arrows indicate the relative extent of the roll-in response when the headgear is tensioned to support the mask on the user's face. The difference in size of the arrows indicates the relative difference in roll-in in each respective region.

Thus, the mask may be configured (for example by virtue of the characteristics of the clip(s) and/or foam cushion) with different degrees of roll-in in different regions of its patient contact surfaces. In the illustrated example of FIG. 85, the mask is configured for greatest degrees of roll-in to be applied in the sides of nose region ZB and/or sides of mouth region ZD, which may be approximately the same. The mask may be configured for smaller degrees of roll-in to be applied in other regions (e.g., nasal bridge region ZA, upper cheek region ZC and/or bottom of mouth region ZE) which may be approximately the same. These roll-in forces may typically be symmetric from side to side of the image of FIG. 85 (e.g., approximately the same on the left side as the right side in the respective regions) However, other force variations may also be configured.

The degree of roll has been intentionally modified to assist with the comfort and with the efficient sealing of the mask. There are a number of ways to achieve a specific degree of rolling.

Generally, around the periphery of the cushion interface, the plane on which the foam cushion sits, may be angled inwardly to the users face at different angles in a manner to promote degrees of roll-in. Some areas (such as sides of mouth) have a more significant angle in order to facilitate a greater roll-in affect.

The flexibility of the soft (e.g. TPE/Silicone) clip to which the foam cushion is assembled is, broadly, shaped as a right angle beam, hence allowing for inward roll (intended via the inwards angling as described above).

The flexible clip material is selected to be flexible and compliant which can also allow for inwards roll (per the intention and descriptions above).

The degree of support to the foam provided by the underlying flexible clip surface can be changed by ensuring that the supporting surface of the flexible clip extends only partially under the foam surface. Thus, some of the foam surface, usually on the inner side of the mask, can be unsupported (i.e., the foam overhangs the flexible clip). When pressure is applied to the foam, the unsupported surfaces may give-in and facilitate the roll-in effect.

Thus, in some examples, the foam cushion assembly can have parameters that vary in at least some sections of the periphery of the clip and/or assembly, such as:

Spring constant of the clip and/or the foam cushion;
Cross-sectional profile of the clip and/or the foam cushion;
wall thickness of the clip;
The angle of the contact surface to which the cushion is attached;
The overhanging of the cushion with respect to the supporting contact surface; and/or
Foam thickness.

4.4.4 Further Optional Foam Mask Features

As previously described, masks may be implemented with a foam cushion whether they are above or below the nose masks as previously described or even nasal only masks. Generally it is desirable to achieve a mask with maximum comfort and compliance/seal performance. Various foam seal forming cushions configurations may be configured to achieve this desire. However, when designing a comfortable foam cushion, there are other trade-offs to consider. One such trade-off is permeability, which is closely associated with the foam's softness and compliance. For achieving desired seal and comfort, a relatively thick layer of foam on the mask can be implemented. Apart from being more heavy and obtrusive, a large layer or foam, even of limited permeability, could be associated with an increased leak and compromise the provided pressure therapy. To address the issues with size and permeability, some versions of the present technology as previously mentioned can employ a flexible intermediary structural component (e.g., clip(s)) between the foam layer and the frame. Such a structure, such as the above described flexible clip(s), attaches to the foam seal forming layer. The balance of rigidity and flexibility of such an intermediary structure (e.g., a flexible clip) can be chosen so that it can serve as a substitute for some of the foam cushion. Thus, a less bulky foam layer can be used. In addition, the clip is generally formed of a non-permeable material. Because of that, and because of the specific concave configurations, discussed earlier in the text, a portion of the clip covers at least a portion of the foam cushion and may reduce the overall leak associated with the foam cushion. The flexible clip may then maintain the benefits of support and compliance, while minimising leak. Some additional optional features of the intermediary structure(s) may be considered with respect to achieving some of the goals of the previously described flexible clips.

5.4.4.1 Clip Flexibility

One disadvantage of simply providing a foam seal forming layer to a hard clip or a frame/shell of a mask is that it has a risk of bottoming out on the hard/rigid portion. Bottoming out occurs when the foam is compressed to such a degree that the patient starts to feel the rigidity or hardness of the underlying clip or frame/shell of the mask. To address this issue, some examples described throughout this specification introduce a soft/flexible clip that flexes under pressure applied to the mask. The arrangement is such that the flexibility and the compliance of the flexible clip compliments that of the foam layer to improve the overall compliance of the mask.

However, the flexibility nature of these flexible clips need not necessarily be a consequence of particularly flexible materials. For example, the function of the flexible clip may be achieved with a semi-rigid or even rigid clip or mask frame/shell instead to which the foam is applied. In such cases, the flexible response may be introduced by structural features, such as locally thinned or profiled sections, that may form a hinge or gusset on a rigid clip or frame to which the foam is attached. Thus, the foam seal forming layer may be directly attached to a rigid clip that has been designed to have flexible sections with structurally introduced compliance in locations where compliance is needed. Thus, the flexible support clip may be formed by a rigid material and the flexibility may be induced by way of introducing one or more compliance regions, such as by introducing one or more lines of weakness or one or more regions of weakness.

Figure 58:
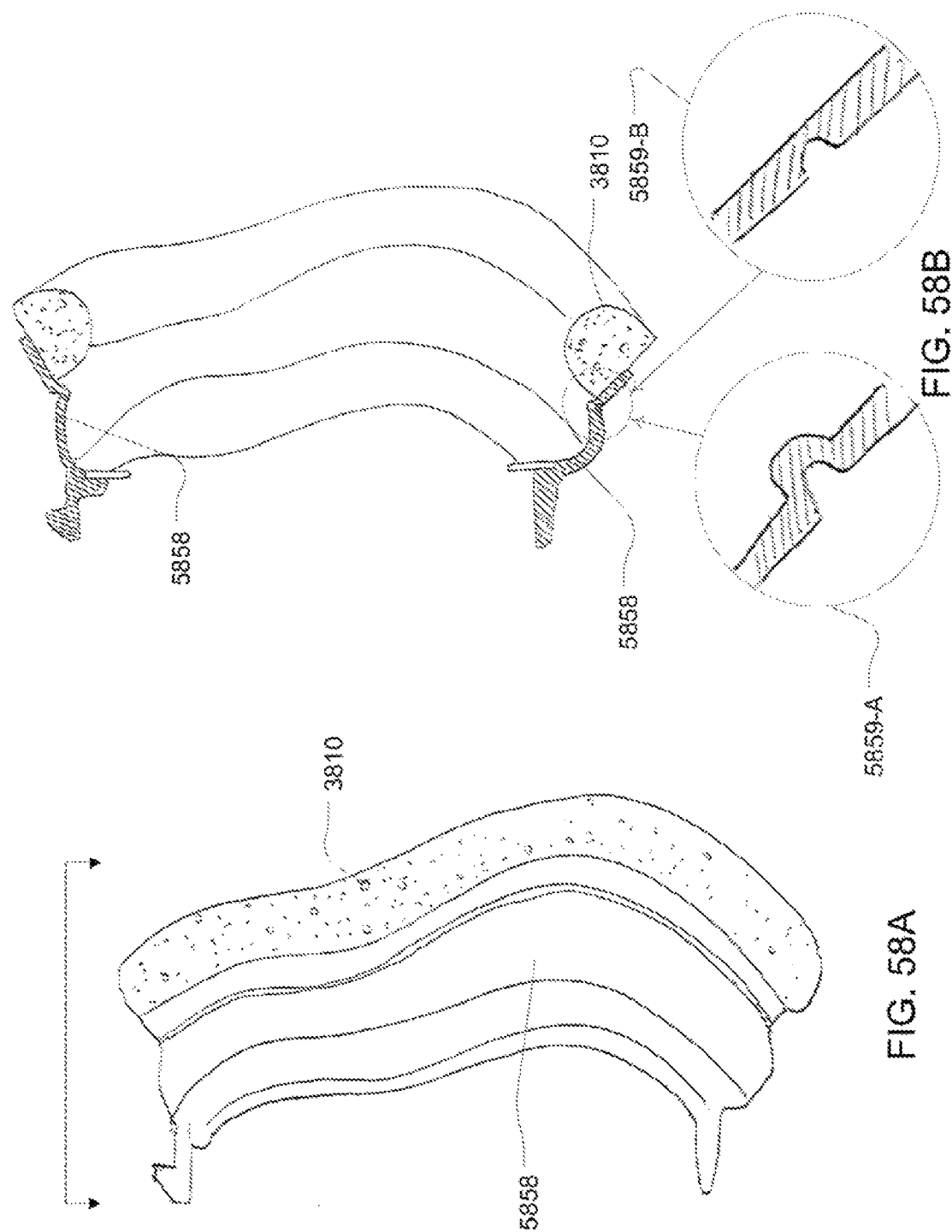

Two different examples of such a configuration are illustrated with respect to FIGS. 58A and 58B. FIG. 58B shows a cross section of the foam cushion assembly of FIG. 58A with a foam cushion 3810 and a rigid clip 5858. The rigid clip 5858 may then attach to a frame (not shown in FIG. 58). This rigid clip 5858 is flexible in that it has structural features designed to promote flexing. As shown in FIG. 58B, the wall of the clip includes a profile to implement a gusset at 5859-A, but the thickness of the wall has not been changed. The other example shown at 5859-B introduces one or more lines of weakness around the periphery of the clip, where the wall is thinner. Each line can be a continuous line or an interrupted one, e.g., a series of weak spots. In such cases, the result can be an increased level of flexibility of wall of the rigid or semi-rigid clip or frame. These structural features can also be implemented to modify the flexibility and the spring constant of an already flexible clip such as any of the clips described throughout this specification.

Another example for imparting flexibility into an otherwise rigid or semi-rigid mask plenum chamber can be to implement flexing sections defined in the recessed rigid clip 6758 or mask shell. For example, such a rigid clip coupled to a foam cushion 3810 is illustrated in FIGS. 67 and 68. As illustrated, the frame/clip can have one or more regions of weakness introduced by having portions of rigid material removed at one or more clip recess(es) 6770. This allows the rigid clip/shell to compress easier under load. Thus, these recess sections can be positioned at regions of discomfort (such as near the nasal bridge or sides of the nose) where more flexibility or compliance is needed. The recesses may be filled with another flexible (but impermeable) material such as a recess membrane 6772 made of, for example, silicone or TPE. Alternatively, the recesses created by the removed sections may be covered by a single flexible sheet. Such a sheet may, for example represent a silicone membrane attached to the inside of the rigid clip.

5.4.4.2 Clip Alternatives

In various assemblies described herein, a clip is described as an intermediary structure for applying foam to a mask frame. For example, the foam mask design has been described as having a foam seal forming layer, attached to a flexible clip that is subsequently attached to a hard clip. The hard clip is removably attachable to the mask frame. The frame in this case may be a rigid part of the mask that provides some level of shape and support to the mask structure and allows for headgear tension to be transferred to the seal forming portion to seal on the face.

Another configuration of a foam mask may include a flexible shell or chamber made from a flexible material (such as TPE or Silicone). Such an assembly may be considered with reference to FIGS. 61, 60 and 60. A flexible chamber or shell 6160 can serve, in part, as the flexible clip, where the flexibility of the shell provides compliance when pressure is applied to the mask. In this case, a headgear frame 6162, which may include a shell aperture 6163, is fit over the shell 6160 as a separate removable structure made of a rigid material to provide support. Whilst the concave silicone chamber of the shell 6160 can serve in part as the C-shaped flexible clip, one substantial difference is that the flexible shell also more completely forms a part of the mask chamber or plenum chamber 3200. For example, it may optionally include a connection port 3600 for coupling with a gas delivery conduit or circuit 4170 and/or a vent 3400.

Although FIG. 60 shows the shell 6160 version of the clip attached to the foam cushion, in some cases a further intermediary may be implemented such as the examples illustrated in FIGS. 63A, 63B and 59. These versions of the mask assembly implement a foam cushion attached directly to a rigid clip 6314. The rigid clip 6314 may then couple with the shell 6160 or other mask frame with engagement features 6319. The foam may be semipermeable, which is correlated to its softness and breathability. However, a permeable foam layer will leak air and air pressure.

In this case, the shell 6160 or other mask frame, can include an additional flexible member 6320 peripherally positioned inside the mask plenum chamber and configured to cover at least a portion of the foam cushion when the rigid clip is assembled/coupled to the shell or mask frame as shown in FIG. 63B. This flexible member 6320 can be an air impermeable skirt, flap or layer positioned within the mask chamber that moves to engage and cover the inner surface of the foam cushion.

The flexible member 6320 may be a flexible membrane made of, for example, TPE or silicone and may be attached to the chamber forming walls of the mask shell/frame, or to a rigid clip 6314 attached to the mask shell/frame. This flexible membrane forms a flap that is adapted to, at least when under pressure, interact with the foam and cover at least partially the under-surface of the foam layer when pressure is applied to the mask. Preferably, the flap will not interact with the face of the patient. The implementation of such a non-permeable layer enhances the overall quality of the seal, which otherwise may be at least partially compromised by the at least partially permeable foam layer.

This sealing layer (flexible member 6320) can also enhance the air-spring effect within the chamber. As the foam sealing portion overhangs off the edge of the hard clip or frame to which it is attached, any force applied to the flap also acts on the foam sealing portion. Having the non-permeable flexible flap cover the foam under-surface (plenum chamber side of foam), will allow for pressure to build up and push the foam into a better sealing engagement when pressure from a flow generator is applied to the mask chamber.

A variation of the flexible member 6320 is seen further in FIG. 59. In this version, flexible member more completely covers the foam cushion by extending internally beyond the supporting surface of the underlying rigid clip. As such, it also extends to at least partially cover the inner lateral surface of the foam cushion. In this position it may be more affected by the flow through the mask from the flow generator so as to move as illustrated in FIG. 59. The length of the flap may be selected on the basis of how thick the foam layer is and whether contact of the flap with the face is desirable. Thus, it may extend to contact the face in some versions and not in others. Such a membrane may be applied to any of the mask described in this specification to reduce foam air leak (i.e., leak through the foam seal forming layer).

As a general requirement, the contours on the foam layer should maximise comfort and effect a seal by matching a patient's facial profile or facial contour. Thus, the foam seal forming layers may preferably be configured into a desired 3-dimensional (3-D) or desired facial profile.

In one example, the flexible clip is moulded to the desired 3-D shape or facial profile so as to impart this shape to a generally flat foam seal forming layer when it is attached to the foam. Alternatively, a 3-D shaped hard clip can impart 3D shape (e.g., a facial contour) to the flexible clip and the foam sealing layer attached to it.

FIGS. 64, 65, 66A and 66B illustrate additional mask examples that show alternative methods to give the foam a desired shape. One such example is to provide one or more rigid over clips that squeeze or clamp the foam cushion into a desired three-dimensional (3D) profile such as when snapped or snap fit into a foam support component such as a mask frame 3816 or shell with snap elements. For example, it has been shown that a foam seal forming layer with a rounded seal forming surface is desirable. Thus, as shown in FIGS. 64, 65, 66A and 66B, multiple clips (e.g., two separate over clips 6470-1, 6470-2) such as an inner peripheral clip (clip 6470-1 and outer peripheral clip (clip 6470-2), can depress or clamp the opposing peripheral edges/sides of a foam body, to effectively round the patient contacting edges of the foam layer. Alternatively, only one of the illustrated clips can be used or the two clips can be arranged in a single clip.

Figure 65:
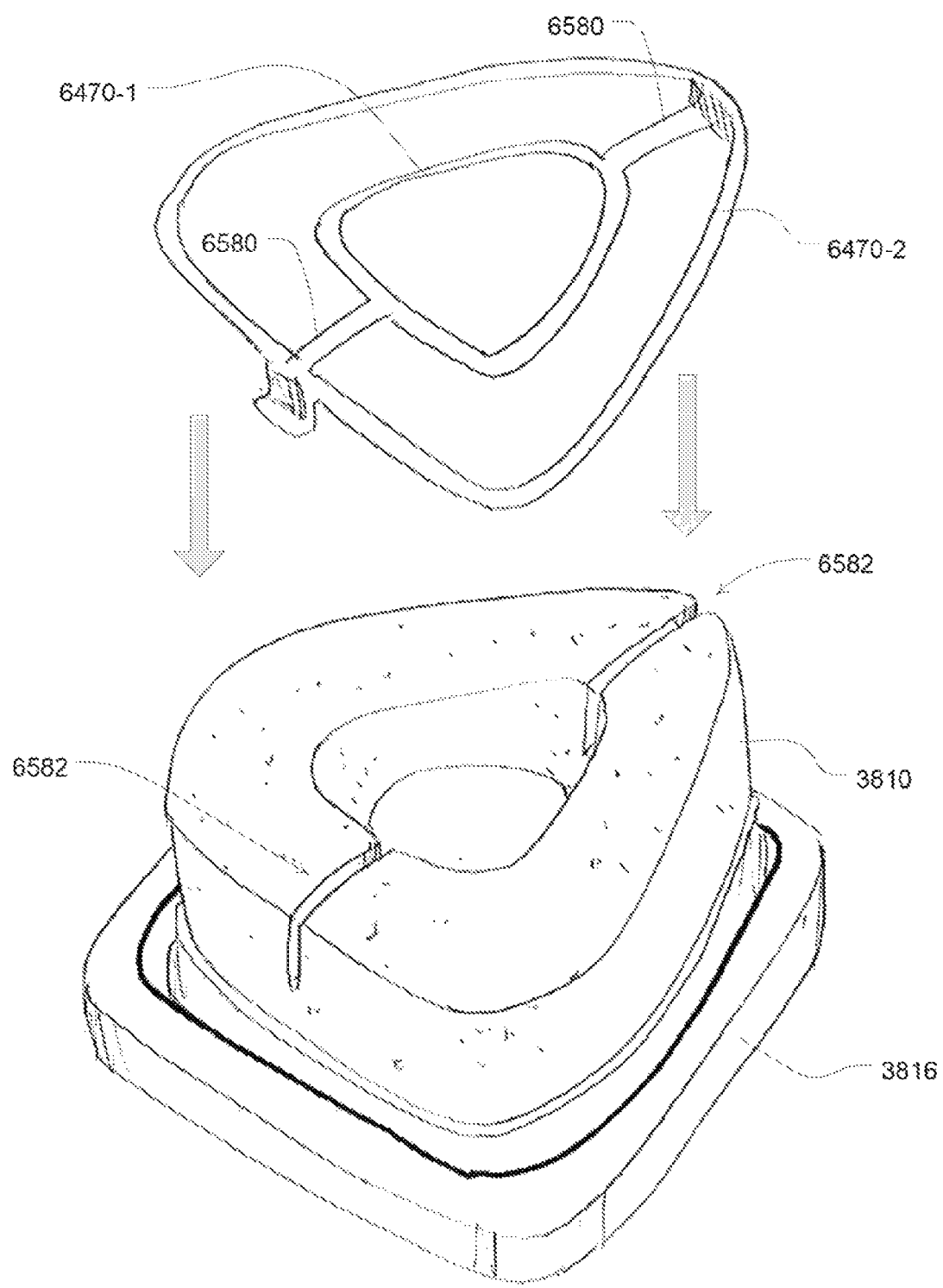
Figure 66A:
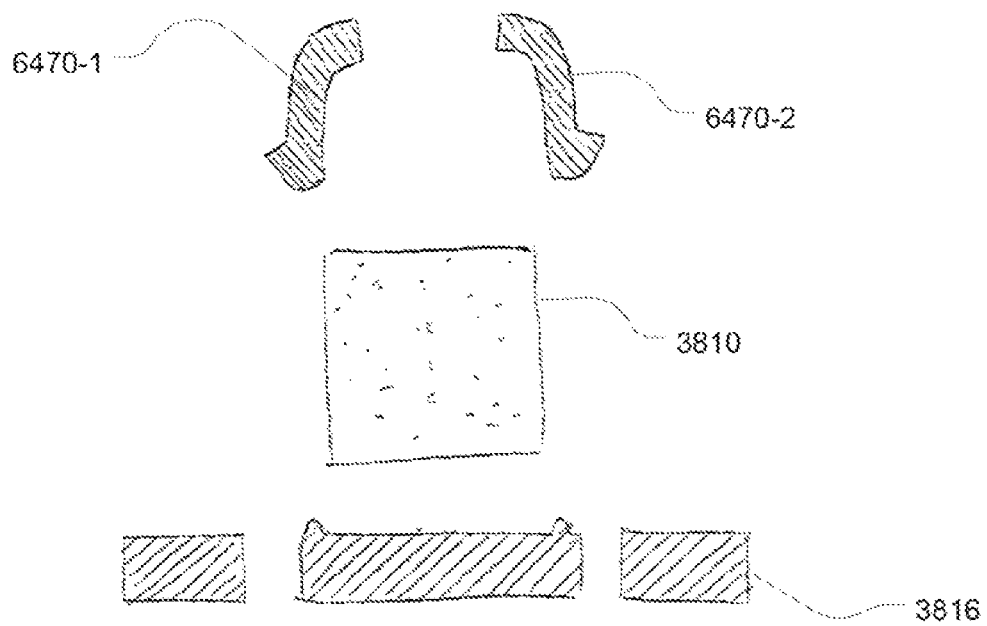
Figure 66B:
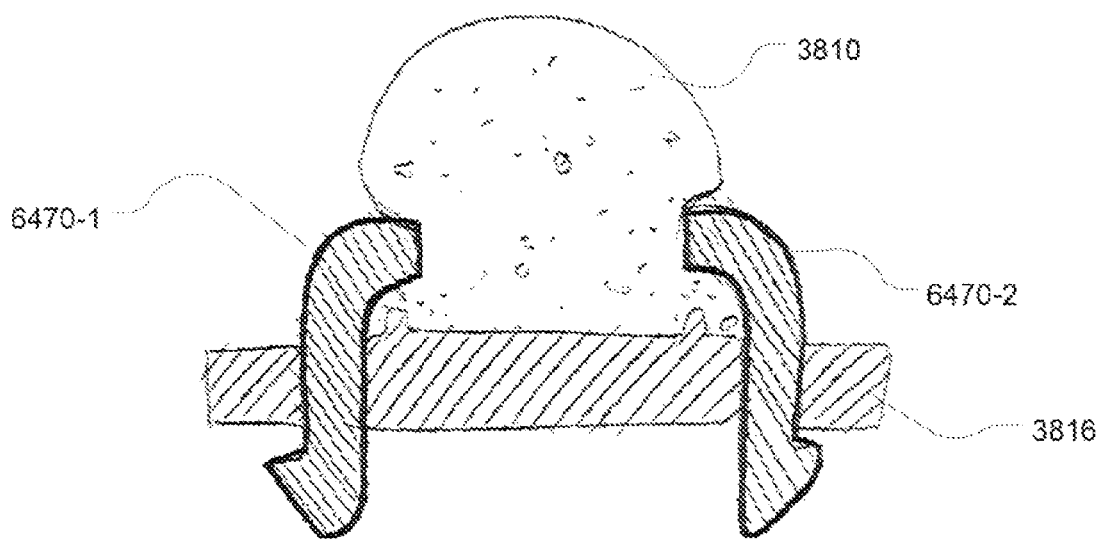

As shown in the example of FIG. 65, the clip 6470 may have one or more over-clip portions 6580 to squash not only the edges, but also one or more top or internal portions of the foam layer toward the mask frame 3816, shell or other mask assembly structure. For example, as illustrated in FIG. 65 at the nasal bridge and in the middle of the lower lip area optional slits 6582 partially through the top side portion of the foam serve as channels for the clip 6470. As a result, the foam may bulge is certain portions and be pressed down in other portions of the mask. This may enhance the compliance and/or comfort of the foam seal forming layer.

Alternatively, one or more of the illustrated over-clip portions can have a 3-D shape (e.g., facial contour), which can provide the same effect (allow the foam to bulge in certain areas and press the foam down in other areas).

5.4.5 Further Foam Cushion Characteristics

Although the cushions described for masks herein may be implemented with many different foam materials, foams with certain performance properties may be particularly well suited when implemented for respiratory treatments given the critical need to promote patient compliance and to ensure effective delivery of medical treatments. In this regard, particularly suitable foams may be characterized by any one or more of its permeability (Liters/min), indentation hardness (Newtons (N)), compression stress strain (Kilo-pascals (Kpa)), density (kilograms per meters$^3$ (kg/m$^3$)), dynamic coefficient of friction (calculated friction (cf)), compression set (percent (%)), tensile strength (Megapascal (Mpa)), elongation @ break (Percent (%)) and/or tear strength (Newtons/millimeter (N/mm)).

5.4.5.1 Permeability

For example, the foam cushion may be configured to have a particular permeability characteristic. The permeability characteristic of the foam may be a measure of the rate of air flowing through a given sample in Liters/minute. Such permeability may be determined by the following permeability test. A test piece can be cut from a piece of foam with a die or a sharp knife into an annular shape (i.e., a ring-shaped geometric foam sample or square sectioned toroid). The test piece is cut nominal to the cell rise direction from a foam sample manufactured at least 72 hours prior. The ring has a height of 25 mm (plus or minus 1.0 mm) from the bottom of the ring to the top in the cell rise direction. The inner open cylinder of the foam ring has that height and a diameter of 70 mm (plus or minus 1.0 mm). The outer edge of the foam ring has a diameter of 110 mm (plus or minus 1.0 mm). Test pieces are free from skin voids and densification lines. The test piece will be in good condition without any visible defects such as burrs, delaminating, tears etc. The test then measures the air flow through the annulus of the foam ring having its constant cross section. The circular shape ensures the pressure is evenly distributed and the foam inflates uniformly. The foam test ring is conditioned, undeflected and undistorted, for at least sixteen hours in an atmosphere of temperature at 23±2° C. and relative humidity at 50±5% prior to testing. The ring may be compressed between plates in a manner to reduce the height of the ring from 25 mm to 17.5 mm during flow testing. A constant air pressure of 20 cmH2O, such as from a flow generator, is applied to the center of the foam ring. Air flow through the ring from the center outward across the foam is then measured with a flow meter in liters/minute. Foam cushions suitable for the present technology may have a permeability characteristic in a range of about 0 to 20 L/m and may preferably have a permeability characteristic in a range of about 0 to 3 L/m.

5.4.5.2 Indentation Hardness

The foam cushion may be configured to have a particular indentation hardness (IDF) characteristic. This characteristic relates to the firmness or stiffness of the material. This characteristic has a significant correlation to comfort, seal and stability needs. Generally, the lower the IDF—the softer the material. Testing may be in general accordance with BS EN ISO 2439: 2008 (method C)—determination of 40% indentation hardness check by compression of samples by 40% of its thickness and recoding the maximum force (N). Foam cushions suitable for the present technology may have an indentation hardness (IDF) characteristic in a range of about 110.48 to 303.11 N, and may preferably have an indentation hardness (IDF) characteristic in a range of about 122.76 to 275.55 N, and still further may more preferably have an indentation hardness (IDF) characteristic in a range of about 143.1-198.88 N.

5.4.5.3 Compression Stress Strain

The foam cushion may be configured to have a particular compression stress strain characteristic. This characteristic relates to how the foam material deflects under stress or load. This characteristic has a significant correlation to comfort, seal and stability needs. The compression stress-strain may be determined in accordance with BS EN ISO 3386: 1997+A1:210. The test speed may be 100 mm/minute. Stress at a compression of 40% may be calculated. Foam cushions suitable for the present technology may have a compression stress-strain characteristic in a range of about 2.32 to 7.26 Kpa, and may preferably have a compression stress-strain characteristic in a range of about 2.574 to 6.6 Kpa, and still further may more preferably have a compression stress-strain characteristic in a range of about 3.15 to 4.29 Kpa.

5.4.5.4 Apparent Density

The foam cushion may be configured to have a particular density characteristic. This characteristic relates to the weight, firmness, "plushness" or tactile "feel" of the material. This characteristic has a significant correlation to comfort, seal and stability needs. The apparent density may be determined in accordance with BS EN ISO 845: 2009. Using measured dimensions (mm) and the weight (g) the density ($kg/m^3$) can be calculated. Foam cushions suitable for the present technology may have a density characteristic in a range of about 24.3 to 117.85 $kg/m^3$, and may preferably have a density characteristic in a range of about 27 to 107.14 $kg/m^3$, and still further may more preferably have a density characteristic in a range of about 50.76 to 66.11 $kg/m^3$.

5.4.5.5 Dynamic Coefficient of Friction

The foam cushion may be configured to have a particular dynamic coefficient of friction characteristic. This characteristic relates to comfort on face and perception of comfort in the hand. This characteristic has a significant correlation to the surface feel or texture of the material. This characteristic has a moderate correlation to seal and stability as a result of relationship between the patient's skin and surface finish of the material. The dynamic coefficient of friction may be determined in accordance with BS EN ISO 8295: 2004. Test pieces may be tested under a load of 1.96 N and a speed of 30 mm/minute on a glass substrate at a temperature of 37 C to 39 C. Force readings may be measured and friction calculated. Foam cushions suitable for the present technology may have a dynamic coefficient of friction characteristic in a range of about 1.86 to 19.12 CF, and may preferably have a dynamic coefficient of friction characteristic in a range of about 2.07 to 17.38 CF, and still further may more preferably have a dynamic coefficient of friction characteristic in a range of about 2.43 to 2.97 CF.

5.4.5.6 Compression Set

The foam cushion may be configured to have a particular compression set characteristic. This characteristic relates to the ability of the foam to recover to its original state post compression and conditioning. If the foam has high/poor compression set it will no longer act as a dynamic seal. If the foam has no compression set, coupled with a strong resilience to deterioration, it will be useable for a long period. The compression set may be determined in accordance with BS EN ISO 1856: 2001. Test spacers may be selected to give a compression of nominally 50% and 75% to each specimen. Compression may occur for a period of time (e.g., 22 hours) at certain temperature and relative humidity (e.g., 22 hours at 23 C (plus or minus 2 C) and 10% R.H.; and 22 hours at 70 C (plus or minus 1 C). After unclamping the test specimens, they may be allowed to recover for 30 minutes at 23 C (plus or minus 2 C) before being re-measured and the compression set % being calculated. Foam cushions suitable for the present technology may have a compression set characteristic in a range of about 0.16 to 17.3%, and may preferably have a compression set characteristic in a range of about 0.18 to 15.73%, and still further may more preferably have a compression set characteristic in a range of about 3.06 to 4.4%.

5.4.5.7 Tensile Strength

The foam cushion may be configured to have a particular tensile strength characteristic. This characteristic relates to the force required to break the foam. This has a moderate correlation to stability and seal. If the cushion has poor tensile strength, it will fail causing leak and poor stability. The tensile strength may be determined in accordance with BS EN ISO 1798: 2008 at a tensile test speed of 500 mm/minute. Load may be recorded and the elongation may be determined by laser extensometry. Foam cushions suitable for the present technology may have a tensile strength characteristic in a range of about 0.03 to 0.27 Mpa, and may preferably have a tensile strength characteristic in a range of about 0.036 to 0.242 Mpa, and still further may more preferably have a tensile strength characteristic in a range of about 0.117 to 0.143 Mpa.

5.4.5.8 Elongation ⊚ Break

The foam cushion may be configured to have a particular elongation ⊚ (at) break characteristic. This characteristic relates the foams ability to elongate before failing. This characteristic has a moderate correlation to stability and seal, as per tensile strength. Foam cushions suitable for the present technology may have an elongation ⊚ break characteristic in a range of about 72.9 to 369.05%, and may preferably have a elongation ⊚ break characteristic in a range of about 81 to 335.5%, and still further may more preferably have a elongation ⊚ break characteristic in a range of about 243 to 335.5%.

5.4.5.9 Tear Strength

The foam cushion may be configured to have a particular tear strength characteristic. This characteristic relates to the foams ability to resist tear under tension. There is a moderate correlation of this characteristic to stability and seal, as per tensile strength and elongation at break. The tear strength may be determined in accordance with BS EN ISO 8067: 2008 (method A) at a test speed of 50 mm/minute. Foam cushions suitable for the present technology may have a tear strength characteristic in a range of about 0.07 to 0.69 N/mm, and may preferably have a tear strength characteristic in a range of about 0.081 to 0.627 N/mm, and still further may more preferably have a tear strength characteristic in a range of about 0.225 to 0.297 N/mm.

5.4.6 Further Clip Characteristics

Although the cushion assembly with the clip(s) described for masks herein may be implemented with many different materials, foam and clip combinations with certain performance properties may be particularly well suited when implemented for respiratory treatments given the critical need to promote patient compliance and to ensure effective delivery of medical treatments. In this regard, particularly suitable cushion assemblies may be characterized by a spring constant characteristic.

In this regard, the spring rate of the cushion assemblies of the present technology, which may be perceived as hardness of the cushion assembly, is more than just a sum of its parts. The parts (e.g., flexible clip and foam cushion) work together to produce a final synergetic effect. Both the foam and the underlying flexible clip can be tuned to each other. For example, if the characteristics of one changes, performance of the whole assembly/system changes. Moreover, the spring rate characteristics of the cushion and the clip assembly (e.g., cushion and flexible clip) can be different at set locations. The spring rate, also known as the spring constant or "k value", may be the force produced per millimeter of deformation of a linear spring and may be determined by equation F=kX. For example, the spring rate may be determined by aligning a probe to act at a particular test location of the cushion/clip assembly, and may be perpendicular to the surface of the frame. The probe may be driven into the location (such as at 50 mm/min). The probe may be stopped when the force exceeds some limit (e.g., 10N). The force/displacement results may be recorded and graphed.

In relation to such a spring constant, example mask assemblies of the present technology are illustrated in the table below. These include a flexible clip+foam cushion assembly, denoted with FC and similar to that of FIG. 47; another flexible clip+cushion assembly, denoted by FF, where the clip is being replaced with a contoured block of foam identical to that of the cushion; a further flexible clip+cushion assembly (labelled as K1) is similar to assembly FF but has a sculpted nasal recess, as illustrated in FIG. 69. These measurements were complimented by the measurements of other mask components, specifically, a flexible clip without foam SC, and a reference 25 mm thick foam slab, denoted in the table as "Foam".

Spring constants were determined in various places of the cushion including bottom center, side of mouth region (points "corner 1" and "corner 2" are on the same side of the mouth with about a 0.5 cm offset from each other in lateral direction), cheek bone region and three vertically aligned points along the nasal bridge region (points nasal bridge 1, nasal bridge 2 and nasal bridge 3 are offset with respect to each other with about 0.5 cm in vertical direction). The spring constant data in the table is summarized in Newtons per millimeter (N/mm). The table indicates for the (foam+clip) assembly with a sculpted nasal recess, a greater spring constant in a mouth region (e.g., side of mouth regions) than in a nasal region (e.g., nasal bridge region) and similar spring constants in a nasal region and a cheek bone region. For the flexible clip only configuration (SC), the table indicates similar spring constants in a nasal region and the corners of the mouth region. It further illustrates a greater spring constant in a cheek region than a nasal region (e.g., nasal bridge region) but a lesser spring constant in a cheek region (e.g., cheek bone region) than a mouth region (e.g., sides of mouth region).

The average numbers in the table are averaged over several samples. Each of the minimum and the maximum numbers correspond to a single measurement shown the smallest or the largest value for the particular location, respectively.

4.5 Foam Cushion Mask

In some versions of the present technology, a mask may be constructed, such as without the need for a mechanical clip, by coupling a frame component (e.g., mask fame or mask shell with a plenum chamber) with a cushion, such as a foam cushion, via mechanical and/or chemical bonding between the two coupled element. In some cases, this may eliminate the need for cushion supports (e.g., a mechanical clip component) and may reduce the size of the mask, require fewer parts, enable less costly production, and minimize or remove the need for adhesives.

In one form of the present technology a mechanical interlock may be created by injecting a mask component forming material into a mould which contains a foam cushion. The injected material may, for example, be formed into a frame component, such as a shell of a plenum chamber, while impregnating a specific section or portion of a cushion, such as a portion of cushion-shaped foam. As the injected material cools it may set within the foam creating a significant mechanical bond in and around sub-surface features/cavities of the foam. In some embodiments mechanical keying between the injected material and cushion may assist in strengthening the mechanical interlocking. Other embodiments described herein may employ coupling through adhesives. Such an injected moulding process described herein may permit bonding without additional adhesives.

In some versions of the present technology an integral bond may be created by injecting a material into a mould which contains a foam cushion. The injected material may be shaped into a frame component of a mask, such as a shell of a plenum chamber. In some such example, one or more materials may be chosen such that a chemical reaction will occur between the injected material and a specific area of a foam of a cushion. Upon completion of the chemical reaction, the frame component may be integrally bonded to the foam cushion as a result of the chemical reaction.

Integral bonds may include primary and/or secondary chemical bonds. For example, possible interactions between the foam of a cushion and material of the frame component, such as silicone/urethane copolymers, may include covalent and/or iconic bonds. Secondary chemical bonds, such as hydrogen bonds, Van der Waals bonds, etc., may also occur between the foam of the cushion and the frame component.

In another form of the present technology, a simultaneous chemical and mechanical bond may be achieved by injecting a material into a mould which contains a foam cushion. The injected material may be shaped into a frame component while a chemical reaction between the injected material and a specific area of the foam cushion occurs. Upon completion of the chemical reaction the frame will be integrally bonded to the foam cushion. The injected material may also impregnate a specific section of the foam creating a mechanical bond. As the injected material cools it may set within the

|  | Bottom | Corner 1 | Corner 2 | Cheek Bone | Nasal Bridge 1 | Nasal Bridge 2 | Nasal Bridge 3 |
| --- | --- | --- | --- | --- | --- | --- | --- |
| FC Average | 0.11 | 0.09 | 0.07 | 0.07 | 0.11 | 0.09 | 0.08 |
| FF Average | 0.13 | 0.07 | 0.08 | 0.1 | 0.18 | 0.14 | 0.1 |
| K1 Average | 0.09 | 0.09 | 0.08 | 0.06 | 0.06 | 0.05 | 0.05 |
| SC Average | 0.12 | 0.74 | 0.77 | 0.26 | 0.13 | 0.09 | 0.07 |
| Min SC | 0.11 | 0.51 | 0.58 | 0.18 | 0.11 | 0.08 | 0.06 |
| Max SC | 0.13 | 0.88 | 1.04 | 0.32 | 0.15 | 0.1 | 0.07 |
| Foam Min | 0.06 | 0.06 | 0.06 | 0.06 | 0.06 | 0.06 | 0.06 |
| Foam Average | 0.13 | 0.13 | 0.13 | 0.13 | 0.13 | 0.13 | 0.13 |
| Foam Max | 0.18 | 0.18 | 0.18 | 0.18 | 0.18 | 0.18 | 0.18 | foam creating a permanent mechanical bond as well as the chemical reaction induced bonding.

In some cases where a support structure (e.g., clip, headgear, forehead support, etc.) is implemented, the foam cushion may be bonded, chemically and/or mechanically, directly to the support structure. In some embodiments the support structure may be wrapped in a fabric such as Spandex or Lycra or a foam lamination. The injected material may chemically and/or mechanically bond with the fabric or foam lamination.

In other embodiments an injected material may be used to bond two different materials together so as to form a 'fir-tree' connection. For example, the joining surface of the material of the cushion may be shaped/drilled/formed etc., to include physical burrows/tunnels to receive injected material. In other embodiments the two different materials may be of differing hardness.

FIGS. 87 and 88 provide an example of a full-face mask 9000 made by combining a frame component 9001 directly to a cushion 9002 formed of foam. In use, the cushion 9002 may be arranged to be in direct contact with the patient's skin and surround an entrance to the airways of the patient so as to facilitate the supply of air at positive pressure to the airways. The frame component 9001 of the current example is a shell that includes a nasal channel 9007, as well as an oral channel 9008. The nasal channel 9007 surrounds the nose of the patient, while the oral channel 9001 surrounds the mouth of the patient. The combination of the frame component 9001 and the cushion 9002 may create a plenum chamber 9003. The joining of the frame component 9001 and the cushion 9002 may create a connection surface 9004. The connection surface 9004 may be created through mechanical and/or chemical bonding of the frame component 9001 to the cushion 9002. Due to the nature of the cushion being substantially or permanently bonded to the frame component 9001, there is little or no uncontrolled air leakage at the connection surface 9004. On the frame component 9001 there may be a connection port 9005. The projection 9006 is from the moulding process and may be removed for use. The connection port may allow coupling to an air circuit of a respiratory treatment apparatus, such as with an elbow or rotatable elbow that may be for example, snap fit, to the frame in the connection port or removable. Though not shown, fasteners, such as for head gear, may be directly connected to the frame and/or cushion.

The frame component 9001 may provide the shape forming structure and surface to hold the cushion (e.g., foam) 9002 in the desired profile for patient sealing. In such an embodiment, the cushion 9002 may provide some or all of the necessary spring and softness to effect the seal and provide comfort to the patient. Otherwise, some of the previously described flexible features (e.g., cantilever components of the clip previously described) may optionally be formed with the frame to assist with the seal and comfort effectiveness. While a full-face mask is shown, in some versions of the present technology nasal masks, nasal puffs, oro-nasal masks, etc. may be formed together with a foam cushion by the methods described herein.

The cushion 9002 may be made of various types of foam. Generally, foams may be separated into two separate classes, thermoset foams and thermoplastic foams. Thermoset foams have been previously cured by heat prior to molding with the frame component. Once cured, thermoset foams generally cannot be melted down, but heat may break down the material. Thermoplastic foams have not been cured and can be melted down. Within these two classes foam may be defined as a semi-open (or semi closed) cell foam. Thermoset and thermoplastic foam may be comprised of a foamed silicone material or a polyurethane foam, etc. Any of such foams may be implemented herein.

In some cases, a very low durometer thermoplastic elastomer (TPE), thermoplastic polyurethane (TPU), thermoplastic vulcanisates (TPV), silicone or rubber material might be implemented for the frame component. The range of hardnesses of the material may be, for example, from around 50 shore A through 85 shore D. In some embodiments, a silicone or silicone/urethane copolymer compound material might be implemented for the frame component.

The compliant nature of foam allows it to, under relatively small tension force, compress into intricate facial features and affect a good seal. This, combined with the easy adaptability and softness experienced by the patient, provides for a relative fast and easy mask set-up. The porosity of the foam also exhibits better breathability than silicone and may permit wicking away of moisture from the face. Thus, the use of foam may be associated with better cooling and reduced discomfort in the areas of contact or sealing.

In certain embodiments the cushion 9002 may be made of various types of foam which provide characteristics which may be beneficial to a face mask. In this regard, the foam may have minimal permeability to assure adequate delivery of a respiratory therapy to a patient and may be made with foam having a small cell size. In an example, a foam that has a hardness between 60-150 N and high density may be used. Such a hardness range may assure that the cushion provides adequate support of the face mask on the user's face, while the high density of the foam may assure minimal permeability. In addition, the cushion may be made of foam which is heat and/or tear resistance. Such a foam may be resistant to discolouring, thereby allowing for longer use of the cushion.

The cushion may also be made from foams which are beneficial to the comfort of a face mask. In this regard, the foam of the cushion may be soft, providing a comfortable contact point between the patient and the cushion 9002. Comfort may also be provided to the patient by using light weight, biocompatible foams which easily contours to the patient's facial shape. The memory (i.e., a return to original shape from deformation) of the foam may also be high to assure the foam maintains the contours of a user's face while not in use. In further embodiments the features of the foams may be consistent through regions of the cushion and/or through the entirety cushion.

The cushions of FIG. 89 are made of foams with different densities. Cushion 9011 is made from dense foam while cushion 9013 is made from less dense foam. Cushion 9012 is made from foam with a density in between that of the foams of cushions 9011 and 9013. The foam cushion may be a semi-open cell foam with limited permeability. The foam cushions may have a permeability characteristic of any of the foams previously described so as to be suitable for providing a pressure treatment to a patient.

As previously described the cushion 9002 may have a generally flat patient contact surface PCS or the edges may be rounded. For example, as illustrated in FIG. 89, the cushion profile may have a generally curved patient contact surface PCS. Other cushion profiles may also be implemented. The frame contact side of the cushion may be generally flat or otherwise conform to the contact surface of the frame. While the cushions of FIG. 89 are generally uni-planar, they may be deformed by the frame to have a multi-planar use configuration (e.g., with an nasolabial angle between the nasal plateau region and the mouth periphery region), in some cases the cushion may be pre-formed or pre-cut in the multi-planar shape consistent with the shape of the frame.

The cushion may be pre-formed by reaction injected moulding. Reaction injection molding requires mixing together polymers. The mixture may then be injected by an impinging mixer into a mould in the desired shape of the cushion. Inside the mould a chemical reaction occurs between the polymers causing the mixture to expand and fill the mould. After an amount of time the mixture cures within the mould in the desired shape of the cushion.

In some cases the cushion may be pre-cut by using a die cutter, such as from a slab of preformed foam. A die cutter may position blades in the desired shape of the cushion. A piece of foam is them compressed against the blades resulting in the blades cutting through the foam. The resulting cutout is in the desired shape of the cushion.

In other cases the cushion may be pre-cut or shaped by grinding foam. A grinding disc may be placed on a grinding wheel or attached to a drill. A piece of foam may then be ground down by the disc into the desired shape of the cushion.

The cushion may also be pre-cut by a compression cutting machine. A template mirroring how the cushion is intended to be shaped may be placed at the bottom of the compression cutting machine. Foam may then be passed into the machine and compressed above the template. A blade may be then passed through the foam above and into the template. The resulting cutout is then in the shape of the desired cushion. The cushions in FIG. 89 were compression cut. Other techniques of pre-cutting and pre-forming cushions may also be used.

The frame component 9001 may be created/formed from plastic. Possible plastics include polypropylene (PP), thermoplastic elastomers (TPE), thermoplastic polyurethane (TPU), thermoplastic polyurethane (TPV). Other types of plastics may also be utilized for creating frame component 9001. Silicone or rubber material might also be utilized in part of or for the entire frame component 9001.

The type of material selected for the frame component 9001, may be dependent on the type of foam utilized for the cushion 9002 and the type of bond desired. Both integral bonds (chemical bonds) and/or mechanical bonds may be possible.

A mechanical bond may involve a plastic and/or silicone interlocking with foam through, for example, a "hook and loop" connection. An example hook and loop connection may be seen in FIGS. 90A-D and 91A-B. In FIGS. 90A-D and 91A-B the connection surface 9004 of the frame 9020 to the cushion 9021 is shown at 40× magnification. As can be seen at 9022, the injected material has, in part, surrounded some fibers of the cushion 9021 creating a situation where the injected material is substantially or permanently connected to the cushion. Depending on the density of the foam selected and the viscosity of the injected material, the impregnation of the injected material into the foam may be non-existent or very deep. Depending on the desired strength of the necessary connection, different densities of foam and different viscosities of plastics, silicones, and/or silicone/urethane copolymers may be utilized.

A chemical bond may involve a material being injected into a mould and reacting to foam within the mould. Chemical reactions may occur under certain conditions such as where compatible types of foams and injected materials are chosen. For example, a TPU may be injected into the mould onto a polyurethane foam cushion. At the connection surface 9023 a chemical reaction may occur integrally bonding the injected material to the foam. However, when incompatible materials are used such as a TPU injected into a mould holding a thermoplastic elastomer cushion, no integral bond will be formed. Thus, the cushion and frame component may be integrally bonded, such as by intramolecular and/or intermolecular bonding.

The connection shown in FIGS. 90A-C and 91A-B was created by overmoulding in which a plastic material is injected into a mould and another material is placed inside the mould for combining with the plastic material. The plastic may then setup around and into the material inside of the mould resulting in the injected material being bonded to the material inside of the mould. The plastic once formed (e.g., the frame component) may then be rigid or semi-rigid. In such a case, the bond forms as a mechanical interlock as the material of the foam becomes intertwined with the material of the frame component during the overmoulding process.

Figure 90A:
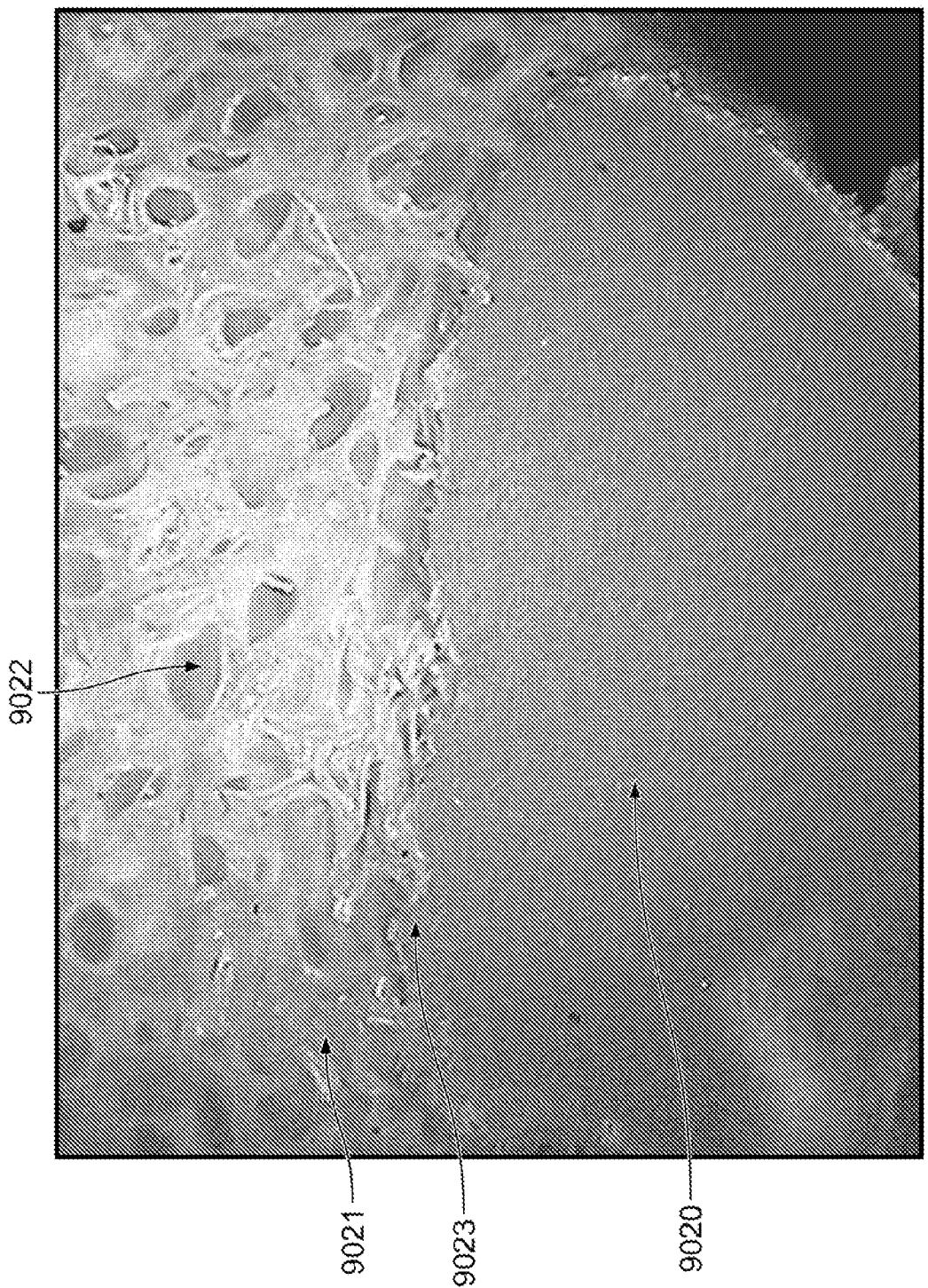
Figure 90B:
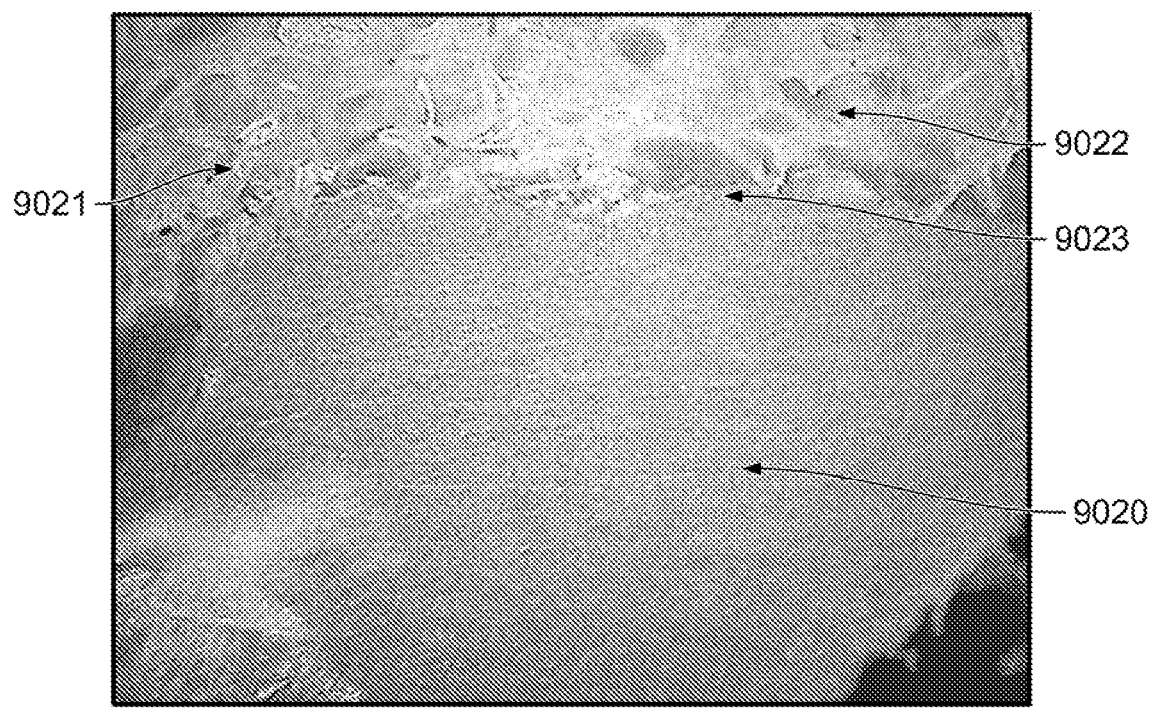
Figure 90C:
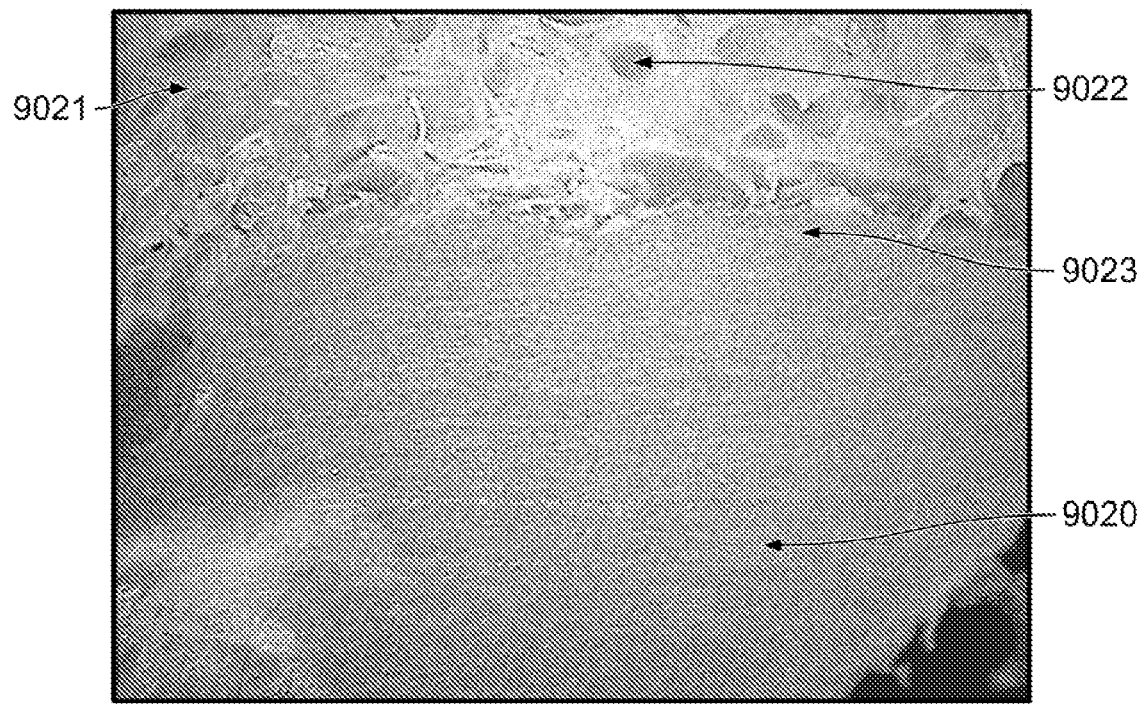
Figure 90D:
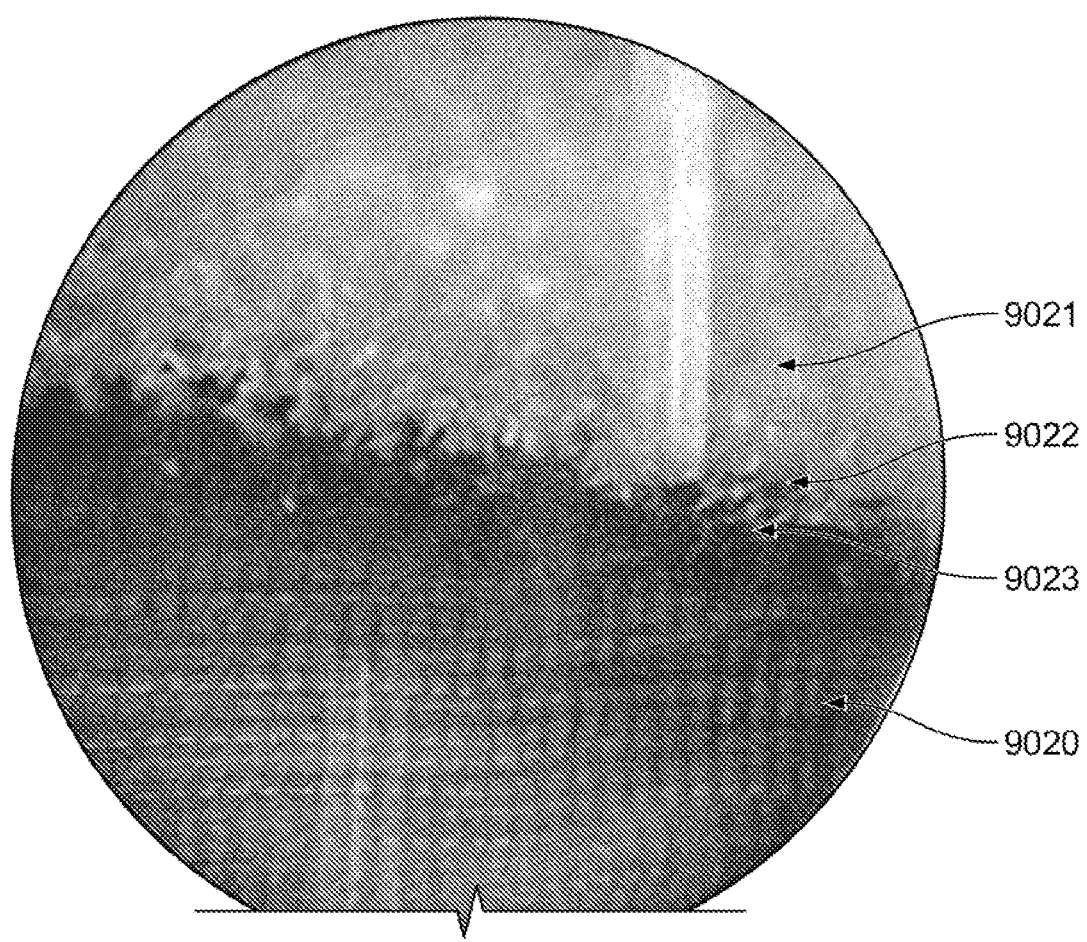
Figure 91A:
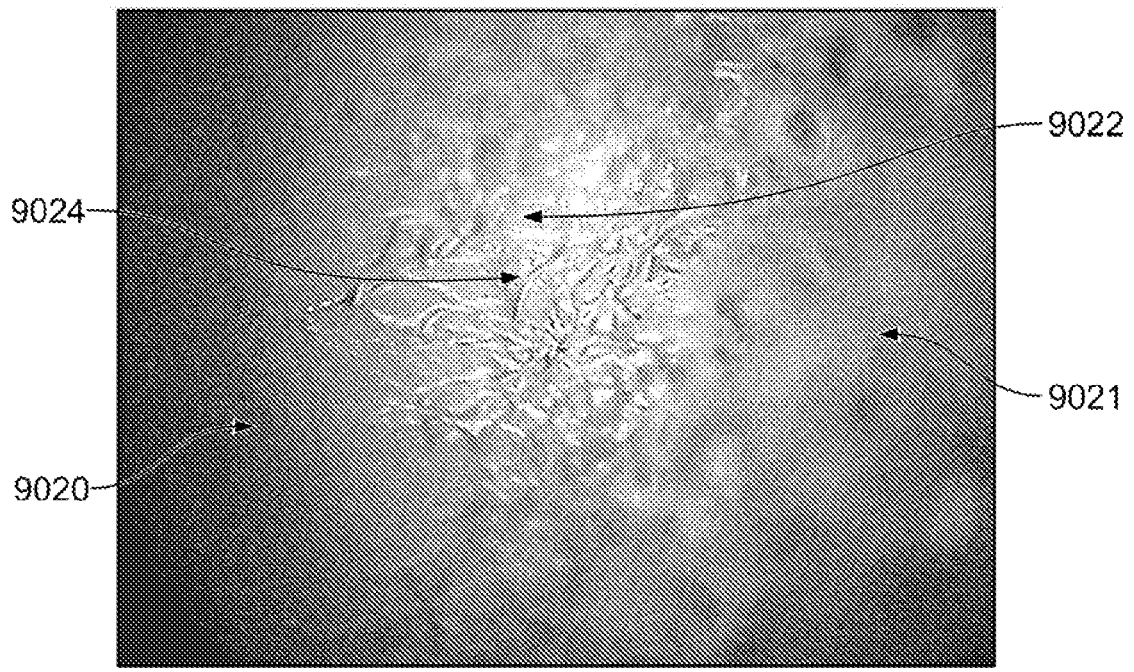
Figure 91B:
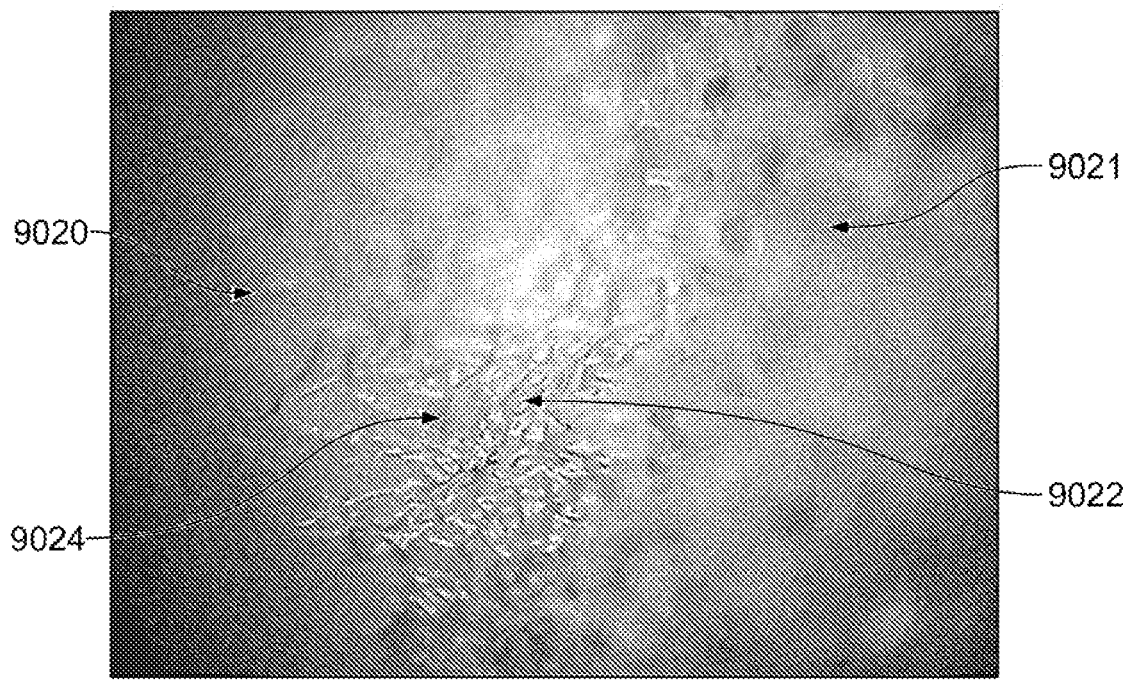

The connection shown in FIG. 90D was created by overmoulding in which a silicone is injected into a mould and another material, in this example, polyurethane foam, is placed inside the mould for combining with the silicone material. The silicone may then setup around and into the material inside of the mould resulting in the injected material being bonded to the material inside of the mould. The silicone once formed (e.g., the frame component) may then be rigid or semi-rigid. In such a case, the bonds may form as mechanical interlocks (i.e., mechanical bonds and/or mechanical keying) and/or integral bonds (i.e., chemical bonds—e.g., primary and/or secondary), as previously described. In some embodiments, a silicone surfactant may optionally be applied to the silicone frame and/or the foam cushion prior to the overmoulding.

FIG. 92 describes the process of overmoulding a plastic onto foam creating a finished mask component. At step 9030, a cushion is acquired in the desired shape. The acquisition may occur through any of the processes described above, such as foam being reaction injected moulded, die cut, compression cut etc.

Upon acquisition of the cushion, the cushion may be placed into a portion of a mould 9031 as shown in FIG. 93. The bottom mould 9040 (e.g., bottom outer core) may include bolt holes 9041, which may be used for clamping the mould closed. The bottom mould 9040 may also include elevated alignment projections 9042 which may help align the bottom mould with another portion of the mould. The bottom mould 9040 may also include bolt holes for clamping an inner core onto the cushion 9002.

The mould may be designed to affect the positioning or shaping of the cushion. In this regard, the shape of the cushion may be adjusted to provide for an optimized profile and fit range. As discussed previously, the cushion conforms to the user's face and serves as a seal between a user's face and the mask, and may also provide comfort to the patient. To assist with shaping and positioning of the cushion, which may start as a flat shape, the bottom mould may include a center mound 9044 and an outer ridge 9045. The center mound and outer ridge may align the cushion as the plastic is injected into the mould by pressing the cushion into the plastic in the desired shape. While the bottom piece of the mould is discussed in this embodiment, the mould may be built so there may be any number of parts that make up the mould.

Step 9032 involves the placing of an inner core 9050 over the cushion 9002 which in the current embodiment is in the bottom mould 9040. Placement of the inner core urges the cushion into a desired shape and into placement in a portion of the mould, thereby deforming a flat cushion so as to form a desired contoured profile more suitable for use with respect to a contour of a patient's face. The inner core 9050 may be designed to form the inner part of the frame component 9001. As shown in FIG. 94, the inner core 9050 may include a nasal region 9052 and an oral region 9056. The inner core may also include an edge ridge 9051, which may compresses the foam and prevent the injected material from spreading onto parts of the foam where it should not contact. As shown on the underside of the inner core, there may also be bolt holes 9055 for connecting the inner core to the bottom mould 9040.

The inner core 9050 may also direct the flow of the injected material. An attachment ridge 9057 may include a cavity 9053. The cavity 9053 may fill with the injected material and direct the injected material into a channel 9054. This cavity then controls the flow of injected material by directing the material where it should go. The attachment ridge 9057 may be elevated above the channel so the injected material may not flow onto the attachment ridge 9057.

Step 9033 involves assembling the formed mold. The formed mold may include the bottom mould 9040, inner core 9050, and top mould 9060 (e.g., top outer core). The bottom mould 9040 and inner core 9050 may be connected through the use of fasteners, such as bolts, inserted through bolt holes 9055 into 9043. The top mould 9060, as described in FIG. 97, may include bolt holes 9061 and recessed alignment ports 9062. The top mold may also include an injection insert 9064, outer shell 9063, and an outer clamping ridge 9065. The injection insert may direct the injected material into the cavity 9053 of the inner core. The outer shell 9063, may provide the shape of the outer portion of the frame component 9001 of the mask, in this case, the shell of a plenum chamber. The outer clamping ridge 9065 may compress the foam and prevent the injected material from spreading onto parts of the foam where it should not form. FIG. 96 shows the inner core 9050, cushion 9002, and bottom mould 9040.

Upon assembly of the bottom mould 9040 to the inner core 9050, the top mould 9060 may be placed over the bottom mould 9040 by aligning the recessed alignment ports 9062 with the elevated alignment projections 9042 of the bottom mould. Fasteners may then be inserted through bolt holes 9061 into bolt holes 9041 to clamp the top mould 9060 to the bottom mould 9040. FIGS. 98A and 98B show an example inner core 9050, bottom mould 9040, and top mould 9060.

Step 9034 of FIG. 92 involves injecting a material, such as the materials described herein, into the formed mold to be shaped into a frame component 9001, as well as to bond with the cushion 9002. The injected material may be inserted through the injection insert 9064 of the top mould.

The temperature at which the injected material is inserted may be dependent upon the type of material being injected as well as the type of foam being utilized for the cushion 9002. For example, if a thermoplastic foam is utilized for the cushion 9002, the temperature of the equipment (i.e., mould) and the injected material must be taken into account, so as not to over-melt the foam, which would destroy the cushion. However, some melting of the thermoplastic foam may result in a better bond between the plastic and the foam. While silicone may be utilized for the frame component 9001, the type of foam utilized for the cushion must be able to withstand the heat of the injected silicone. The range of temperatures for the plastic being injected may be around 260° C. to 300° C., while the machinery is around 20° C. to 60° C., for example. These temperatures are dependent upon the material being injected and the material utilized for the cushion 9002.

The temperature at which the injected material is inserted is less of a concern when thermoset foam is utilized as the cushion 9002. As previously described, thermoset foam has already been cured and is less susceptible to heat than thermoplastic foams.

While injecting a material for overmoulding, the pressure of the injection may be considered. Low injection pressure may be utilized to avoid distorting the cushion 9002, as well as to avoid overcoming the cushion's tensile and tear strength. Suitable example foam cushion tensile and tear strength characteristics have be previously described.

The injection pressure may, for example, be in the range of 20 MPa to 50 MPa. The injection pressure may be controlled by adjusting the speed of the injection material, the size of the part being created, and the size of the gate allowing the material to flow.

Step 9035 involves the time from the injection of the material through to the time the material has set and cooled. This time period is called a cycle time. The cycle time may be dependent upon the type of injected material utilized. For example, a dense rubber may take longer to set than a less dense plastic. The rubber may also take longer to cool than a plastic. Accordingly rubber may have a longer cycle time than plastic. If the cooling time of the overmoulding process may be long, cooling equipment, such as refrigeration, liquid nitrogen, or cooling racks may be necessary to shorten the time required to set and cool the injected material.

In steps 9036 and 9037, once the injected material has set and cooled, the formed mould may be disassembled by removing the inserted bolts. The finished component product may then be ejected from the inner core.

While the embodiments described above show the injected material bonding to a cushion, the injected material may be used to bond two materials together in a 'fir-tree' connection. For example, injected plastic may be bonded to a pre-formed silicone mask on a first side and a cushion on the opposing side. The materials joined by the injected material may both be flexible and/or hard, or one may be flexible, while the other may be hard.

4.6 Glossary

For the purposes of the present technology disclosure, in certain forms of the present technology, one or more of the following definitions may apply. In other forms of the present technology, alternative definitions may apply.

4.6.1 General

Air: In certain forms of the present technology, air supplied to a patient may be atmospheric air, and in other forms of the present technology atmospheric air may be supplemented with oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

4.6.2 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricula or Pinna: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion.

4.6.3 Anatomy of the Skull

Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

4.6.4 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

4.6.5 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240

Polycarbonate: a typically transparent thermoplastic polymer of Bisphenol-A Carbonate.

4.6.6 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to a mean portion of a patient interface having walls enclosing a volume of space, the volume having air therein pressurised above atmospheric pressure in use. A shell may form part of the walls of a mask plenum chamber. In one form, a region of the patient's face forms one of the walls of the plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will preferably be taken to mean a curved structure having bending, tensile and compressive stiffness, for example, a portion of a mask that forms a curved structural wall of the mask. Preferably, compared to its overall dimensions it is relatively thin. In some forms, a shell may be faceted. Preferably such walls are airtight, although in some forms they may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. Preferably there is little or no leak flow of air from the swivel in use.

Tie: A tie will be taken to be a structural component designed to resist tension.

Vent: (noun) the structure that allows a deliberate controlled rate leak of air from an interior of the mask, or conduit to ambient air, to allow washout of exhaled carbon dioxide ($CO_2$) and supply of oxygen ($O_2$).

4.6.7 Terms Used in Relation to Patient Interface

Curvature (of a surface): A region of a surface having a saddle shape, which curves up in one direction and curves down in a different direction, will be said to have a negative curvature. A region of a surface having a dome shape, which curves the same way in two principle directions, will be said to have a positive curvature. A flat surface will be taken to have zero curvature.

Floppy: A quality of a material, structure or composite that is the combination of features of:
Readily conforming to finger pressure.
Unable to retain its shape when caused to support its own weight.
Not rigid.
Able to be stretched or bent elastically with little effort.
The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during positive airway pressure therapy.

4.7 Other Remarks

A portion of the disclosure of this patent document contains material which is subject to copyright protection.

The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The expressions "soft" and "flexible", as well as their derivatives, when used in this specification to describe the first support clip 3812 (FIG. 40), are intended to have the meaning of the expression "resilient" as specifically defined in section "Terms used in relation to patient interface". This is to say, the flexible supporting clip is able to deform substantially elastically, and to quickly release substantially all of the energy upon unloading.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

The invention claimed is:

1. A mask apparatus for a respiratory treatment comprising:
   a frame component adapted to couple with a respiratory treatment apparatus so as to permit communication of a pressurized gas to a respiratory system of a patient from the respiratory treatment apparatus; and
   a foam cushion adapted to conform to a facial surface of the patient for delivery of the pressurized gas,
   wherein the frame component is overmoulded to the foam cushion to form a chemical bond and a mechanical bond at a surface of the frame component and the foam cushion,
   wherein when the frame component is overmoulded to the foam cushion, material of the frame component is set in and around sub-surface features of the foam cushion such that the mechanical bond comprises an impregnation of a sub-surface of the foam cushion with material of the frame component,
   wherein the impregnated sub-surface of the foam cushion comprises an edge of the foam cushion on a frame contact side that is opposite to a patient contact side of the foam cushion,
   wherein the foam cushion has a density characteristic in a range of approximately 24.3 to 117.85 kg/m$^3$ and a permeability characteristic in a range of approximately 0 to 20 L/min under a constant air pressure of 20 cmH$_2$O wherein the chemical bond comprises a primary chemical bond.

2. The mask apparatus of claim 1 wherein the foam cushion comprises a triangular ring having a common nasal and mouth aperture.

3. The mask apparatus of claim 1 wherein the frame component comprises a shell of a plenum chamber.

4. The mask apparatus of claim 1 wherein the foam cushion is formed of a thermoset foam.

5. The mask apparatus of claim 1 wherein the frame component is formed of a plastic material.

6. The mask apparatus of claim 1 wherein the frame component is formed of a silicone material.

7. The mask apparatus of claim 1 wherein the chemical bond comprises a secondary chemical bond.

8. The mask apparatus of claim 1 wherein the mechanical bond comprises an interlock of a sub-surface of the foam cushion with material of the frame component.

9. The mask apparatus of claim 1 wherein the mechanical bond comprises mechanical keying.

10. The mask apparatus of claim 1 wherein when the frame component is overmoulded to the foam cushion, material of the frame component surrounds at least some fibers of the foam cushion such that the mechanical bond comprises hook and loop connections.

11. The mask apparatus of claim 1 wherein the frame component and foam cushion are joined without adhesive.

12. The mask apparatus of claim 1 wherein material of the frame component comprises thermoplastic polyurethane.

13. The mask apparatus of claim 1 wherein the foam cushion is a semi-open cell foam formed by a mixture of open and closed cells.

14. The mask apparatus of claim 1 wherein the foam cushion comprises a generally flat seal-forming surface.

15. The mask apparatus of claim 1 wherein the foam cushion comprises a generally curved seal-forming surface.

16. The mask apparatus of claim 1 further comprising a respiratory treatment apparatus configured to generate a controlled supply of breathable gas at a pressure above atmospheric pressure, the respiratory treatment apparatus including a gas delivery conduit coupled with the frame component to direct the breathable gas to the frame component.

17. A method of manufacturing a mask apparatus for a respiratory treatment comprising:
positioning a foam cushion within a cavity of a mould, the cavity of the mould for forming a mask frame component; and
injecting a material into the mould to form the mask frame component;
whereby the formed frame component is overmoulded to the foam cushion forming a chemical bond and a mechanical bond at a surface of the frame component and the foam cushion,
wherein when the frame component is overmoulded to the foam cushion, material of the frame component is set in and around sub-surface features of the foam cushion such that the mechanical bond comprises an impregnation of a sub-surface of the foam cushion with material of the frame component,
wherein the impregnated sub-surface of the foam cushion comprises an edge of the foam cushion on a frame contact side that is opposite to a patient contact side of the foam cushion,
wherein the foam cushion has a density characteristic in a range of approximately 24.3 to 117.85 kg/m³ and a permeability characteristic in a range of approximately 0 to 20 L/min under a constant air pressure of 20 cmH$_2$O wherein the chemical bond comprises a primary chemical bond.

18. The method of claim 17 wherein the foam cushion comprises a triangular ring having a common nasal and mouth aperture.

19. The method of claim 17 wherein the mould includes a form of a shell of a plenum chamber.

20. The method of claim 17 wherein the foam cushion is formed of a thermoset foam.

21. The method of claim 17 wherein the injected material is a plastic.

22. The method of claim 17 wherein the injected material is a silicone.

23. The method of claim 17 wherein the chemical bond comprises a secondary chemical bond.

24. The method of claim 17 wherein the mechanical bond comprises an interlock of a sub-surface of the foam cushion with material of the frame component.

25. The method of claim 17 wherein the mechanical bond comprises mechanical keying.

26. The method of claim 17 wherein when the frame component is overmoulded to the foam cushion, material of the frame component surrounds at least some fibers of the foam cushion such that the mechanical bond comprises hook and loop connections.

27. The method of claim 17 wherein the frame component and foam cushion are joined for use without adhesive.

28. The method of claim 17 wherein the injected material of the frame component comprises thermoplastic polyurethane.

29. The method of claim 17 wherein the injected material of the frame component comprises silicon/polyurethane copolymer.

30. The method of claim 17 wherein the foam cushion is a semi-open cell foam formed by a mixture of open and closed cells.

31. The method of claim 17 wherein the injecting occurs at a pressure range of 20 to 50 mega-pascals.

32. The method of claim 31 wherein the injecting occurs at a pressure of about 20 mega-pascals.

33. The method of claim 17 further comprising inserting a plenum chamber shaped inner moulding core against the foam cushion.

34. The mask apparatus of claim 1, wherein the impregnation is to a predetermined depth within the foam cushion that is based on the density characteristic of the foam cushion and a viscosity of the material of the frame component.

* * * * *